United States Patent
Shelton, IV et al.

(10) Patent No.: US 10,835,246 B2
(45) Date of Patent: Nov. 17, 2020

(54) STAPLE CARTRIDGES AND ARRANGEMENTS OF STAPLES AND STAPLE CAVITIES THEREIN

(71) Applicant: Ethicon Endo-Surgery, LLC, Guaynabo, PR (US)

(72) Inventors: Frederick E. Shelton, IV, Hillsboro, OH (US); Jason L. Harris, Lebanon, OH (US); Janna B. Volz, West Chester, OH (US); Jordan B. Wong, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 517 days.

(21) Appl. No.: 15/385,939

(22) Filed: Dec. 21, 2016

(65) Prior Publication Data

US 2018/0168629 A1   Jun. 21, 2018

(51) Int. Cl.
    *A61B 17/072*   (2006.01)
    *A61B 17/068*   (2006.01)
    *A61B 34/30*    (2016.01)
    *A61B 17/29*    (2006.01)
    (Continued)

(52) U.S. Cl.
    CPC ...... *A61B 17/07207* (2013.01); *A61B 17/072* (2013.01); *A61B 2017/00017* (2013.01); *A61B 2017/0046* (2013.01); *A61B 2017/00398* (2013.01); *A61B 2017/00464* (2013.01); *A61B 2017/00473* (2013.01); *A61B 2017/00477* (2013.01); *A61B 2017/0645* (2013.01); *A61B 2017/0725* (2013.01); *A61B 2017/07228* (2013.01); *A61B 2017/07235* (2013.01); *A61B 2017/07242* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01); *A61B 2017/2927* (2013.01)

(58) Field of Classification Search
    CPC  A61B 2017/07271; A61B 2017/07235; A61B 2017/07228
    USPC ............................................. 227/175.1–182.1
    See application file for complete search history.

(56) References Cited

U.S. PATENT DOCUMENTS 4,305,539 A * 12/1981 Korolkov ............. A61B 17/072
                                              227/109
5,364,003 A * 11/1994 Williamson, IV ... A61B 17/072
                                              227/178.1
(Continued)

FOREIGN PATENT DOCUMENTS

CN   202313537 U * 7/2012  ........... A61B 17/072
CN   204158441 U * 2/2015  ....... A61B 17/07207
(Continued)

*Primary Examiner* — Stephen F. Gerrity
*Assistant Examiner* — Joshua G Kotis

(57) ABSTRACT

A staple cartridge is disclosed. The staple cartridge can have a longitudinal axis and a cartridge body having a deck, wherein a plurality of staple cavities can be defined in the cartridge body. The staple cavities can be arranged in a plurality of patterns, and the patterns can include a first pattern and a second pattern longitudinally offset from the first pattern. The second pattern can be different than the first pattern. The first pattern can consist of a longitudinally-repetitive pattern of angularly-oriented staple cavities and/or the second pattern can consist of parallel staple cavities.

14 Claims, 45 Drawing Sheets

(51) Int. Cl.
*A61B 17/064* (2006.01)
*A61B 17/00* (2006.01)

(56) References Cited

U.S. PATENT DOCUMENTS

| | | | | |
|---|---|---|---|---|
| 5,389,098 A * | 2/1995 | Tsuruta | A61B 17/00234 | 606/41 |
| 5,551,622 A * | 9/1996 | Yoon | A61B 17/072 | 227/176.1 |
| 8,540,133 B2 * | 9/2013 | Bedi | A61B 17/07207 | 227/180.1 |
| 2006/0011699 A1 * | 1/2006 | Olson | A61B 17/07207 | 227/180.1 |
| 2008/0023522 A1 * | 1/2008 | Olson | A61B 17/07207 | 227/175.1 |
| 2011/0009853 A1 * | 1/2011 | Bertolero | A61B 17/122 | 606/14 |
| 2011/0192882 A1 * | 8/2011 | Hess | A61B 17/072 | 227/176.1 |
| 2012/0080493 A1 * | 4/2012 | Shelton, IV | A61B 17/07207 | 227/176.1 |
| 2012/0241499 A1 * | 9/2012 | Baxter, III | A61B 17/0643 | 227/176.1 |
| 2014/0081176 A1 * | 3/2014 | Hassan | A61M 25/10181 | 600/593 |
| 2014/0180281 A1 * | 6/2014 | Rusin | A61B 18/1442 | 606/45 |
| 2015/0150620 A1 * | 6/2015 | Miyamoto | A61B 17/07207 | 606/51 |
| 2015/0282809 A1 * | 10/2015 | Shelton, IV | A61B 17/068 | 227/176.1 |
| 2015/0297236 A1 * | 10/2015 | Harris | A61B 17/0644 | 227/176.1 |
| 2015/0351758 A1 * | 12/2015 | Shelton, IV | A61B 17/00491 | 606/219 |
| 2015/0351764 A1 * | 12/2015 | Shelton, IV | A61B 17/00491 | 227/176.1 |
| 2016/0199084 A1 * | 7/2016 | Takei | A61B 18/085 | 606/170 |
| 2017/0128121 A1 * | 5/2017 | Takashino | A61B 18/10 | |

FOREIGN PATENT DOCUMENTS

| | | | | |
|---|---|---|---|---|
| JP | 6010269 B1 * | 10/2016 | | A61B 18/10 |
| RU | 2069981 C1 * | 12/1996 | | A61B 17/072 |

* cited by examiner

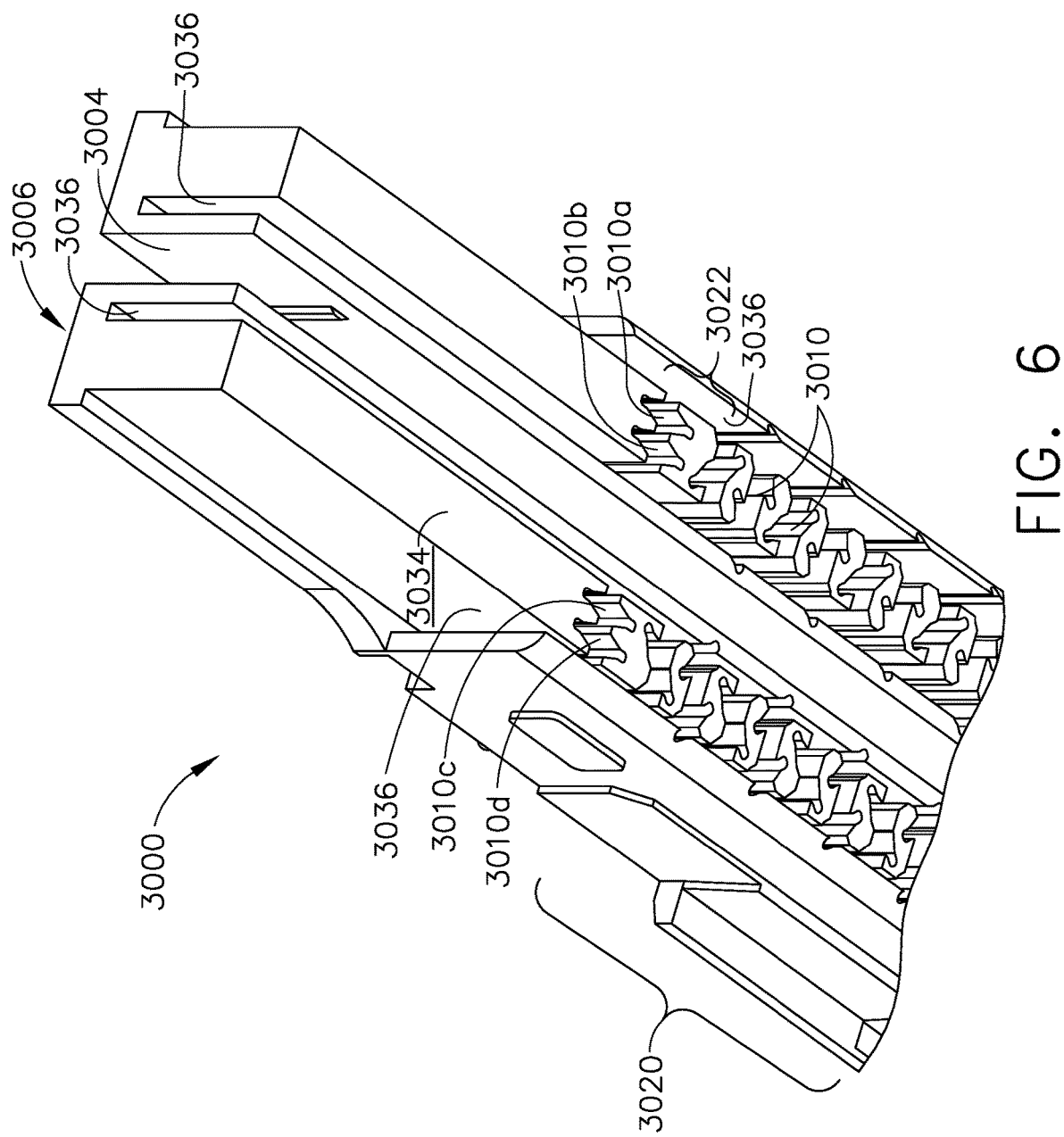

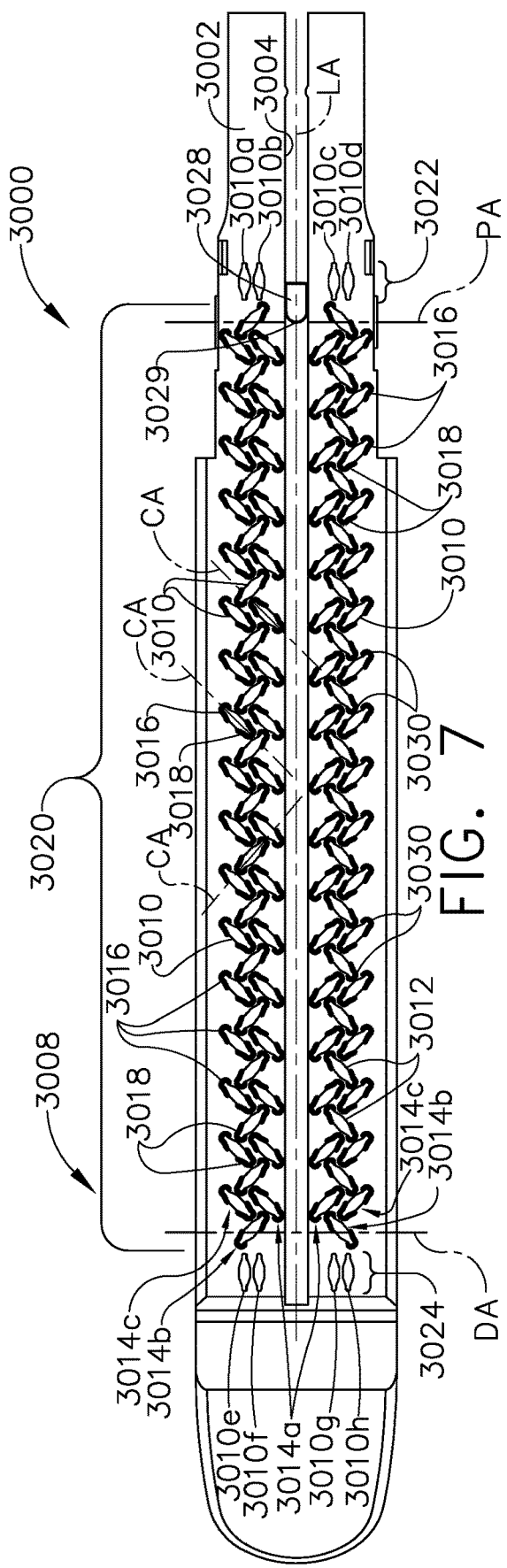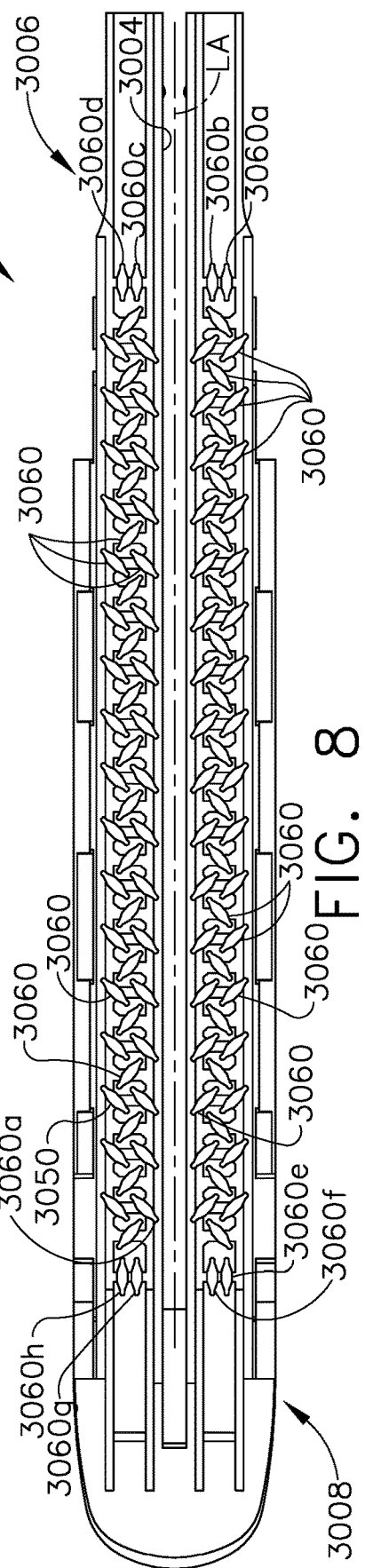

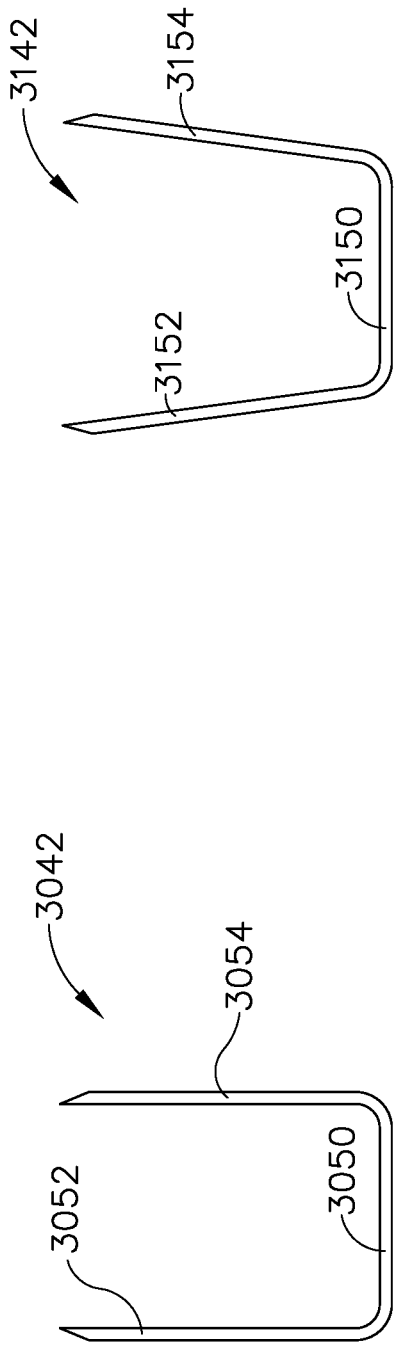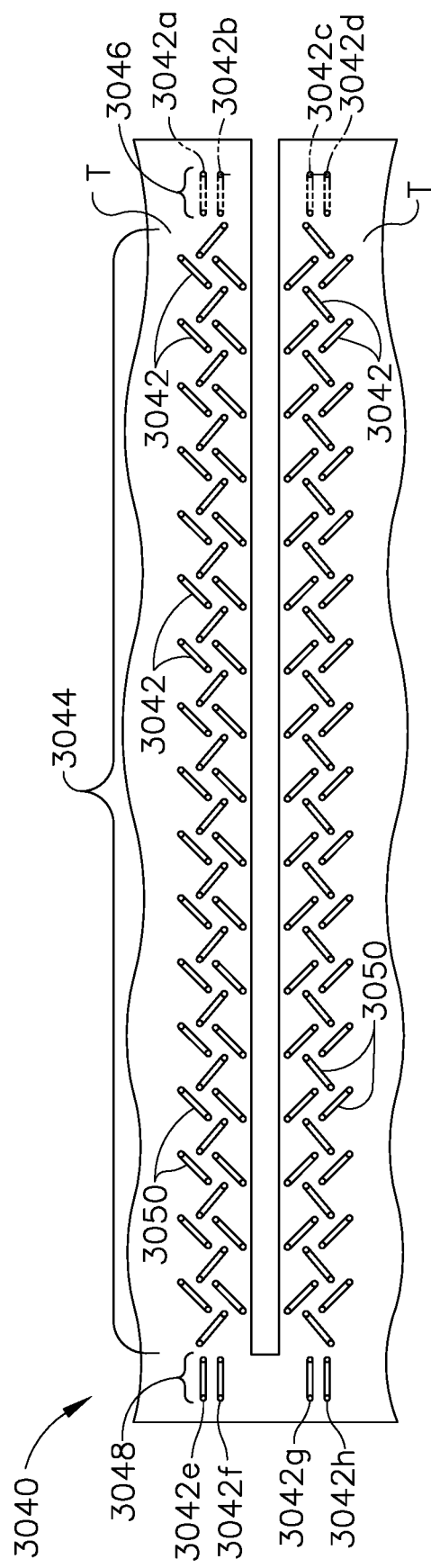

STAPLE CARTRIDGES AND ARRANGEMENTS OF STAPLES AND STAPLE CAVITIES THEREIN

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 6 is a partial perspective bottom view of the staple cartridge body of FIG. 5;

FIG. 7 is a top plan view of the staple cartridge body of FIG. 5 and depicting a cutting element positioned in a longitudinal slot of the cartridge body;

FIG. 8 is a bottom plan view of the staple cartridge body of FIG. 5 and depicting drivers positioned in the staple cavities;

FIG. 9 is a staple line implanted in stapled tissue and generated by the staple cartridge body of FIG. 5 and depicting certain staples that are likely to be missing from the staple line with phantom lines;

FIG. 10 is a side elevation view of a staple in the staple line of FIG. 9;

FIG. 11 is a side elevation view of a staple;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
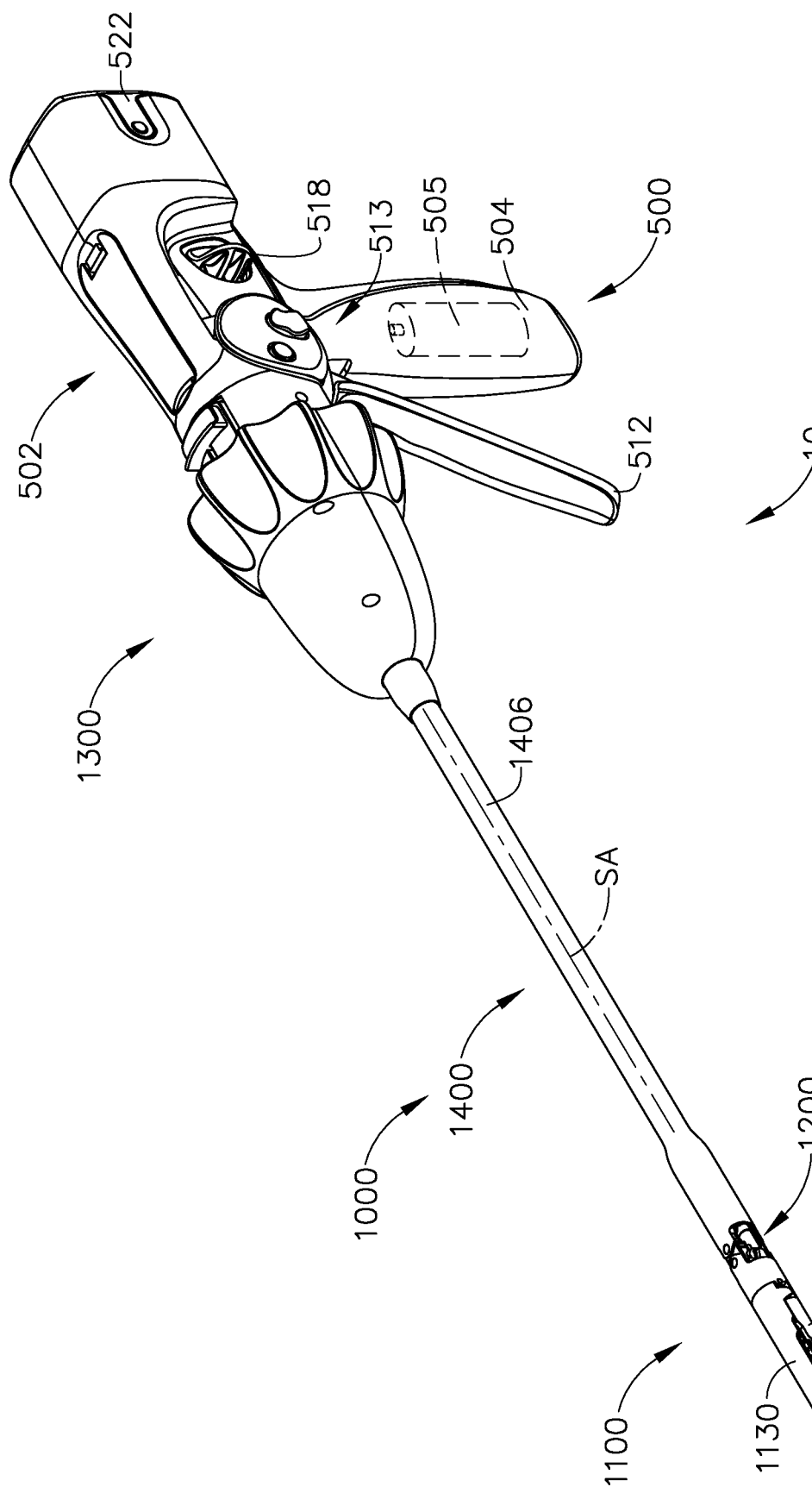
FIG. 1 is a perspective view of an interchangeable surgical tool assembly embodiment operably coupled to a handle assembly embodiment.

Applicant of the present application owns the following U.S. Patent Applications that were filed on Dec. 21, 2016 and which are each herein incorporated by reference in their respective entireties:

U.S. patent application Ser. No. 15/386,185, entitled SURGICAL STAPLING INSTRUMENTS AND REPLACEABLE TOOL ASSEMBLIES THEREOF;

U.S. patent application Ser. No. 15/386,230, entitled ARTICULATABLE SURGICAL STAPLING INSTRUMENTS;

U.S. patent application Ser. No. 15/386,221, entitled LOCKOUT ARRANGEMENTS FOR SURGICAL END EFFECTORS;

U.S. patent application Ser. No. 15/386,209, entitled SURGICAL END EFFECTORS AND FIRING MEMBERS THEREOF;

U.S. patent application Ser. No. 15/386,198, entitled LOCKOUT ARRANGEMENTS FOR SURGICAL END EFFECTORS AND REPLACEABLE TOOL ASSEMBLIES; and U.S. patent application Ser. No. 15/386,240, entitled SURGICAL END EFFECTORS AND ADAPTABLE FIRING MEMBERS THEREFOR.

Applicant of the present application owns the following U.S. Patent Applications that were filed on Dec. 21, 2016 and which are each herein incorporated by reference in their respective entireties:

U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS;

U.S. patent application Ser. No. 15/385,943, entitled SURGICAL STAPLING INSTRUMENTS AND STAPLE-FORMING ANVILS;

U.S. patent application Ser. No. 15/385,950, entitled SURGICAL TOOL ASSEMBLIES WITH CLOSURE STROKE REDUCTION FEATURES;

U.S. patent application Ser. No. 15/385,945, entitled STAPLE CARTRIDGES AND ARRANGEMENTS OF STAPLES AND STAPLE CAVITIES THEREIN;

U.S. patent application Ser. No. 15/385,946, entitled SURGICAL STAPLING INSTRUMENTS AND STAPLE-FORMING ANVILS;

U.S. patent application Ser. No. 15/385,951, entitled SURGICAL INSTRUMENTS WITH JAW OPENING FEATURES FOR INCREASING A JAW OPENING DISTANCE;

U.S. patent application Ser. No. 15/385,953, entitled METHODS OF STAPLING TISSUE;

U.S. patent application Ser. No. 15/385,954, entitled FIRING MEMBERS WITH NON-PARALLEL JAW ENGAGEMENT FEATURES FOR SURGICAL END EFFECTORS;

U.S. patent application Ser. No. 15/385,955, entitled SURGICAL END EFFECTORS WITH EXPANDABLE TISSUE STOP ARRANGEMENTS;

U.S. patent application Ser. No. 15/385,948, entitled SURGICAL STAPLING INSTRUMENTS AND STAPLE-FORMING ANVILS;

U.S. patent application Ser. No. 15/385,956, entitled SURGICAL INSTRUMENTS WITH POSITIVE JAW OPENING FEATURES;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT; and U.S. patent application Ser. No. 15/385,947, entitled STAPLE CARTRIDGES AND ARRANGEMENTS OF STAPLES AND STAPLE CAVITIES THEREIN.

Applicant of the present application owns the following U.S. Patent Applications that were filed on Dec. 21, 2016 and which are each herein incorporated by reference in their respective entireties:

U.S. patent application Ser. No. 15/385,896, entitled METHOD FOR RESETTING A FUSE OF A SURGICAL INSTRUMENT SHAFT;

U.S. patent application Ser. No. 15/385,898, entitled STAPLE FORMING POCKET ARRANGEMENT TO ACCOMMODATE DIFFERENT TYPES OF STAPLES;

U.S. patent application Ser. No. 15/385,899, entitled SURGICAL INSTRUMENT COMPRISING IMPROVED JAW CONTROL;

U.S. patent application Ser. No. 15/385,901, entitled STAPLE CARTRIDGE AND STAPLE CARTRIDGE CHANNEL COMPRISING WINDOWS DEFINED THEREIN;

U.S. patent application Ser. No. 15/385,902, entitled SURGICAL INSTRUMENT COMPRISING A CUTTING MEMBER;

U.S. patent application Ser. No. 15/385,904, entitled STAPLE FIRING MEMBER COMPRISING A MISSING CARTRIDGE AND/OR SPENT CARTRIDGE LOCKOUT;

U.S. patent application Ser. No. 15/385,905, entitled FIRING ASSEMBLY COMPRISING A LOCKOUT;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT;

U.S. patent application Ser. No. 15/385,908, entitled FIRING ASSEMBLY COMPRISING A FUSE; and U.S. patent application Ser. No. 15/385,909, entitled FIRING ASSEMBLY COMPRISING A MULTIPLE FAILED-STATE FUSE.

Applicant of the present application owns the following U.S. Patent Applications that were filed on Dec. 21, 2016 and which are each herein incorporated by reference in their respective entireties:

U.S. patent application Ser. No. 15/385,920, entitled STAPLE FORMING POCKET ARRANGEMENTS;

U.S. patent application Ser. No. 15/385,913, entitled ANVIL ARRANGEMENTS FOR SURGICAL STAPLERS;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT;

U.S. patent application Ser. No. 15/385,893, entitled BILATERALLY ASYMMETRIC STAPLE FORMING POCKET PAIRS;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS;

U.S. patent application Ser. No. 15/385,911, entitled SURGICAL STAPLERS WITH INDEPENDENTLY ACTUATABLE CLOSING AND FIRING SYSTEMS;

U.S. patent application Ser. No. 15/385,927, entitled SURGICAL STAPLING INSTRUMENTS WITH SMART STAPLE CARTRIDGES;

U.S. patent application Ser. No. 15/385,917, entitled STAPLE CARTRIDGE COMPRISING STAPLES WITH DIFFERENT CLAMPING BREADTHS;

U.S. patent application Ser. No. 15/385,900, entitled STAPLE FORMING POCKET ARRANGEMENTS COMPRISING PRIMARY SIDEWALLS AND POCKET SIDEWALLS;

U.S. patent application Ser. No. 15/385,931, entitled NO-CARTRIDGE AND SPENT CARTRIDGE LOCKOUT ARRANGEMENTS FOR SURGICAL STAPLERS;

U.S. patent application Ser. No. 15/385,915, entitled FIRING MEMBER PIN ANGLE;

U.S. patent application Ser. No. 15/385,897, entitled STAPLE FORMING POCKET ARRANGEMENTS COMPRISING ZONED FORMING SURFACE GROOVES;

U.S. patent application Ser. No. 15/385,922, entitled SURGICAL INSTRUMENT WITH MULTIPLE FAILURE RESPONSE MODES;

U.S. patent application Ser. No. 15/385,924, entitled SURGICAL INSTRUMENT WITH PRIMARY AND SAFETY PROCESSORS;

U.S. patent application Ser. No. 15/385,912, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS;

U.S. patent application Ser. No. 15/385,910, entitled ANVIL HAVING A KNIFE SLOT WIDTH;

U.S. patent application Ser. No. 15/385,903, entitled CLOSURE MEMBER ARRANGEMENTS FOR SURGICAL INSTRUMENTS; and U.S. patent application Ser. No. 15/385,906, entitled FIRING MEMBER PIN CONFIGURATIONS.

Applicant of the present application owns the following U.S. Patent Applications that were filed on Dec. 21, 2016 and which are each herein incorporated by reference in their respective entireties:

U.S. patent application Ser. No. 15/386,188, entitled STEPPED STAPLE CARTRIDGE WITH ASYMMETRICAL STAPLES;

U.S. patent application Ser. No. 15/386,192, entitled STEPPED STAPLE CARTRIDGE WITH TISSUE RETENTION AND GAP SETTING FEATURES;

U.S. patent application Ser. No. 15/386,206, entitled STAPLE CARTRIDGE WITH DEFORMABLE DRIVER RETENTION FEATURES;

U.S. patent application Ser. No. 15/386,226, entitled DURABILITY FEATURES FOR END EFFECTORS AND FIRING ASSEMBLIES OF SURGICAL STAPLING INSTRUMENTS;

U.S. patent application Ser. No. 15/386,222, entitled SURGICAL STAPLING INSTRUMENTS HAVING END EFFECTORS WITH POSITIVE OPENING FEATURES; and U.S. patent application Ser. No. 15/386,236, entitled CONNECTION PORTIONS FOR DISPOSABLE LOADING UNITS FOR SURGICAL STAPLING INSTRUMENTS.

Applicant of the present application owns the following U.S. Patent Applications that were filed on Dec. 21, 2016 and which are each herein incorporated by reference in their respective entireties:

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM;

U.S. patent application Ser. No. 15/385,890, entitled SHAFT ASSEMBLY COMPRISING SEPARATELY ACTUATABLE AND RETRACTABLE SYSTEMS;

U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM;

U.S. patent application Ser. No. 15/385,894, entitled SHAFT ASSEMBLY COMPRISING A LOCKOUT; and U.S. patent application Ser. No. 15/385,895, entitled SHAFT ASSEMBLY COMPRISING FIRST AND SECOND ARTICULATION LOCKOUTS.

Applicant of the present application owns the following U.S. Patent Applications that were filed on Dec. 21, 2016 and which are each herein incorporated by reference in their respective entireties:

U.S. patent application Ser. No. 15/385,916, entitled SURGICAL STAPLING SYSTEMS;

U.S. patent application Ser. No. 15/385,918, entitled SURGICAL STAPLING SYSTEMS;

U.S. patent application Ser. No. 15/385,919, entitled SURGICAL STAPLING SYSTEMS;

U.S. patent application Ser. No. 15/385,921, entitled SURGICAL STAPLE CARTRIDGE WITH MOVABLE CAMMING MEMBER CONFIGURED TO DISENGAGE FIRING MEMBER LOCKOUT FEATURES;

U.S. patent application Ser. No. 15/385,923, entitled SURGICAL STAPLING SYSTEMS;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT;

U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS;

U.S. patent application Ser. No. 15/385,932, entitled ARTICULATABLE SURGICAL END EFFECTOR WITH ASYMMETRIC SHAFT ARRANGEMENT;

U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK;

U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM;

U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION; and U.S. patent application Ser. No. 15/385,936, entitled ARTICULATABLE SURGICAL INSTRUMENTS WITH ARTICULATION STROKE AMPLIFICATION FEATURES.

Applicant of the present application owns the following U.S. Patent Applications that were filed on Jun. 24, 2016 and which are each herein incorporated by reference in their respective entireties:

U.S. patent application Ser. No. 15/191,775, entitled STAPLE CARTRIDGE COMPRISING WIRE STAPLES AND STAMPED STAPLES;

U.S. patent application Ser. No. 15/191,807, entitled STAPLING SYSTEM FOR USE WITH WIRE STAPLES AND STAMPED STAPLES;

U.S. patent application Ser. No. 15/191,834, entitled STAMPED STAPLES AND STAPLE CARTRIDGES USING THE SAME;

U.S. patent application Ser. No. 15/191,788, entitled STAPLE CARTRIDGE COMPRISING OVERDRIVEN STAPLES; and U.S. patent application Ser. No. 15/191,818, entitled STAPLE CARTRIDGE COMPRISING OFFSET LONGITUDINAL STAPLE ROWS.

Applicant of the present application owns the following U.S. Patent Applications that were filed on Jun. 24, 2016 and which are each herein incorporated by reference in their respective entireties:

U.S. Design patent application Ser. No. 29/569,218, entitled SURGICAL FASTENER; U.S. Design patent application Ser. No. 29/569,227, entitled SURGICAL FASTENER; U.S. Design patent application Ser. No. 29/569,259, entitled SURGICAL FASTENER CARTRIDGE; and U.S. Design patent application Ser. No. 29/569,264, entitled SURGICAL FASTENER CARTRIDGE.

Applicant of the present application owns the following patent applications that were filed on Apr. 1, 2016 and which are each herein incorporated by reference in their respective entirety:

U.S. patent application Ser. No. 15/089,325, entitled METHOD FOR OPERATING A SURGICAL STAPLING SYSTEM;

U.S. patent application Ser. No. 15/089,321, entitled MODULAR SURGICAL STAPLING SYSTEM COMPRISING A DISPLAY;

U.S. patent application Ser. No. 15/089,326, entitled SURGICAL STAPLING SYSTEM COMPRISING A DISPLAY INCLUDING A RE-ORIENTABLE DISPLAY FIELD;

U.S. patent application Ser. No. 15/089,263, entitled SURGICAL INSTRUMENT HANDLE ASSEMBLY WITH RECONFIGURABLE GRIP PORTION;

U.S. patent application Ser. No. 15/089,262, entitled ROTARY POWERED SURGICAL INSTRUMENT WITH MANUALLY ACTUATABLE BAILOUT SYSTEM;

U.S. patent application Ser. No. 15/089,277, entitled SURGICAL CUTTING AND STAPLING END EFFECTOR WITH ANVIL CONCENTRIC DRIVE MEMBER;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS;

U.S. patent application Ser. No. 15/089,258, entitled SURGICAL STAPLING SYSTEM COMPRISING A SHIFTABLE TRANSMISSION;

U.S. patent application Ser. No. 15/089,278, entitled SURGICAL STAPLING SYSTEM CONFIGURED TO PROVIDE SELECTIVE CUTTING OF TISSUE;

U.S. patent application Ser. No. 15/089,284, entitled SURGICAL STAPLING SYSTEM COMPRISING A CONTOURABLE SHAFT;

U.S. patent application Ser. No. 15/089,295, entitled SURGICAL STAPLING SYSTEM COMPRISING A TISSUE COMPRESSION LOCKOUT;

U.S. patent application Ser. No. 15/089,300, entitled SURGICAL STAPLING SYSTEM COMPRISING AN UNCLAMPING LOCKOUT;

U.S. patent application Ser. No. 15/089,196, entitled SURGICAL STAPLING SYSTEM COMPRISING A JAW CLOSURE LOCKOUT;

U.S. patent application Ser. No. 15/089,203, entitled SURGICAL STAPLING SYSTEM COMPRISING A JAW ATTACHMENT LOCKOUT;

U.S. patent application Ser. No. 15/089,210, entitled SURGICAL STAPLING SYSTEM COMPRISING A SPENT CARTRIDGE LOCKOUT;

U.S. patent application Ser. No. 15/089,324, entitled SURGICAL INSTRUMENT COMPRISING A SHIFTING MECHANISM;

U.S. patent application Ser. No. 15/089,335, entitled SURGICAL STAPLING INSTRUMENT COMPRISING MULTIPLE LOCKOUTS;

U.S. patent application Ser. No. 15/089,339, entitled SURGICAL STAPLING INSTRUMENT;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS;

U.S. patent application Ser. No. 15/089,304, entitled SURGICAL STAPLING SYSTEM COMPRISING A GROOVED FORMING POCKET;

U.S. patent application Ser. No. 15/089,331, entitled ANVIL MODIFICATION MEMBERS FOR SURGICAL STAPLERS;

U.S. patent application Ser. No. 15/089,336, entitled STAPLE CARTRIDGES WITH ATRAUMATIC FEATURES;

U.S. patent application Ser. No. 15/089,312, entitled CIRCULAR STAPLING SYSTEM COMPRISING AN INCISABLE TISSUE SUPPORT;

U.S. patent application Ser. No. 15/089,309, entitled CIRCULAR STAPLING SYSTEM COMPRISING ROTARY FIRING SYSTEM; and U.S. patent application Ser. No. 15/089,349, entitled CIRCULAR STAPLING SYSTEM COMPRISING LOAD CONTROL.

Applicant of the present application also owns the U.S. Patent Applications identified below which were filed on Dec. 31, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS;

U.S. patent application Ser. No. 14/984,525, entitled MECHANISMS FOR COMPENSATING FOR DRIVETRAIN FAILURE IN POWERED SURGICAL INSTRUMENTS; and U.S. patent application Ser. No. 14/984,552, entitled SURGICAL INSTRUMENTS WITH SEPARABLE MOTORS AND MOTOR CONTROL CIRCUITS.

Applicant of the present application also owns the U.S. Patent Applications identified below which were filed on Feb. 9, 2016 which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR;

U.S. patent application Ser. No. 15/019,228, entitled SURGICAL INSTRUMENTS WITH MULTIPLE LINK ARTICULATION ARRANGEMENTS;

U.S. patent application Ser. No. 15/019,196, entitled SURGICAL INSTRUMENT ARTICULATION MECHANISM WITH SLOTTED SECONDARY CONSTRAINT;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY;

U.S. patent application Ser. No. 15/019,215, entitled SURGICAL INSTRUMENTS WITH NON-SYMMETRICAL ARTICULATION ARRANGEMENTS;

U.S. patent application Ser. No. 15/019,227, entitled ARTICULATABLE SURGICAL INSTRUMENTS WITH SINGLE ARTICULATION LINK ARRANGEMENTS;

U.S. patent application Ser. No. 15/019,235, entitled SURGICAL INSTRUMENTS WITH TENSIONING ARRANGEMENTS FOR CABLE DRIVEN ARTICULATION SYSTEMS;

U.S. patent application Ser. No. 15/019,230, entitled ARTICULATABLE SURGICAL INSTRUMENTS WITH OFF-AXIS FIRING BEAM ARRANGEMENTS; and U.S. patent application Ser. No. 15/019,245, entitled SURGICAL INSTRUMENTS WITH CLOSURE STROKE REDUCTION ARRANGEMENTS.

Applicant of the present application also owns the U.S. Patent Applications identified below which were filed on Feb. 12, 2016 which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS;

U.S. patent application Ser. No. 15/043,259, entitled MECHANISMS FOR COMPENSATING FOR DRIVETRAIN FAILURE IN POWERED SURGICAL INSTRUMENTS;

U.S. patent application Ser. No. 15/043,275, entitled MECHANISMS FOR COMPENSATING FOR DRIVETRAIN FAILURE IN POWERED SURGICAL INSTRUMENTS; and U.S. patent application Ser. No. 15/043,289, entitled MECHANISMS FOR COMPENSATING FOR DRIVETRAIN FAILURE IN POWERED SURGICAL INSTRUMENTS.

Applicant of the present application owns the following patent applications that were filed on Jun. 18, 2015 and which are each herein incorporated by reference in their respective entirety:

U.S. patent application Ser. No. 14/742,925, entitled SURGICAL END EFFECTORS WITH POSITIVE JAW OPENING ARRANGEMENTS;

U.S. patent application Ser. No. 14/742,941, entitled SURGICAL END EFFECTORS WITH DUAL CAM ACTUATED JAW CLOSING FEATURES;

U.S. patent application Ser. No. 14/742,914, entitled MOVABLE FIRING BEAM SUPPORT ARRANGEMENTS FOR ARTICULATABLE SURGICAL INSTRUMENTS;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT;

U.S. patent application Ser. No. 14/742,885, entitled DUAL ARTICULATION DRIVE SYSTEM ARRANGEMENTS FOR ARTICULATABLE SURGICAL INSTRUMENTS; and U.S. patent application Ser. No. 14/742,876, entitled PUSH/PULL ARTICULATION DRIVE SYSTEMS FOR ARTICULATABLE SURGICAL INSTRUMENTS.

Applicant of the present application owns the following patent applications that were filed on Mar. 6, 2015 and which are each herein incorporated by reference in their respective entirety:

U.S. patent application Ser. No. 14/640,746, entitled POWERED SURGICAL INSTRUMENT, now U.S. Patent Application Publication No. 2016/0256184;

U.S. patent application Ser. No. 14/640,795, entitled MULTIPLE LEVEL THRESHOLDS TO MODIFY OPERATION OF POWERED SURGICAL INSTRUMENTS, now U.S. Patent Application Publication No. 2016/02561185;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Patent Application Publication No. 2016/0256154;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Patent Application Publication No. 2016/0256071;

U.S. patent application Ser. No. 14/640,831, entitled MONITORING SPEED CONTROL AND PRECISION INCREMENTING OF MOTOR FOR POWERED SURGICAL INSTRUMENTS, now U.S. Patent Application Publication No. 2016/0256153;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Patent Application Publication No. 2016/0256187;

U.S. patent application Ser. No. 14/640,817, entitled INTERACTIVE FEEDBACK SYSTEM FOR POWERED SURGICAL INSTRUMENTS, now U.S. Patent Application Publication No. 2016/0256186;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Patent Application Publication No. 2016/0256155;

U.S. patent application Ser. No. 14/640,837, entitled SMART SENSORS WITH LOCAL SIGNAL PROCESSING, now U.S. Patent Application Publication No. 2016/0256163;

U.S. patent application Ser. No. 14/640,765, entitled SYSTEM FOR DETECTING THE MIS-INSERTION OF A STAPLE CARTRIDGE INTO A SURGICAL STAPLER, now U.S. Patent Application Publication No. 2016/0256160;

U.S. patent application Ser. No. 14/640,799, entitled SIGNAL AND POWER COMMUNICATION SYSTEM POSITIONED ON A ROTATABLE SHAFT, now U.S. Patent Application Publication No. 2016/0256162; and U.S. patent application Ser. No. 14/640,780, entitled SURGICAL INSTRUMENT COMPRISING A LOCKABLE BATTERY HOUSING, now U.S. Patent Application Publication No. 2016/0256161.

Applicant of the present application owns the following patent applications that were filed on Feb. 27, 2015, and which are each herein incorporated by reference in their respective entirety:

U.S. patent application Ser. No. 14/633,576, entitled SURGICAL INSTRUMENT SYSTEM COMPRISING AN INSPECTION STATION, now U.S. Patent Application Publication No. 2016/0249919;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Patent Application Publication No. 2016/0249915;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Patent Application Publication No. 2016/0249918;

U.S. patent application Ser. No. 14/633,555, entitled SYSTEM FOR MONITORING WHETHER A SURGICAL INSTRUMENT NEEDS TO BE SERVICED, now U.S. Patent Application Publication No. 2016/0249916;

U.S. patent application Ser. No. 14/633,542, entitled REINFORCED BATTERY FOR A SURGICAL INSTRUMENT, now U.S. Patent Application Publication No. 2016/0249908;

U.S. patent application Ser. No. 14/633,548, entitled POWER ADAPTER FOR A SURGICAL INSTRUMENT, now U.S. Patent Application Publication No. 2016/0249909;

U.S. patent application Ser. No. 14/633,526, entitled ADAPTABLE SURGICAL INSTRUMENT HANDLE, now U.S. Patent Application Publication No. 2016/0249945;

U.S. patent application Ser. No. 14/633,541, entitled MODULAR STAPLING ASSEMBLY, now U.S. Patent Application Publication No. 2016/0249927; and U.S. patent application Ser. No. 14/633,562, entitled SURGICAL APPARATUS CONFIGURED TO TRACK AN END-OF-LIFE PARAMETER, now U.S. Patent Application Publication No. 2016/0249917.

Applicant of the present application owns the following patent applications that were filed on Dec. 18, 2014 and which are each herein incorporated by reference in their respective entirety:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Patent Application Publication No. 2016/0174977;

U.S. patent application Ser. No. 14/574,483, entitled SURGICAL INSTRUMENT ASSEMBLY COMPRISING LOCKABLE SYSTEMS, now U.S. Patent Application Publication No. 2016/0174969;

U.S. patent application Ser. No. 14/575,139, entitled DRIVE ARRANGEMENTS FOR ARTICULATABLE SURGICAL INSTRUMENTS, now U.S. Patent Application Publication No. 2016/0174978;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Patent Application Publication No. 2016/0174976;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Patent Application Publication No. 2016/0174972;

U.S. patent application Ser. No. 14/575,143, entitled SURGICAL INSTRUMENTS WITH IMPROVED CLOSURE ARRANGEMENTS, now U.S. Patent Application Publication No. 2016/0174983;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Patent Application Publication No. 2016/0174975;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Patent Application Publication No. 2016/0174973;

U.S. patent application Ser. No. 14/574,493, entitled SURGICAL INSTRUMENT ASSEMBLY COMPRISING A FLEXIBLE ARTICULATION SYSTEM, now U.S. Patent Application Publication No. 2016/0174970; and U.S. patent application Ser. No. 14/574,500, entitled SURGICAL INSTRUMENT ASSEMBLY COMPRISING A LOCKABLE ARTICULATION SYSTEM, now U.S. Patent Application Publication No. 2016/0174971.

Applicant of the present application owns the following patent applications that were filed on Mar. 1, 2013 and which are each herein incorporated by reference in their respective entirety:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Patent Application Publication No. 2014/0246471;

U.S. patent application Ser. No. 13/782,323, entitled ROTARY POWERED ARTICULATION JOINTS FOR SURGICAL INSTRUMENTS, now U.S. Patent Application Publication No. 2014/0246472;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Patent Application Publication No. 2014/0246478;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entirety:

U.S. patent application Ser. No. 13/803,097, entitled ARTICULATABLE SURGICAL INSTRUMENT COMPRISING A FIRING DRIVE, now U.S. Patent Application Publication No. 2014/0263542;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Patent Application Publication No. 2014/0263564;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Patent Application Publication No. 2014/0263538;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Patent Application Publication No. 2014/0263565;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Patent Application Publication No. 2014/0277017.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Patent Application Publication No. 2014/0263539.

Applicant of the present application also owns the following patent applications that were filed on Mar. 26, 2014 and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Patent Application Publication No. 2015/0272581;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Patent Application Publication No. 2015/0272574;

U.S. patent application Ser. No. 14/226,075, entitled MODULAR POWERED SURGICAL INSTRUMENT WITH DETACHABLE SHAFT ASSEMBLIES, now U.S. Patent Application Publication No. 2015/0272579;

U.S. patent application Ser. No. 14/226,093, entitled FEEDBACK ALGORITHMS FOR MANUAL BAILOUT SYSTEMS FOR SURGICAL INSTRUMENTS, now U.S. Patent Application Publication No. 2015/0272569;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Patent Application Publication No. 2015/0272578;

U.S. patent application Ser. No. 14/226,097, entitled SURGICAL INSTRUMENT COMPRISING INTERACTIVE SYSTEMS, now U.S. Patent Application Publication No. 2015/0272570;

U.S. patent application Ser. No. 14/226,126, entitled INTERFACE SYSTEMS FOR USE WITH SURGICAL INSTRUMENTS, now U.S. Patent Application Publication No. 2015/0272572;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Patent Application Publication No. 2015/0277471;

U.S. patent application Ser. No. 14/226,076, entitled POWER MANAGEMENT THROUGH SEGMENTED CIRCUIT AND VARIABLE VOLTAGE PROTECTION, now U.S. Patent Application Publication No. 2015/0280424;

U.S. patent application Ser. No. 14/226,111, entitled SURGICAL STAPLING INSTRUMENT SYSTEM, now U.S. Patent Application Publication No. 2015/0272583; and U.S. patent application Ser. No. 14/226,125, entitled SURGICAL INSTRUMENT COMPRISING A ROTATABLE SHAFT, now U.S. Patent Application Publication No. 2015/0280384.

Applicant of the present application also owns the following patent applications that were filed on Sep. 5, 2014 and which are each herein incorporated by reference in their respective entirety:

U.S. patent application Ser. No. 14/479,103, entitled CIRCUITRY AND SENSORS FOR POWERED MEDICAL DEVICE, now U.S. Patent Application Publication No. 2016/0066912;

U.S. patent application Ser. No. 14/479,119, entitled ADJUNCT WITH INTEGRATED SENSORS TO QUANTIFY TISSUE COMPRESSION, now U.S. Patent Application Publication No. 2016/0066914;

U.S. patent application Ser. No. 14/478,908, entitled MONITORING DEVICE DEGRADATION BASED ON COMPONENT EVALUATION, now U.S. Patent Application Publication No. 2016/0066910;

U.S. patent application Ser. No. 14/478,895, entitled MULTIPLE SENSORS WITH ONE SENSOR AFFECTING A SECOND SENSOR'S OUTPUT OR INTERPRETATION, now U.S. Patent Application Publication No. 2016/0066909;

U.S. patent application Ser. No. 14/479,110, entitled POLARITY OF HALL MAGNET TO DETECT MISLOADED CARTRIDGE, now U.S. Patent Application Publication No. 2016/0066915;

U.S. patent application Ser. No. 14/479,098, entitled SMART CARTRIDGE WAKE UP OPERATION AND DATA RETENTION, now U.S. Patent Application Publication No. 2016/0066911;

U.S. patent application Ser. No. 14/479,115, entitled MULTIPLE MOTOR CONTROL FOR POWERED MEDICAL DEVICE, now U.S. Patent Application Publication No. 2016/0066916; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entirety:

U.S. patent application Ser. No. 14/248,590, entitled MOTOR DRIVEN SURGICAL INSTRUMENTS WITH LOCKABLE DUAL DRIVE SHAFTS, now U.S. Patent Application Publication No. 2014/0305987;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Patent Application Publication No. 2014/0305989;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Patent Application Publication No. 2014/0305988;

U.S. patent application Ser. No. 14/248,588, entitled POWERED LINEAR SURGICAL STAPLER, now U.S. Patent Application Publication No. 2014/0309666;

U.S. patent application Ser. No. 14/248,591, entitled TRANSMISSION ARRANGEMENT FOR A SURGICAL INSTRUMENT, now U.S. Patent Application Publication No. 2014/0305991;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Patent Application Publication No. 2014/0305994;

U.S. patent application Ser. No. 14/248,587, entitled POWERED SURGICAL STAPLER, now U.S. Patent Application Publication No. 2014/0309665;

U.S. patent application Ser. No. 14/248,586, entitled DRIVE SYSTEM DECOUPLING ARRANGEMENT FOR A SURGICAL INSTRUMENT, now U.S. Patent Application Publication No. 2014/0305990; and U.S. patent application Ser. No. 14/248,607, entitled MODULAR MOTOR DRIVEN SURGICAL INSTRUMENTS WITH STATUS INDICATION ARRANGEMENTS, now U.S. Patent Application Publication No. 2014/0305992.

Applicant of the present application also owns the following patent applications that were filed on Apr. 16, 2013 and which are each herein incorporated by reference in their respective entirety:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Applicant of the present application also owns the following patent applications that were filed on Sep. 2, 2015 and which are each herein incorporated by reference in their respective entirety:

U.S. patent application Ser. No. 14/843,168, entitled SURGICAL STAPLE CARTRIDGE WITH IMPROVED STAPLE DRIVER CONFIGURATIONS;

U.S. patent application Ser. No. 14/843,196, entitled SURGICAL STAPLE DRIVER ARRAYS;

U.S. patent application Ser. No. 14/843,216, entitled SURGICAL STAPLE CARTRIDGE STAPLE DRIVERS WITH CENTRAL SUPPORT FEATURES;

U.S. patent application Ser. No. 14/843,243, entitled SURGICAL STAPLE CONFIGURATIONS WITH CAMMING SURFACES LOCATED BETWEEN PORTIONS SUPPORTING SURGICAL STAPLES; and U.S. patent application Ser. No. 14/843,267, entitled SURGICAL STAPLE CARTRIDGES WITH DRIVER ARRANGEMENTS FOR ESTABLISHING HERRINGBONE STAPLE PATTERNS.

Applicant of the present application also owns the following patent applications that were filed on Sep. 26, 2014 and which are each herein incorporated by reference in their respective entirety:

U.S. patent application Ser. No. 14/498,070, entitled CIRCULAR FASTENER CARTRIDGES FOR APPLYING RADIALLY EXPANDABLE FASTENER LINES; now U.S. Patent Application Publication No. 2016/0089146;

U.S. patent application Ser. No. 14/498,087, entitled SURGICAL STAPLE AND DRIVER ARRANGEMENTS FOR STAPLE CARTRIDGES; now U.S. Patent Application Publication No. 2016/0089147;

U.S. patent application Ser. No. 14/498,105, entitled SURGICAL STAPLE AND DRIVER ARRANGEMENTS FOR STAPLE CARTRIDGES; now U.S. Patent Application Publication No. 2016/0089148;

U.S. patent application Ser. No. 14/498,121, entitled FASTENER CARTRIDGE FOR CREATING A FLEXIBLE STAPLE LINE; now U.S. Patent Application Publication No. 2016/0089141

U.S. patent application Ser. No. 14/498,145, entitled METHOD FOR CREATING A FLEXIBLE STAPLE LINE; now U.S. Patent Application Publication No. 2016/0089142; and U.S. patent application Ser. No. 14/498,107, entitled SURGICAL STAPLING BUTTRESSES AND ADJUNCT MATERIALS; now U.S. Patent Application Publication No. 2016/0089143.

Applicant of the present application also owns U.S. Pat. No. 8,590,762, which issued Nov. 26, 2013, entitled STAPLE CARTRIDGE CAVITY CONFIGURATIONS, which is herein incorporated by reference in its respective entirety.

Applicant of the present application also owns U.S. Pat. No. 8,727,197, which issued May 20, 2014, entitled STAPLE CARTRIDGE CAVITY CONFIGURATION WITH COOPERATIVE SURGICAL STAPLE, which is herein incorporated by reference in its respective entirety.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

FIG. 1 depicts one form of an interchangeable surgical tool assembly 1000 that is operably coupled to a motor driven handle assembly 500. The tool assembly 1000 may also be effectively employed with a tool drive assembly of a robotically controlled or automated surgical system. For example, the surgical tool assemblies disclosed herein may be employed with various robotic systems, instruments, components and methods such as, but not limited to, those disclosed in U.S. Pat. No. 9,072,535, entitled SURGICAL STAPLING INSTRUMENTS WITH ROTATABLE STAPLE DEPLOYMENT ARRANGEMENTS, which is hereby incorporated by reference herein in its entirety. The handle assembly 500, as well as the tool drive assembly of a robotic system may also be referred to herein as "control systems" or "control units".

Figure 2:
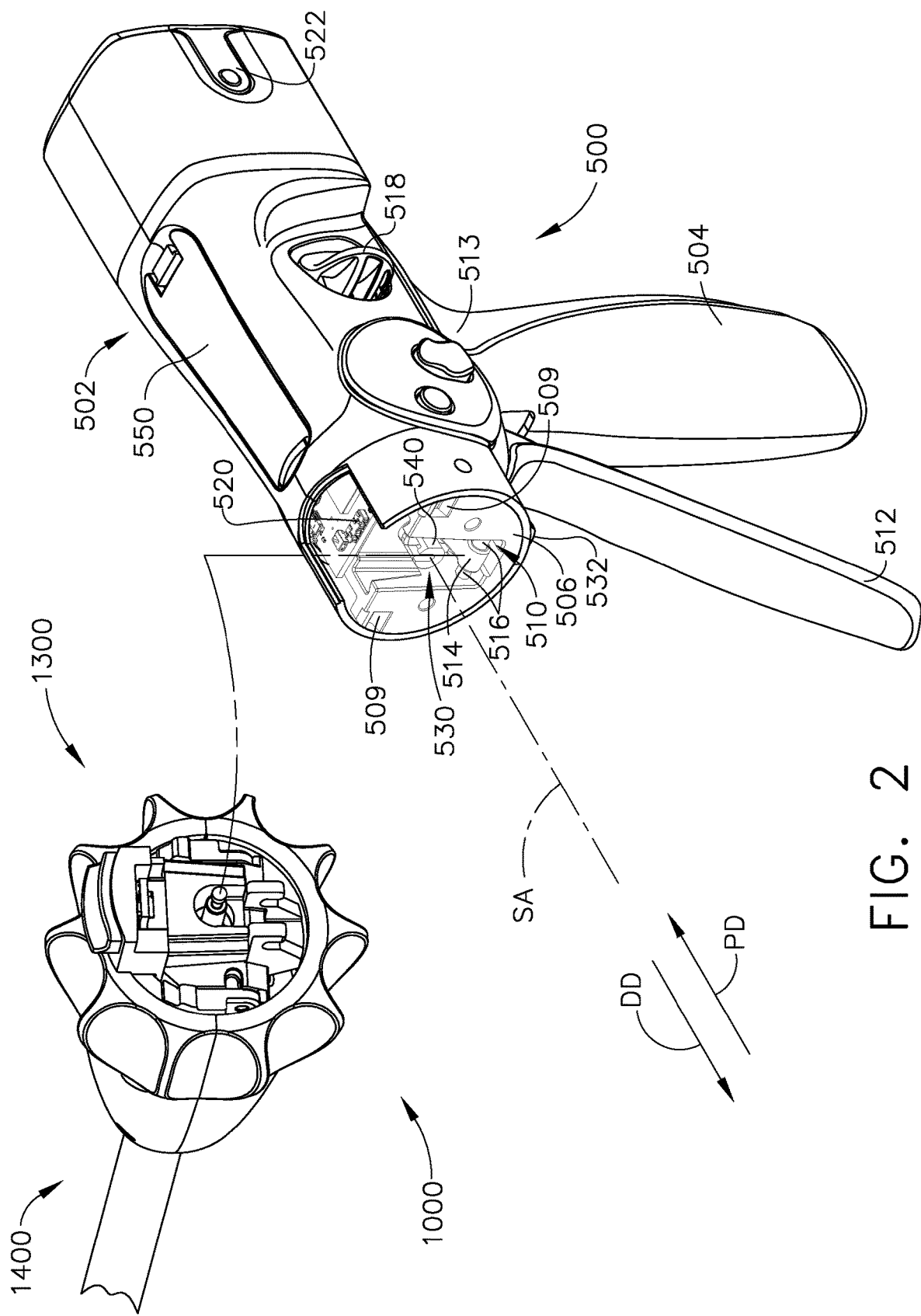
FIG. 2 is an exploded assembly view of portions of the handle assembly and interchangeable surgical tool assembly of FIG. 1.

FIGS. 1 and 2 illustrate attachment of the interchangeable surgical tool assembly 1000 to the handle assembly 500. The handle assembly 500 may comprise a handle housing 502 that includes a pistol grip portion 504 that can be gripped and manipulated by the clinician. The handle assembly 500 may further include a frame 506 that operably supports the plurality of drive systems. For example, the frame 506 can operably support a "first" or closure drive system, generally designated as 510, which may be employed to apply closing and opening motions to the interchangeable surgical tool assembly 1000 that is operably attached or coupled to the handle assembly 500. In at least one form, the closure drive system 510 may include an actuator in the form of a closure trigger 512 that is pivotally supported by the frame 506. Such arrangement enables the closure trigger 512 to be manipulated by a clinician such that when the clinician grips the pistol grip portion 504 of the handle assembly 500, the closure trigger 512 may be easily pivoted from a starting or "unactuated" position to an "actuated" position and more particularly, to a fully compressed or fully actuated position. In various forms, the closure drive system 510 further includes a closure linkage assembly 514 that is pivotally coupled to the closure trigger 512 or otherwise operably interfaces therewith. As further discussed in contemporaneously-filed U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS, which is hereby incorporated by reference herein in its entirety, the closure linkage assembly 514 includes a transverse attachment pin 516 that facilitates attachment to a corresponding drive system on the surgical tool assembly. In use, to actuate the closure drive system 510, the clinician depresses the closure trigger 512 towards the pistol grip portion 504. As described in further detail in U.S. patent application Ser. No. 14/226,142, entitled SURGICAL INSTRUMENT COMPRISING A SENSOR SYSTEM, now U.S. Patent Application Publication No. 2015/0272575, which is hereby incorporated by reference in its entirety herein, when the clinician fully depresses the closure trigger 512 to attain a "full" closure stroke, the closure drive system 510 is configured to lock the closure trigger 512 into the fully depressed or fully actuated position. When the clinician desires to unlock the closure trigger 512 to permit it to be biased to the unactuated position, the clinician simply activates a closure release button assembly 518 which enables the closure trigger 512 to return to unactuated position. The closure release button assembly 518 may also be configured to interact with various sensors that communicate with a microcontroller 520 in the handle assembly 500 for tracking the position of the closure trigger 512. Further details concerning the configuration and operation of the closure release button assembly 518 may be found in U.S. Patent Application Publication No. 2015/0272575.

In at least one form, the handle assembly 500 and the frame 506 may operably support another drive system referred to herein as a firing drive system 530 that is configured to apply firing motions to corresponding portions of the interchangeable surgical tool assembly that is attached thereto. As was described in detail in U.S. Patent Application Publication No. 2015/0272575, the firing drive system 530 may employ an electric motor 505 (FIG. 1) that is located in the pistol grip portion 504 of the handle assembly 500. In various forms, the motor 505 may be a DC brushed driving motor having a maximum rotation of, approximately, 25,000 RPM, for example. In other arrangements, the motor 505 may include a brushless motor, a cordless motor, a synchronous motor, a stepper motor, or any other suitable electric motor. The motor 505 may be powered by a power source 522 that in one form may comprise a removable power pack. The power pack may support a plurality of Lithium Ion ("LI") or other suitable batteries therein. A number of batteries, which may be connected in series, may be used as the power source 522 for the handle assembly 500. In addition, the power source 522 may be replaceable and/or rechargeable.

The electric motor 505 is configured to axially drive a longitudinally movable drive member 540 in distal and proximal directions depending upon the polarity of the motor. For example, when the motor 505 is driven in one rotary direction, the longitudinally movable drive member 540 will be axially driven in the distal direction "DD". When the motor 505 is driven in the opposite rotary direction, the longitudinally movable drive member 540 will be axially driven in a proximal direction "PD". The handle assembly 500 can include a switch 513 which can be configured to reverse the polarity applied to the electric motor 505 by the power source 522 or otherwise control the motor 505. The handle assembly 500 can also include a sensor or sensors (not shown) that is configured to detect the position of the drive member 540 and/or the direction in which the drive member 540 is being moved. Actuation of the motor 505 can be controlled by a firing trigger 532 that is pivotally supported on the handle assembly 500. The firing trigger 532 may be pivoted between an unactuated position and an actuated position. The firing trigger 532 may be biased into the unactuated position by a spring (not shown) or other biasing arrangement such that when the clinician releases the firing trigger 532, it may be pivoted or otherwise returned to the unactuated position by the spring or biasing arrangement. In at least one form, the firing trigger 532 can be positioned "outboard" of the closure trigger 512 as was discussed above. As discussed in U.S. Patent Application Publication No. 2015/0272575, the handle assembly 500 may be equipped with a firing trigger safety button (not shown) to prevent inadvertent actuation of the firing trigger 532. When the closure trigger 512 is in the unactuated position, the safety button is contained in the handle assembly 500 where the clinician cannot readily access it and move it between a safety position preventing actuation of the firing trigger 532 and a firing position wherein the firing trigger 532 may be fired. As the clinician depresses the closure trigger 512, the safety button and the firing trigger 532 may pivot down wherein they can then be manipulated by the clinician.

In at least one form, the longitudinally movable drive member 540 may have a rack of teeth (not shown) formed thereon for meshing engagement with a corresponding drive gear arrangement (not shown) that interfaces with the motor 505. Further details regarding those features may be found in U.S. Patent Application Publication No. 2015/0272575. At least one form also includes a manually-actuatable "bailout" assembly that is configured to enable the clinician to manually retract the longitudinally movable drive member 540 should the motor 505 become disabled. The bailout assembly may include a lever or bailout handle assembly that is stored within the handle assembly 500 under a releasable door 550. The lever is configured to be manually pivoted into ratcheting engagement with the teeth in the drive member 540. Thus, the clinician can manually retract the drive member 540 by using the bailout handle assembly to ratchet the drive member 540 in the proximal direction "PD". U.S. patent application Ser. No. 12/249,117, entitled POWERED SURGICAL CUTTING AND STAPLING APPARATUS WITH MANUALLY RETRACTABLE FIRING SYSTEM, now U.S. Patent Application Publication No. 2010/0089970, the entire disclosure of which is hereby incorporated by reference herein, discloses bailout arrangements and other components, arrangements and systems that may also be employed with the tool assembly 1000.

The interchangeable surgical tool assembly 1000 includes a shaft mounting portion 1300 that is operably attached to an elongate shaft assembly 1400. A surgical end effector 1100 that comprises an elongate channel 1102 that is configured to operably support a staple cartridge 1110 therein is operably attached to the elongate shaft assembly 1400. See FIGS. 3 and 4. The end effector 1100 may further include an anvil 1130 that is pivotally supported relative to the elongate channel 1102. The elongate channel 1102/staple cartridge assembly 1110 and the anvil 1130 may also be referred to as "jaws". The interchangeable surgical tool assembly 1000 may further include an articulation joint 1200 and an articulation lock 1210 (FIGS. 3 and 4) which can be configured to releasably hold the end effector 1100 in a desired articulated position about an articulation axis B-B which is transverse to a shaft axis SA. Details regarding the construction and operation of the articulation lock 1210 may be found in in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the entire disclosure of which is hereby incorporated by reference herein. Additional details concerning the articulation lock 1210 may also be found in U.S. patent application Ser. No. 15/019,196, filed Feb. 9, 2016, entitled SURGICAL INSTRUMENT ARTICULATION MECHANISM WITH SLOTTED SECONDARY CONSTRAINT, the entire disclosure of which is hereby incorporated by reference herein.

A firing member 1760 is configured to operably interface with a sled assembly 1120 that is operably supported within the body 1111 of the surgical staple cartridge 1110. The sled assembly 1120 is slidably displaceable within the surgical staple cartridge body 1111 from a proximal starting position adjacent the proximal end 1112 of the cartridge body 1111 to an ending position adjacent a distal end 1113 of the cartridge body 1111. See FIG. 4. The cartridge body 1111 operably supports therein a plurality of staple drivers 1170 (FIGS. 81-83) that are aligned in rows on each side of a centrally disposed slot 1114. The centrally disposed slot 1114 enables the firing member 1760 to pass therethrough and cut the tissue that is clamped between the anvil 1130 and the staple cartridge 1110. The drivers are associated with corresponding pockets or cavities 1116 that open through the upper deck surface 1115 of the cartridge body 1111. Each of the staple drivers supports one or more surgical staple or fastener thereon. The sled assembly 1120 includes a plurality of sloped or wedge-shaped cams 1122 wherein each cam 1122 corresponds to a particular line of fasteners or drivers located on a side of the slot 1114. When the firing member 1760 is fired or driven distally, the firing member 1760 drives the sled assembly 1120 distally as well. As the firing member 1760 moves distally through the cartridge 1110, the tissue cutting feature 1766 cuts the tissue that is clamped between the anvil assembly 1130 and the cartridge 1110, and the sled assembly 1120 drives the drivers upwardly in the cartridge which drive the corresponding staples or fasteners into forming contact with the anvil assembly 1130.

Figure 81:
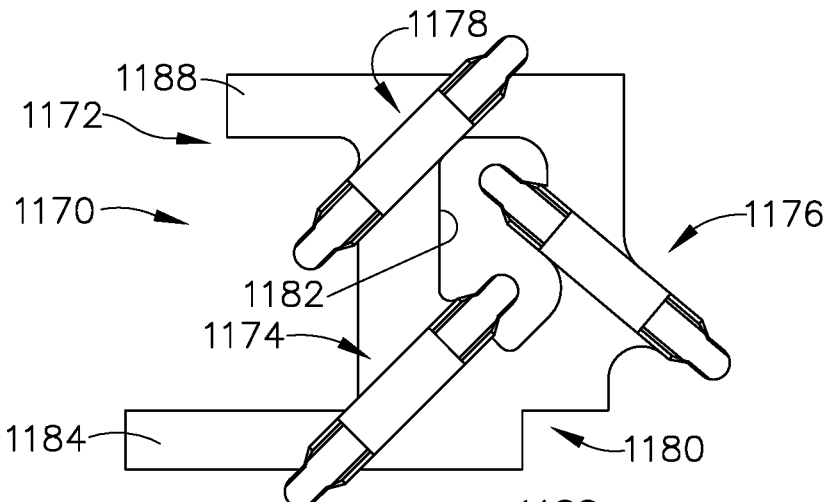
FIG. 81 is a top view of a staple driver embodiment.
Figure 82:
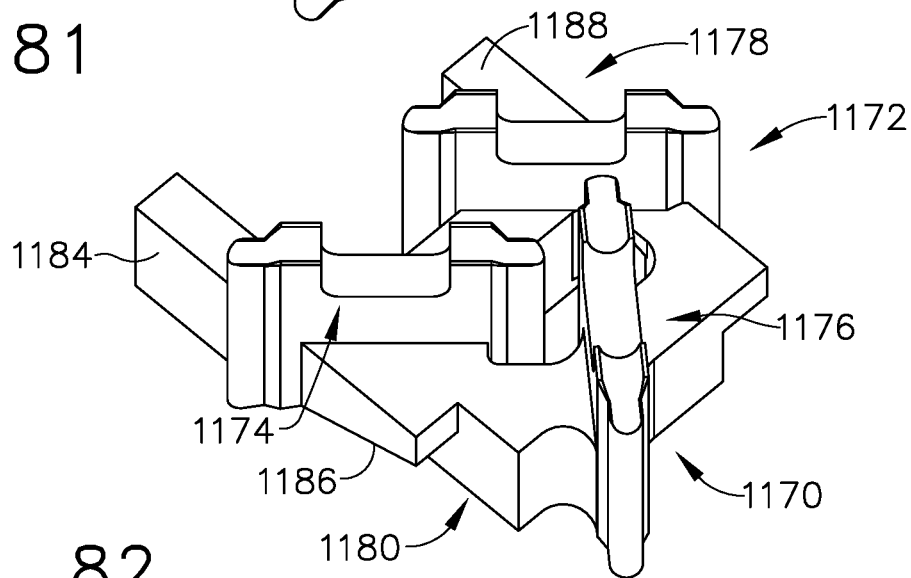
FIG. 82 is a top perspective view of the staple driver embodiment of FIG. 81.
Figure 83:
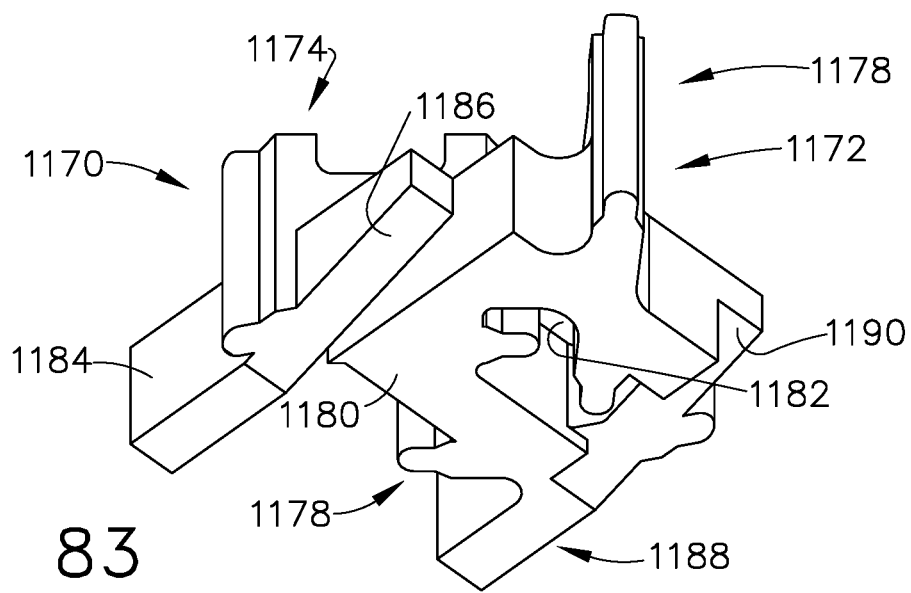
FIG. 83 is a bottom perspective view of the staple driver embodiment of FIGS. 81 and 82.

In the illustrated example, the cartridge body 1111 operably supports therein a plurality of staple drivers that are aligned in rows on each side of a centrally disposed slot 1114. FIGS. 81-83 illustrate one example of a staple driver 1170 that may be employed to support staples on one side of a surgical staple cartridge. The drivers located on the opposite side of the centrally disposed slot 1114 may comprise mirror images of drivers 1170. Other staple driver configurations may also be effectively employed as well. As can be seen in FIGS. 81-83, one form of a staple driver 1700 comprises a staple driver body 1172. The driver body 1172 includes a first or innermost staple support portion 1174 that is configured to support a staple (not shown) thereon. A second or central staple support portion 1176 is configured to support another staple (not shown) thereon and a third support portion 1870 that is configured to support a third staple (not shown) thereon. The first staple support portion 1174, the second staple support portion 1176 and the third staple support portion 1178 are all coupled together by a connector portion 1180. In at least one arrangement, the connector portion 1180 is formed with a centrally disposed opening or aperture 1182 that is configured to slidably receive a corresponding first driver guide (not shown) that is formed in the cartridge body. The connector portion 1180 includes a first cam portion 1184 that has a first camming surface or ramp 1186 formed thereon. The connector portion 1180 also includes a second cam portion 1188 that has a second a second camming surface 1190 formed thereon. The camming surfaces 1186, 1190 have the same slope or angle or they may have different slopes/angles. In at least one embodiment, each staple driver 1170 is integrally formed from or molded from, for example, Ultem®, with no fill. However, other materials such as, for example, Ultem® with a glass or mineral fill or Nylon or Nylon with a glass file could be used. In other arrangements, the various portions of the staple drivers 1170 may be separately fabricated from other materials and be attached together by adhesive, solder, etc. Further details concerning the staple drivers 1170 as well as other driver embodiments that may be effectively employed with the various embodiments disclosed herein may be found in U.S. patent application Ser. No. 14/843, 243, filed Sep. 2, 2015, entitled SURGICAL STAPLE CONFIGURATIONS WITH CAMMING SURFACES LOCATED BETWEEN PORTIONS SUPPORTING SURGICAL STAPLES, the entire disclosure of which is hereby incorporated by reference herein.

The staple cavities 1116 are angularly oriented relative to the shaft axis SA. More specifically, the staple cavities 1116 are oriented at oblique angles relative to the shaft axis SA and form a herringbone pattern in the deck surface 1115. Various alternative patterns for staple cavities in a staple cartridge body are described herein.

Variations to the arrangement and/or geometry of staples in a staple line can affect the flexibility and sealing properties of the staple line. For example, a staple line comprised of linear staples can provide a limited amount of flexibility or stretch because the staple line can flex or stretch between the linear staples. Consequently, a limited portion of the staple line (e.g., the portion between staples) is flexible. A staple line comprised of angularly-oriented staples can also flex or stretch between the staples. However, the angularly-oriented staples are also able to rotate, which provides an additional degree of stretch within the staple line. A staple line comprised of angularly-oriented staples can stretch in excess of 60%, for example. In certain instances, a staple line comprised of angularly-oriented staples can stretch at least 25% or at least 50%, for example. The arrangement of staples includes the relative orientation of the staples and the spacing between the staples, for example. The geometry of the staples includes the size and shape of the staples, for example. The flexibility and sealing properties of a staple line can change at longitudinal and/or lateral positions based on the arrangement and/or geometry of the staples. In certain instances, it is desirable to alter the flexibility and/or sealing properties of a staple line at one or more locations along the staple line. For example, it can be desirable to maximize the flexibility of the staple line or a portion thereof. Additionally or alternatively, it can be desirable to minimize the flexibility of the staple line or a portion thereof. It can also be desirable to maximize the sealing properties of the staple line or a portion thereof. Additionally or alternatively, it can be desirable to minimize the sealing properties of the staple line or a portion thereof.

The arrangement of staple cavities in a staple cartridge corresponds to the arrangement of staples in a staple line generated by the staple cartridge. For example, the spacing and relative orientation of staple cavities in a staple cartridge corresponds to the spacing and relative orientation of staples in a staple line generated by the staple cartridge. In various instances, a staple cartridge can include an arrangement of staples cavities that is selected and/or designed to optimize the flexibility and/or sealing properties of the resultant staple line. A surgeon may select a staple cartridge having a particular arrangement of staple cavities based on the surgical procedure to be performed and/or the properties of the tissue to be treated during the surgical procedure, for example.

In certain instances, it can be desirable to generate a staple line with different staple patterns. A staple line can include a first pattern of staples for a first portion thereof and a second pattern of staples for a second portion thereof. The first pattern and the second pattern can be longitudinally offset. For example, the first pattern can be positioned at the proximal or distal end of the staple line. In other instances, the first pattern and the second pattern can be laterally offset and, in still other instances, the first pattern and the second pattern can be laterally offset and longitudinally offset. A staple line can include at least two different patterns of staples.

In certain instances, the majority of staples in a staple line can form a major pattern and other staples in the staple line can form one or more minor patterns. The major pattern can span a significant portion of the staple line and can include a longitudinally-repetitive sub-pattern. In certain instances, the minor pattern, or irregularity, can deviate from the major pattern. The minor pattern can be an anomaly at one or more locations along the length of the staple line, for example. The different patterns in a staple line can be configured to produce different properties at predefined locations. For example, the major pattern can be a highly flexible or elastic pattern, which can permit extensive stretching of the stapled tissue, and the minor pattern can be less flexible or less elastic. It can be desirable for the majority of the staple line to be highly flexible and for one or more limited portions to be less flexible, for example. In other instances, the minor pattern can be more flexible than the major pattern. In certain instances, because the minor pattern extends along a shorter portion of the staple line, the flexibility of the minor pattern may not impact, or may not significantly impact, the overall flexibility of the entire staple line.

Referring now to FIGS. 5-8, a staple cartridge body 3000 for use with a surgical end effector is depicted. The staple cartridge body 3000 includes a deck 3002 and a slot 3004, which extends through the deck 3002 from a proximal end 3006 toward a distal end 3008 of the cartridge body 3000. The slot 3004 extends along the longitudinal axis LA (FIG. 7) of the cartridge body 3000. Staple cavities 3010 are defined in the cartridge body 3000 and each staple cavity 3010 defines an opening 3012 in the deck 3002.

The majority of the staple cavities 3010 are arranged in a first pattern, or major pattern, 3020. The first pattern 3020 is a longitudinally-repetitive pattern of angularly-oriented staple cavities 3010. Longitudinally-repetitive patterns are patterns in which a sub-pattern or arrangement is longitudinally repeated. For example, an arrangement of three staple cavities on each side of the slot 3004 (an inner staple cavity, an intermediate staple cavity, and an outer staple cavity) can be repeated along at least a portion of the length of the staple cartridge body 3000. Various longitudinally-repetitive patterns of angularly-oriented staples cavities are described in U.S. patent application Ser. No. 14/498,145, filed Sep. 26, 2014, now U.S. Patent Application Publication No. 2016/0089142, entitled METHOD FOR CREATING A FLEXIBLE STAPLE LINE, which is incorporated by reference herein in its entirety. The openings 3012 of the staple cavities 3010 in the first pattern 3020 form a herringbone pattern having six rows of angularly-oriented staple cavity openings 3012 in the cartridge deck 3002. An inner row 3014a, an intermediate row 3014b, and an outer row 3014c of staple cavities 3010 are positioned on each side of the slot 3004.

Each staple cavity opening 3012 has a proximal end 3016 and a distal end 3018. The proximal end 3016 and the distal end 3018 of the staple cavities 3010 in the first pattern 3020 are laterally offset. Stated differently, each staple cavity 3010 in the first pattern 3020 is angularly oriented relative to the longitudinal axis LA (FIG. 7). A cavity axis CA (FIG. 7) extends between the proximal end 3016 and the distal end 3018 of each opening 3012. The cavity axes CA are obliquely oriented relative to the slot 3004. More specifically, the openings 3012 in the inner rows 3014a of staple cavities 3010 and the outer rows 3014c of staple cavities 3010 are oriented at 45 degrees, or about 45 degrees, relative to the longitudinal axis LA, and the openings 3012 in the intermediate rows 3014b of staple cavities 3010 are oriented at 90 degrees, or about 90 degrees, relative to the openings 3012 of the inner rows 3014a and the outer rows 3014a.

Certain staple cavities 3010 in the cartridge body 3000 are oriented at an angle that is anomalous or irregular with respect to the staple cavities 3010 in the first pattern 3020. More specifically, the angular orientation of proximal staple cavities 3010a, 3010b, 3010c, and 3010d and distal staples cavities 3010e, 3010f, 3010g, and 3010h does not conform to the herringbone arrangement of the staple cavities 3010 in the first pattern 3020. Rather, the proximal staple cavities 3010a-3010d and the distal staple cavities 3010e-3010h are angularly offset from the staple cavities 3010 in the first pattern 3020. The proximal staple cavities 3010a, 3010b, 3010c, and 3010d are obliquely oriented relative to the staples cavities 3010 in the first pattern 3020, and the distal staple cavities 3010e, 3010f, 3010g, and 3010h are also obliquely oriented relative to the staples cavities 3010 in the first pattern 3020. The proximal and distal staple cavities 3010a-3010h are oriented parallel to the slot 3004 and to the longitudinal axis LA.

The proximal staple cavities 3010a-3010d form a proximal pattern 3022 that is distinct from the first pattern 3020, and the distal staple cavities 3010e-3010h form a distal pattern 3024 that is also distinct from the first pattern 3020. In the depicted arrangement, the proximal pattern 3022 includes a first pair of parallel, longitudinally-aligned staple cavities 3010a, 3010b on a first side of the slot 3004 and a second pair of parallel, longitudinally-aligned staple cavities 3010c, 3010d on a second side of the longitudinal slot 3004. The distal pattern 3024 also includes a first pair of parallel, longitudinally-aligned staple cavities 3010e, 3010f on the first side of the longitudinal slot 3004 and a second pair of parallel, longitudinally-aligned staple cavities 3010g, 3010h on the second side of the longitudinal slot 3004. In other instances, the distal pattern 3024 can be different from the proximal pattern 3022.

The proximal pattern 3022 and the distal pattern 3024 are symmetric relative to the longitudinal axis LA. In other instances, the proximal pattern 3022 and/or the distal pattern 3024 can be asymmetric relative to the longitudinal axis LA. For example, the staple cavities 3010e and 3010f can be longitudinally offset from the staple cavities 3010g and 3010h and/or the staple cavities 3010a and 3010b can be longitudinally offset from the staple cavities 3010c and 3010d. Additionally or alternatively, in certain instances, the staple cartridge body 3000 can include either the proximal pattern 3022 or the distal pattern 3024. In other instances, the staple cavities 3010 defined in the staple cartridge body 3000 can include additional and/or different patterns of staple cavities 3010.

Figure 5:
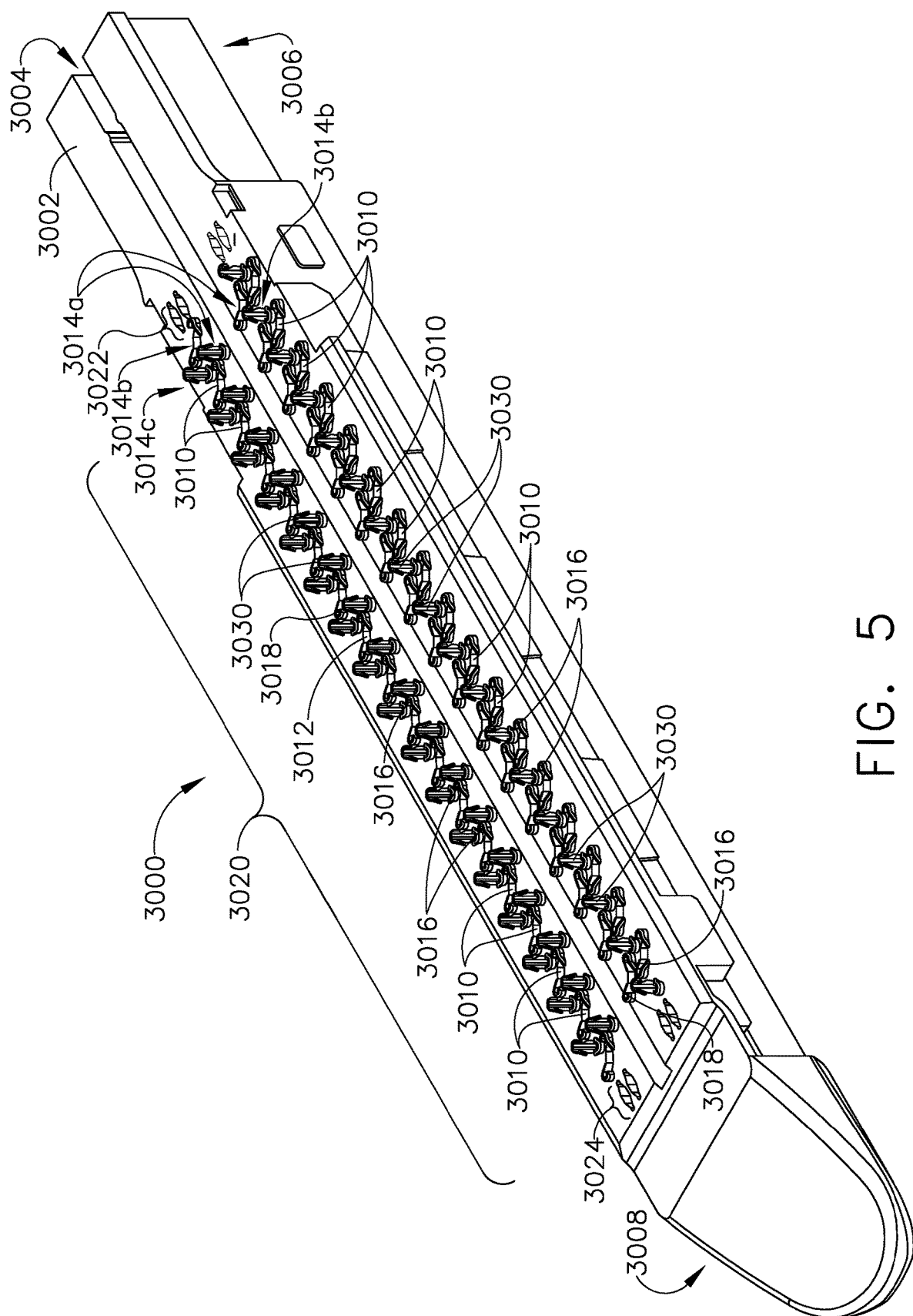
FIG. 5 is a perspective view of a staple cartridge body having a plurality of staple cavities defined therein.

Referring primarily to FIG. 5, atraumatic extenders 3030 extend or protrude from the deck 3002 around a portion of the staple cavities 3010 in the first pattern 3020. The atraumatic extenders 3030 surround the proximal and distal ends 3016 and 3018, respectively, of the openings 3012 of the staple cavities 3010 in the first pattern 3020. The atraumatic extenders 3030 may be configured to grip tissue that is clamped by the end effector. Additionally or alternatively, in certain instances, the tips of the staple legs can protrude from the cartridge body 3000. In such instances, the atraumatic extenders 3030 may be configured to extend flush with and/or beyond the tips of the staple legs to prevent the tips from prematurely penetrating tissue. Consequently, larger staples, e.g., staples having longer legs, can be positioned in the staple cavities 3010 having atraumatic extenders 3030 positioned therearound. For example, referring again to FIG. 5, larger staples can be positioned in the staple cavities 3010 in the first pattern 3020 than the staples in the staple cavities in the proximal pattern 3022 and the distal pattern 3024 without risking premature piercing of tissue by the longer staple legs. In certain instances, atraumatic extenders 3030 can be positioned around staples cavities 3010 in the proximal pattern 3022 and/or the distal pattern 3024, and larger staples can be positioned in one of more of those staple cavities 3010a-3010h, as well.

The staple cartridge body 3000 can be configured to generate a staple line having different properties along the length thereof. A staple line 3040 generated by the staple cartridge body 3000 and embedded in tissue T is depicted in FIG. 9. The staple line 3040 is comprised of staples 3042, and an exemplary staple 3042 for use with various staple cartridges described herein is depicted in FIG. 10. The staple 3042 can be comprised of a bent wire, for example. The wire can have a diameter of 0.0079 inches, or approximately 0.0079 inches. In other instances, the wire can have a diameter of 0.0089 inches, or approximately 0.0089 inches. In still other instances, the wire can have a diameter of 0.0094, or approximately 0.0094 inches. In certain instances, the wire can have a diameter of less than 0.0079 inches or more than 0.0094 inches. The reader will appreciate that the diameter of the wire can dictate the diameter of the staple. The staple 3042 is a substantially U-shaped staple having a base 3050, a first leg 3052 extending from a first end of the base 3050, and a second leg 3054 extending from a second end of the base 3050. The first leg 3052 is substantially parallel to the second leg 3054 and substantially perpendicular to the base 3050. When implanted in tissue T, the angular orientation of the base 3050 corresponds to the angular orientation of the staple cavity opening 3012 from which the staple 3042 was fired.

Another exemplary staple 3142 for use with various staple cartridges described herein is depicted in FIG. 11. The staple 3142 is a substantially V-shaped staple having a base 3150, a first leg 3152 extending from a first end of the base 3050, and a second leg 3154 extending from a second end of the base 3150. The first leg 3152 is obliquely oriented relative to the second leg 3154 and the base 3150. When implanted in tissue T, the orientation of the base 3150 corresponds to the orientation of the staple cavity opening 3012 from which the staple 3142 was fired. The reader will appreciate that staples having different geometries can also be fired from the staple cartridges described herein.

Referring again to FIG. 9, the staple line 3040 includes a first portion 3044, a proximal portion 3046, and a distal portion 3048. The first portion 3044 is generated from the first pattern, or major pattern, 3020 and extends along a substantial portion of the staple line 3040. Owing to the angular orientation of the staples 3042 in the first portion 3044, the first portion 3044 is substantially flexible or compliant. For example, because the angularly-oriented staples 3042 can rotate within the stapled tissue T while minimizing trauma to the tissue T, the first portion 3044 is configured to stretch or extend longitudinally and/or laterally as the stapled tissue stretches.

The proximal portion 3046 is generated from the proximal pattern 3022 and forms the proximal end of the staple line 3040. The distal portion 3048 is generated from the distal pattern 3024 and forms the distal end of the staple 3040. Owing to the parallel orientation of the staples 3042 in the proximal portion 3046 and the distal portion 3048 of the staple line 3040, the proximal portion 3046 and the distal portion 3046 of the staple line 3040 can be less flexible than the first portion 3044. However, the reduced flexibility of the proximal portion 3046 and the distal portion 3048 may not impact, or not substantially impact, the overall flexibility of the staple line 3040. Moreover, as described herein, the proximal portion 3046 and the distal portion 3048 may not extend adjacent to the cutline and, in certain instances, the proximal portion 3046 may be absent or missing from the staple line 3040.

A firing element, such as the firing member 1760 (FIG. 4), is configured to move along at least a portion of the slot 3004 to fire the staples 3042 from the staple cavities 3010. The firing element can include and/or engage one of more wedge sleds and/or camming surfaces, such as the sled assembly 1120 having wedge-shaped cams 1122 (FIG. 4). The cams of the sled are configured to drive the staples upward toward a staple-forming surface, such as into forming pockets in the anvil 1130 (FIGS. 1, 3 and 4), for example. Referring to FIG. 6, the staple cartridge body 3000 includes a plurality of channels 3036 along a bottom surface 3034 through which the wedge-shaped cams can move during a firing stroke.

Figure 3:
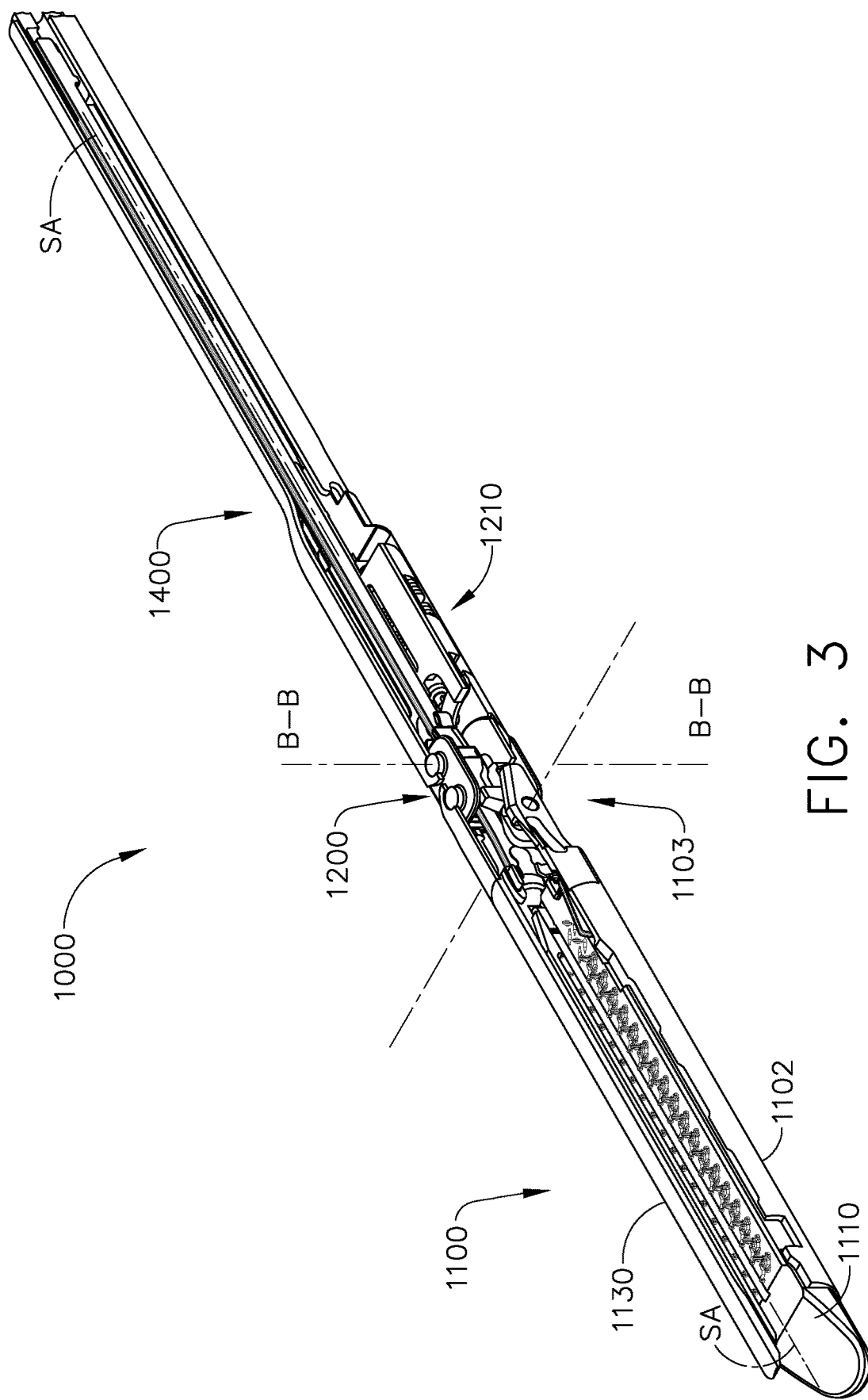
FIG. 3 is a perspective view of a distal portion of the interchangeable surgical tool assembly embodiment depicted in FIGS. 1 and 2 with portions thereof omitted for clarity.
Figure 4:
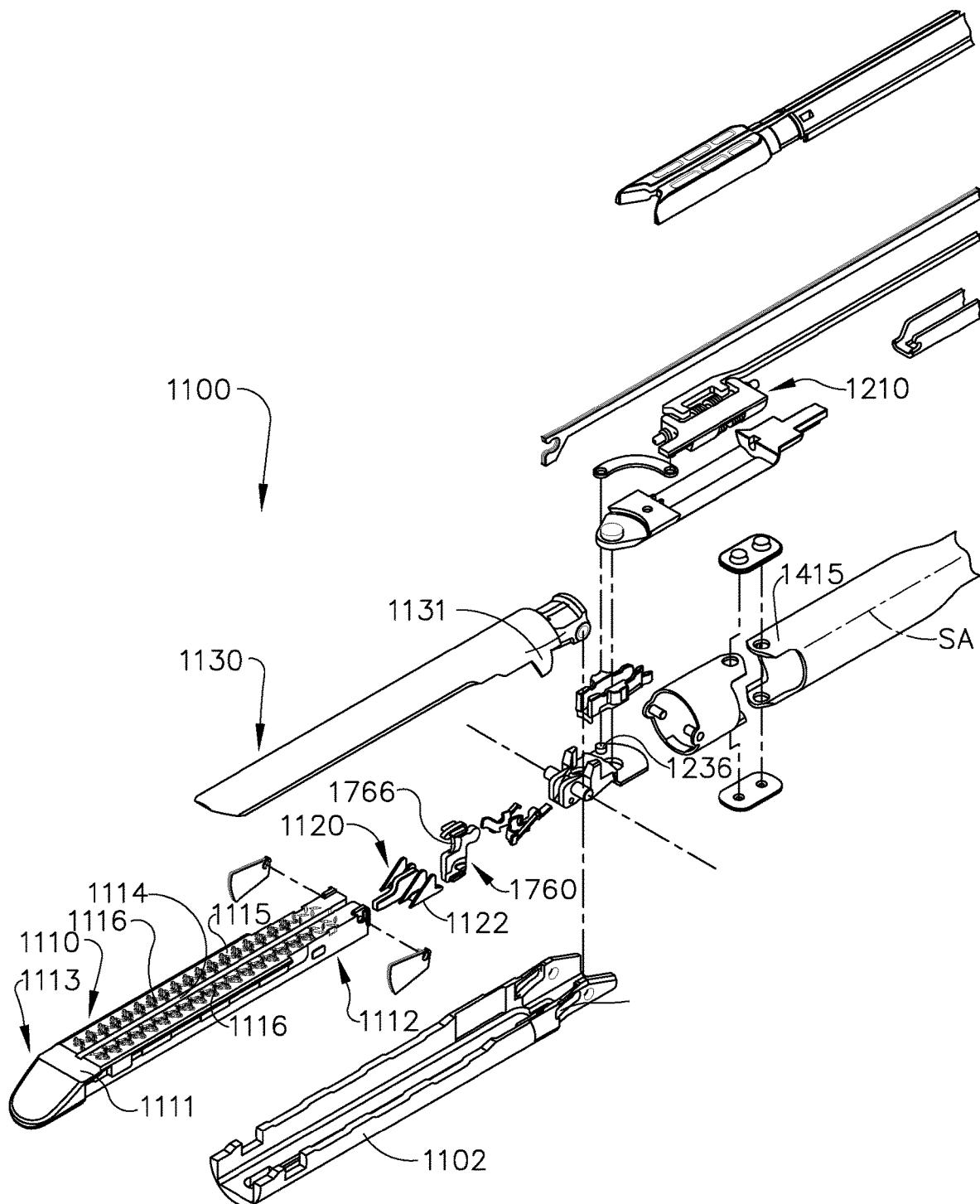
FIG. 4 is an exploded assembly view of a distal portion of the interchangeable surgical tool assembly of FIG. 1.

In use, target tissue is clamped between the staple cartridge body 3000 and an anvil, such as the anvil 1130 (FIGS. 1, 3 and 4). The tissue overlapping the staple cavities 3010 is stapled. If tissue is not positioned over certain staple cavities 3010, staples fired from those staple cavities 3010 may not engage the tissue. An anvil typically contains downwardly extending sidewalls commonly referred to as "tissue stops". The tissue stops are configured to block the target tissue from getting too far proximal between the anvil and cartridge. For example, referring to the end effector 1100 in FIG. 4, the anvil 1130 includes tissue stops 1131, which extend toward the staple cartridge 1110. When the anvil 1130 is closed toward the cartridge 1110, the tissue stops 1131 on either side of the anvil 1130 extend downward past the cartridge deck surface 1115 and form a wall or barrier, which prevents tissue from being positioned too far proximal between the anvil 1130 and cartridge 1110. The distal ends of the tissue stops 1131 define a proximal starting point for the cutline. A proximal axis PA corresponding to the distal ends of the tissue stops 1131 is depicted in FIG. 7. Because target tissue is not positioned proximal to the proximal axis PA, the staples that are fired from the staple cavities located proximal to the proximal axis PA, i.e., the proximal staple cavities 3010a-3010d, are not fired into the target tissue. In such instances, staples fired from the proximal pattern 3022 do not form a part of the staple line.

A cutting element 3028 (FIG. 7) is also configured to move along the longitudinal slot 3004. In various instances, the cutting element 3028 can be an integral part of the firing element, such as the tissue cutting feature 1766 on the firing member 1760 (FIG. 4), for example. The cutting element 3028 has a distal cutting edge 3029 that is configured to incise tissue clamped by the end effector and stapled by the staples 3042. Referring primarily to FIG. 7, the cutting edge 3029 of the cutting element 3028 is configured to move between a proximal position near the proximal end portion 3006 of the cartridge body 3000 and a distal position near the distal end portion 3008 of the cartridge body 3000. The distal-most position of the cutting edge 3029 is defined by a distal termination point for the cutline. A distal axis DA corresponding to the distal termination point of the cutting edge 3029 is depicted in FIG. 7. Tissue positioned distal to the distal axis DA is not incised by the cutting element 3028 during the firing stroke.

The first pattern 3020 of staple cavities 3010 extends between the proximal axis PA and the distal axis DA. Moreover, at least one staple cavity 3010 in the first pattern 3020 overlaps the proximal axis PA and the distal axis DA. In other instances, more than one longitudinally-repetitive pattern of staple cavities 3010 can be positioned between the proximal axis PA and the distal axis DA. The proximal pattern 3022 is positioned proximal to the proximal axis PA, and the distal pattern 3024 is positioned distal to the distal axis DA. In such instances, staples fired from the distal staple cavities 3010e-3010h are not configured to staple incised tissue. Moreover, staples fired from the proximal staple cavities 3010a-3010d are not configured to staple the target tissue. Accordingly, such staples may not impact the flexibility and/or sealing quality of the resultant staple line.

In certain instances, it can be desirable to generate a staple line having a first flexibility adjacent to the cutline and a different flexibility proximal to and/or distal to the cutline. For example, a staple line that includes at least two parallel staples on each side of the cutline and positioned distal to the distal end of the cutline, may provide certain advantages. In certain instances, a staple arrangement that provides less flexibility may prevent and/or limit the propagation of the cutline and/or tearing of the tissue. Additionally, the tissue adjacent to an uncut portion may experience less stress and/or strain than the tissue adjacent to the cutline and, thus, may require less flexibility to prevent and/or limit tissue trauma. More specifically, tissue adjacent to the cutline may experience more forces during the cutting stroke and, thus, increased flexibility may prevent trauma to the tissue. Additionally, the tissue adjacent to the cutline may stretch as it heals and thus, increased flexibility may facilitate the healing process. For tissue that experiences fewer forces, such as the tissue distal to the cutline, for example, the reduced flexibility may reinforce or strengthen the staple line and prevent distal propagation of the cutline.

In the depicted arrangement, the proximal pattern 3022 includes two irregular staple cavities on each side of the knife slot 3004 adjacent to the proximal end of the first pattern 3020 and the distal pattern 3024 includes two irregular staple cavities on each side of the knife slot 3004 adjacent to the distal end of the first pattern 3020. In other instances, the proximal pattern 3022 and/or the distal pattern 3024 can consist of a single irregular staple cavity on one or both sides of the knife slot 3004. In still other instances, the proximal pattern 3022 and/or the distal pattern 3024 can include three or more irregular staple cavities on one or both sides of the knife slot 3004. The proximal pattern 3022 and/or the distal pattern 3024 can include longitudinally repetitive sub-patterns. For example, the proximal pattern 3022 and/or the distal pattern 3024 can include multiple columns of parallel staple cavity openings 3012. In certain instances, the staple cartridge body 3000 can have a single irregular pattern, which can be positioned at either the proximal end or distal end of the first pattern 3020.

In certain instances, one or more staple cavities in the proximal pattern 3022 and/or the distal pattern 3024 can be non-parallel to the knife slot 3004. For example, such staple cavities can be oriented perpendicular to the knife slot 3004 or at an oblique angle relative to the knife slot 3004. Additionally or alternatively, certain staple cavities in the proximal pattern 3022 and/or the distal pattern 3024 can be non-parallel to each other Referring primarily to FIG. 8, staple drivers 3060 are positioned in the staple cavities 3010 of the cartridge body 3000. The staple drivers 3060 are positioned to support the staples 3042 (FIGS. 9 and 10) therein and to drive the staples 3042 from the staple cavities 3010 during a firing stroke. Owing to the different patterns of staple cavities 3010 in the cartridge body 3000, e.g., the patterns 3020, 3022 and 3024, the staple drivers 3060 can have different geometries and/or orientations. For example, the staple drivers 3060 positioned in the staple cavities 3010 of the first pattern 3020 may include connected drivers as described in U.S. patent application Ser. No. 14/498,145, filed Sep. 26, 2014, now U.S. Patent Application Publication No. 2016/0089142, entitled METHOD FOR CREATING A FLEXIBLE STAPLE LINE, which is incorporated by reference herein in its entirety. Each connected driver can include an inner driver positioned in a staple cavity 3010 in the inner row 3014a, an intermediate driver positioned in a staple cavity 3010 in the intermediate row 3014b, and an outer driver positioned in a staple cavity 3010 in the outer row 3014c. A connecting flange can connect the intermediate driver to at least one inner driver and at least one outer driver. In other instances, the staple drivers positioned in the staple cavities in the first pattern 3020 may include individual drivers, wherein each driver drives a single staple. In still other instances, the staples can be direct-drive staples, which can be driven by direct contact with a wedge sled and/or camming surfaces, as described in U.S. patent application Ser. No. 14/138,475, filed on Dec. 23, 2013, now U.S. Patent Application Publication No. 2015/0173749, entitled SURGICAL STAPLES AND STAPLE CARTRIDGES and U.S. patent application Ser. No. 14/498,145, which are incorporated by reference herein in their respective entireties.

The drivers 3060 positioned in the staple cavities 3010 are dimensioned and positioned for driving engagement by the sled and camming surfaces thereof. For example, the drivers 3060 are positioned in the staple cavities 3010 of the first pattern 3020. Proximal drivers 3060a, 3060b, 3060c, and 3060d are positioned in the staple cavities 3010a, 3010b, 3010c, and 3010d, respectively, of the proximal pattern 3022, and distal drivers 3060e, 3060f, 3060g, and 3060h are positioned in the staple cavities 3010e, 3010f, 3010g, and 3010h, respectively, of the distal pattern 3024. Referring again to FIG. 4, the sled assembly 1120 and the wedge-shaped cams 1122 thereof can be configured to lift the drivers 3060 in the staple cavities 3010. In such instances, the cams 1122 are configured to drivingly engage the drivers 3060 along the length of the cartridge body 3000. More specifically, the cams 1122 initially engage and drive the proximal drivers 3060a, 3060b, 3060c, and 3060d to fire the staples in the proximal pattern 3022, then engage and drive the drivers 3060 to fire the staples in the first pattern 3022, and finally engage and drive the distal drivers 3060e, 3060f, 3060g, and 3060h to fire the staples in the distal pattern 3024. Although the proximal drivers 3060a, 3060b, 3060c, and 3060d and/or the distal drivers 3060e, 3060f, 3060g, and 3060h have a different geometry than the drivers 3060 in the first pattern 3020 of staple cavities 3010, the sled and camming surfaces thereof are compatible with the different drivers in the cartridge body 3000.

Referring again to FIG. 4, the sled assembly 1120 includes four camming surfaces 1122. A first pair of camming surfaces 1122 are positioned for driving engagement with the staple drivers on the first side of the longitudinal axis LA, and a second pair of camming surfaces 1122 are positioned for driving engagement with the staple drivers on the second side of the longitudinal axis LA. The camming surfaces 1122 in each pair are longitudinally offset. In other instances, the camming surfaces 1122 can be longitudinally aligned. Each pair of camming surfaces 1122 is configured to lift a triple driver (see, e.g., the driver 1170 in FIGS. 81-83), i.e., a connected driver supporting a staple in the inner row 3014a of staple cavities 3010, a staple in the intermediate row 3014b of staple cavities 3010, and a staple in the outer row 3014c of staple cavities 3010. The camming surfaces 1122 are also configured to lift the proximal drivers 3060a, 3060b, 3060c, and 3060d and the distal drivers 3060e, 3060f, 3060g, and 3060h. In other instances, the sled assembly 1120 can include more than or less than four camming surfaces.

Figure 14:
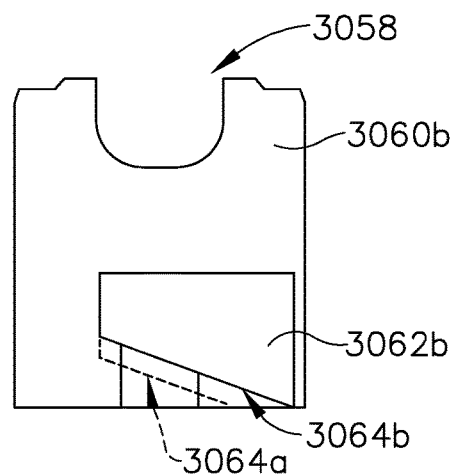
FIG. 14 is a side elevation view of the drivers of FIG. 13 and depicting an offset ramped surface with a phantom line.
Figure 15:
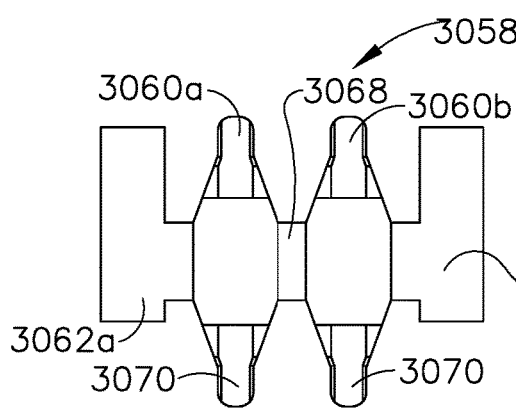
FIG. 15 is a plan view of the drivers of FIG. 13.
Figure 16:
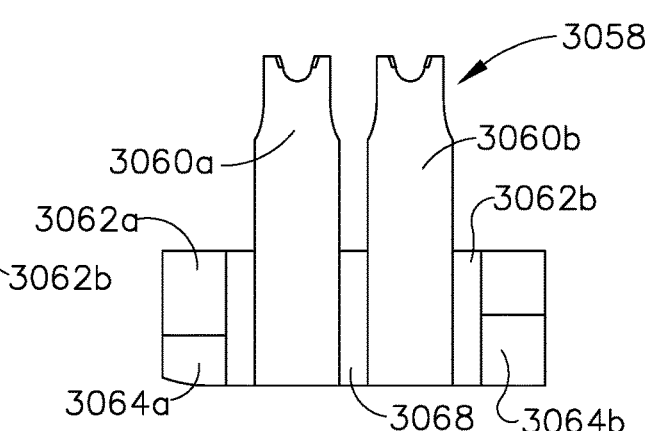
FIG. 16 is a front elevation view of the drivers of FIG. 13.

The proximal drivers 3060a-3060d and the distal drivers 3060e-3060h are connected drivers 3058. An exemplary connected driver 3058 is depicted in FIGS. 13-16. The connected driver 3058 includes the first driver 3060a and the second driver 3060b. A connecting flange 3068 extends between the two drivers 3060a and 3060b. Because the first and second drivers 3060a and 3060b are connected, the staples supported by the first and second drivers 3060a, 3060b are fired simultaneously by the sled assembly. Each driver 3060a and 3060b also includes a cradle 3070 for supporting the base of the staple. A guide 3062a and 3062b extends laterally from each driver 3060a and 3060b, respectively. The first guide 3062a extends in a first direction and forms an outside portion of the connected driver 3058 and the second guide 3062b extends in a second, opposite direction and forms an inside portion of the connected driver 3058. Ramped surfaces 3064a and 3064b on the guides 3062a and 3062b, respectively, are positioned for driving contact with the camming surfaces of the sled assembly. The guides 3062a and 3062b are driven upward in the channels 3036 (FIG. 6) of the cartridge body 3000 when moved to a fired position by the sled assembly. The channels 3036 form a vertical support structure through which the guides 3062a, 3062b are driven by the camming surfaces. As described herein, the camming surfaces can be longitudinally offset. In such instances, the ramped surfaces 3064a, 3064b are correspondingly offset, as depicted in FIGS. 14 and 16. In other instances, the ramped surfaces 3064a and 3064b can be aligned.

Figure 12:
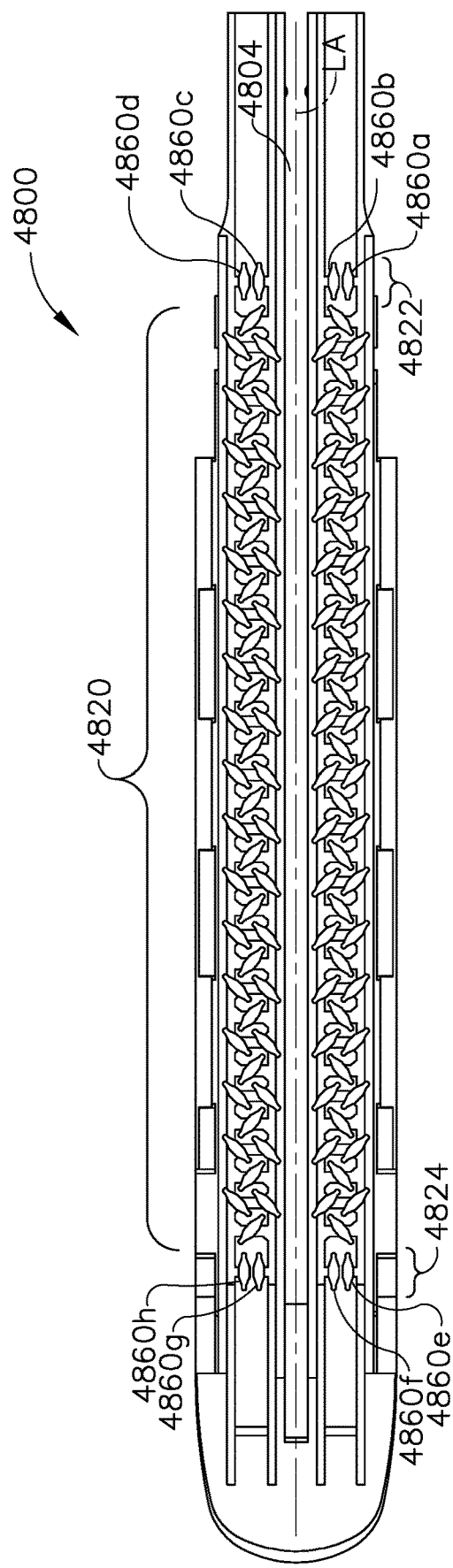
FIG. 12 is a bottom plan view of a staple cartridge body having a plurality of staple cavities defined therein and depicting drivers positioned in the staple cavities.
Figure 13:
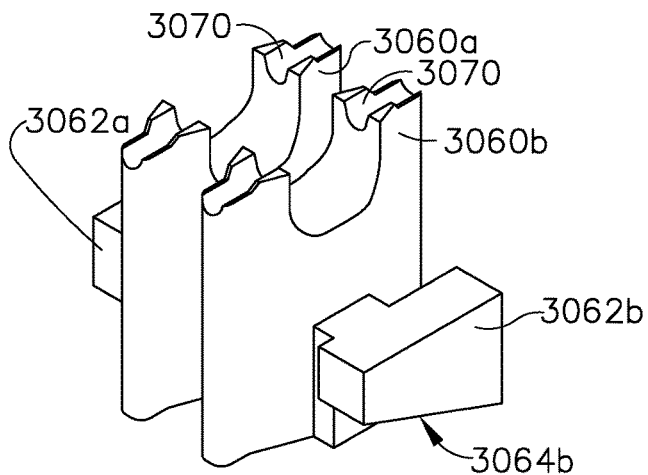
FIG. 13 is a perspective view of the drivers in the proximal staple cavities of FIG. 8.

In other instances, the proximal drivers and/or the distal drivers in a staple cartridge may not be connected. For example, referring to FIG. 12, a staple cartridge 4800 is depicted. The staple cartridge body 4800 is similar in many aspects to the staple cartridge body 3000. For example, the staple cartridge body 4800 includes a first pattern 4820 of angularly-oriented staple cavities, which are arranged in a herringbone pattern. A slot 4804 extends along the longitudinal axis LA of the cartridge body 4800. The staple cartridge body 4800 also includes proximal staple cavities arranged in a proximal pattern 4822 and distal staple cavities arranged in a distal pattern 4824. The proximal pattern 4822 includes a first pair of parallel, longitudinally-aligned staple cavities on a first side of the slot 4804 and a second pair of parallel, longitudinally-aligned staple cavities on a second side of the longitudinal slot 4804. The distal pattern 4824 also includes a first pair of parallel, longitudinally-aligned staple cavities on the first side of the slot 4804 and a second pair of parallel, longitudinally-offset staple cavities on the second side of the longitudinal slot 4804. The proximal pattern 4822 and the distal pattern 4824 are symmetric relative to the longitudinal axis LA. In other instances, the proximal pattern 4822 and/or the distal pattern 4824 can be asymmetric relative to the longitudinal axis LA.

Figure 17:
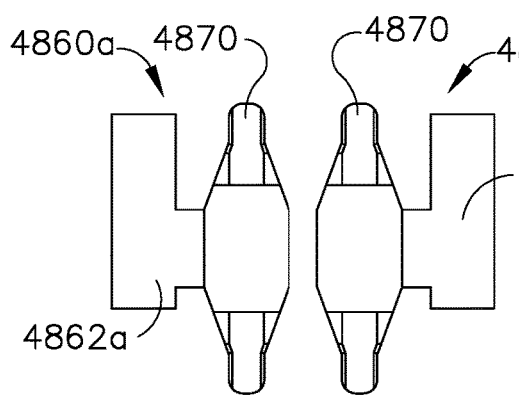
FIG. 17 is a plan view of the drivers in the proximal staple cavities of the staple cartridge body of FIG. 12.
Figure 18:
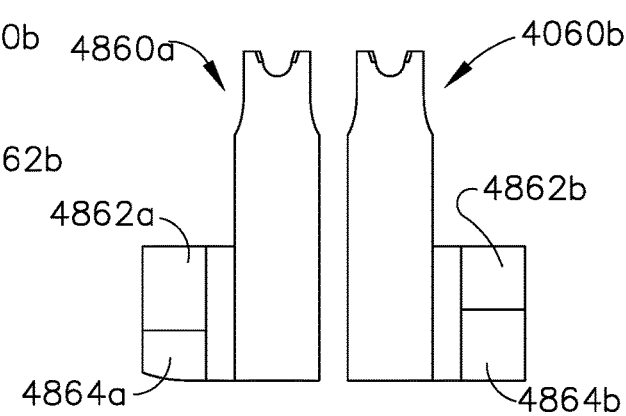
FIG. 18 is a front elevation view of the drivers of FIG. 17.

Drivers 4860 are positioned in the staple cavities 4810 of the first pattern 4820. The drivers 4860 in the staple cavities 4810 of the first pattern 4820 are triple drivers, as described herein. Proximal drivers 4860a, 4860b, 4860c, and 4860d are positioned in the staple cavities of the proximal pattern 4822, and distal drivers 4860e, 4860f, 4860g, and 4860h are positioned in the staple cavities of the distal pattern 4824. The proximal drivers 4860a-4860d and the distal drivers 4860e-4860h are single drivers. Exemplary single drivers 4860a and 4860b are depicted in FIGS. 17 and 18.

Each driver 4860a and 4860b includes a cradle 4870 for supporting the base of the staple. A guide 4862a and 4862b extends laterally from each driver 4860a and 4860b, respectively. The first guide 4862a extends in a first direction and forms an outside portion of the first driver 4860a and the second guide 4862b extends in a second, opposite direction and forms an outside portion of the second driver 4860b. Ramped surfaces 4864a and 4864b on the guides 4862a and 4862b, respectively, are positioned for driving contact with the camming surfaces of a sled assembly. The guides 4862a and 4862b are driven upward in channels in the cartridge body 4800, such as the channels 3036 in the cartridge 3000 (FIG. 6), when the drivers 4860a and 4860b are moved to a fired position by the sled assembly. The channels form a vertical support structure through which the guides 4862a and 4862b are driven by the camming surfaces. Such channels can stabilize the guides 4862a and 4862b and, thus, stabilize the individual drivers 4860a and 4860b, respectively, during deployment. As described herein, the camming surfaces can be longitudinally offset. In such instances, the ramped surfaces 4864a, 4864b are correspondingly offset, as depicted in FIG. 18. In other instances, the ramped surfaces 4864a and 4864b can be aligned.

Because the first and second drivers 4860a, 4860b are separate, the staples supported by the first and second drivers 4860a, 4860b can be fired independently. In certain instances, the first driver 4860a and the second driver 4860b can be fired sequentially. It can be advantageous to fire an inner staple before an outer staple, for example, which can be accomplished with the separate drivers 4860a and 4860b. In other instances, an outer staple can be fired before an inner staple with the separate drivers 4860a and 4860b. The firing order can be modified by adjusting the relationship between the camming surfaces and the ramped surfaces 3864a and 4864b, for example.

Figure 19:
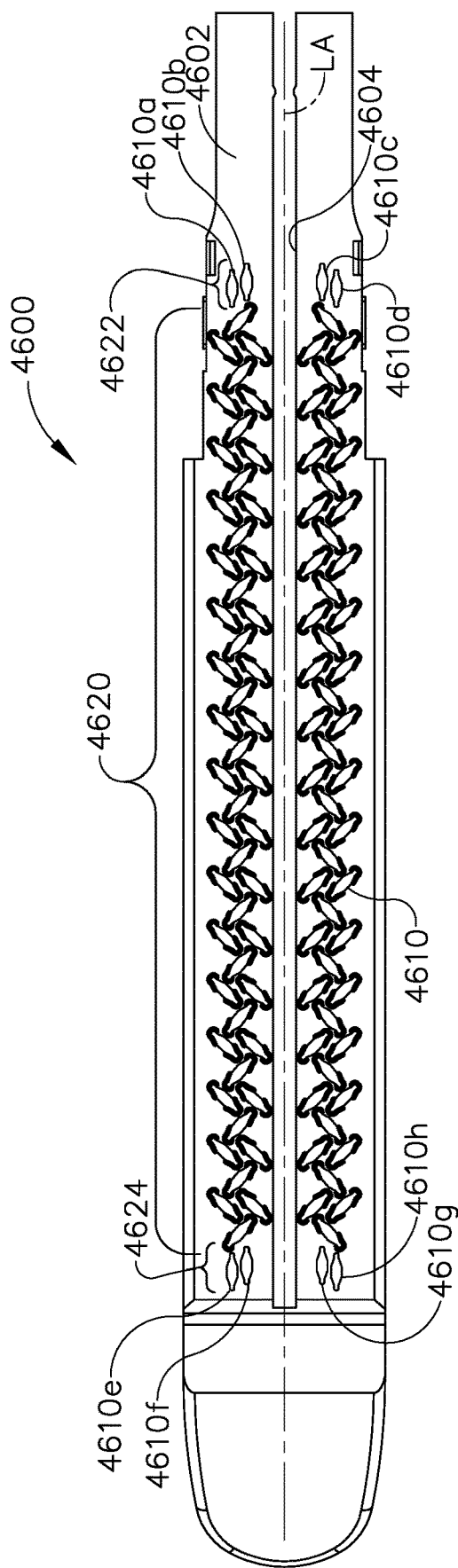
FIG. 19 is a top plan view of a staple cartridge body having a plurality of staple cavities defined therein.
Figure 20:
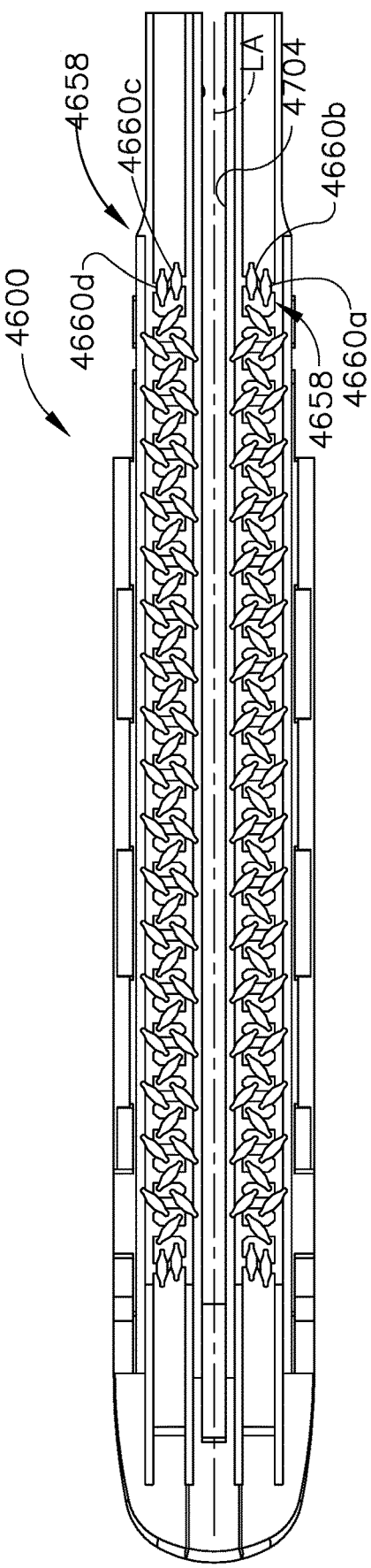
FIG. 20 is a bottom plan view of the staple cartridge body of FIG. 19 and depicting drivers positioned in the staple cavities.

In various instances, the staple cavities in a distal pattern and/or a proximal pattern may not be longitudinally-aligned and/or may not be parallel. For example, referring now to FIGS. 19 and 20, a staple cartridge body 4600 is depicted. The staple cartridge body 4600 is similar in many aspects to the staple cartridge body 3000. For example, the staple cartridge body 4600 includes a first pattern 4620 of angularly-oriented staple cavities 4610, which are arranged in a herringbone pattern. A slot 4604 extends through a deck 4602 of the staple cartridge body 4600 along the longitudinal axis LA of the cartridge body 4600. The staple cartridge body 4600 also includes proximal staple cavities 4610a-4610d arranged in a proximal pattern 4622 and distal staple cavities 4610e-4610h arranged in a distal pattern 4624. The proximal pattern 4622 includes a first pair of parallel, longitudinally-offset staple cavities 4610a, 4610b on a first side of the slot 4604 and a second pair of parallel, longitudinally-offset staple cavities 4610c, 4610d on a second side of the longitudinal slot 4604. The distal pattern 4624 also includes a first pair of parallel, longitudinally-offset staple cavities 4610e, 4610f on the first side of the slot 4604 and a second pair of parallel, longitudinally-offset staple cavities 4610g, 4610h on the second side of the longitudinal slot 4604. The proximal pattern 4622 and the distal pattern 4624 are symmetric relative to the longitudinal axis LA. In other instances, the proximal pattern 4622 and the distal pattern 4624 can be asymmetric relative to the longitudinal axis LA.

Figures 21, 22:
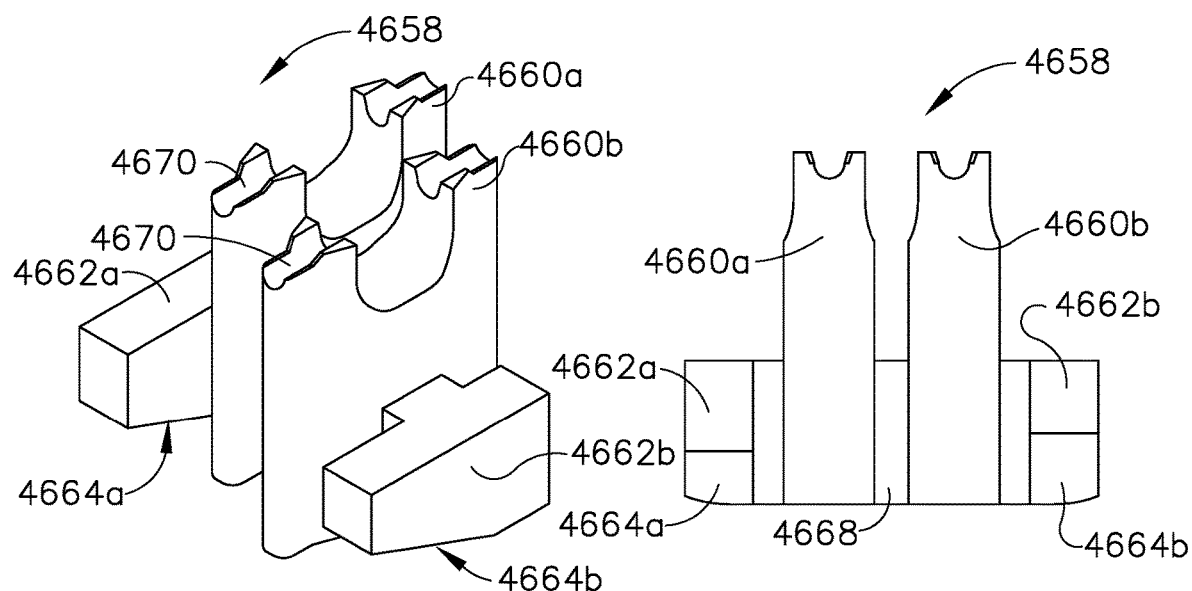
FIG. 21 is a perspective view of the drivers in the proximal staple cavities of FIG. 20.
FIG. 22 is a front elevation view of the drivers of FIG. 21.
Figures 23, 24:
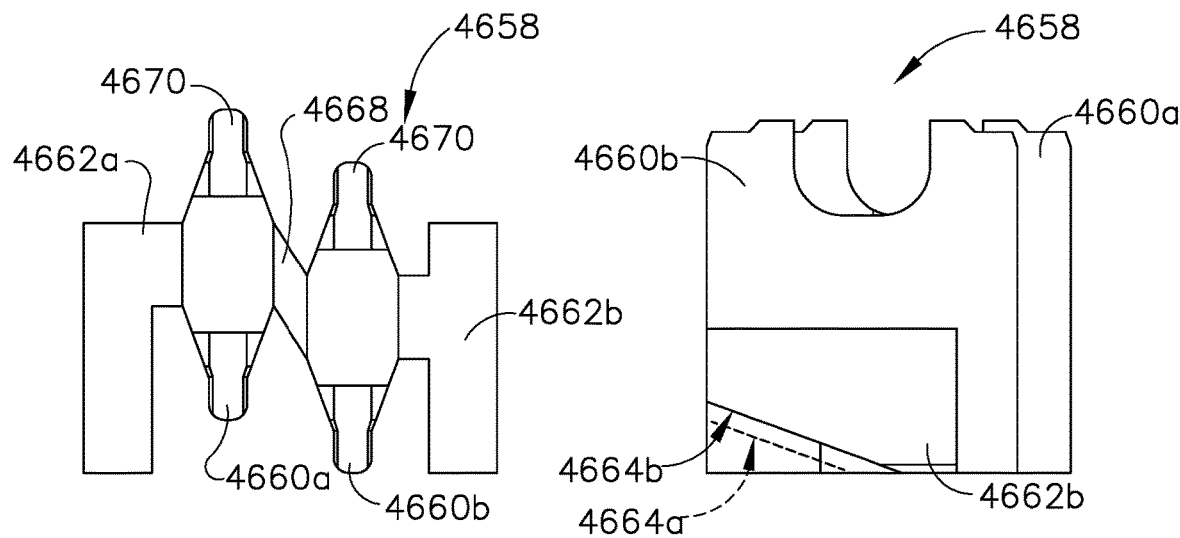
FIG. 23 is a plan view of the drivers of FIG. 21.
FIG. 24 is a side elevation view of the drivers of FIG. 21 and depicting an offset ramped surface with a phantom line.

Connected drivers 4658 are positioned in the proximal and distal staple cavities 4610a-4610h. An exemplary connected driver 4658 is depicted in FIGS. 21-24. The connected driver 4658 includes the first driver 4660a and the second driver 4660b. A connecting flange 4668 extends between the two offset drivers 4660a and 4660b. Because the drivers 4660a and 4660b are connected, the staples supported by the drivers 4660a, 4660b are fired simultaneously by the sled assembly. Each driver 4660a and 4660b includes a cradle 4670 for supporting the base of the staple. A guide 4662a and 4662b extends laterally from each driver 4660a and 4660b, respectively. The first guide 4662a extends in a first direction and forms an outside portion of the connected driver 4658 and the second guide 4662b extends in a second, opposite direction and forms an inside portion of the connected driver 4658. Ramped surfaces 4664a and 4664b on the guides 4662a and 4662b, respectively, are positioned for driving contact with the camming surfaces of a sled assembly. The guides 4662a and 4662b are driven upward in channels in the cartridge body 4800, such as the channels 3036 in the staple cartridge 3000 (FIG. 6), for example, when the drivers 4660a, 4660b are moved to a fired position by the sled assembly. The channels form a vertical support structure through which the guides 4662a, 4662b are supported as they are driven by the camming surfaces. As described herein, the camming surfaces can be longitudinally offset. In such instances, the ramped surfaces 4664a, 4664b are correspondingly offset, as depicted in FIGS. 22 and 24. In other instances, the ramped surfaces 4664a and 4664b can be aligned.

Figure 25:
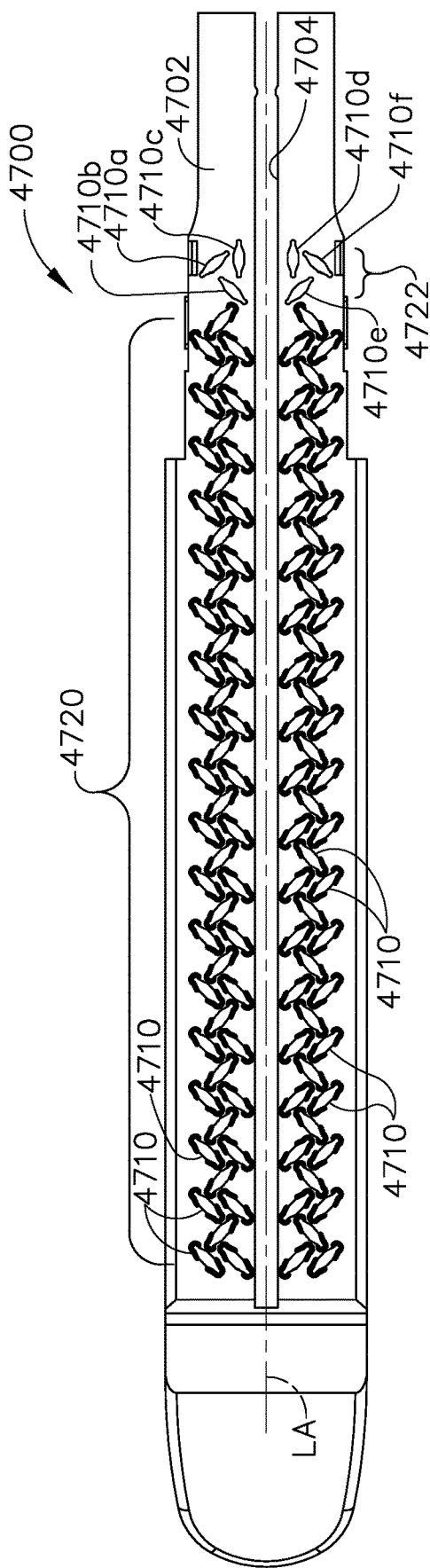
FIG. 25 is a top plan view of a staple cartridge body having a plurality of staple cavities defined therein.
Figure 26:
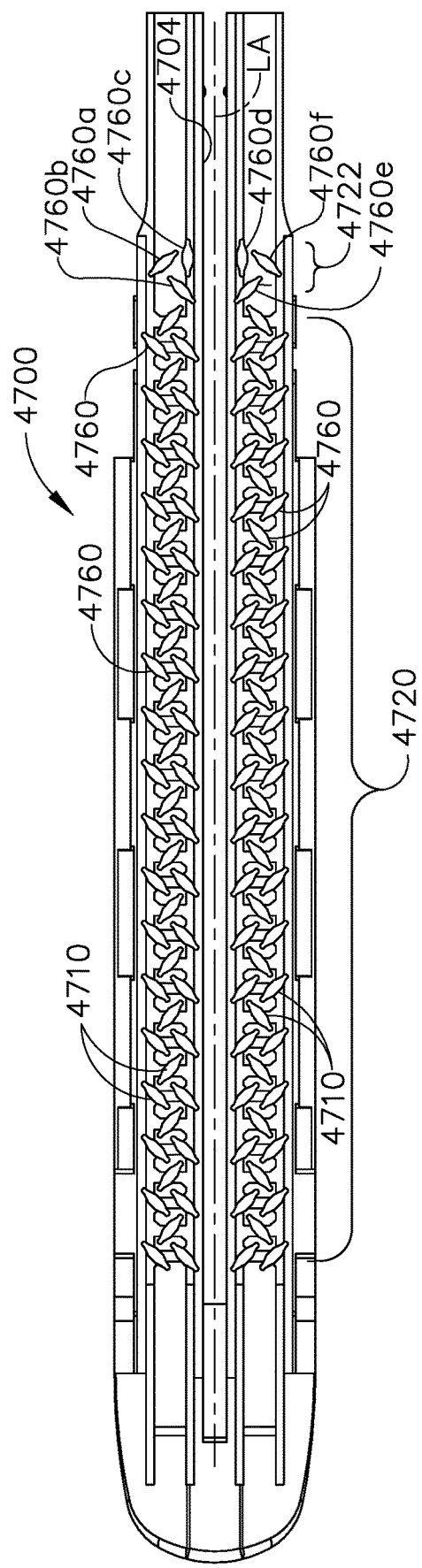
FIG. 26 is a bottom plan view of the staple cartridge body of FIG. 25 and depicting drivers positioned in the staple cavities.

Referring now to FIGS. 25 and 26, a staple cartridge body 4700 is depicted. The staple cartridge body 4700 is similar in many aspects to the staple cartridge body 3000. For example, the staple cartridge body 4700 includes a first pattern 4720 of angularly-oriented staple cavities 4710, which are arranged in a herringbone pattern. A slot 4704 extends through a deck 4702 of the staple cartridge body 4700 along the longitudinal axis LA of the cartridge body 4700. The staple cartridge body 4700 also includes proximal staple cavities 4710a-4710f arranged in a proximal pattern 4722. The proximal pattern 4722 includes inner staple cavities 4710c and 4710d, which are oriented parallel to the longitudinal axis LA. The proximal pattern 4722 also includes angularly-oriented outer staple cavities 4710a and 4710f, and angularly-oriented intermediate cavities 4710b and 4710e. The outer staple cavities 4710a and 4710f and the intermediate staple cavities 4710b and 4710e are oriented at oblique angles relative to the longitudinal axis LA. The angularly-oriented outer staple cavities 4710a and 4710f are also oriented at oblique angles relative to the cavity axes of the staple cavities 4710 in the first pattern 4720. The outer staple cavities 4710a and 4710f are less angled than the staple cavities 4710 in the first pattern 4720. In other words, the outer staple cavities 4710a and 4710f are oriented at an angle that is closer to parallel with the longitudinal axis LA than the staple cavities 4710 in the first pattern 4720. In such instances, the proximal pattern 4722 can be less flexible than the first pattern 4720.

The intermediate staple cavities 4710b and 4710e are oriented parallel to certain staple cavities 4710 in the first pattern 4020. For example, the intermediate staple cavities 4710b and 4710e are oriented parallel to the staple cavities 4710 in an inner row in the first pattern 4720. Though certain staple cavities in the proximal pattern 4722 are not angularly offset from the staple cavities in the first pattern 4020, the proximal pattern 4722, when considered as a whole, is different than the first pattern 4020 and is different than the longitudinally-repetitive sub-patterns within the first pattern 4020.

The proximal pattern 4722 includes three staple cavities positioned on each side of the slot 4704. In other instances, less than three staple cavities or more than three staple cavities can be arranged in the proximal pattern 4722 on one or both sides of the slot 4704. The proximal pattern 4722 does not include a longitudinally-repetitive sub-pattern. In other instances, the proximal pattern 4722 can be longitudinally repetitive. Additionally, the proximal pattern 4722 is symmetric relative to the longitudinal axis LA. In other instances, the proximal pattern 4722 can be asymmetric relative to the longitudinal axis LA.

Drivers 4760 are positioned in the staple cavities 4710 in the cartridge body 4700. The drivers 4760 in the staple cavities 4710 of the first pattern 4720 are triple drivers, as described herein. Proximal drivers 4760a, 4760b, 4760c, 4760d, 4710e, and 4710f are positioned in the proximal staple cavities 4710a, 4710b, 4710c, 4710d, 4710e, and 4710f respectively, of the proximal pattern 4722. The proximal drivers 4760a-4760f are single drivers. In certain instances, the proximal drivers 4760c and 4760d in the inner cavities 4710c and 4710d, respectively, can be single drivers, the proximal drivers 4760a and 4760b can be connected drivers, and the proximal drivers 4760e and 4760f can be connected drivers. In still other instances, the proximal drivers 4760a, 4760b, and 4760c can comprise a first connected driver, and the distal drivers 4760d, 4760e, and 4760f can comprise a second connected driver.

The reader will appreciate that the various patterns of staple cavities described herein can be combined and/or interchanged. In certain instances, one or more irregular patterns of staple cavities can be defined at the proximal and/or distal end of a staple cartridge body. Additionally or alternatively, one or more irregular patterns, or minor patterns, can be sandwiched or inserted within a major pattern.

The angular orientation of staples in a staple line can influence the flexibility or compliance of the stapled tissue along the staple line. For example, the flexibility of a staple line can increase when staples are oriented at an oblique angle relative to the longitudinal axis and/or cutline. Such an angular orientation can provide flexibility or extendability, within certain limits, in response to forces, such as tension and/or torsion, along and/or adjacent to the cutline. More specifically, the flexibility in the staple line can permit stretching, buckling, folding, and/or twisting of the stapled tissue. Generally, as the angular orientation of a staple approaches 45 degrees or 135 degrees relative to the longitudinal axis of the staple line and/or the cutline, the flexibility of the stapled tissue increases. A staple line comprised of angularly-oriented staples can be considered a compliant or elastic staple line, for example.

In certain instances, the flexibility of a staple line can vary laterally relative to the cutline. For example, one or more staples in a first portion of the staple line can be oriented at a first angle relative to the cutline and one or more staples in a second portion of the staple line can be oriented at a different angle relative to the cutline. The first portion of the staple line can have a first flexibility and the second portion of the staple line can have a different flexibility. In certain instances, the first portion can be laterally offset from the second portion. For example, the first portion of the staple line can include a first row of staples or portion of the first row, and the second portion of the staple line can include a second row of staples or portion of the second row. In such instances, the flexibility of the staple line along the first row of staples can be different than the flexibility of the staple line along the second row of staples.

Figure 27:
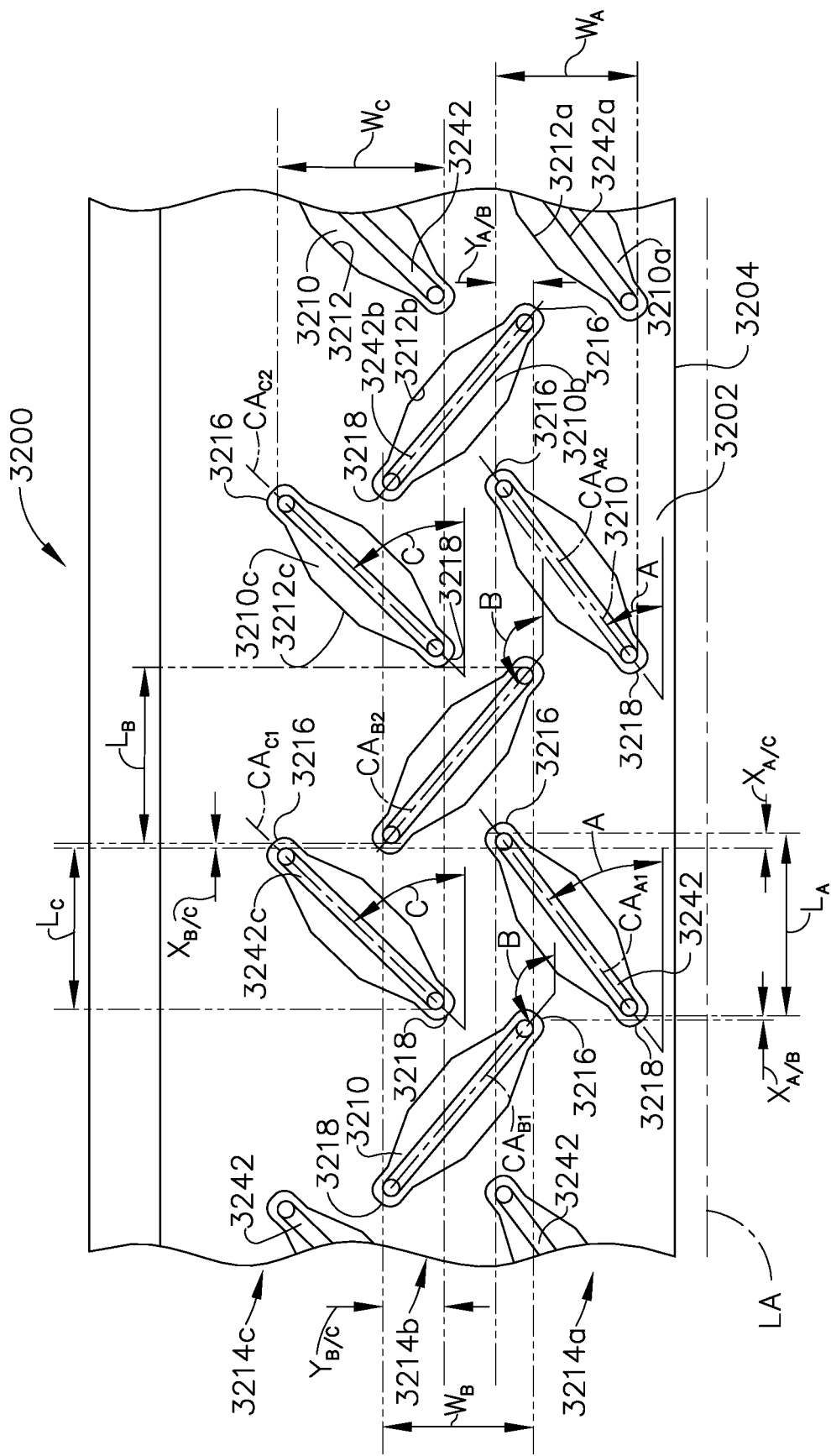
FIG. 27 is a plan view of a portion of a staple cartridge body having a plurality of angularly-oriented staple cavities defined therein and depicting staples in the staple cavities.

Referring now to FIG. 27, a portion of a staple cartridge body 3200 is depicted. The staple cartridge body 3200 includes a deck 3202 and a longitudinal slot 3204. The longitudinal slot 3204 extends along the longitudinal axis LA. Staple cavities 3210 are defined in the staple cartridge body 3200, and each staple cavity 3210 defines an opening 3212 in the deck 3202. A staple 3242 is positioned in each staple cavity 3210. The staple 3242 can be similar in many aspects to the staple 3042 (FIG. 10) or the staple 3142 (FIG. 11). In certain instances, the legs of each staple 3242 can be biased against the inside wall of the staple cavity 3210. The reader will appreciate that the arrangement of staples 3242 in the staple cavities 3210 corresponds to the arrangement of staples 3242 in a staple line when the staples 3242 are fired from the staple cartridge body 3200 and into tissue. More specifically, the bases of each staple 3242 in a resultant staple line are collinear, or substantially collinear, with the cavities axes CA.

The staple cavity openings 3212 are arranged in three rows 3214a, 3214b, and 3214c on a first side of the longitudinal slot 3204. Inner openings 3212a define the perimeter of inner cavities 3210a in the inner row 3214a, intermediate openings 3212b define the perimeter of intermediate cavities 3210b in the intermediate row 3214b, and outer openings 3212c define the perimeter of outer cavities 3210c in the outer row 3214c. Inner staples 3242a are positioned in the inner cavities 3210a, intermediate staples 3242b are positioned in the intermediate cavities 3210b, and outer staples 3242c are positioned in the outer cavities 3210c. Although not shown in FIG. 27, in at least one instance, the staple cavities 3210 on the opposing side of the slot 3204 form a mirror image reflection of the staple cavities 3210 on the first side of the longitudinal slot 3204. Consequently, the arrangement of staples 3242 in a resultant staple line is symmetric relative to the cutline. In other instances, the staple line can be asymmetric relative to the cutline.

Each staple cavity opening 3212 has a first end, or proximal end, 3216 and a second end, or distal end, 3218. A cavity axis CA extends between the proximal end 3216 and the distal end 3218 of each opening 3212. The staple cavity openings 3212 in each respective row are parallel. For example, the inner cavities 3210a are oriented at an angle A relative to the longitudinal axis LA. Stated differently, the cavity axes (e.g., $CA_{A1}$ and $CA_{A2}$) of the inner openings 3212a are oriented at the angle A relative to the longitudinal axis LA. The intermediate cavities 3210b are oriented at an angle B relative to the longitudinal axis LA. Stated differently, the cavity axes (e.g., $CA_{B1}$ and $CA_{B2}$) of the intermediate openings 3212b are oriented at the angle B relative to the longitudinal axis LA. The outer cavities 3210c are oriented at an angle C relative to the longitudinal axis LA.

Stated differently, the cavity axes (e.g., $CA_{C1}$ and $CA_{C2}$) defined by the outer openings 3212 are oriented at the angle C relative to the longitudinal axis LA.

The angles A, B, and C are different. Consequently, the inner openings 3212a are obliquely oriented relative to the outer openings 3212c. Because the cavity axes CA of the outer openings 3212c (e.g., axes $CA_{C1}$ and $CA_{C2}$) are not parallel to the cavity axes of the inner openings 3212a (e.g., axes $CA_{A1}$ and $CA_{A2}$), the openings 3212 in the staple cartridge body 3200 form a modified or skewed herringbone pattern. The cavity axes $CA_{B1}$ and $CA_{B2}$ of the intermediate openings 3212b can be oriented perpendicular, or substantially perpendicular, to either the inner openings 3212a or the outer openings 3212c. For example, the angle B can be a supplementary angle to either angle A or angle C. In other instances, the angle B may not be a supplementary angle to either angle A or angle C.

Owing to the different angles A, B, and C, the widths $W_A$, $W_B$, $W_C$ of the staple rows in the staple line can be different. For example, the inner staples 3242a form a row of staples having a width $W_A$, the intermediate staples 3242b form a row of staples having a width $W_B$, and the outer staples 3242c form a row of staples having a width $W_C$. The widths $W_A$ and $W_C$ are different because the angle A is different than the angle C. In certain instances, the width $W_B$ is different than the widths $W_A$ and $W_C$. In other instances, the width $W_B$ can match one of the widths $W_A$ or $W_C$. For example, if the angle B is a supplementary angle to angle A, the width $W_B$ matches the width $W_A$. Similarly, if the angle B is a supplementary angle to angle C, the width $W_B$ matches the width $W_C$.

Furthermore, owing to the different angles A, B, and C, the longitudinal lengths $L_A$, $L_B$, and $L_C$ of the staples 3242a, 3242b, and 3242c, respectively, are different. For example, the inner staples 3242a have a longitudinal length $L_A$, the intermediate staples 3242b have a longitudinal length $L_B$, and the outer staples 3242c have a longitudinal length $L_C$. The longitudinal lengths $L_A$ and $L_C$ are different because the angle A is different than the angle C. Because the longitudinal lengths $L_A$ and $L_C$ are different, the inner staples 3242a are at least partially longitudinally staggered or offset relative to the outer staples 3242c. Stated differently, at least one end of each inner staple 3242a is not aligned with a corresponding end of an outer staple 3242b. Because the ends are not aligned, the longitudinal overlap and/or gap with respect to the intermediate staples 3242b differs between the inner staples 3242a and the outer staples 3242c. In certain instances, the longitudinal length $L_B$ is different than the lengths $L_A$ and $L_C$. In other instances, the longitudinal length $L_B$ can match one of the longitudinal lengths $L_A$ or $L_C$. For example, if the angle B is a supplementary angle to angle A, the longitudinal length $L_B$ matches the longitudinal length $L_A$. Similarly, if the angle B is a supplementary angle to angle C, the longitudinal length $L_B$ matches the longitudinal length $L_C$.

The length of the staple bases may also impact the widths $W_A$, $W_B$, and $W_C$ and the longitudinal lengths $L_A$, $L_B$, and $L_C$. In the staple cartridge body 3200, the inner staples 3242a, the intermediate staples 3242b, and the outer staples 3242c have the same length base. For example, identical staples can be positioned in each staple cavity 3210. In other instances, as further described herein, staples having different geometries and/or sizes, such as bases of different lengths, for example, can be positioned in certain staple cavities in a cartridge body.

Referring still to FIG. 27, the angular orientation of the staple cavities 3210a, 3210b, and 3210c, and the corresponding widths $W_A$, $W_B$, and $W_C$ and longitudinal lengths $L_A$, $L_B$, and Lc, respectively, can impact the amount of lateral and longitudinal overlap in the staple line. The longitudinal and lateral overlap between the staples 3242 also depends on the spacing of the staple cavities 3210. Generally, a greater overlap between adjacent staples corresponds to less direct fluid pathways, which can correspond to greater tissue sealing properties. A greater overlap can also decrease the flexibility of the staple line because the tissue may be more constrained in the overlapped region. Moreover, a greater overlap can correspond to less spacing between the staples. In certain instances, it can be desirable to modify the degree of lateral and/or longitudinal overlap in a staple line. As the overlap varies, the flexibility and sealing properties of the staple line can also vary.

The overlap or degree of overlap described herein can refer to a positive overlap or a negative overlap, for example. When staples and/or rows of staples define a negative overlap, the staples and/or rows of staples may be spaced apart such that they do not overlap and a gap is defined therebetween. In still other instances, the staples or rows of staples can be aligned such that the overlap is equal to the diameter of the staples.

The reader will further appreciate that the degree of overlap with respect to the staples or rows of staples in a staple cartridge corresponds to the degree of overlap with respect to the staple cavities or rows of staple cavities in the staple cartridge. For example, relative differences in the lateral and/or longitudinal overlaps between staples or rows of staples correspond to the relative differences in the lateral and/or longitudinal overlaps in the staple cavities or rows of staple cavities in the staple cartridge. In certain instances, at least a portion of the staple legs can be positioned against and/or biased into the inside walls of the staple cavities at the proximal and distal ends of the staple cavity. In such instances, a distance measured with respect to the outside edges of the staples equal the distance measured with respect to the inside edges of the corresponding staple cavities. In other instances, the difference between such distances can be minimal or insignificant.

In certain instances, the degree of overlap can be minimized, such as when ends of the staples are aligned. When the ends of the staples are aligned, the overlap is equal, or substantially equal, to the diameter of the staples. For example, if the staples are comprised of a wire having a diameter of about 0.0079 inches, the overlap can be about 0.0079 inches. In other instances, the overlap can be less than the diameter of staples. For example, the overlap can be less than about 0.0079 inches. In still other instances, the degree of overlap can be a non-overlap or negative overlap, i.e., a space or gap between the ends of the staples. In still other instances, a minimized overlap can be equal to or less than one-third of the staple length. For example, the overlap can be less 33% of the staple length. In other instances, the overlap can be less than 25% or less than 10% of the staple length. In still other instances, the overlap can be more than 33% of the staple length, for example.

In certain instances, a staple line can include a first degree of overlap between the inner and intermediate rows of staples and a second degree of overlap between the intermediate and outer rows of staples. The second degree of overlap can be different from the first degree of overlap in a lateral and/or longitudinal direction. Consequently, an inner portion of the staple line can comprise a different flexibility than an outer portion of the staple line. Moreover, the tissue sealing properties of the inner portion can be different than the tissue sealing properties of the outer portion.

Referring again to FIG. 27, the angle A is less than the angle C. Consequently, the width $W_A$ is less than the width $W_C$ and the length $L_A$ is greater than the length $L_C$. The angle A can be 35 degrees to 40 degrees, for example, and the angle C can be 43 degrees to 47 degrees, for example. In other instances, the angle A can be less than 35 degrees or more than 40 degrees and/or the angle C can be less than 43 degrees or more than 47 degrees. The difference between the angle A and the angle C can be between three degrees and twelve degrees. For example, the difference can be about eight degrees. In still other instances, the difference between the angle A and the angle C can be less than three degrees or more than twelve degrees.

Referring still to FIG. 27, the staples 3242 in each respective row are aligned. More specifically, the proximal ends of the inner staples 3242a are longitudinally aligned, the distal ends of the inner staples 3242a are longitudinally aligned, the proximal ends of the intermediate staples 3242b are longitudinally aligned, the distal ends of the intermediate staples 3242b are longitudinally aligned, the proximal ends of the outer staples 3242c are longitudinally aligned, and the distal ends of the outer staples 3242c are longitudinally aligned. The aligned staples 3242 in each row 3214a, 3214b, and 3214c of staple cavities 3310 are configured to form rows of aligned staples 3242 in a staple line. Owing to the angular orientation of the staples 3242 and the spacing therebetween, the rows of staples 3242 laterally overlap. The inner staples 3242a laterally overlap the intermediate staples 3242b by a lateral overlap $Y_{A/B}$ and the outer staples 3242c laterally overlap the intermediate staples 3242b by a lateral overlap $Y_{B/C}$. The lateral overlap $Y_{A/B}$ between the inner staples 3242a and the intermediate staples 3242b is greater than the lateral overlap $Y_{B/C}$ between the outer staples 3242c and the intermediate staples 3242b. In such instances, the outer staples are positioned closer to the intermediate staples than the inner staples are positioned to the intermediate staples. In other instances, the lateral overlap $Y_{A/B}$ can be less than or equal to the lateral overlap $Y_{B/C}$.

The intermediate staples 3242b are longitudinally staggered with respect to the inner staples 3242a and the outer staples 3242c. In particular, each intermediate staple 3242b is positioned longitudinally equidistant between adjacent inner staples 3242a and longitudinally equidistant between adjacent outer staples 3242c. Owing to the angular orientation of the staples 3242 and the spacing therebetween, the staples 3242 do not longitudinally overlap. The inner staples 3242a are spaced apart from the intermediate staples 3242b by a longitudinal gap $X_{A/B}$ and the outer staples 3242c are spaced apart from the intermediate staples 3242b by a longitudinal gap $X_{B/C}$. The longitudinal gap $X_{A/B}$ between the inner staples 3242a and the intermediate staples 3242b is less than the longitudinal gap $X_{B/C}$ between the outer staples 3242c and the intermediate staples 3242b. In other instances, the longitudinal gap $X_{A/B}$ can be greater than or equal to the longitudinal gap $X_{B/C}$. In certain instances, the intermediate staples 3242b can longitudinally overlap the inner staples 3242a and/or the outer staples 3242c.

The lateral overlaps and longitudinal gaps generated by the arrangement of staple cavities in FIG. 27 can be sufficient to sufficiently obstruct the fluid pathways across the staple line to seal the tissue. In various instances, the lateral and/or longitudinal overlaps and/or gaps can be configured to selectively optimize the sealing properties of the staple line. Additionally or alternatively, the lateral and/or longitudinal overlaps and/or gaps can be configured to selectively optimize the flexibility of the staple line. Moreover, the overlaps can be minimized. In certain instances, the lateral overlaps can be less than one-third of the staple length and, in at least one instance, can equal approximately the diameter of the staple.

Figure 28:
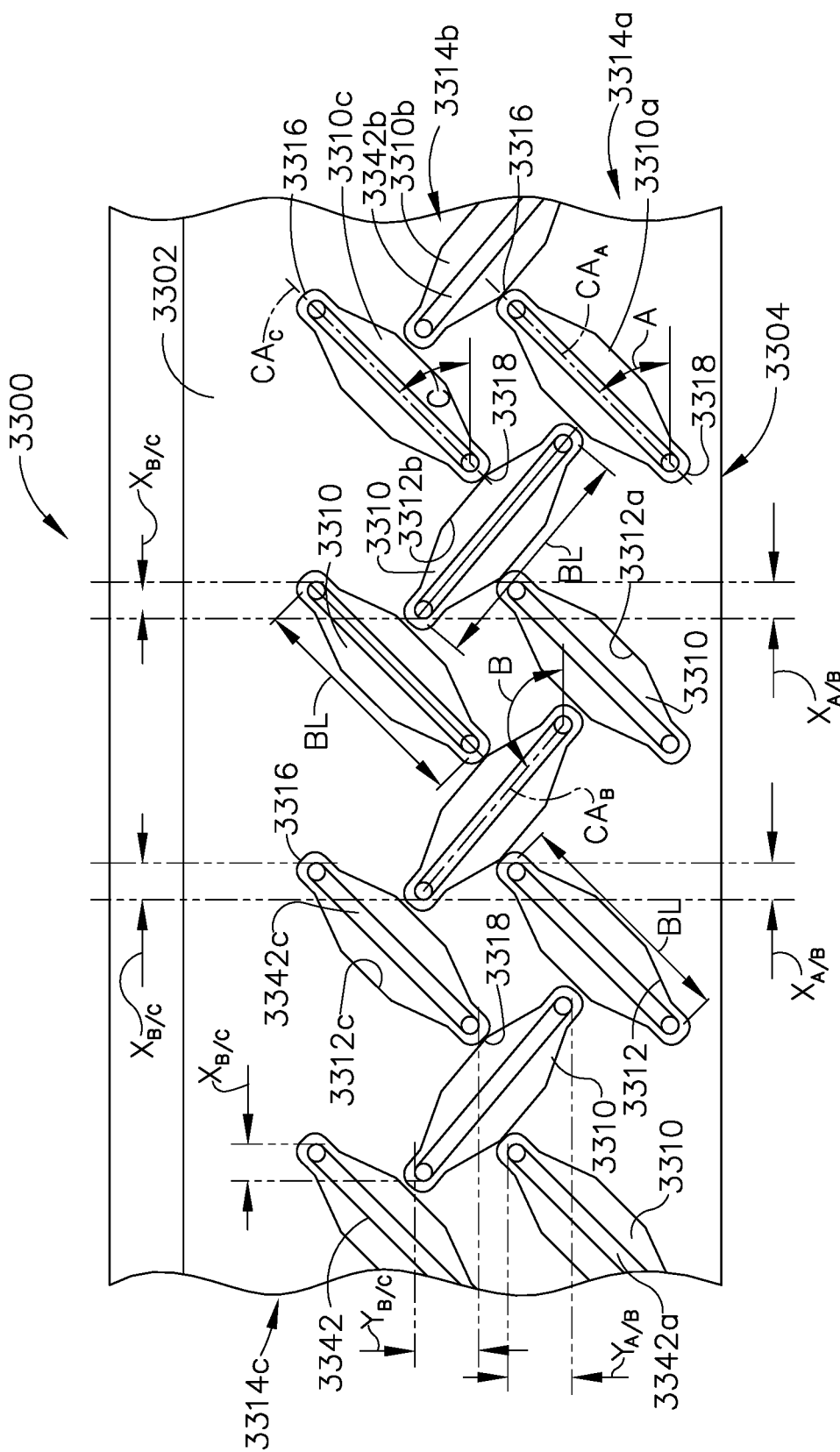
FIG. 28 is a plan view of a portion of a staple cartridge body having a plurality of angularly-oriented staple cavities defined therein and depicting staples in the staple cavities.

Referring now to FIG. 28, a portion of a staple cartridge body 3300 is depicted. The staple cartridge body 3300 includes a deck 3302 and a longitudinal slot 3304. The longitudinal slot 3304 extends along the longitudinal axis LA. Staple cavities 3310 are defined in the staple cartridge body 3300, and each staple cavity 3310 includes an opening 3312 in the deck 3302. A staple 3342 is positioned in each staple cavity 3310. The staple 3342 can be similar in many aspects to the staple 3042 (FIG. 10) or the staple 3142 (FIG. 11). In certain instances, the legs of each staple 3342 can be biased against the inside wall of the staple cavity 3310. The reader will appreciate that the arrangement of staples 3342 in the staple cavities 3310 corresponds to the arrangement of staples 3342 in a staple line when the staples 3342 are fired from the staple cartridge body 3300 and into tissue. More specifically, the bases of each staple 3342 in a resultant staple line are collinear, or substantially collinear, with the cavities axes CA.

The staple cavity openings 3312 are arranged in three rows 3314a, 3314b, and 3314c on a first side of the longitudinal slot 3304. Inner openings 3312a define the perimeter of inner cavities 3310a in the inner row 3314a, intermediate openings 3312b define the perimeter of intermediate cavities 3310b in the intermediate row 3314b, and outer openings 3312c define the perimeter of outer cavities 3310c in the outer row 3314c. Inner staples 3342a are positioned in the inner cavities 3310a, intermediate staples 3342b are positioned in the intermediate cavities 3310b, and outer staples 3342c are positioned in the outer cavities 3310c. Although not shown in FIG. 28, in at least one instance, the staple cavities 3310 on the opposing side of the slot 3304 form a mirror image reflection of the staple cavities 3310 on the first side of the longitudinal slot 3304. Consequently, the arrangement of staples 3342 in a resultant staple line is symmetric relative to the cutline. In other instances, the staple line can be asymmetric relative to the cutline.

Each staple cavity opening 3312 has a first end, or proximal end, 3316 and a second end, or distal end, 3318. A cavity axis CA extends between the proximal end 3316 and the distal end 3318 of each opening 3312. The staple cavity openings 3312 in each respective row are parallel. For example, the inner cavities 3310a are oriented at an angle A relative to the longitudinal axis LA. Stated differently, the cavity axes (e.g., $CA_A$) of the inner openings 3312a are oriented at the angle A relative to the longitudinal axis LA. The intermediate cavities 3310b are oriented at an angle B relative to the longitudinal axis LA. Stated differently, the cavity axes (e.g., $CA_B$) of the intermediate openings 3312b are oriented at the angle B relative to the longitudinal axis LA. The outer cavities 3310c are oriented at an angle C relative to the longitudinal axis LA. Stated differently, the cavity axes (e.g., $CA_C$) defined by the outer openings 3312c are oriented at the angle C relative to the longitudinal axis LA.

In the staple cartridge body 3300, the angle A is equal to the angle C, and the angle B is a supplementary angle to the angles A and C. Consequently, the inner openings 3312a are parallel to outer openings 3312c and the intermediate openings 3312b are perpendicular to the inner and outer openings 3312a and 3312c, respectively. The staple cavity openings 3312 in the staple cartridge body 3300 form a herringbone pattern. Moreover, referring still to FIG. 28, the staples 3342 in each row 3314a, 3314b, 3314c have the same length base BL. The widths of the staple rows are equal, and the longitudinal lengths of the staples 3342 are also equal.

Referring still to FIG. 28, the longitudinal overlap $X_{A/B}$ between the inner staples 3342a and the intermediate staples 3342b is equal to the longitudinal overlap $X_{B/C}$ between the outer staples 3342c and the intermediate staples 3342b. Moreover, the lateral overlap $Y_{A/B}$ between the inner staples 3342a and the intermediate staples 3342b is equal to the lateral overlap $Y_{B/C}$ between the outer staples 3342c and the intermediate staples 3342b. In such instances, the intermediate staples 3342b are positioned equidistantly close to the inner staples 3342a and the outer staples 3342c.

Referring still to FIG. 28, the spacing between the staple cavities 3310 in the cartridge body 3300 is minimized. For example, the proximal and distal ends 3316, 3318 of the staple cavity openings 3312 are positioned adjacent to other staple cavities 3312. In certain instances, adjacent staple cavities can be in abutting contact. By minimizing the spacing between the staple cavities 3310, the density of the staple cavities 3310 and the degree of overlap between the staple cavities 3310 in the arrangement of FIG. 28 is maximized. Although the degree of overlap is maximized, because of the close proximity of the staple cavities, the lateral overlap is still less than one-third of the staple length.

In other instances, the angular orientation of the staple cavities in at least one row of staple cavities can differ from the angular orientation of the staple cavities in other rows. Additionally or alternatively, the length of the staple bases in at least one row of staple cavities can differ from the length of the staple bases in at least one other row. Additionally or alternatively, the staple cavities may not be equidistantly staggered or offset from adjacent staple cavities in each adjacent row. Such variations to the staple cartridge and staples therein can generate staple lines with varying properties laterally with respect to the cutline.

In certain instances, the staples in an inner portion of the staple line, such as the staples fired from the inner rows of staple cavities, for example, can have a different base length than the staples in an outer portion of the staple line. For example, the staples in the inner row of staple cavities on each side of a knife slot can have a longer base than the staples in the other rows of staple cavities. The longer bases can provide greater sealing capabilities because more tissue can be captured by the staples, for example. Additionally or alternatively, the longer bases can reinforce the staple line and reduce the flexibility thereof.

Figure 29:
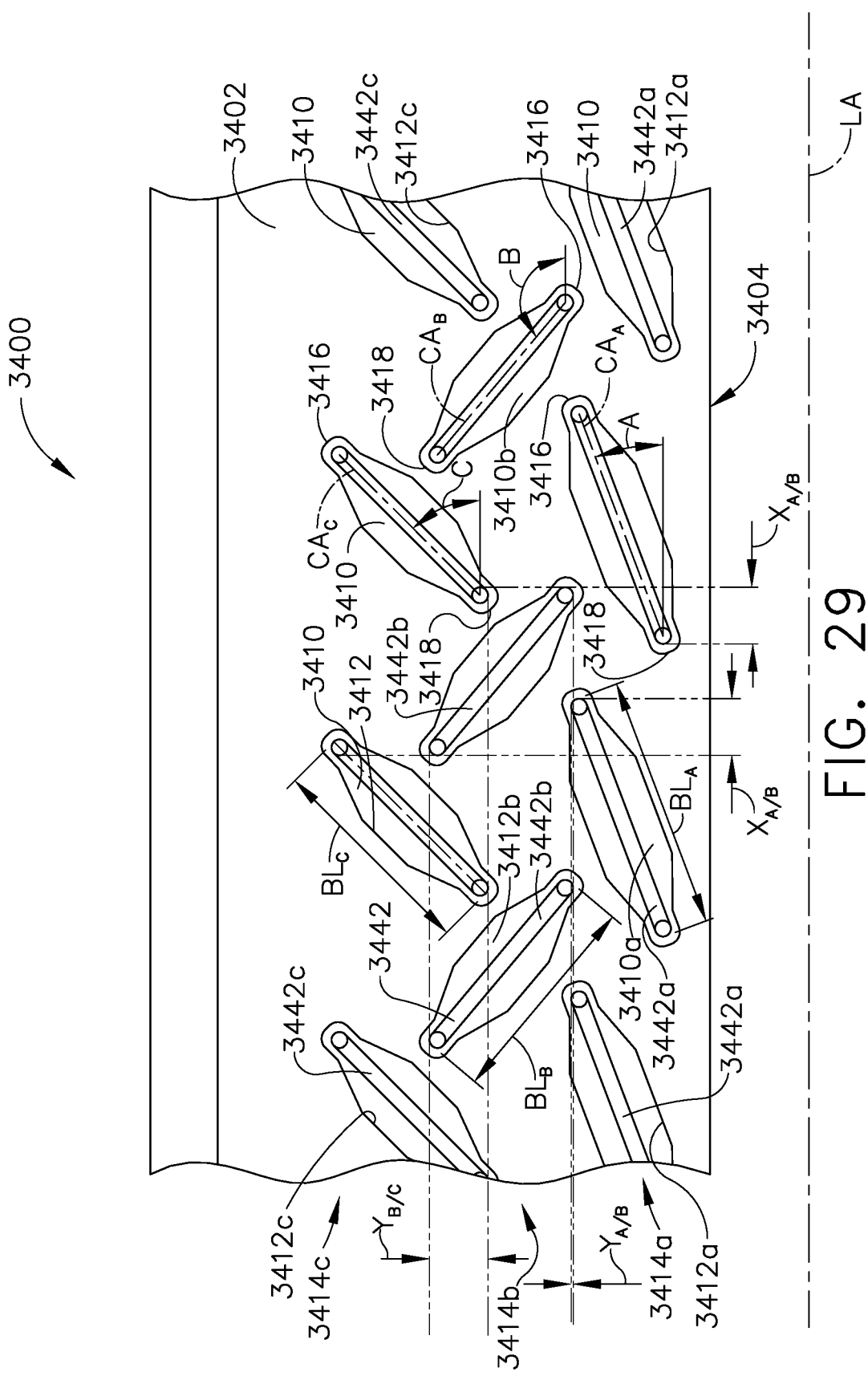
FIG. 29 is a plan view of a portion of a staple cartridge body having a plurality of angularly-oriented staple cavities defined therein and depicting staples in the staple cavities.

Referring now to FIG. 29, a portion of a staple cartridge body 3400 is depicted. The staple cartridge body 3400 includes a deck 3402 and a longitudinal slot 3404. The longitudinal slot 3404 extends along the longitudinal axis LA. Staple cavities 3410 are defined in the staple cartridge body 3400, and each staple cavity 3410 defines an opening 3412 in the deck 3402. A staple 3442 is positioned in each staple cavity 3410. The staple 3442 can be similar in many aspects to the staple 3042 (FIG. 10) or the staple 3142 (FIG. 11). In certain instances, the legs of each staple 3442 can be biased against the inside wall of the staple cavity 3410. The reader will appreciate that the arrangement of staples 3442 in the staple cavities 3410 corresponds to the arrangement of staples 3442 in a staple line when the staples 3442 are fired from the cartridge body 3400 and into tissue. More specifically, the bases of each staple 3442 in a resultant staple line are collinear, or substantially collinear, with the cavities axes CA.

The staple cavity openings 3412 are arranged in three rows 3414a, 3414b, and 3414c on a first side of the longitudinal slot 3404. Inner openings 3412a define the perimeter of inner cavities 3410a in the inner row 3414a, intermediate openings 3412b define the perimeter of intermediate cavities 3410b in the intermediate row 3414b, and outer openings 3412c define the perimeter of outer cavities 3410c in the outer row 3414c. Inner staples 3442a are positioned in the inner cavities 3410a, intermediate staples 3442b are positioned in the intermediate cavities 3410b, and outer staples 3442c are positioned in the outer cavities 3410c. Although not shown in FIG. 29, in at least one instance, the staple cavities 3410 on the opposing side of the slot 3404 form a mirror image reflection of the staple cavities 3410 on the first side of the longitudinal slot 3404. Consequently, the arrangement of staples 3442 in a resultant staple line is symmetric relative to the cutline. In other instances, the staple line can be asymmetric relative to the cutline.

Each staple cavity opening 3412 has a first end, or proximal end, 3416 and a second end, or distal end, 3418. A cavity axis CA extends between the proximal end 3416 and the distal end 3418 of each opening 3412. The staple cavity openings 3412 in each row are parallel. For example, the inner cavities 3410a are oriented at an angle A relative to the longitudinal axis LA. Stated differently, the cavity axes (e.g., $CA_A$) of the inner openings 3412a are oriented at the angle A relative to the longitudinal axis LA. The intermediate cavities 3410b are oriented at an angle B relative to the longitudinal axis LA. Stated differently, the cavity axes (e.g., $CA_B$) of the intermediate openings 3412b are oriented at the angle B relative to the longitudinal axis LA. The outer cavities 3410c are oriented at an angle C relative to the longitudinal axis LA. Stated differently, the cavity axes (e.g., $CA_C$) defined by the outer openings 3412c are oriented at the angle C relative to the longitudinal axis LA.

The angles A, B, and C are different. The inner openings 3412a are obliquely oriented relative to the outer openings 3412c. The angle A is less than the angle C. Because the axes of outer openings 3412c (e.g., axis $CA_C$) are not parallel to the axes of inner openings 3412a (e.g., axis $CA_A$), the staple cavity openings 3412 in the staple cartridge body 3400 form a modified or skewed herringbone pattern. The cavity axes $CA_B$ of the intermediate openings 3412b can be oriented perpendicular, or substantially perpendicular, to either the inner openings 3412a or the outer openings 3412c. For example, the angle B can be a supplementary angle to either angle A or C. In other instances, the angle B may not be a supplementary angle to either angle A or C.

Referring still to FIG. 29, the inner staples 3442a have a base length $BL_A$, the intermediate staples 3442b have a base length $BL_B$, and the outer staples 3442c have a base length $BL_C$. The base length $BL_A$ is greater than the base length $BL_B$ and the base length $BL_C$. In other words, the inner staples 3442a are longer than the intermediate staples 3442b and the outer staples 3442c. Moreover, the staple cavities 3410 housing the inner staples 3442a are correspondingly larger to accommodate the longer length base $BL_A$.

The arrangement of staple cavities 3410 in the cartridge body 3400 provides a longitudinal overlap $X_{A/B}$ between inner staples 3442a and the intermediate staples 3442b at both the proximal and distal ends of the intermediate staples 3442b. The intermediate staples 3442b are equidistantly spaced and longitudinally staggered between two adjacent inner staples 3442a. The intermediate staples 3442b are also equidistantly spaced and longitudinally staggered between two adjacent outer staples 3442c. The proximal end of each outer staple 3442c is longitudinally aligned with the distal end of an intermediate staple 3442b and the distal end of each outer staple 3442c is longitudinally aligned with the proximal end of another intermediate staple 3442b. In other words, such staples are longitudinally aligned and the longitudinal overlap is equal to the diameter of the staples 3442. The arrangement of staples cavities 3410 in the cartridge body 3400 also provides a lateral gap $Y_{A/B}$ between the inner row 3414a and the intermediate row 3414b and a lateral overlap $Y_{B/C}$ between the outer row 3414c and the intermediate row 3414b. In such instances, the intermediate staples 3442b are positioned closer to the outer staples 3442c than to the inner staples 3442a.

Referring still to FIG. 29, a staple line generated by the staple cartridge body 3400 can have different properties laterally with respect to the cutline. In particular, the staple line may have a greater sealing effectiveness along the cutline than laterally outward from the cutline. Furthermore, the staple line may have a greater flexibility laterally away from the cutline than inward toward the cutline. For example, because the bases $BL_A$ of the inner staples 3442a are longer than the bases $BL_B$ and $BL_C$ of the intermediate staples 3442b and the outer staples 3442c, respectively, an inner portion of the staple line may have greater sealing effectiveness and/or less flexibility than an outer portion of the staple line. Additionally or alternatively, because the inner staples 3442a are oriented at an angle that is less than the outer staples 3442c and is closer to a parallel orientation than the outer staples 3442c, an inner portion of the staple line may have greater sealing effectiveness and/or less flexibility than an outer portion of the staple line. Additionally or alternatively, because the intermediate staples 3442b longitudinally overlap the inner staples 3442a but do not longitudinally overlap the outer staples 3442c, an inner portion of the staple line may have greater sealing effectiveness and/or less flexibility than an outer portion of the staple line. The amount of overlap can be minimized. For example, the overlap can be less than one-third of the staple length and, in at least one instance, can equal approximately the diameter of the staple.

In certain instances, the staples in an outer portion of the staple line, such as the staples fired from the outer rows of staple cavities, for example, can have a different base length than the staples in an inner portion of the staple line. For example, the staples in the outer row of staple cavities on each side of a knife slot can have a shorter base than the staples in the other rows of staple cavities. The shorter bases can provide increased flexibility of the staple line, for example.

Figure 30:
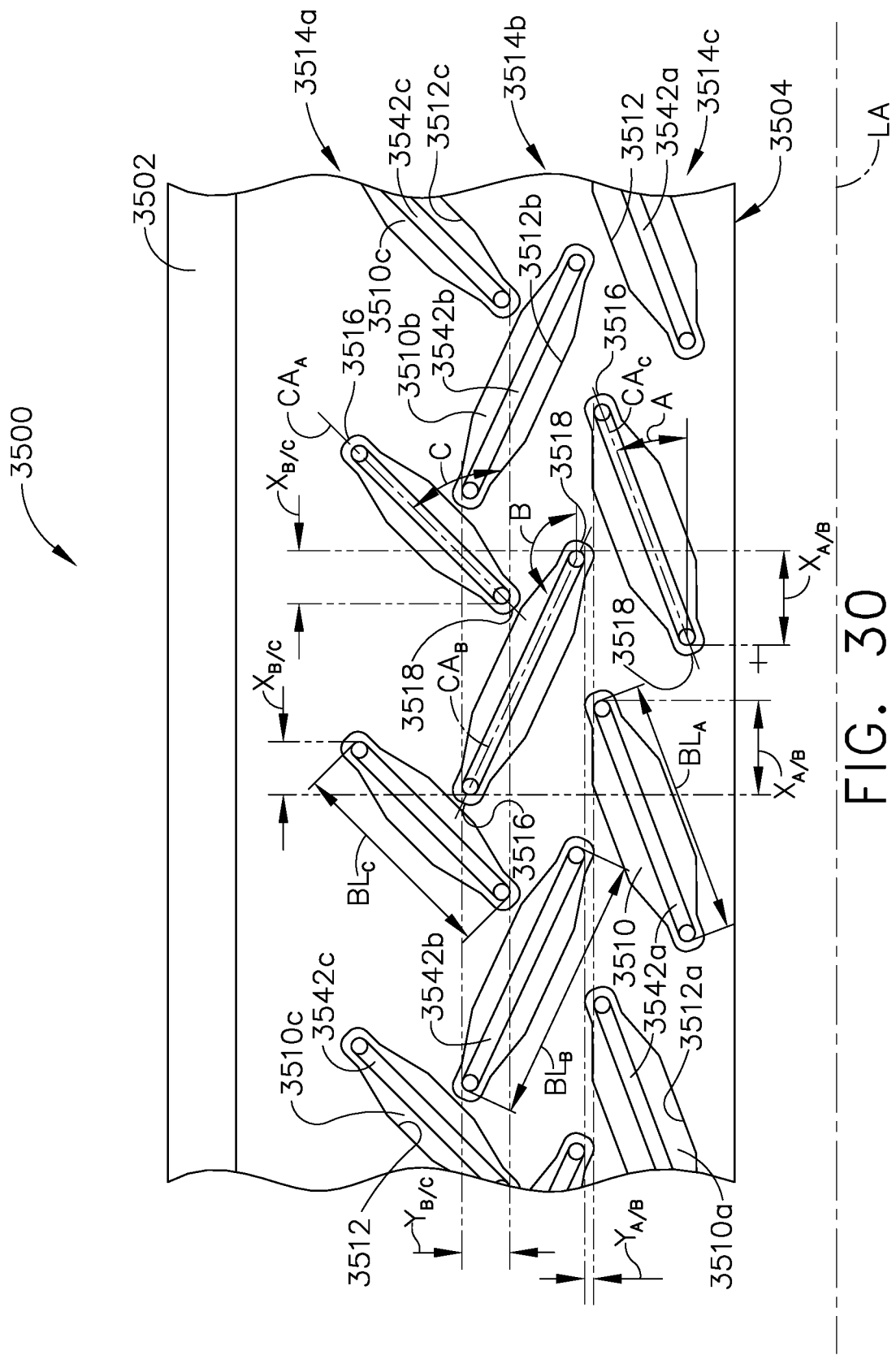
FIG. 30 is a plan view of a portion of a staple cartridge body having a plurality of angularly-oriented staple cavities defined therein and depicting staples in the staple cavities.

Referring now to FIG. 30, a portion of a staple cartridge body 3500 is depicted. The staple cartridge body 3500 includes a deck 3502 and a longitudinal slot 3504. The longitudinal slot 3504 extends along the longitudinal axis LA. Staple cavities 3510 are defined in the staple cartridge body 3500, and each staple cavity 3510 defines an opening 3512 in the deck 3502. A staple 3542 is positioned in each staple cavity 3510. The staple 3542 can be similar in many aspects to the staple 3042 (FIG. 10) or the staple 3142 (FIG. 11). In certain instances, the legs of each staple 3542 can be biased against the inside wall of the staple cavity 3510. The reader will appreciate that the arrangement of staples 3542 in the staple cavities 3510 corresponds to the arrangement of staples 3542 in a staple line when the staples 3542 are fired from the cartridge body 3500 and into tissue. More specifically, the bases of each staple 3542 in a resultant staple line are collinear, or substantially collinear, with the cavities axes CA.

The staple cavity openings 3512 are arranged in three rows 3514a, 3514b, and 3514c on a first side of the longitudinal slot 3504. Inner openings 3512a define the perimeter of inner cavities 3510a in the inner row 3514a, intermediate openings 3512b define the perimeter of intermediate cavities 3510b in the intermediate row 3514b, and outer openings 3512c define the perimeter of outer cavities 3510c in the outer row 3514c. Inner staples 3542a are positioned in the inner cavities 3510a, intermediate staples 3542b are positioned in the intermediate cavities 3510b, and outer staples 3542c are positioned in the outer cavities 3510c. Although not shown in FIG. 30, in at least one instance, the staple cavities 3510 on the opposing side of the slot 3504 form a mirror image reflection of the staple cavities 3510 on the first side of the longitudinal slot 3504. Consequently, the arrangement of staples 3542 in a resultant staple line is symmetric relative to the cutline. In other instances, the staple line can be asymmetric relative to the cutline.

Each staple cavity opening 3512 has a first end, or proximal end, 3516 and a second end, or distal end, 3518. A cavity axis CA extends between the proximal end 3516 and the distal end 3518 of each opening 3512. The staple cavity openings 3512 in each row are parallel. For example, the inner cavities 3510a are oriented at an angle A relative to the longitudinal axis LA. Stated differently, the cavity axes (e.g., $CA_A$) of the inner openings 3512a are oriented at the angle A relative to the longitudinal axis LA. The intermediate cavities 3510b are oriented at an angle B relative to the longitudinal axis LA. Stated differently, the cavity axes (e.g., $CA_B$) of the intermediate openings 3512b are oriented at the angle B relative to the longitudinal axis LA. The outer cavities 3510c are oriented at an angle C relative to the longitudinal axis LA. Stated differently, the cavity axes (e.g., $CA_C$) defined by the outer openings 3512c are oriented at the angle C relative to the longitudinal axis LA.

The angles A, B, and C may be different. The inner openings 3512a are obliquely oriented relative to the outer openings 3512c. The angle A is less than the angle C. Because the axes of the outer openings 3512c (e.g., axis $CA_C$) are not parallel to the axes of the inner openings 3512a (e.g., axis $CA_A$), the staple cavity openings 3512 in the staple cartridge body 3500 form a modified or skewed herringbone pattern. The cavity axes $CA_B$ of the intermediate openings 3512b can be oriented perpendicular, or substantially perpendicular, to either the inner openings 3512a or the outer openings 3512c. For example, the angle B can be a supplementary angle to either angle A or C. In other instances, the angle B may not be a supplementary angle to either angle A or C.

The inner staples 3542a have a base length $BL_A$, the intermediate staples 3542b have a base length $BL_B$, and the outer staples 3542c have a base length $BL_C$. The base length $BL_C$ is less than the base length $BL_B$ and the base length $BL_A$. In other words, the outer staples 3542c are shorter than the intermediate staples 3542b and the inner staples 3542a. Moreover, the staple cavities 3510 housing the outer staples 3542c are correspondingly shorter to accommodate the shorter length base $BL_C$.

The arrangement of staple cavities 3510 in the cartridge body 3500 provides a longitudinal overlap $X_{A/B}$ between the inner staples 3542a and the intermediate staples 3542b at both the proximal and distal ends of the intermediate staples 3542b. The intermediate staples 3542b are equidistantly spaced and longitudinally staggered between two adjacent inner staples 3542a. The arrangement of staple cavities 3510 in the cartridge body 3500 also provides a longitudinal overlap $X_{B/C}$ between the intermediate staples 3542b and the outer staples 3542c at both the proximal and distal ends of the intermediate staples 3542b. The intermediate staples 3542b are also equidistantly spaced and longitudinally staggered between two adjacent outer staples 3542c. Owing to the angular orientation and spacing of the staples 3542, the longitudinal overlap $X_{A/B}$ is greater than the longitudinal overlap $X_{B/C}$. The arrangement of staples cavities 3510 in the cartridge body 3500 also provides a lateral gap $Y_{A/B}$ between the inner staples 3542a and the intermediate staples 3542b and a lateral overlap $Y_{B/C}$ between the outer staples 3542c and the intermediate staples 3542b. In such instances, the intermediate staples 3542b are positioned closer to the outer staples 3542c than to the inner staples 3542a.

Referring still to FIG. 30, a staple line generated by the staple cartridge body 3500 can have different properties laterally with respect to the cutline. In particular, the staple line may have a greater sealing effectiveness along the cutline than laterally outward from the cutline. Furthermore, the staple line may have a greater flexibility laterally away from the cutline than inward toward the cutline. For example, because the bases $BL_C$ of the outer staples 3542c are shorter than the bases $BL_A$ and $BL_B$ of the intermediate staples 3542b and the outer staples 3542c, respectively, an inner portion of the staple line may have greater sealing effectiveness and/or less flexibility than an outer portion of the staple line. Additionally or alternatively, because the inner staples 3542a are oriented at an angle that is less than the outer staples 3542c and is closer to a parallel orientation than the outer staples 3542c, an inner portion of the staple line may have greater sealing effectiveness and/or less flexibility than an outer portion of the staple line. Additionally or alternatively, because the intermediate staples 3542b longitudinally overlap the inner staples 3542a more than the intermediate staples 3542b longitudinally overlap the outer staples 3542c, an inner portion of the staple line may have greater sealing effectiveness and/or less flexibility than an outer portion of the staple line.

In various instances, the properties of the staple line can be customized in each row of staples. The staples in each row of staple cavities on one side of a knife slot can have different base lengths. Additionally, the staples in each row of staple cavities on one side of a knife slot can be oriented at different angles relative to the knife slot. Moreover, the spacing between the cavities can be varied row-to-row. For example, the size and orientation of the staples in each row can be selected to optimize the flexibility of the staple line and sealing properties in each row based on the row's position laterally from the cutline toward the outer boundary of the staple line. In certain instances, the sealing effectiveness can be maximized or emphasized along the cutline, for example, and the flexibility of the staple line can be maximized or emphasized along the outer boundary of the staple line, for example. Alternatively, in certain instances, the sealing effectiveness can be maximized or emphasized along the outer boundary of the staple line and/or the flexibility of the staple line can be maximized or emphasized along the cutline.

Figure 31:
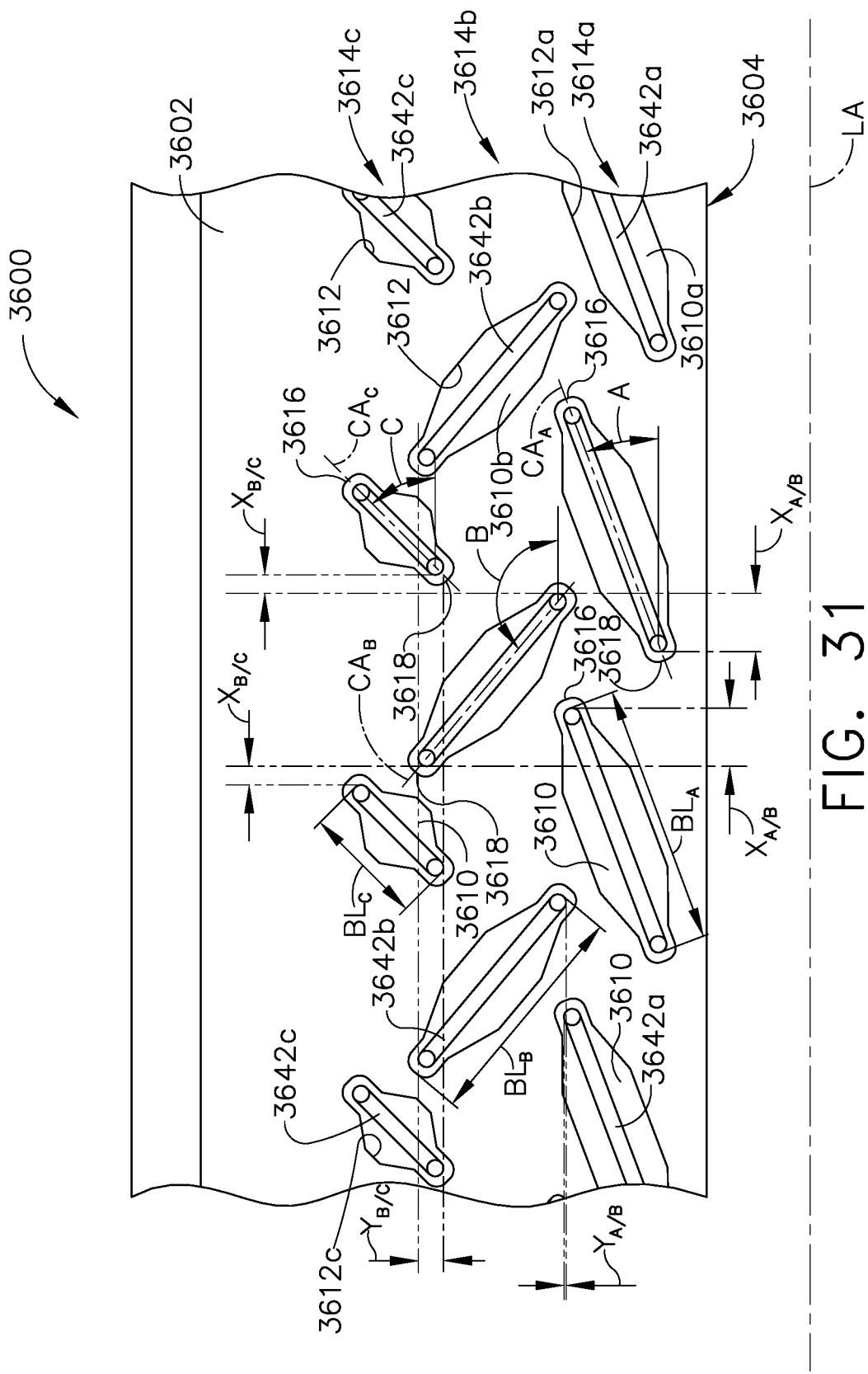
FIG. 31 is a plan view of a portion of a staple cartridge body having a plurality of angularly-oriented staple cavities defined therein and depicting staples in the staple cavities.

Referring now to FIG. 31, a portion of a staple cartridge body 3600 is depicted. The staple cartridge body 3600 includes a deck 3602 and a longitudinal slot 3604. The longitudinal slot 3604 extends along the longitudinal axis LA. Staple cavities 3610 are defined in the staple cartridge body 3600, and each staple cavity 3610 defines an opening 3612 in the deck 3602. A staple 3642 is positioned in each staple cavity 3610. The staple 3642 can be similar in many aspects to the staple 3042 (FIG. 10) or the staple 3142 (FIG. 11). In certain instances, the legs of each staple 3642 can be biased against the inside wall of the staple cavity 3610. The reader will appreciate that the arrangement of staples 3642 in the staple cavities 3610 corresponds to the arrangement of staples 3642 in a staple line when the staples 3642 are fired from the cartridge body 3600 and into tissue. More specifically, the bases of each staple 3642 in a resultant staple line are collinear, or substantially collinear, with the cavities axes CA.

The staple cavity openings 3612 are arranged in three rows 3614a, 3614b, 3614c on a first side of the longitudinal slot 3604. Inner openings 3612a define the perimeter of inner cavities 3610a in the inner row 3614a, intermediate openings 3612b define the perimeter of intermediate cavities 3610b in the intermediate row 3614b, and outer openings 3612c define the perimeter of outer cavities 3610c in the outer row 3614c. Inner staples 3642a are positioned in the inner cavities 3610a, intermediate staples 3642b are positioned in the intermediate cavities 3610b, and outer staples 3642c are positioned in the outer cavities 3610c. Although not shown in FIG. 31, in at least one instance, the staple cavities 3610 on the opposing side of the slot 3604 form a mirror image reflection of the staple cavities 3610 on the first side of the longitudinal slot 3604. Consequently, the arrangement of staples 3642 in a resultant staple line is symmetric relative to the cutline. In other instances, the staple line can be asymmetric relative to the cutline.

Each staple cavity opening 3612 has a first end, or proximal end, 3616 and a second end, or distal end, 3618. A cavity axis CA extends between the proximal end 3616 and the distal end 3618 of each opening 3612. The staple cavity openings 3612 in each row are parallel. For example, the inner cavities 3610a are oriented at an angle A relative to the longitudinal axis LA. Stated differently, the cavity axes (e.g., $CA_A$) of the inner openings 3612a are oriented at the angle A relative to the longitudinal axis LA. The intermediate cavities 3610b are oriented at an angle B relative to the longitudinal axis LA. Stated differently, the cavity axes (e.g., $CA_B$) of the intermediate openings 3612b are oriented at the angle B relative to the longitudinal axis LA. The outer cavities 3610c are oriented at an angle C relative to the longitudinal axis LA. Stated differently, the cavity axes (e.g., $CA_C$) defined by the outer openings 3612c are oriented at the angle C relative to the longitudinal axis LA.

The angles A, B, and C may be different. The inner openings 3612a are obliquely oriented relative to the outer openings 3612c. The angle A is less than the angle C. Because the axes of the outer openings 3612c (e.g., axis $CA_C$) are not parallel to the axes of the inner openings 3612a (e.g., axis $CA_A$), the staple cavity openings 3612 in the staple cartridge body 3600 form a modified or skewed herringbone pattern. The cavity axes $CA_B$ of the intermediate openings 3612b can be oriented perpendicular, or substantially perpendicular, to either the inner openings 3612a or the outer openings 3612c. For example, the angle B can be a supplementary angle to either angle A or C. In other instances, the angle B may not be a supplementary angle to either angle A or C.

The inner staples 3642a have a base length $BL_A$, the intermediate staples 3642b have a base length $BL_B$, and the outer staples 3642c have a base length $BL_C$. The base length $BL_C$ is less than the base length $BL_B$, and the base length $BL_B$ is less than the base length $BL_A$. In other words, the length of the staples 3642 increases laterally toward the longitudinal slot 3604. Moreover, the staple cavities 3610 correspondingly increase in length laterally toward the longitudinal slot 3604 to accommodate the larger staples.

The arrangement of staple cavities 3610 in the cartridge body 3600 provides a longitudinal overlap $X_{A/B}$ between the inner staples 3642a and the intermediate staples 3642b at both the proximal and distal ends of the intermediate staples 3642b. The intermediate staples 3642b are equidistantly spaced and longitudinally staggered between two adjacent inner staples 3642a. The arrangement of staple cavities 3610 in the cartridge body 3600 also provides a longitudinal gap $X_{B/C}$ between the intermediate staples 3642b and the outer staples 3642c at both the proximal and distal ends of the intermediate staples 3642b. The intermediate staples 3642b are also equidistantly spaced and longitudinally staggered between two adjacent outer staples 3642c. Owing to the variations in the angular orientation of the staples, the spacing of the staples, and the length of the staples, the longitudinal overlap $X_{A/B}$ is greater than the longitudinal gap $X_{B/C}$. In other instances, the longitudinal overlap $X_{A/B}$ can be equal to or less than the longitudinal overlap $X_{B/C}$. The arrangement of staples cavities 3610 in the cartridge body 3600 also provides a lateral gap $Y_{A/B}$ between the inner row 3614a and the intermediate row 3614b and a lateral overlap $Y_{B/C}$ between the outer row 3614c and the intermediate row 3614b.

Referring still to FIG. 31, a staple line generated by the staple cartridge body 3600 can have different properties laterally with respect to the cutline. In particular, the staple line may have a greater sealing effectiveness adjacent to the cutline than laterally outward from the cutline. Furthermore, the staple line may have a greater flexibility laterally away from the cutline than inward toward the cutline. For example, because the length of the bases $BL_A$, $BL_B$, and $BL_C$ of the staples 3642a, 3642b, and 3642c, respectively, increases laterally inward toward the cutline, an inner portion of the staple line may have greater sealing effectiveness than an outer portion of the staple line. Additionally or alternatively, because the angular orientation of the staples 3642a, 3642b, and 3642c increases laterally outward away from the cutline, an outer portion of the staple line may have greater flexibility than an inner portion of the staple line.

As described herein, staples are removably positioned in a staple cartridge and fired from the staple cartridge during use. In various instances, the staples can be driven out of staple cavities in the staple cartridge and into forming contact with an anvil. For example, a firing element can translate through the staple cartridge during a firing stroke to drive the staples from the staple cartridge toward an anvil. In certain instances, the staples can be supported by staple drivers and the firing element can lift the staple drivers to eject or remove the staples from the staple cartridge.

An anvil can include a staple-forming surface having staple-forming pockets defined therein. In certain instances, the staple-forming pockets can be stamped in the anvil. For example, the staple-forming pockets can be coined in a flat surface of the anvil. The reader will appreciate that certain features of the staple-forming pockets can be a deliberate consequence of a coining process. For example, a certain degree of rounding at corners and/or edges of the staple-forming produce can be an intentional result of the coining process. Such features can also be designed to better form the staples to their formed configurations, including staples that become skewed and/or otherwise misaligned during deployment.

Each staple in the staple cartridge can be aligned with a staple-forming pocket of the anvil. In other words, the arrangement of staple cavities and staples in a staple cartridge for an end effector can correspond or match the arrangement of staple-forming pockets in an anvil of the end effector. More specifically, the angular orientation of each staple cavity can match the angular orientation of the respective staple-forming pocket. For example, when the staple cavities are arranged in a herringbone pattern, the staple-forming pockets can also be arranged in a herringbone pattern.

When staples are driven from the staple cartridge and into forming contact with the anvil, the staples can be formed into a fired configuration. In various instances, the fired configuration can be a B-form configuration, in which the tips of the staple legs are bent toward the staple base or crown to form a capital letter B having symmetrical upper and lower loops. In other instances, the fired configuration can be a modified B-form, such as a skewed B-form configuration, in which at least a portion of a staple leg torques out of plane with the staple base, or an asymmetrical B-form configuration, in which the upper and lower loops of the capital letter B are asymmetric. Tissue can be captured or clamped within the formed staple.

The arrangement of staples and/or staple cavities in a staple cartridge can be configured to optimize the corresponding arrangement of staple-forming pockets in the forming surface of a complementary anvil. For example, the angular orientation and spacing of staples in a staple cartridge can be designed to optimize the forming surface of an anvil. In certain instances, the footprint of the staple-forming pockets in an anvil can be limited by the geometry of the anvil. In instances in which the staple-forming pockets are obliquely-oriented relative to a longitudinal axis, the width of the anvil can limit the size and spacing of the obliquely-oriented staple-forming pockets. For example, the width of an intermediate row of staple-forming pockets can define a minimum distance between a first row (e.g. an outer row) on one side of the intermediate row and a second row (e.g. an inner row) on the other side of the intermediate row. Moreover, the rows of staple-forming pockets are confined between an inside edge on the anvil, such as a knife slot, and an outside edge of the anvil.

In various instances, the pockets can be adjacently nested along a staple-forming surface of the anvil. For example, an intermediate pocket can be nested between an inner pocket and an outer pocket. The angular orientation of the pockets can vary row-to-row to facilitate the nesting thereof. For example, the staple-forming pockets in an inner row can be oriented at a first angle, the staple-forming pockets in an intermediate row can be oriented at a second angle, and the staple-forming pockets in an outer row can be oriented at a third angle. The first angle, the second angle, and the third angle can be different, which can facilitate the close arrangement of the staple-forming pockets.

Referring again to the staple cartridges depicted in FIGS. 27-31, the varying angles of the staples and the staple cavities in each row can be selected to optimize the nesting of the staple-forming pockets in a complementary anvil. For each staple cartridge depicted in FIGS. 27-31, a complementary anvil can be configured to have a corresponding arrangement of staple-forming pockets. Moreover, the staple-forming pockets in the complementary anvils can be larger than the staple cavities depicted in FIGS. 27-31 to ensure that the staple legs land or fall within the staple-forming pockets. For example, the staple legs may be biased outward, such as in the case of V-shaped staples (see FIG. 11) and the larger footprint of the staple-forming pockets can catch the outwardly-biased staple legs during firing. In various instances, the staple-forming pockets can be 0.005 inches to 0.015 inches longer than the corresponding staple cavities and/or staples. Additionally or alternatively, the staple-receiving cups of each staple-forming pocket can be 0.005 inches to 0.015 inches wider than the corresponding staple cavities. In other instances, the difference in length and/or width can be less than 0.005 inches or more than 0.015 inches.

In instances in which the size of the staples varies within a staple cartridge (see, e.g., FIGS. 29-31), the size of the staple-forming pockets can correspondingly vary within a complementary anvil. Varying the size of the staple-forming pockets can further facilitate the nesting thereof. For example, in instances in which staple-forming pockets in an intermediate row are shorter than the staple-forming pockets in an inner row or an outer row, the width of the intermediate row of staple-forming pockets can be reduced, which can minimize the requisite spacing between the inner row and the outer row.

The spacing of the staple-forming pockets can also be configured to optimize the nesting thereof. For example, the pockets arranged in an inner row can be longitudinally staggered relative to the pockets arranged in an outer row. Moreover, the pockets in the inner row can partially longitudinally overlap the pockets in the outer row. The pockets in an intermediate row can be longitudinally staggered relative to the pockets in the inner row and the pockets in the outer row. For example, the pockets in the intermediate row can be equidistantly longitudinally offset from the pockets in the outer row and the pockets in the inner row.

Figure 80:
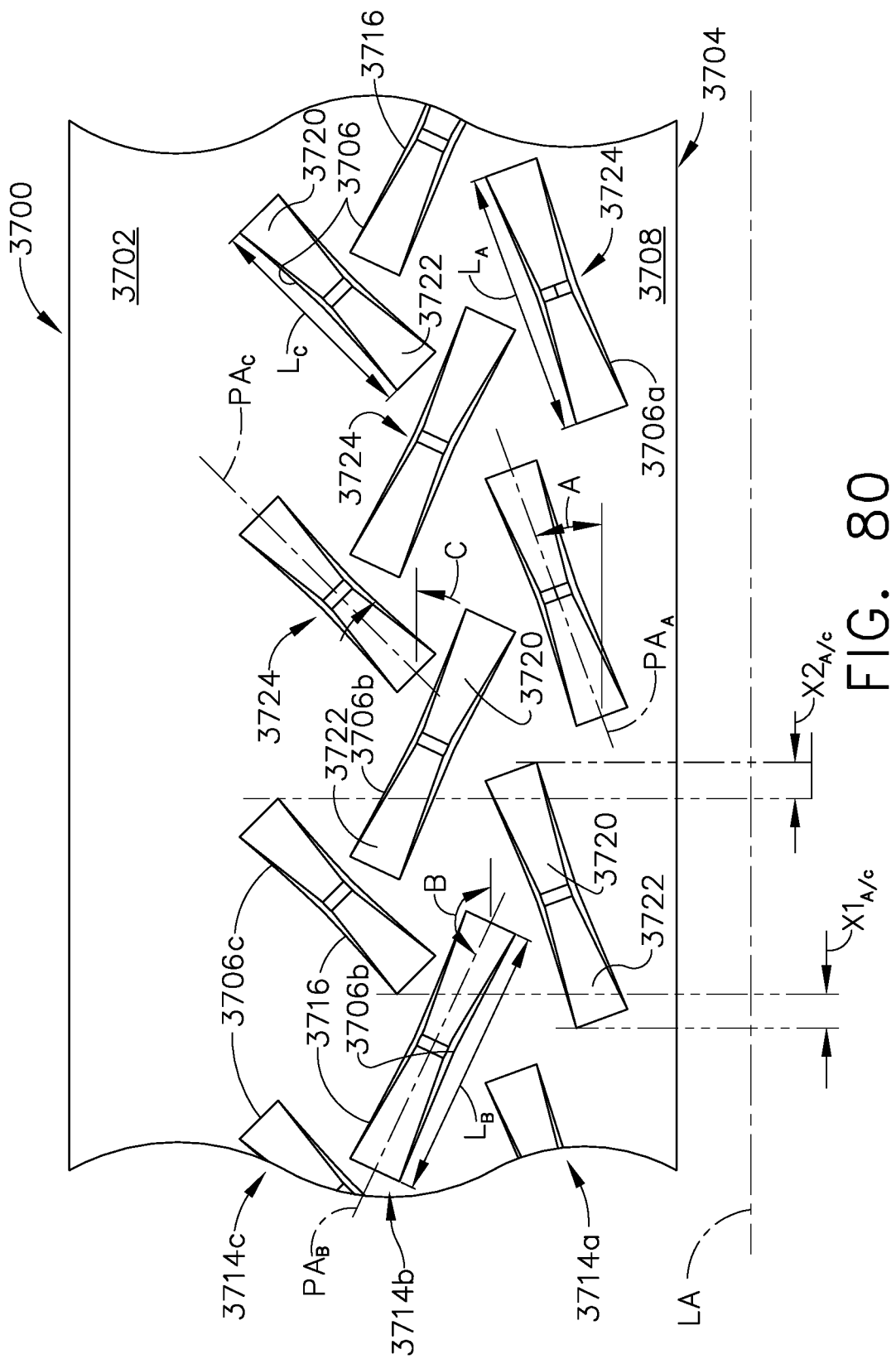
FIG. 80 is a plan view of a portion of an anvil having a plurality of staple-forming pockets defined therein.

Referring now to FIG. 80, an anvil 3700 is depicted. The anvil 3700 can be complementary to the staple cartridge 3500 (FIG. 30). For example, the arrangement of staple-forming pockets 3706 in the anvil 3700 can correspond to the arrangement of staples 3542 and staple cavities 3510 (FIG. 30) in the staple cartridge 3500. The anvil 3700 includes a staple-forming surface 3702 and a longitudinal slot 3704. The longitudinal slot 3704 extends along the longitudinal axis LA of the anvil 3700. In certain instances, a firing element and/or cutting element can translate through the longitudinal slot 3704 during at least a portion of a firing stroke. Staple-forming pockets 3706 are defined in the staple-forming surface 3702. The staple-forming surface 3702 also includes a non-forming portion 3708 that extends around the pockets 3706. The non-forming portion 3708 extends entirely around each pocket 3706 in FIG. 80. In other words, the non-forming portion 3708 surrounds the staple-forming pockets 3706. In other instances, at least a portion of two or more adjacent pockets 3706 can be in abutting contact such that a non-forming portion 3708 is not positioned therebetween.

The forming ratio of the staple-forming surface 3702 can be optimized. By optimizing the forming ratio, more staples can be formed and/or formed to their desired configurations. In certain instances, the surface area of the non-forming portion 3708 of the anvil 3700 can be minimized with respect to the staple-forming pockets 3706. Additionally or alternatively, the footprint of the staple-forming pockets 3706 can be extended or enlarged to maximize the portion of the staple-forming surface 3702 that is designed to catch and form the staples.

The pockets 3706 depicted in FIG. 80 are arranged in three rows 3714a, 3714b, 3714c on a first side of the longitudinal slot 3704. The first row 3714a is an inner row, the second row 3714b is an intermediate row, and the third row 3714c is an outer row. Inner pockets 3706a are positioned in the inner row 3714a, intermediate pockets 3706b are positioned in the intermediate row 3714b, and outer pockets 3706c are positioned in the outer row 3714c. The pockets 3706 are arranged in a herringbone arrangement along the staple-forming surface 3702 of the anvil 3700. Although not shown in FIG. 80, in at least one instance, the pockets 3706 on the opposing side of the slot 3704 can form a mirror image reflection of the pockets 3706 on the first side of the longitudinal slot 3704. In other instances, the arrangement of pockets 3706 in the staple-forming surface 3702 can be asymmetrical relative to the slot 3704 and, in certain instances, the anvil 3700 may not include the longitudinal slot 3704. In various instances, the pockets 3706 can be arranged in less than or more than three rows on each side of the slot 3704.

Each pocket 3706 includes a perimeter 3716, which defines the boundary of the pocket 3706b. Each pocket 3706 also includes a proximal cup 3720, a distal cup 3722, and a neck portion 3724 connecting the proximal cup 3720 and the distal cup 3722. When a staple is driven into forming contact with the staple-forming surface 3702, the proximal cup 3720 is aligned with a proximal staple leg, and the distal cup 3722 is aligned with a distal staple leg. The tips of the staple legs are positioned and configured to land in the respective cups 3720, 3722. Stated differently, the proximal cup 3720 is configured to receive a proximal staple leg and the distal cup 3722 is configured to receive a distal staple leg. The cups 3720 and 3722 are also configured to direct or funnel the staple legs toward the pocket axis PA and a central portion of the pocket 3806, such as the neck portion 3724, and to deform the staple legs into the formed configuration.

The geometry, spacing, and/or orientation of the pockets 3706 can vary row-to-row. A pocket axis PA extends from the proximal cup 3720, through the neck portion 3724, and to the distal cup 3722 of each pocket 3706. The pockets 3706 in each row are parallel. For example, the inner pockets 3706a are oriented at an angle A relative to the longitudinal axis LA. Stated differently, the pocket axes (e.g., $PA_A$) of the inner pockets 3706a are oriented at the angle A relative to the longitudinal axis LA. The intermediate pockets 3706b are oriented at an angle B relative to the longitudinal axis LA. Stated differently, the pocket axes (e.g., $PA_B$) of the inner pockets 3706b are oriented at the angle B relative to the longitudinal axis LA. The outer pockets 3706c are oriented at an angle C relative to the longitudinal axis LA. Stated differently, the pocket axes (e.g., $PA_C$) of the inner pockets 3706a are oriented at the angle C relative to the longitudinal axis LA.

The angles A, B, and C may be different. The inner pockets 3706a are obliquely oriented relative to the outer pockets 3706c. The angle A is less than the angle C. Because the axes of the outer pockets 3706c (e.g., axis $PA_C$) are not parallel to the axes of the inner pockets 3706a (e.g., axis $PA_A$), the staple-forming pockets 3706 in the anvil 3700 form a modified or skewed herringbone pattern. The pocket axes $PA_B$ of the intermediate pockets 3706b are obliquely oriented relative to the inner pockets 3706a and outer pockets 3706c. In other instances, the pocket axes $PA_B$ of the intermediate pockets 3706b can be oriented perpendicular, or substantially perpendicular, to either the inner pocket 3706a or the outer pocket 3706c. For example, the angle B can be a supplementary angle to either angle A or C.

The inner pockets 3706a have a length $L_A$, the intermediate pockets 3706b have a length $L_B$, and the outer pockets 3706c have a length $L_C$. The length $L_C$ is less than the length $L_B$ and the length $L_A$. In other words, the outer pockets 3706c are shorter than the intermediate pockets 3706b and the inner pockets 3706a. In certain instances, the lengths $L_A$, $L_B$, and $L_C$ can be different. In other instances, the lengths $L_A$, $L_B$, and $L_C$ can be the same. In still other instances, the length $L_B$ can be less than the length $L_A$ and/or $L_B$, and/or the length $L_A$ can be less than the length $L_A$ and/or $L_C$. The lengths $L_A$, $L_B$, and $L_C$ can be selected to optimize the nesting of the pockets 3706.

The spacing of the staple-forming pockets 3706 can also be configured to optimize the nesting thereof. For example, the inner pockets 3706a can be longitudinally staggered relative to the outer pockets 3706c. Moreover, the inner pockets 3706a can partially longitudinally overlap the outer pockets 3706c. Referring to FIG. 80, a first end of the inner pocket 3706a is longitudinally offset from the corresponding end of the outer pocket 3706c by a distance $X1_{A/C}$. Moreover, a second end of the inner pocket 3706a is longitudinally offset from the corresponding end of the outer pocket 3706c by a distance $X2_{A/C}$. The distance $X2_{A/C}$ is less than the distance $X1_{A/C}$. In other instances, the distance $X2_{A/C}$ can be equal to or greater than the distance $X1_{A/C}$. The intermediate pockets 3706b are longitudinally staggered relative to the inner pockets 3706a and the outer pockets 3706c. More specifically, the intermediate pockets 3706b are equidistantly longitudinally offset between adjacent inner pockets 3706a and between adjacent outer pockets 3706c. In other instances, the intermediate pockets 3706b may be non-equidistantly offset between adjacent inner pockets 3706a and between adjacent outer pockets 3706c.

The arrangement of pockets 3706 is configured to nest the pockets 3706 such that the pockets 3706 fit within a predefined space. For example, in certain instances, the width of the anvil can be minimized or otherwise restrained to fit within a surgical trocar and/or within a narrow surgical field, and the arrangement of staple-forming pockets 3706 (and the corresponding arrangement of staples and/or staple cavities) can fit within a narrow anvil.

Referring now to FIGS. 32-35C, staple-forming pockets 3806 in a portion of an anvil 3800 are shown. The anvil 3800 includes a staple-forming surface 3802 and a longitudinal slot 3804. The longitudinal slot 3804 extends along the longitudinal axis LA of the anvil 3800. In certain instances, a firing element and/or cutting element can translate through the longitudinal slot 3804 during at least a portion of a firing stroke. The staple-forming pockets 3806 are defined in the staple-forming surface 3802, which also includes a non-forming portion 3808 that extends around the pockets 3806. The non-forming portion 3808 extends entirely around each pocket 3806. In other words, the non-forming portion 3808 surrounds the staple-forming pockets 3806. In other instances, at least a portion of two or more adjacent pockets can be in abutting contact such that a non-forming portion is not positioned therebetween. In certain instances, the non-forming portion 3808 can extend across one or more of the pockets 3806.

The "forming ratio" of the staple-forming surface 3802 (the ratio of the non-forming portion 3808 to the forming portion, i.e., the pockets 3806) can be optimized. By optimizing the forming ratio, more staples can be formed and/or formed to their desired configurations. In certain instances, the surface area of the non-forming portion 3808 of the anvil 3800 can be minimized with respect to the staple-forming pockets 3806. Additionally or alternatively, the footprint of the staple-forming pockets 3806 can be extended or enlarged to maximize the portion of the staple-forming surface 3802 that is designed to catch and form the staples. Such arrangement, for example, may prevent inadvertent malformed staples that, for whatever reason, miss or fall outside of their corresponding forming pocket during the firing process.

Figure 32:
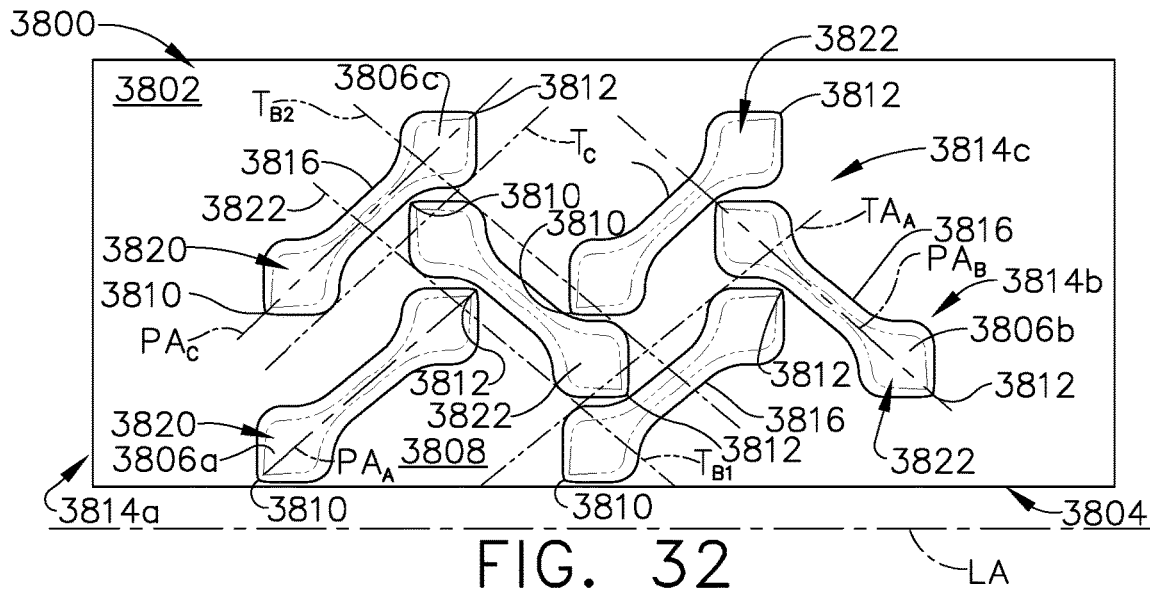
FIG. 32 is a plan view of a portion of an anvil having a plurality of staple-forming pockets defined therein.

The pockets 3806 depicted in FIG. 32 are arranged in three rows 3814a, 3814b, and 3814c on a first side of the longitudinal slot 3804. The first row 3814a is an inner row, the second row 3814b is an intermediate row, and the third row 3814c is an outer row. Inner pockets 3806a are positioned in the inner row 3814a, intermediate pockets 3806b are positioned in the intermediate row 3814b, and outer pockets 3806c are positioned in the outer row 3814c. Although not shown in FIG. 32, in at least one instance, the pockets 3806 on the opposing side of the slot 3804 can form a mirror image reflection of the pockets 3806 on the first side of the longitudinal slot 3804. In other instances, the arrangement of pockets 3806 in the staple-forming surface 3802 can be asymmetrical relative to the slot 3804 and, in certain instances, the anvil 3800 may not include the longitudinal slot 3804. In various instances, the pockets 3806 can be arranged in less than or more than three rows on each side of the slot 3804.

The pockets 3806 depicted in FIG. 32 are identical. Each pocket 3806 defined in the staple-forming surface 3802 has the same geometry. In other instances, the geometry of the pockets 3806 can vary row-to-row and/or longitudinally along the length of the anvil 3800. For example, in certain instances, the depth of the pockets 3806 or portions thereof can vary along the length of the anvil 3800 to accommodate for variations in gap distance between the anvil and the staple cartridge along the length of an end effector and/or tissue flow, as described herein.

An exemplary pocket 3806b is shown in FIGS. 33-35C. The pocket 3806b has a first end, or proximal end, 3810 and a second end, or distal end, 3812. A pocket axis PA extends between the proximal end 3810 and the distal end 3814 of the pocket 3806b. Referring again to FIG. 32, the pockets 3806 in each respective row are parallel. For example, the pocket axes (e.g., $PA_A$) of the inner pockets 3806a are parallel to each other, the pocket axes (e.g., $PA_B$) of the intermediate pockets 3806b are parallel to each other, and the pocket axes (e.g., $PA_C$) of the outer pockets 3806c are parallel to each other. The pocket axes PA are obliquely oriented relative to the slot 3804. Moreover, the axes $PA_B$ of the intermediate pockets 3806b are oriented perpendicular to the axes $PA_A$ and $PA_C$ of the inner pockets 3806a and the outer pockets 3806c, respectively. As such, the pockets 3806 are arranged in a herringbone arrangement along the staple-forming surface 3802.

The pocket 3806b includes a perimeter 3816, which defines the boundary of the pocket 3806b. The pocket 3806b also includes a proximal cup 3820, a distal cup 3822, and a neck portion 3824 connecting the proximal cup 3820 and the distal cup 3822. When a staple is driven into forming contact with the staple-forming surface 3802, the proximal cup 3820 is aligned with a proximal staple leg, and the distal cup 3822 is aligned with a distal staple leg. The tips of the staple legs are positioned and configured to land in the respective cups 3820, 3822. Stated differently, the proximal cup 3820 is configured to receive a proximal staple leg and the distal cup 3822 is configured to receive a distal staple leg. The cups 3820 and 3822 are also configured to direct or funnel the staple legs toward the pocket axis PA and a central portion of the pocket 3806, such as the neck portion 3824, and to deform the staple legs into the formed configuration.

The pockets 3806 include extended landing zones for the staple legs. Referring to the pocket 3806b depicted in FIG. 33, the pocket 3806b includes a proximal extended landing zone 3830 and a distal extended landing zone 3832. The proximal extended landing zone 3830 is positioned in a proximal portion of the proximal cup 3820, and the distal extended landing zone 3832 is positioned in a distal portion of the distal cup 3822. The extended landing zones 3830 and 3832 define a substantially triangular perimeter. Moreover, the extended landing zones 3830 and 3832 terminate along the pocket axis PA at a point to form corners of the pocket 3806b.

In other instances, the extended landing zones 3830 and 3832 can define straight and/or contoured perimeters, for example, and may extend laterally and/or longitudinally relative to the pocket axis PA. In instances where a staple or portion thereof is skewed during firing, the extended landing zones 3830, 3832 can salvage, or at least attempt to salvage, the formation of the skewed staple.

Figure 34:
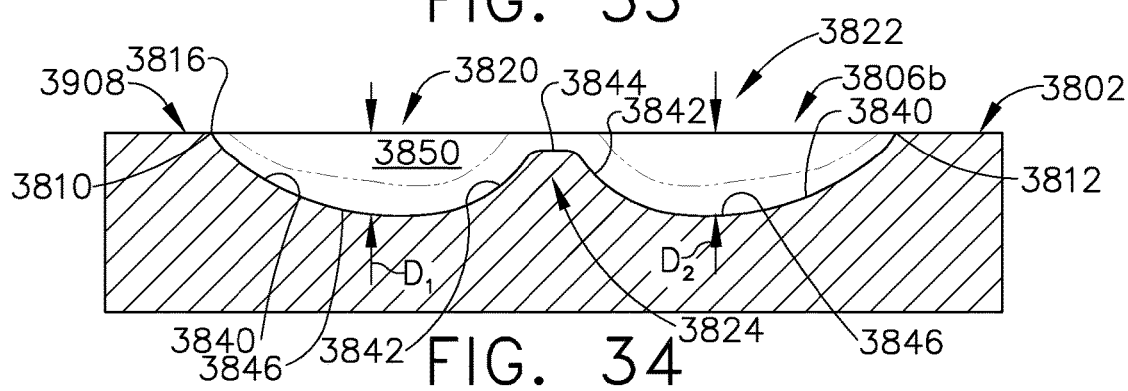
FIGS. 34-35C are cross-sectional views of the pocket of FIG. 33.

Referring primarily to FIG. 34, each cup 3820, 3822 of the pocket 3806b defines an entrance ramp 3840 and an exit ramp 3842. The exit ramp 3842 is steeper than the entrance ramp 3840. When forming a staple, the tip of a staple leg can enter the respective cup 3820, 3822 along the entrance ramp 3840 and exit the respective cup 3820, 3822 along the exit ramp 3842. At an apex 3846 between the entrance ramp 3840 and the exit ramp 3842, the tips of the staple legs are deformed toward the staple base to assume the formed configuration, such as a B-form or modified B-form, for example. The proximal cup 3820 defines a proximal depth $D_1$ at the apex 3846 thereof measured relative to the non-forming portion 3808 of the staple-forming surface 3802, and the distal cup 3822 defines a distal depth $D_2$ at the apex 3846 thereof measured relative to the non-forming portion 3808 of the staple-forming surface 3802. In the pocket 3806b, the proximal depth $D_1$ and the distal depth $D_2$ are equal. In other instances, the proximal depth $D_1$ and the distal depth $D_2$ can be different.

The pocket 3806b also defines a bridge 3844 in the neck portion 3824 between the proximal cup 3820 and the distal cup 3822. The bridge 3844 is offset from the non-forming portion 3808 of the staple-forming surface 3802. More specifically, the bridge 3844 is positioned below or recessed relative to the non-forming portion 3808. In other instances, the bridge 3844 can be aligned with the non-forming portion 3808 and/or can protrude away from the non-forming portion 3808 toward the opposing jaw of the end effector.

Figure 35C:
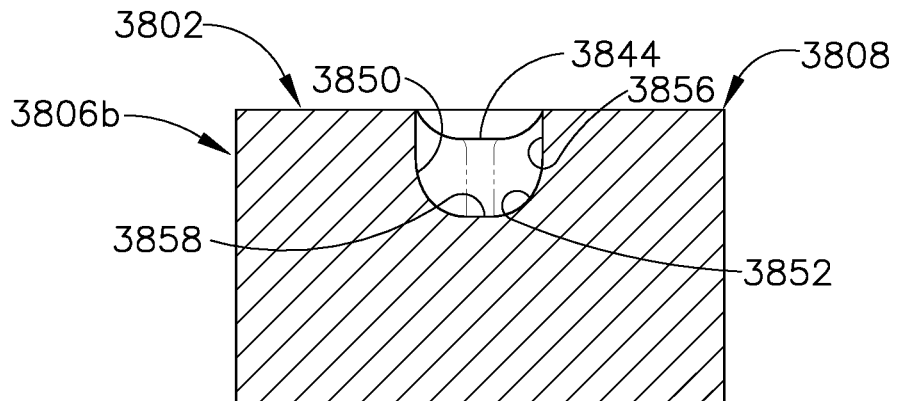
Figure 35B:
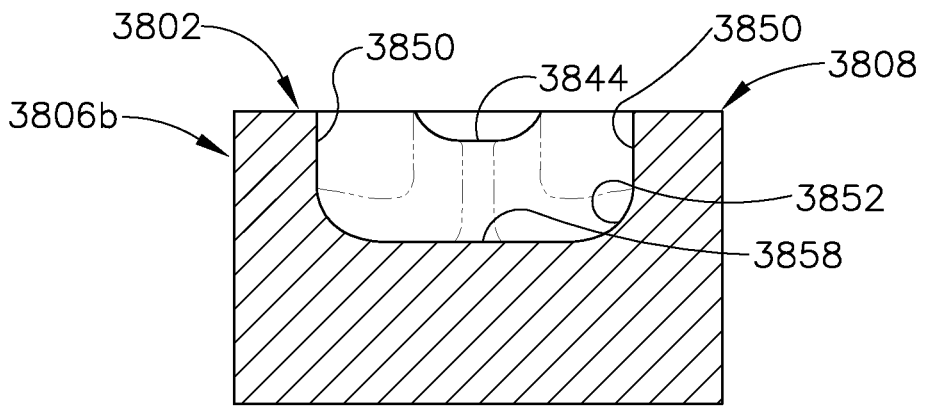
Figure 35A:
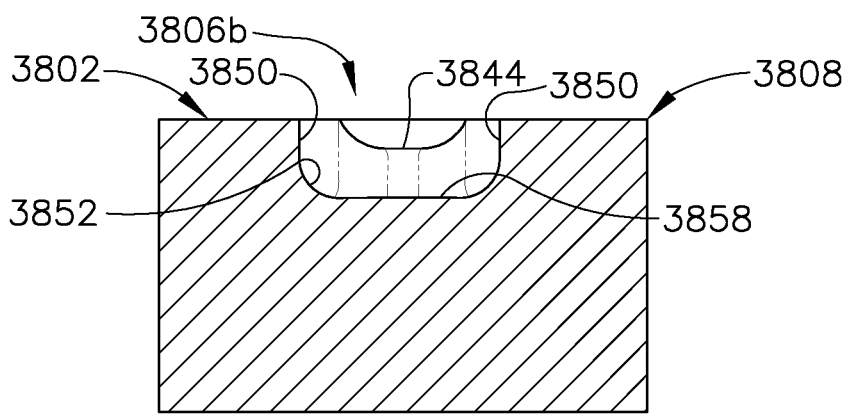

Referring primarily to FIGS. 35A-35C, the pocket 3806b includes sidewalls 3850. The sidewalls 3850 are oriented perpendicular to the non-forming portion 3808 of the staple-forming surface 3802. The sidewalls 3850 widen toward a central region 3821 of each cup 3820, 3822, and narrow from the central region 3821 of each cup 3820, 3822 toward the neck portion 3824. The widened central region 3821 provides an enlarged footprint for receiving the tip of a staple leg. The extended landing zones 3830, 3832 also enlarge the footprint of the respective cups 3820, 3822 for receiving the staple tips. As the cups 3820, 3822 narrow toward the neck portion 3824, the cups 3820, 3822 are configured to funnel and/or guide the tips of the staple legs toward and/or along the pocket axis PA and into a formed configuration. As the cups 3820 and 3822 widen and then narrow toward the neck portion 3824, the perimeter 3816 of the pocket 3806b defines a contour or arced profile. In other instances, the perimeter 3816 of the pocket 3806b can extend along linear, non-contoured profiles having non-rounded corners, for example.

The pocket 3806b defines fillets 3852 (FIGS. 35A-35C) between the sidewalls 3850 and the bottom surface of the pocket 3806b. The fillets 3852 are configured to guide the staple legs along the desired path in the pocket 3806b. For example, if a staple leg lands along the fillet 3852 or is diverted to the fillet 3852, the fillet 3852 can smoothly guide the staple leg toward the pocket axis PA.

Referring again to FIG. 33, the pocket 3806b is symmetric about the pocket axis PA. For example, the perimeter 3816 of the pocket 3806b is symmetric about the pocket axis PA. Moreover, the pocket 3806b is symmetric about a central axis CA through the neck portion 3824 and perpendicular to the pocket axis PA. For example, the perimeter 3816 of each pocket 3806 is symmetric about the central axis CA, and the proximal cup 3820 has the same geometry as the distal cup 3822.

In other instances, the proximal cup 3820 can be different than the distal cup 3822. For example, referring again to FIG. 34, the distal depth $D_2$ can be less than the proximal depth $D_1$. In various instances, the variation in the depth of a staple-forming pocket can accommodate for variations in gap distance between the anvil and the staple cartridge along the length of an end effector when tissue is clamped therebetween. For example, an anvil may bow or bend away from the staple cartridge as the anvil approaches the distal end of the end effector. Variations to the depth of the staple-forming pockets 3806 can be configured to ensure that an appropriate forming height is maintained in view of the anticipated or expected bowing or bending of the anvil 3800.

Additionally or alternatively, the variation in the depth of a staple-forming pocket can accommodate for tissue movement or flow relative to the end effector. More specifically, when tissue is clamped between the jaws of the end effector, fluid in the clamped tissue can flow or move toward adjacent, unclamped tissue. The tissue can flow laterally toward the longitudinal sides of the anvil 3800, distally toward the distal end of the anvil 3800, and/or proximally toward the proximal end of the anvil 3800. In certain instances, tissue can flow relative to the anvil 3800 when the cutting edge is advanced distally through the tissue. In such instances, tissue may flow laterally, distally, and/or proximally, but it primarily flows distally due to the distal movement of the cutting edge. In instances where the cutting edge moves proximally to incise tissue, the movement or flow of the tissue would be generally proximal during the cutting stroke. Different depths $D_1$ and $D_1$ in the pocket 3806 can accommodate for the distal flow of the tissue, which can shift or skew the staple legs embedded therein distally.

In various instances, tissue movement or flow at the distal end of an end effector can be larger than the tissue movement or flow at the proximal end of the end effector. Such instances can arise as a result of the distal movement of the firing member within the end effector. Although the firing member is configured to progressively staple and incise the tissue as it is moved distally, the firing member can also plow or push the tissue distally. This pushing or plowing effect may begin at the proximal end of the end effector and may compound as the firing member is moved distally such that the largest pushing or plowing effect is realized at the distal end of the end effector. Consequently, the tissue flow can be increased toward the distal end of the end effector. To accommodate for such an increase in tissue flow, the geometries of the staple pockets can vary longitudinally along the length of a row. In instances where the proximal and distal cups of the staple pockets are different to accommodate for tissue flow, a gradient in pocket asymmetries may be utilized within a row of pockets to compensate for the gradient in tissue movement and staple shifting.

In certain instances, different staple geometries can be utilized with the different pocket geometries. The use of different staples to accommodate for tissue flow along the length of an end effector is described in U.S. patent application Ser. No. 14/318,996, entitled FASTENER CARTRIDGES INCLUDING EXTENSIONS HAVING DIFFERENT CONFIGURATIONS, filed Jun. 30, 2014, which is hereby incorporated by reference herein in its entirety. In other instances, identical staples can be utilized with different pocket geometries along the length of an anvil.

Figure 33:
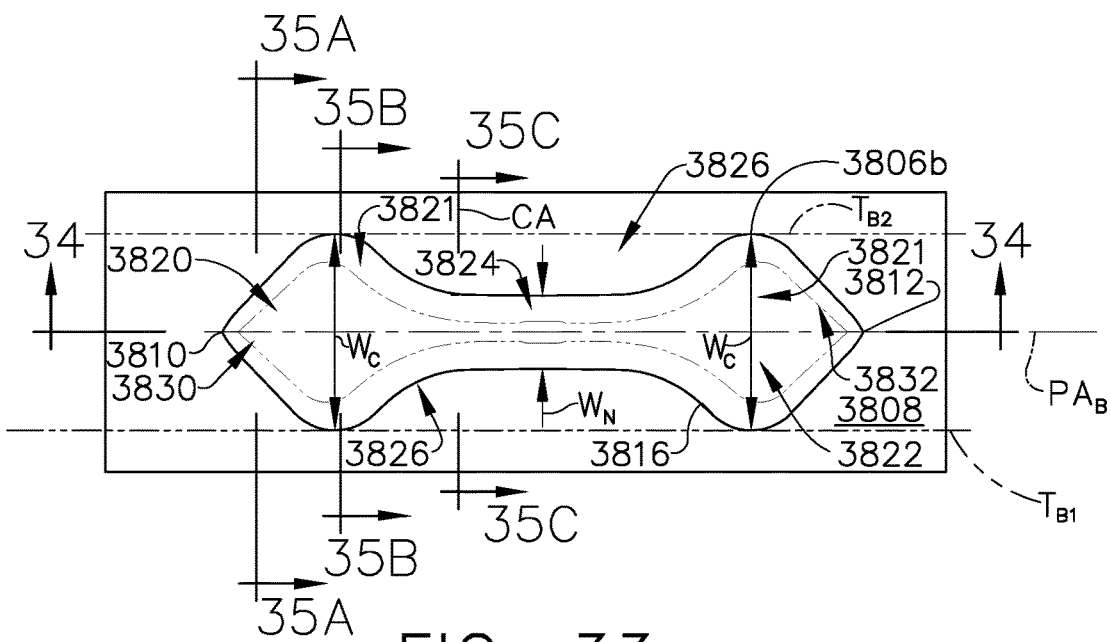
FIG. 33 is a detail view of a pocket of FIG. 32.

Referring again to FIG. 33, the neck portion 3824 defines a width $W_N$ and the proximal and distal cups 3820 and 3822 define a width $W_C$. The width $W_N$ is less than the width $W_C$. Consequently, the central portion of the pocket 3806b is narrower than the proximal and distal cups 3820 and 3822. The narrowed perimeter 3816 of the pocket 3806b at the neck portion 3824 defines a receiving peninsula 3826 between a portion of the proximal cup 3820 and a portion of the distal cup 3822. Owing to the symmetry of the pocket 3806b, symmetrical receiving peninsulas 3826 are positioned on each side of the pocket 3806b. The receiving peninsulas 3826 are bounded by the perimeter 3816 of the pocket 3806b and a tangent axis (e.g., $T_A$, $T_{B1}$, $T_{B2}$, and $T_C$), which is tangential to the widest portion of the proximal and distal cups 3820 and 3822 on a side of the pocket 3806. A first tangent axis $T_{B1}$ is positioned on a first side of the pocket 3806b and a second tangent axis $T_{B2}$ is positioned on the opposite side of the pocket 3806b. The first and second tangent axes $T_{B1}$ and $T_{B2}$ depicted in FIG. 33 are parallel to the pocket axis $PA_B$.

Referring again to FIG. 32, the perimeters 3816 of the pockets 3806 are nested or interlocked along the staple-forming surface 3802. In particular, each pocket 3806 extends into the receiving peninsula 3826 of an adjacent pocket 3806. For example, the intermediate pockets 3806b are nested between the inner pockets 3806a and the outer pockets 3806c. Stated differently, the intermediate pockets 3806b extend into the receiving peninsula 3826 of an adjacent inner pocket 3806a and into the receiving peninsula 3826 of an adjacent outer pocket 3806c. Moreover, the inner pockets 3806a and the outer pockets 3806b are nested with the intermediate pockets 3806b. More specifically, the inner pockets 3806a extend into the receiving peninsula 3826 of an adjacent intermediate pocket 3806b, and the outer pockets 3806c extend into the receiving peninsula 3826 of an adjacent intermediate pocket 3806b.

The distal cup 3822 of the intermediate pocket 3806b extend across the tangent axis $T_A$ and into the receiving peninsula 3826 of the adjacent inner pocket 3806a. Moreover, the proximal cup 3820 of the intermediate pocket 3806b extends across the tangent axis $T_C$ and into the receiving peninsula 3826 of the adjacent outer pocket 3806c. Additionally, the distal cup 3822 of the inner pockets 3806a extends across the tangent axis $T_{B1}$ and into the receiving peninsula 3826 of the adjacent intermediate pocket 3806b. Furthermore, the proximal cup 3820 of the outer pockets 3806c extends across the tangent axis $T_{B2}$ and into the receiving peninsula 3826 of the adjacent intermediate pocket 3806b. In various instances, the distal extended landing zone 3832 of the intermediate pocket 3806b is positioned in the receiving peninsula 3826 of an inner pocket 3806a, the proximal extended landing zone 3830 of the intermediate pocket 3806b is positioned in the receiving peninsula 3826 of an outer pocket 3806c, the distal extended landing zone 3832 of an inner pocket 3806a is positioned in the receiving peninsula 3826 of an intermediate pocket 3806b, and the proximal extended landing zone 3830 of the outer pocket 3806c is positioned in the receiving peninsula 3826 of an intermediate pocket 3806b.

The geometry of the pockets 3806 facilitates the nesting of the pockets 3806 in the staple-forming surface 3802. For example, because the pockets 3806 include a narrowed neck portion 3824 between two enlarged cups 3820 and 3822, one of the enlarged cups 3820, 3822 of another pocket 3806 can be positioned adjacent to the narrowed neck portion 3824. For example, one of the enlarged cups 3820, 3822 can be aligned with and/or received by a portion of an adjacent pocket 3806. In such instances, the surface area of the staple-forming surface 3802 that is covered by the pockets 3806 can be optimized. For example, the surface area of the staple-forming surface 3802 that is covered by the pockets 3806 is maximized. The "forming ratio" of the staple-forming surface 3802 is the ratio of the non-forming portion 3808 to the forming portion, i.e., the pockets 3806. The forming ratio is about 1.7:1. In other instances, the forming ratio can be less than 1.7:1 or more than 1.7:1. For example, in at least one instance, more than 50% of the staple-forming surface 3802 can be covered with staple-forming pockets 3806.

The nesting of staple-forming pockets discussed herein can refer to the nesting of adjacent pocket perimeters. For example, where a first pocket defines an inward contour, i.e., a contour extending inward toward the pocket axis, an adjacent second pocket can protrude toward and/or into the region adjacent to the inward contour. Additionally or alternatively, a portion of the second pocket, such as an end of the second pocket, can be aligned with the narrowed region of the first pocket. Consequently, the second pocket can be positioned nearer to the pocket axis of the first pocket than if the end of the second pocket was aligned with a wider region of the first pocket.

Referring now to FIGS. 36-39C, staple-forming pockets 3906 in a portion of an anvil 3900 are depicted. The anvil 3900 includes a staple-forming surface 3902 and a longitudinal slot 3904. The longitudinal slot 3904 extends along the longitudinal axis LA of the anvil 3900. In certain instances, a firing element and/or cutting element can translate through the longitudinal slot 3904 during at least a portion of a firing stroke. The staple-forming pockets 3906 are defined in the staple-forming surface 3902. The staple-forming surface 3902 also includes a non-forming portion 3908 that extends around the pockets 3906. The non-forming portion 3908 extends entirely around each pocket 3906 in FIG. 36. In other words, the non-forming portion 3908 surrounds the staple-forming pockets 3906. In other instances, at least a portion of two or more adjacent pockets 3906 can be in abutting contact such that a non-forming portion 3908 is not positioned therebetween.

The forming ratio of the staple-forming surface 3902 can be optimized. By optimizing the forming ratio, more staples can be formed and/or formed to their desired configurations. In certain instances, the surface area of the non-forming portion 3908 of the anvil 3900 can be minimized with respect to the staple-forming pockets 3906. Additionally or alternatively, the footprint of the staple-forming pockets 3906 can be extended or enlarged to maximize the portion of the staple-forming surface 3902 that is designed to catch and form the staples.

Figure 36:
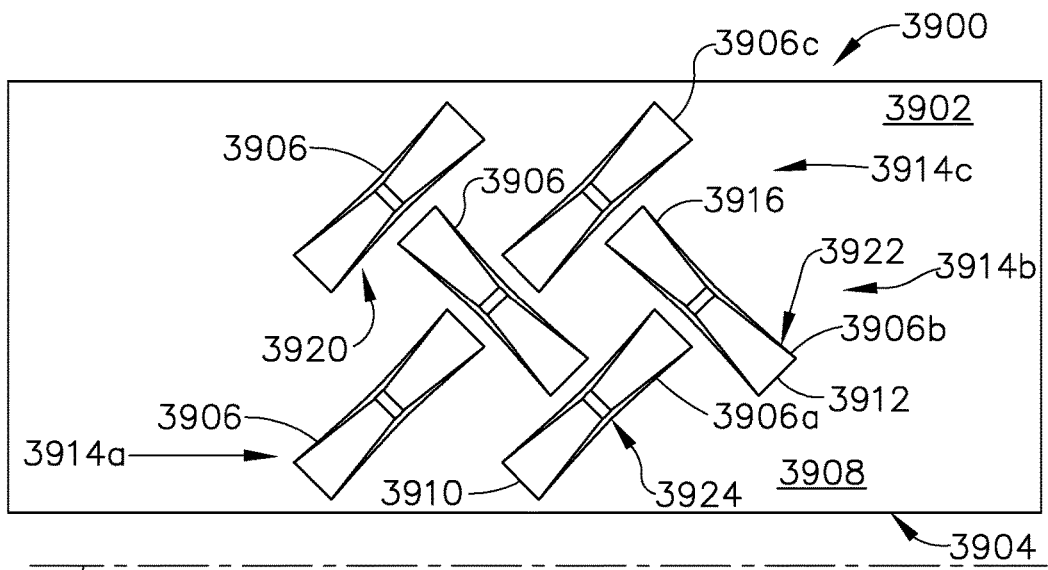
FIG. 36 is a plan view of a portion of an anvil having a plurality of staple-forming pockets defined therein.
Figure 37:
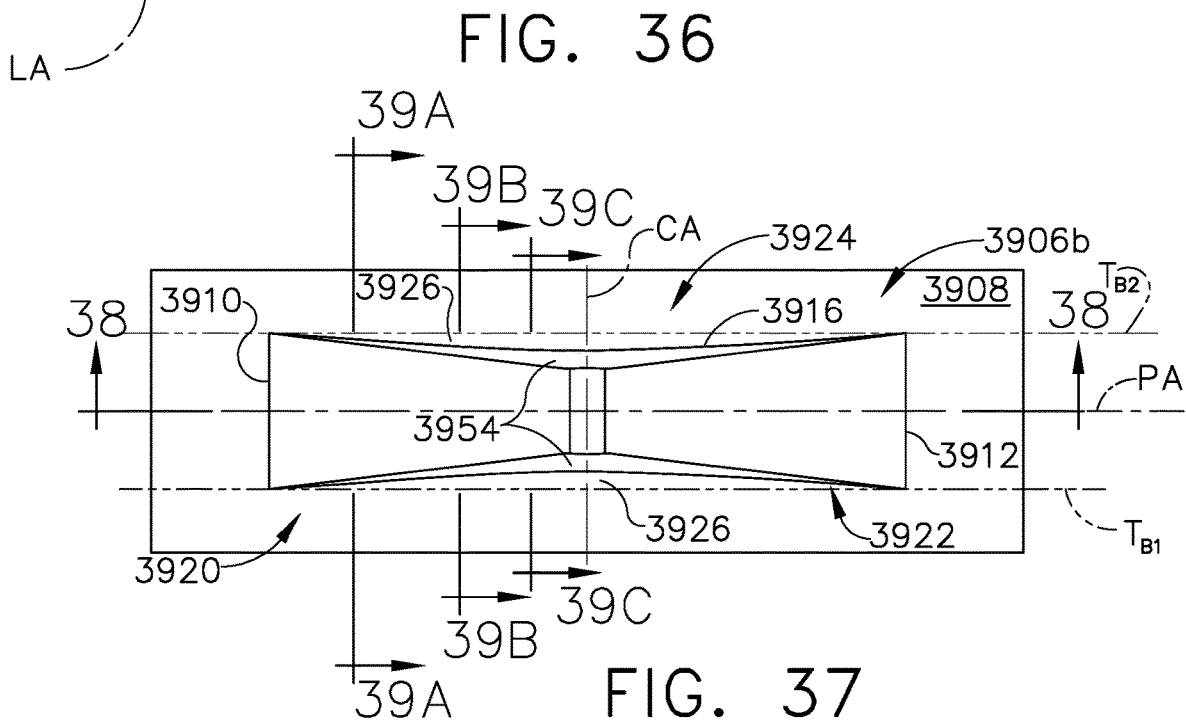
FIG. 37 is a detail view of a pocket of FIG. 36.

The pockets 3906 depicted in FIG. 36 are arranged in three rows 3914a, 3914b, 3914c on a first side of the longitudinal slot 3904. The first row 3914a is an inner row, the second row 3914b is an intermediate row, and the third row 3914c is an outer row. Inner pockets 3906a are positioned in the inner row 3914a, intermediate pockets 3906b are positioned in the intermediate row 3914b, and outer pockets 3906c are positioned in the outer row 3914c. Similar to the anvil 3800, the pockets 3906 are arranged in a herringbone arrangement along the staple-forming surface 3902 of the anvil 3900. Although not shown in FIG. 36, in at least one instance, the pockets 3906 on the opposing side of the slot 3904 can form a mirror image reflection of the pockets 3906 on the first side of the longitudinal slot 3904. In other instances, the arrangement of pockets 3906 in the staple-forming surface 3902 can be asymmetrical relative to the slot 3904 and, in certain instances, the anvil 3900 may not include the longitudinal slot 3904. In various instances, the pockets 3906 can be arranged in less than or more than three rows on each side of the slot 3904.

The pockets 3906 depicted in FIG. 36 are identical. Each pocket 3906 defined in the staple-forming surface 3802 has the same geometry. In other instances, the geometry of the pockets 3906 can vary row-to-row and/or longitudinally along the length of the anvil 3900. For example, in certain instances, the depth of the pockets 3906 or portions thereof can vary along the length of the anvil 3900 to accommodate for variations in gap distance between the anvil and the staple cartridge along the length of an end effector and/or tissue flow, as described herein.

An exemplary pocket 3906b is shown in FIGS. 37-39C. The pocket 3906b has a first end, or proximal end, 3910 and a second end, or distal end, 3912. A pocket axis PA (FIG. 37) extends between the proximal end 3910 and the distal end 3912 of the pocket 3906b. The pocket 3906b includes a perimeter 3916, which defines the boundary of the pocket 3906. The pocket 3906b also includes a proximal cup 3920, a distal cup 3922, and a neck portion 3924 connecting the proximal cup 3920 and the distal cup 3922. When a staple is driven into forming contact with the staple-forming surface 3902, the proximal cup 3920 is aligned with a proximal staple leg, and the distal cup 3922 is aligned with a distal staple leg. The cups 3920 and 3922 are configured to direct or funnel the staple legs toward the pocket axis PA and a central portion of the pocket 3906, such as the neck portion 3924, and to deform the staple legs into the formed configuration.

Figure 38:
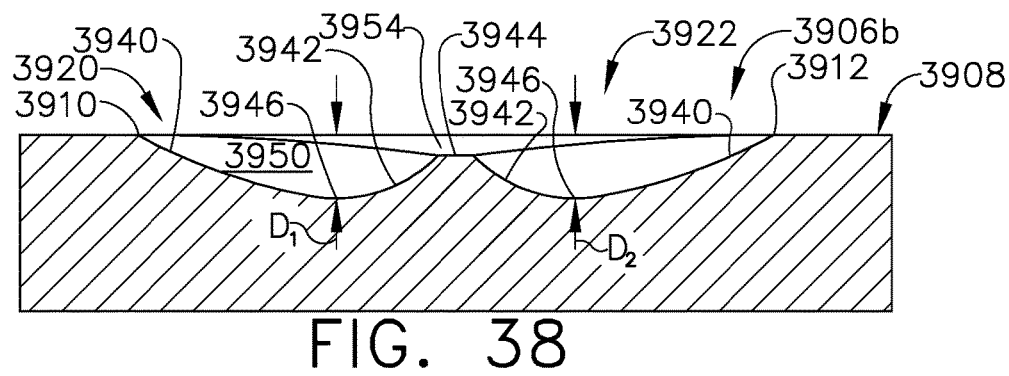
FIGS. 38-39C are cross-sectional views of the pocket of FIG. 37.

Referring primarily to FIG. 38, each cup 3920, 3922 of the pocket 3906b defines an entrance ramp 3940 and an exit ramp 3942. The exit ramp 3942 is steeper than the entrance ramp 3940. When forming a staple, the tip of a staple leg can enter the respective cup 3920, 3922 along the entrance ramp 3940 and exit the respective cup 3920, 3922 along the exit ramp 3942. At an apex 3946 between the entrance ramp 3940 and the exit ramp 3942, the tips of the staple legs are deformed toward the staple base to assume the formed configuration, such as a B-form or modified B-form, for example. The proximal cup 3920 defines a proximal depth $D_1$ at the apex 3946 thereof measured relative to the non-forming portion 3908 of the staple-forming surface 3902, and the distal cup 3922 defines a distal depth $D_2$ at the apex 3946 thereof measured relative to the non-forming portion 3908 of the staple-forming surface 3902. In the pocket 3906, the proximal depth $D_1$ and the distal depth $D_2$ are equal. In other instances, the proximal depth $D_1$ and the distal depth $D_2$ can be different. The pocket 3906b also defines a bridge 3944 in the neck portion 3924 between the proximal cup 3920 and the distal cup 3922. The bridge 3944 is offset from the non-forming portion 3908 of the staple-forming surface 3902. More specifically, the bridge 3944 is positioned below or recessed relative to the non-forming portion 3908.

Figure 39C:
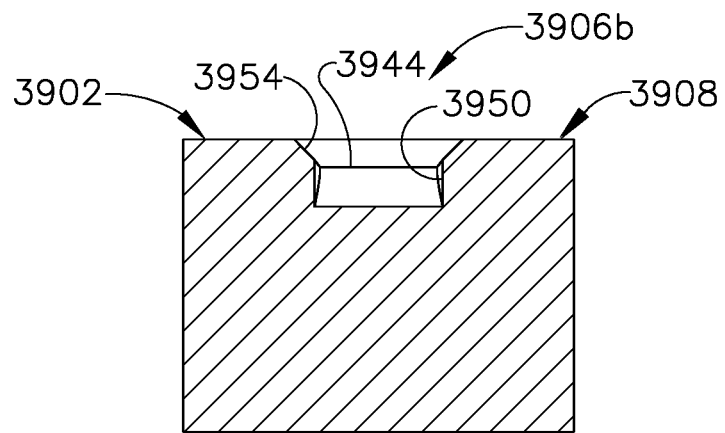
Figure 39B:
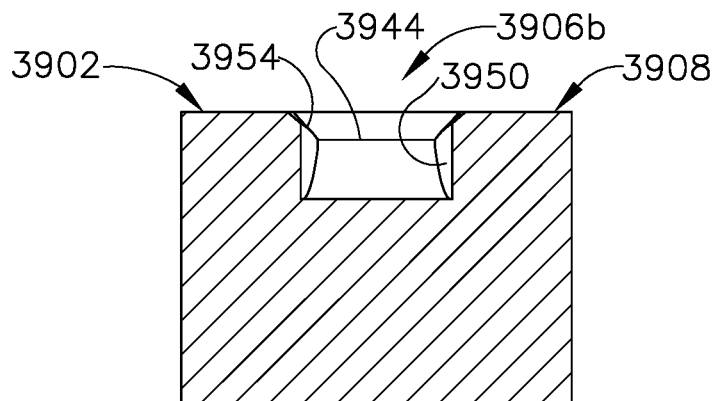
Figure 39A:
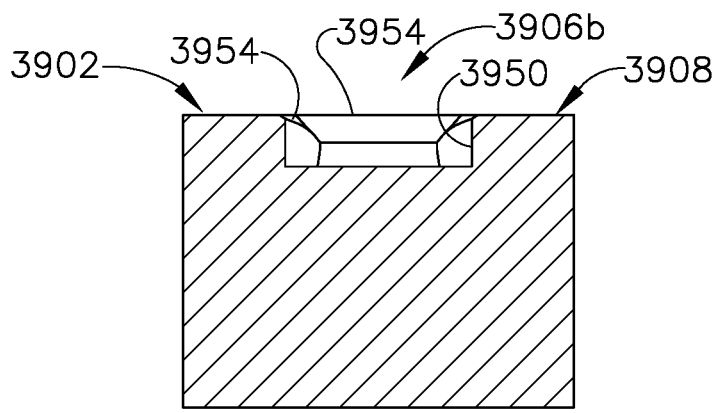

Referring primarily to FIGS. 39A-39C, the pocket 3906b includes sidewalls 3950. The sidewalls 3950 are oriented perpendicular to the non-forming portion 3908 of the staple-forming surface 3902. The sidewalls 3950 narrow linearly from the outer ends of each cup 3920, 3922 toward the neck portion 3924. Consequently, the widest portion of the cups 3920, 3922 is at the proximal and distal ends 3910, 3912 of the pocket 3906b, respectively. The profile 3916 of the pocket 3906b defines a bow-tie shape perimeter. The widened region at the proximal and distal ends 3910, 3912 provides an enlarged footprint for receiving the tip of a staple leg. In various instances, the widened portions of the cups 3920 and 3922 define extended landing zones for receiving the staple tips. As the cups 3920, 3922 narrow toward the neck portion 3924, the cups 3920, 3922 are configured to funnel and/or guide the tips of the staple legs toward and/or along the pocket axis PA into a formed configuration. The pocket 3906b defines a chamfered edge 3954 along the sides of the pocket 3906b. The chamfered edge 3954 serves to enlarge the footprint of the pocket 3906b and guide the tips of the staple legs toward the pocket axis PA.

Referring again to FIG. 37, the pocket 3906b is symmetric about the pocket axis PA. For example, the perimeter 3916 of the pocket 3906b is symmetric about the pocket axis PA. Moreover, the pocket 3906b is symmetric about a central axis CA through the neck portion 3924 and perpendicular to the pocket axis PA. For example, the perimeter 3916 of the pocket 3906b is symmetric about the central axis CA, and the proximal cup 3920 has the same geometry as the distal cup 3922. In other instances, the proximal cup 3920 can be different than the distal cup 3922. For example, referring again to FIG. 38, the distal depth $D_2$ can be less than the proximal depth $D_1$ to accommodate for variations in gap distance between the anvil and the staple cartridge and/or tissue flow, as described herein.

Referring again to FIG. 37, the width of the neck portion 3924 is less than the width of the cups 3920 and 3922. Consequently, the central portion of the pocket 3906b is narrower than the proximal and distal cups 3920 and 3922. The narrowed perimeter 3916 of the pocket 3906b at the neck portion 3924 defines a receiving peninsula 3926 between a portion of the proximal cup 3920 and a portion of the distal cup 3922. Owing to the symmetry of the pocket 3906b, symmetrical receiving peninsulas 3926 are positioned on each side of the pocket 3906b. The receiving peninsulas 3926 are bounded by the perimeter 3916 of the pocket 3906b and a tangent axis (e.g., $T_{B1}$ and $T_{B2}$), which is tangential to the widest portion of the proximal and distal cups 3920 and 3922 on a side of the pocket 3906b. A first tangent axis $T_{B1}$ is positioned on a first side of the pocket 3906b and a second tangent axis $T_{B2}$ is positioned on the opposite side of the pocket 3906b. The first and second tangent axes $T_{B1}$ and $T_{B2}$ are parallel to the pocket axis PA.

Referring again to FIG. 36, each pocket 3906 extends toward the receiving peninsula 3926 of an adjacent pocket 3906. For example, the intermediate pockets 3906b are aligned with the neck portions 3924 of the inner pockets 3906a and the outer pockets 3906c. Moreover, the inner pockets 3906a and the outer pockets 3906b extend toward the receiving peninsula 3926 of one of the intermediate pockets 3906b. More specifically, the pocket axes PA of the intermediate pockets 3906b are aligned with the neck portions 3924 of adjacent inner and outer pockets 3906a and 3906c, respectively, the pocket axes PA of the inner pockets 3906a are aligned with the neck portion 3924 of an adjacent intermediate pocket 3906b, and the pocket axes PA of the outer pockets 3906c are aligned with the neck portion 3924 of an adjacent intermediate pocket 3906b. In certain instances, a portion of one or more of the pockets 3906 can extend into the receiving peninsula of an adjacent pocket 3906.

The geometry of the pockets 3906 facilitates the close arrangement of the pockets 3906 in the staple-forming surface 3902. For example, because the pockets 3906 include a narrowed neck portion 3924 between two enlarged cups 3920 and 3922, the enlarged cup 3920, 3922 of another pocket 3906 can be positioned adjacent to the narrowed neck portion 3924. For example, an enlarged cup 3920, 3922 can be aligned with and/or received by a portion of the adjacent pocket 3906. Consequently, the surface area of the staple-forming surface 3902 that is covered by the pockets 3906 can be optimized. For example, the surface area of the staple-forming surface 3902 that is covered by pockets 3906 is maximized. The "forming ratio" is the ratio of the non-forming portion 3908 to the forming portion, i.e., the pockets 3906. In various instances, the forming ratio can be at least 1:1, for example.

In certain instances, though the pockets 3906 are positioned in close proximity to each other, because the neck portion 3924 narrows, there is space for the non-forming portion 3908 between adjacent pockets 3906. For example, the non-forming portion 3908 can extend between the neck portion 3924 of an inner pocket 3906a and the distal cup 3922 of an adjacent intermediate pocket 3906b. The non-forming portion 3908 between adjacent pockets 3906 can provide sufficient spacing between pockets 3906 to strengthen and/or reinforce the anvil 3900.

Referring now to FIGS. 40-43C, staple-forming pockets 4006 in a portion of an anvil 4000 are depicted. The pockets 4006 and arrangement thereof in the anvil 4000 are similar in many aspects to the pockets 3906 and arrangement thereof in the anvil 3900. For example, the anvil 4000 includes a staple-forming surface 4002 and a longitudinal slot 4004. The longitudinal slot 4004 extends along the longitudinal axis LA of the anvil 4000. In certain instances, a firing element and/or cutting element can translate through the longitudinal slot 4004 during at least a portion of a firing stroke. The staple-forming pockets 4006 are defined in the staple-forming surface 4002. The staple-forming surface 4002 also includes a non-forming portion 4008 that extends around the pockets 4006. The non-forming portion 4008 extends entirely around each pocket 4006 in FIG. 40. In other words, the non-forming portion 4008 surrounds the staple-forming pockets 4006. In other instances, at least a portion of two or more adjacent pockets 4006 can be in abutting contact such that a non-forming portion 4008 is not positioned therebetween.

The forming ratio of the staple-forming surface 4002 can be optimized. By optimizing the forming ratio, more staples can be formed and/or formed to their desired configurations. In certain instances, the surface area of the non-forming portion 4008 of the anvil 4000 can be minimized with respect to the staple-forming pockets 4006. Additionally or alternatively, the footprint of the staple-forming pockets 4006 can be extended or enlarged to maximize the portion of the staple-forming surface 4002 that is designed to catch and form the staples.

The pockets 4006 are arranged in an inner row 4014a, an intermediate row 4014b, and an outer row 4014c on a first side of the longitudinal slot 4004. Inner pockets 4006a are positioned in the inner row 4014a, intermediate pockets 4006b are positioned in the intermediate row 4014b, and outer pockets 4006c are positioned in the outer row 4014c. Similar to the anvil 3800, the pockets 4006 are arranged in a herringbone arrangement along the staple-forming surface 4002 of the anvil 4000. Although not shown in FIG. 40, in at least one instance, the pockets 4006 on the opposing side of the slot 4004 can form a mirror image reflection of the pockets 4006 on the first side of the longitudinal slot 4004. In other instances, the arrangement of pockets 4006 in the staple-forming surface 4002 can be asymmetrical relative to the slot 4004 and, in certain instances, the anvil 4000 may not include the longitudinal slot 4004. In various instances, the pockets 4006 can be arranged in less than or more than three rows on each side of the slot 4004.

Figure 40:
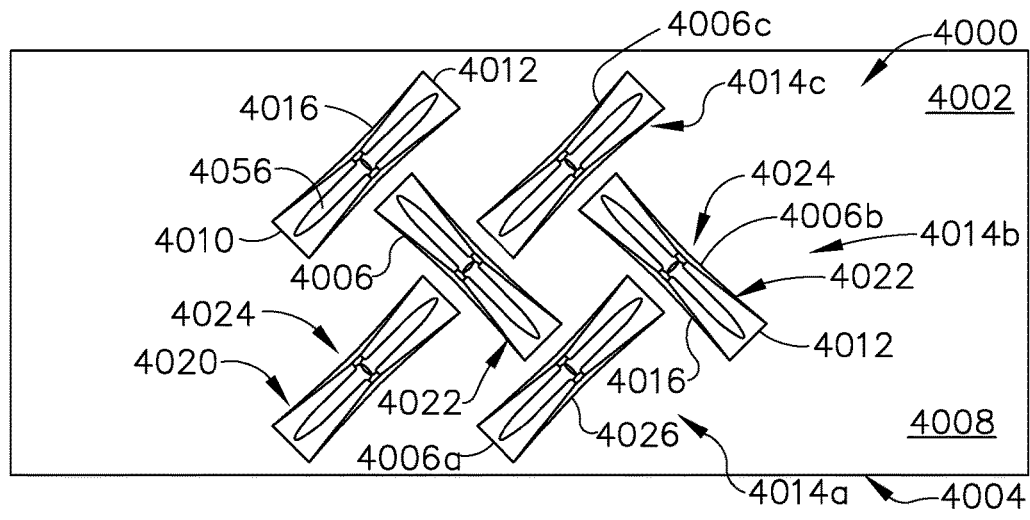
FIG. 40 is a plan view of a portion of an anvil having a plurality of staple-forming pockets defined therein.

The pockets 4006 depicted in FIG. 40 are identical. Each pocket 4006 defined in the staple-forming surface 4002 has the same geometry. In other instances, the geometry of the pockets 4006 can vary row-to-row and/or longitudinally along the length of the anvil 4000. For example, in certain instances, the depth of the pockets 4006 or portions thereof can vary along the length of the anvil 4000 to accommodate for variations in gap distance between the anvil and the staple cartridge along the length of an end effector and/or tissue flow, as described herein.

An exemplary pocket 4006b is shown in FIGS. 41-43C. The pocket 4006b has a first end, or proximal end, 4010 and a second end, or distal end, 4012. A pocket axis PA (FIG. 41) extends between the proximal end 4010 and the distal end 4012 of the pocket 4006b. The pocket 4006b includes a perimeter 4016, which defines the boundary of the pocket 4006b. The pocket 4006b also includes a proximal cup 4020, a distal cup 4022, and a neck portion 4024 connecting the proximal cup 4020 and the distal cup 4022. When a staple is driven into forming contact with the staple-forming surface 4002, the proximal cup 4020 is aligned with a proximal staple leg, and the distal cup 4022 is aligned with a distal staple leg. The cups 4020 and 4022 are configured to direct or funnel the staple legs toward the pocket axis PA and a central portion of the pocket 4006, such as the neck portion 4024, and to deform the staple legs into the formed configuration.

Figure 42:
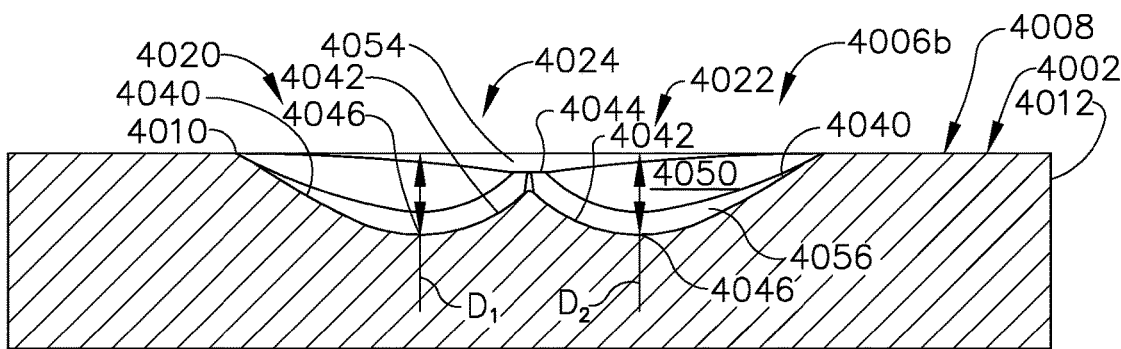
FIGS. 42-43C are cross-sectional views of the pocket of FIG. 41.

Referring primarily to FIG. 42, each cup 4020, 4022 of the pocket 4006b defines an entrance ramp 4040 and an exit ramp 4042. When forming a staple, the tip of a staple leg can enter the respective cup 4020, 4022 along the entrance ramp 4040 and exit the respective cup 4020, 4022 along the exit ramp 4042. At an apex 4046 between the entrance ramp 4040 and the exit ramp 4042, the tips of the staple legs are deformed toward the staple base to assume the formed configuration, such as a B-form or modified B-form, for example. The pocket 4006b also defines a bridge 4044 between the proximal cup 4020 and the distal cup 4022. The bridge 4044 is offset from the non-forming portion 4008. More specifically, the bridge 4044 is positioned below or recessed relative to the non-forming portion 4008.

Figure 43C:
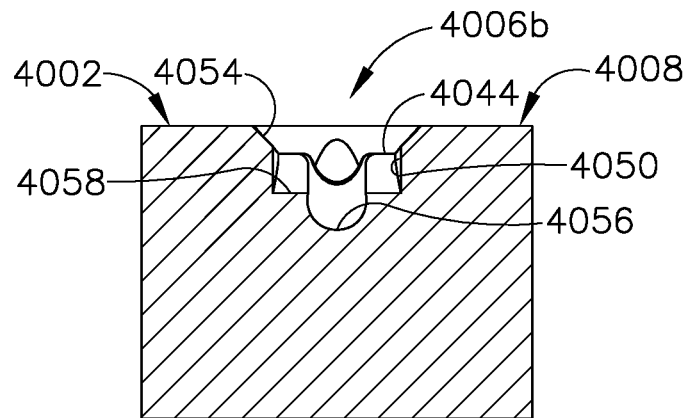
Figure 43B:
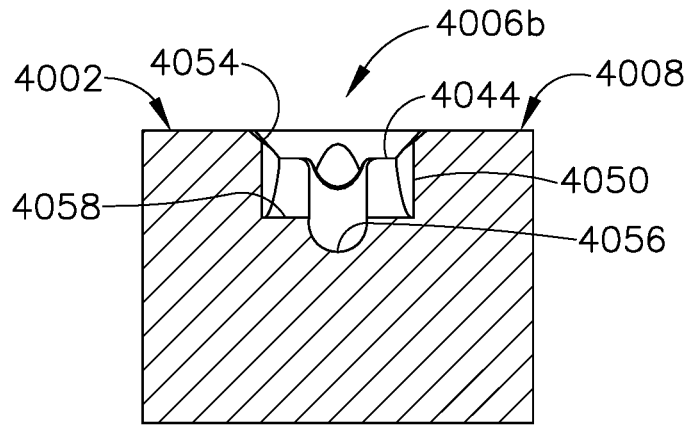
Figure 43A:
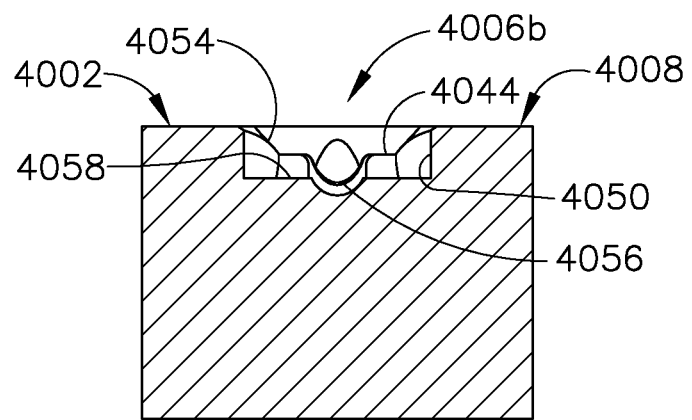

Referring primarily to FIGS. 43A-43C, the pocket 4006b includes sidewalls 4050, which are oriented perpendicular to the non-forming portion 4008 of the staple-forming surface 4002. The sidewalls 4050 narrow from the outer ends of each cup 4020, 4022 toward the neck portion 4024. Consequently, the widest portion of the cups 4020, 4022 is at the proximal and distal ends 4010, 4012 of the pocket 4006b, respectively. The profile 4016 of the pocket 4006b defines a bow-tie shape perimeter. The widened region at the proximal and distal ends 4010, 4012 provides an enlarged footprint for receiving the tip of a staple leg. In various instances, the widened portions of the cups 4020, 4022 define extended landing zones for receiving the staple tips. As the cups 4020, 4022 narrow toward the neck portion 4024, the cups 4020, 4022 are configured to funnel and/or guide the tips of the staple legs toward and/or along the pocket axis PA and into a formed configuration.

The pocket 4006b defines a chamfered edge 4054 along the sides of the pocket 4006b. Additionally, the pocket 4006b includes a groove 4056 in the bottom surface 4058 thereof. The groove 4056 extends from the proximal cup 4020 over the bridge 4024 and into the distal cup 4022. The groove 4056 is configured to constrain and guide the staple legs as they move to the deformed configuration.

In various instances, the diameter of the groove 4056 can be less than the diameter of the staple engaged with the groove 4056. For example, a staple can have a diameter of at least 0.0079 inches, and the diameter of the groove 4056 can be less than 0.0079 inches. The diameter of the groove 4056 can be about 0.007 inches, about 0.005 inches, or less than 0.005 inches. In certain instances, the staple can have a diameter of more than 0.0079 inches, such as about 0.0089 inches or about 0.0094 inches, for example. In various instances, the diameter of the staple can be less than 0.0079 inches or more than 0.0094 inches. In end effectors in which different staple geometries are utilized with the same staple-forming pocket geometry, the width of the groove in the pocket can be less than the smallest diameter staple. In still other instances, the width of the groove 4056 can vary staple-to-staple within a row and/or row-to-row.

Referring again to FIG. 41, the pocket 4006b is symmetric about the pocket axis PA. For example, the perimeter 4016 of the pocket 4006b is symmetric about the pocket axis PA. Moreover, the pocket 4006b is symmetric about a central axis CA through the neck portion 4024 and perpendicular to the pocket axis PA. For example, the perimeter 4016 of the pocket 4006b is symmetric about the central axis CA, and the proximal cup 4020 has the same geometry as the distal cup 4022. In other instances, the proximal cup 4020 can be different than the distal cup 4022. For example, referring again to FIG. 42, the distal depth $D_2$ can be less than the proximal depth $D_1$ to accommodate for variations in gap distance between the anvil and the staple cartridge and/or tissue flow, as described herein.

Figure 41:
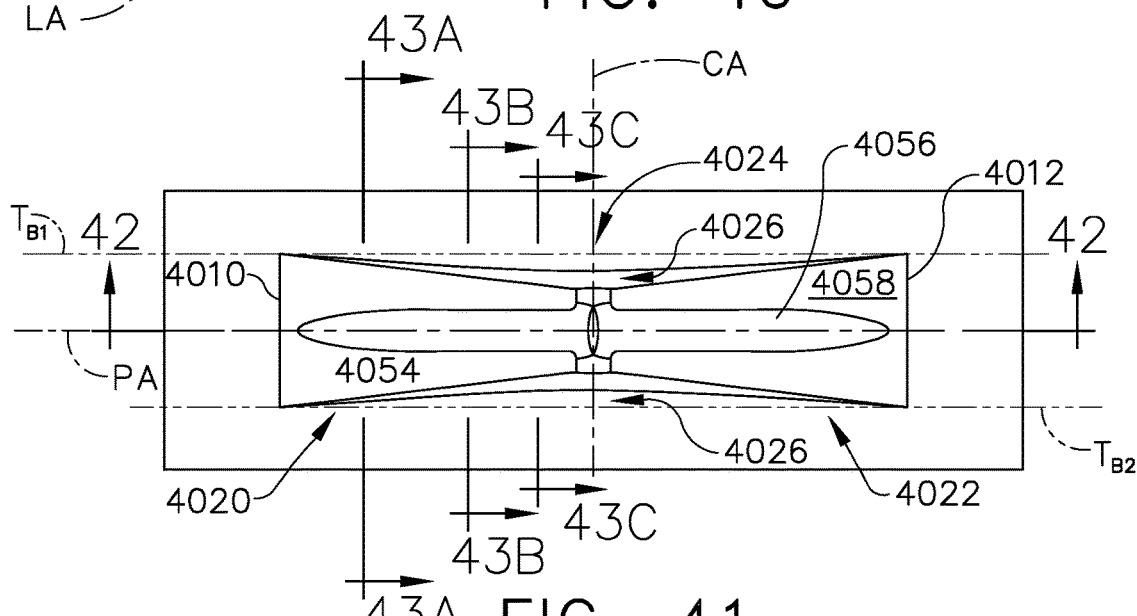
FIG. 41 is a detail view of a pocket of FIG. 40.

Referring again to FIG. 41, the neck portion 4024 of the pocket 4006b is narrower than the proximal and distal cups 4020 and 4022. The narrowed perimeter 4016 of the pocket 4006b defines a receiving peninsula 4026 between a portion of the proximal cup 4020 and a portion of the distal cup 4022. Owing to the symmetry of the pocket 4006b, symmetrical receiving peninsulas 4026 are positioned on each side of the pocket 4006b. The receiving peninsulas 4026 are bounded by the perimeter 4016 of the pocket 4006b and a tangent axis (e.g., $T_{B1}$ and $T_{B2}$), which is tangential to the widest portion of the proximal and distal cups 4020 and 4022 on a side of the pocket 4006b. A first tangent axis $T_{B1}$ is positioned on a first side of the pocket 4006b and a second tangent axis $T_{B2}$ is positioned on the opposite side of the pocket 4006b. The first and second tangent axes $T_{B1}$ and $T_{B2}$ depicted in FIG. 41 are parallel to the pocket axis PA.

Referring again to FIG. 40, each pocket 4006 extends toward the receiving peninsula 4026 of an adjacent pocket 4006. For example, the intermediate pockets 4006b are aligned with the neck portions 4024 of the inner pockets 4006a and the outer pockets 4006c. Moreover, the inner pockets 4006a and the outer pockets 4006b extend toward the receiving peninsula 4026 of one of the intermediate pockets 4006b. More specifically, the inner pockets 4006a are aligned with the neck portion 4024 of an adjacent intermediate pocket 4006b, and the outer pockets 4006c are aligned with the neck portion 4024 of an adjacent intermediate pocket 4006b. In certain instances, a portion of the pockets 4006 can extend into the receiving peninsula 4026 of an adjacent pocket 4006. Similar to the pockets 3906 in the anvil 3900, the geometry of the pockets 4006 facilitates the close arrangement of the pockets 4006 in the staple-forming surface 4002. The "forming ratio" is the ratio of the non-forming portion 4008 to the forming portion, i.e., the pockets 4006. In various instances, the forming ratio can be at least 1:1, for example.

Referring now to FIGS. 44-47C, staple-forming pockets 4106 in a portion of an anvil 4100 are depicted. The pockets 4106 and arrangement thereof in the anvil 4100 are similar in many aspects to the pockets 4006 and arrangement thereof in the anvil 4000. For example, the anvil 4100 includes a staple-forming surface 4102 and a longitudinal slot 4104. The longitudinal slot 4104 extends along the longitudinal axis LA of the anvil 4100. In certain instances, a firing element and/or cutting element can translate through the longitudinal slot 4104 during at least a portion of a firing stroke. Staple-forming pockets 4106 are defined in the staple-forming surface 4102. The staple-forming surface 4102 also includes a non-forming portion 4108 that extends around the pockets 4106. The non-forming portion 4108 extends entirely around each pocket 4106 in FIG. 41. In other words, the non-forming portion 4108 surrounds the staple-forming pockets 4106. In other instances, at least a portion of two or more adjacent pockets 4106 can be in abutting contact such that a non-forming portion 4108 is not positioned therebetween.

The forming ratio of the staple-forming surface 4102 can be optimized. By optimizing the forming ratio, more staples can be formed and/or formed to their desired configurations. In certain instances, the surface area of the non-forming portion 4108 of the anvil 4100 can be minimized with respect to the staple-forming pockets 4106. Additionally or alternatively, the footprint of the staple-forming pockets 4106 can be extended or enlarged to maximize the portion of the staple-forming surface 4102 that is designed to catch and form the staples.

Figure 44:
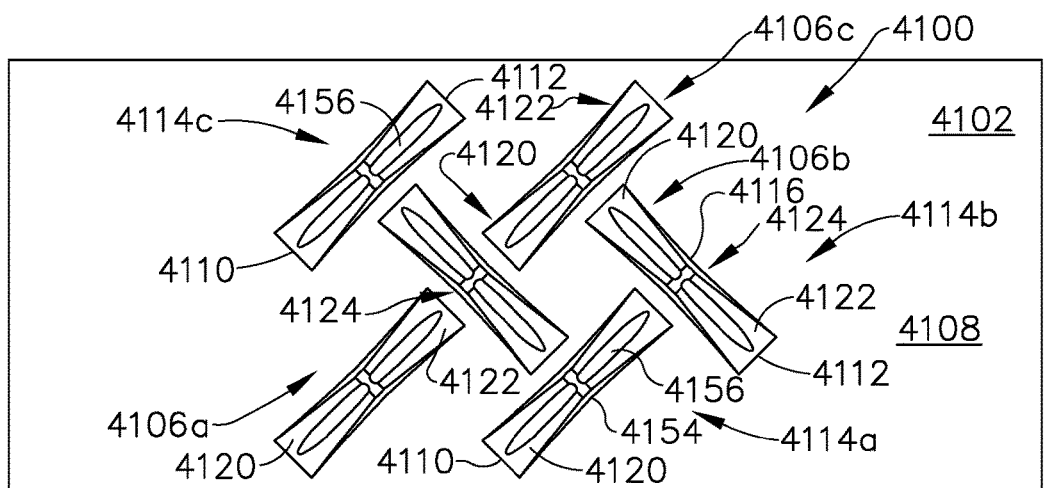
FIG. 44 is a plan view of a portion of an anvil having a plurality of staple-forming pockets defined therein.

The pockets 4106 depicted in FIG. 44 are arranged in an inner row 4114a, an intermediate row 4114b, and an outer row 4114c on a first side of the longitudinal slot 4104. Inner pockets 4106a are positioned in the inner row 4114a, intermediate pockets 4106b are positioned in the intermediate row 4114b, and outer pockets 4106c are positioned in the outer row 4114c. Similar to the anvil 3800, the pockets 4106 are arranged in a herringbone arrangement along the staple-forming surface 4102 of the anvil 4100. Although not shown in FIG. 44, in at least one instance, the pockets 4106 on the opposing side of the slot 4104 can form a mirror image reflection of the pockets 4106 on the first side of the longitudinal slot 4104. In other instances, the arrangement of pockets 4106 in the staple-forming surface 4102 can be asymmetrical relative to the slot 4104 and, in certain instances, the anvil 4100 may not include the longitudinal slot 4104. In various instances, the pockets 4106 can be arranged in less than or more than three rows on each side of the slot 4104.

The pockets 4106 depicted in FIG. 44 are identical. Each pocket 4106 defined in the staple-forming surface 4102 has the same geometry. In other instances, the geometry of the pockets 4106 can vary row-to-row and/or longitudinally along the length of the anvil 4100. For example, in certain instances, the depth of the pockets 4106 or portions thereof can vary along the length of the anvil 4100 to accommodate for variations in gap distance between the anvil and the staple cartridge along the length of an end effector and/or tissue flow, as described herein.

An exemplary pocket 4106b is shown in FIGS. 45-47C. The pocket 4106b has a first end, or proximal end, 4110 and a second end, or distal end, 4112. A pocket axis PA (FIG. 45) extends between the proximal end 4110 and the distal end 4112 of the pocket 4106b. The pocket 4106b includes a perimeter 4116, which defines the boundary of the pocket 4106b. The pocket 4106 also includes a proximal cup 4120, a distal cup 4122, and a neck portion 4124 connecting the proximal cup 4120 and the distal cup 4122. When a staple is driven into forming contact with the staple-forming surface 4102, the proximal cup 4120 is aligned with a proximal staple leg, and the distal cup 4122 is aligned with a distal staple leg. The cups 4120, 4122 are configured to direct or funnel the staple legs toward the pocket axis PA and a central portion of the pocket 4106, such as the neck portion 4124, and to deform the staple legs into the formed configuration.

Figure 46:
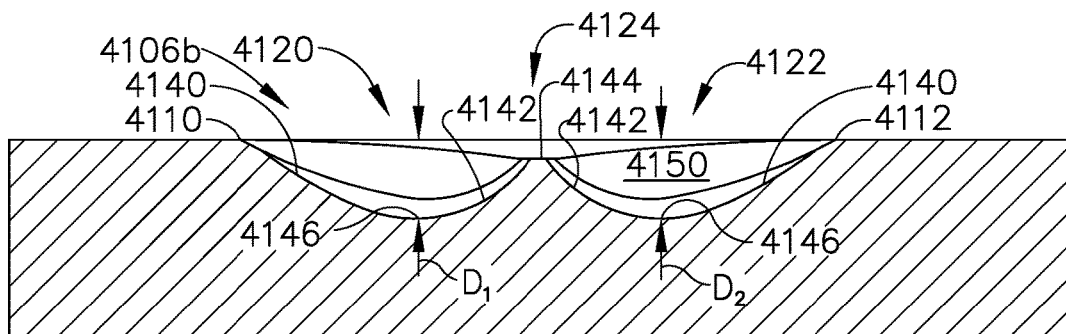
FIGS. 46-47C are cross-sectional views of the pocket of FIG. 45.

Referring primarily to FIG. 46, each cup 4120, 4122 of the pocket 4106b defines an entrance ramp 4140 and an exit ramp 4142. The exit ramp 4142 is steeper than the entrance ramp 4140. When forming a staple, the tip of a staple leg can enter the respective cup 4120, 4122 along the entrance ramp 4140 and exit the respective cup 4120, 4122 along the exit ramp 4142. At an apex 4146 between the entrance ramp 4140 and the exit ramp 4142, the tips of the staple legs are deformed toward the staple base to assume the formed configuration, such as a B-form or modified B-form, for example. The pocket 4106b also defines a bridge 4144 in the neck portion 4124 between the proximal cup 4120 and the distal cup 4122. The bridge 4144 is offset from the non-forming portion 4108. More specifically, the bridge 4144 is positioned below or recessed relative to the non-forming portion 4108.

Figure 47C:
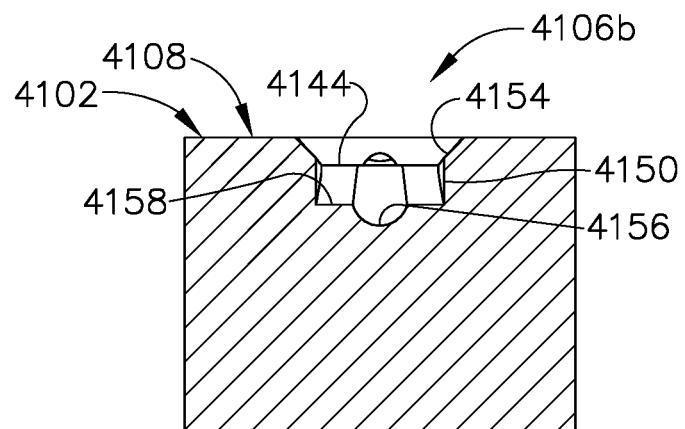
Figure 47B:
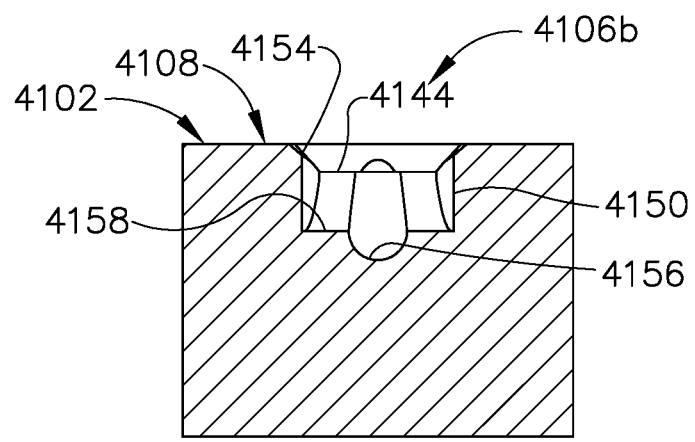
Figure 47A:
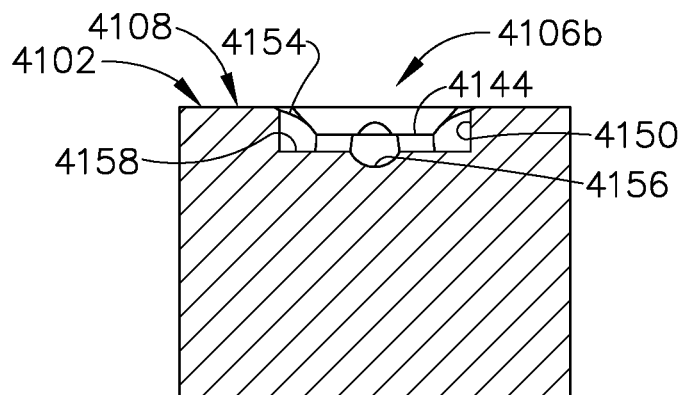

Referring primarily to FIGS. 47A-47C, the pocket 4106b includes sidewalls 4150, which are oriented perpendicular to the non-forming portion 4108 of the staple-forming surface 4102. The sidewalls 4150 narrow from the outer ends of each cup 4120, 4122 toward the neck portion 4124. Consequently, the widest portion of the cups 4120 and 4122 is at the proximal and distal ends 4110 and 4112, respectively, of the pocket 4106b. The profile 4116 of the pocket 4106b defines a bow-tie shape perimeter. The widened region at the proximal and distal ends 4110, 4112 provides an enlarged footprint for receiving the tip of a staple leg. In various instances, the widened portions of the cups 4120, 4122 define extended landing zones for receiving the staple tips. As the cups 4120, 4122 narrow toward the neck portion 4124, the cups 4120, 4122 are configured to funnel and/or guide the tips of the staple legs toward and/or along the pocket axis PA and into a formed configuration.

Referring again to FIG. 47A-47C, the pocket 4106b defines a chamfered edge 4154 along the sides of the pocket 4106b. Additionally, the pocket 4106b includes a groove 4156 in the bottom surface 4158 thereof. The groove 4156 is defined in the proximal cup 4120 and the distal cup 4122. In the depicted embodiment, the groove 4156 does not extend across the bridge 4144 of the pocket 4106b. The groove 4156 is configured to constrain and guide the staple legs as they move to the deformed configuration. For example, the staple legs can slide through the groove 4156 as the staples move along at least a portion of the entrance ramp 4140 and the exit ramp 4142. In various instances, the diameter of the groove 4156 can be less than the diameter of the staple engaged with the groove 4156. In end effectors in which different staple geometries are utilized with the same staple-forming pocket geometry, the width of the groove in the pocket can be less than the smallest diameter staple. In various instances, the staple legs are deformed toward the staple base before reaching the bridge 4144 and, thus, do not engage the bridge 4144 of the pocket 4106b.

Referring again to FIG. 45, the pocket 4106b is symmetric about the pocket axis PA. For example, the perimeter 4116 of the pocket 4106b is symmetric about the pocket axis PA. Moreover, the pocket 4106b is symmetric about a central axis CA through the neck portion 4124 and perpendicular to the pocket axis PA. For example, the perimeter 4116 of the pocket 4106b is symmetric about the central axis CA, and the proximal cup 4120 has the same geometry as the distal cup 4122. In other instances, the proximal cup 4120 can be different than the distal cup 4122. For example, referring again to FIG. 42, the distal depth $D_2$ can be less than the proximal depth $D_1$ to accommodate for variations in gap distance between the anvil and the staple cartridge and/or tissue flow, as described herein.

Figure 45:
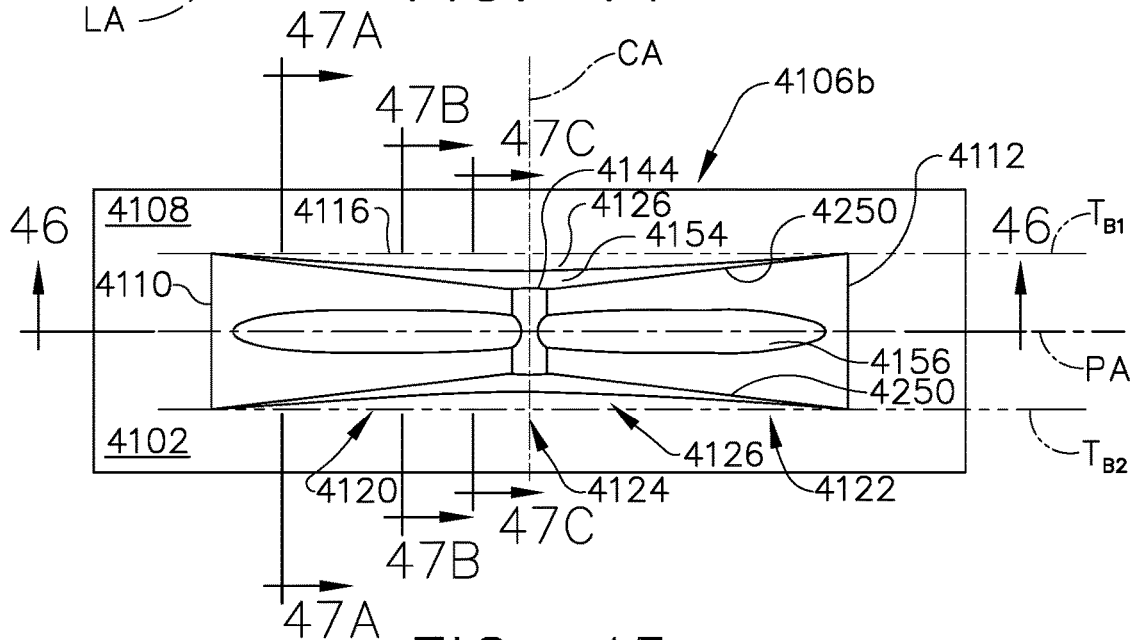
FIG. 45 is a detail view of a pocket of FIG. 44.

Referring again to FIG. 45, the neck portion 4124 of the pocket 4106b is narrower than the proximal and distal cups 4120 and 4122. The narrowed perimeter 4116 of the pocket 4106b defines a receiving peninsula 4126 between a portion of the proximal cup 4120 and a portion of the distal cup 4122. Owing to the symmetry of the pocket 4106b, symmetrical receiving peninsulas 4126 are positioned on each side of the pocket 4106b. The receiving peninsulas 4126 are bounded by the perimeter 4116 of the pocket 4106b and a tangent axis (e.g., $T_{B1}$ and $T_{B2}$), which is tangential to the widest portion of the proximal and distal cups 4120 and 4122 on a side of the pocket 4106b. A first tangent axis $T_{B1}$ is positioned on a first side of the pocket 4106b and a second tangent axis $T_{B2}$ is positioned on the opposite side of the pocket 4106b. The first and second tangent axes $T_{B1}$ and $T_{B2}$ depicted in FIG. 45 are parallel to the pocket axis PA.

Referring again to FIG. 44, each pocket 4106 extends toward the receiving peninsula 4126 of an adjacent pocket 4106. For example, the intermediate pockets 4106b are aligned with the neck portion 4124 of the inner pockets 4106a and the outer pockets 4106c. Moreover, the inner pockets 4106a and the outer pockets 4106b extend toward the receiving peninsula 4126 of one of the intermediate pockets 4106b. More specifically, the inner pockets 4106a are aligned with the neck portion 4124 of an adjacent intermediate pocket 4106b, and the outer pockets 4106c are aligned with the neck portion 4124 of an adjacent intermediate pocket 4106b. In certain instances, a portion of the pockets 4106 can extend into the receiving peninsula 4126 of an adjacent pocket 4106. Similar to the pockets 3906 in the anvil 3900, the geometry of the pockets 4106 facilitates the close arrangement of the pockets 4106 in the staple-forming surface 4102. The "forming ratio" is the ratio of the non-forming portion 4108 to the forming portion, i.e., the pockets 4106. In various instances, the forming ratio can be at least 1:1, for example.

Referring now to FIGS. 48-51C, staple-forming pockets 4206 in a portion of an anvil 4200 are depicted. The pockets 4206 and arrangement thereof in the anvil 4200 are similar in many aspects to the pockets 4106 and arrangement thereof in the anvil 4100. For example, the anvil 4200 includes a staple-forming surface 4202 and a longitudinal slot 4204. The longitudinal slot 4204 extends along the longitudinal axis LA of the anvil 4200. In certain instances, a firing element and/or cutting element can translate through the longitudinal slot 4204 during at least a portion of a firing stroke. The staple-forming pockets 4206 are defined in the staple-forming surface 4202. The staple-forming surface 4202 also includes a non-forming portion 4208 that extends around the pockets 4206. The non-forming portion 4208 extends entirely around each pocket 4206 in FIG. 48. In other words, the non-forming portion 4208 surrounds the staple-forming pockets 4206. In other instances, at least a portion of two or more adjacent pockets 4206 can be in abutting contact such that a non-forming portion 4208 is not positioned therebetween.

The forming ratio of the staple-forming surface 4202 can be optimized. By optimizing the forming ratio, more staples can be formed and/or formed to their desired configurations. In certain instances, the surface area of the non-forming portion 4208 of the anvil 4200 can be minimized with respect to the staple-forming pockets 4206. Additionally or alternatively, the footprint of the staple-forming pockets 4206 can be extended or enlarged to maximize the portion of the staple-forming surface 4202 that is designed to catch and form the staples.

Figure 48:
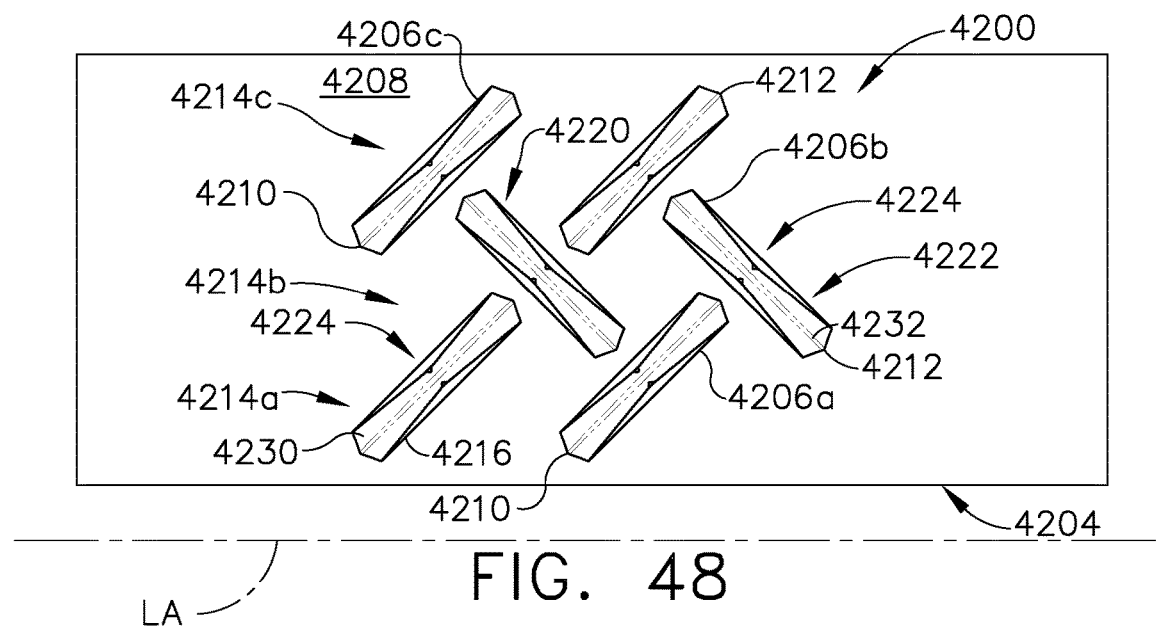
FIG. 48 is a plan view of a portion of an anvil having a plurality of staple-forming pockets defined therein.

The pockets 4206 depicted in FIG. 48 are arranged in an inner row 4214a, an intermediate row 4214b, and an outer row 4214c on a first side of the longitudinal slot 4204. Inner pockets 4206a are positioned in the inner row 4214a, intermediate pockets 4206b are positioned in the intermediate row 4214b, and outer pockets 4206c are positioned in the outer row 4214c. Similar to the anvil 3800, the pockets 4206 are arranged in a herringbone arrangement along the staple-forming surface 4202 of the anvil 4200. Although not shown in FIG. 48, in at least one instance, the pockets 4206 on the opposing side of the slot 4204 can form a mirror image reflection of the pockets 4206 on the first side of the longitudinal slot 4204. In other instances, the arrangement of pockets 4206 in the staple-forming surface 4202 can be asymmetrical relative to the slot 4204 and, in certain instances, the anvil 4200 may not include the longitudinal slot 4204. In various instances, the pockets 4206 can be arranged in less than or more than three rows on each side of the slot 4204.

The pockets 4206 depicted in FIG. 48 are identical. Each pocket 4206 defined in the staple-forming surface 4202 has the same geometry. In other instances, the geometry of the pockets 4206 can vary row-to-row and/or longitudinally along the length of the anvil 4200. For example, in certain instances, the depth of the pockets 4206 or portions thereof can vary along the length of the anvil 4200 to accommodate for variations in gap distance between the anvil and the staple cartridge along the length of an end effector and/or tissue flow, as described herein.

An exemplary pocket 4206b is shown in FIGS. 49-51C. The pocket 4206b has a first end, or proximal end, 4210 and a second end, or distal end, 4212. A pocket axis PA (FIG. 49) extends between the proximal end 4210 and the distal end 4212 of each pocket 4206. The pocket 4206b includes a perimeter 4216, which defines the boundary of the pocket 4206b. The pocket 4206b also includes a proximal cup 4220, a distal cup 4222, and a neck portion 4224 connecting the proximal cup 4220 and the distal cup 4222. When a staple is driven into forming contact with the staple-forming surface 4202, the proximal cup 4220 is aligned with a proximal staple leg, and the distal cup 4222 is aligned with a distal staple leg. The cups 4220, 4222 are configured to direct or funnel the staple legs toward the pocket axis PA and a central portion of the pocket 4206, such as the neck portion 4224, and to deform the staple legs into the formed configuration.

Figure 50:
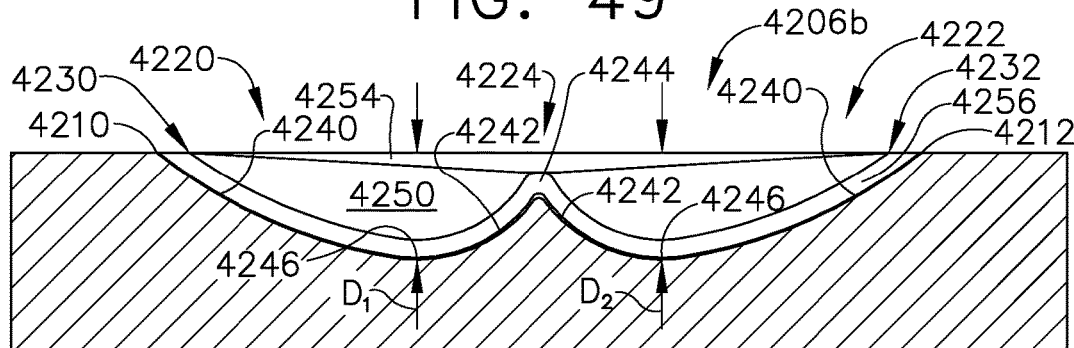
FIGS. 50-51C are cross-sectional views of the pocket of FIG. 49.

Referring primarily to FIG. 50, each cup 4220, 4222 of the pocket 4206b defines an entrance ramp 4240 and an exit ramp 4242. The exit ramp 4242 is steeper than the entrance ramp 4240. When forming a staple, the tip of a staple leg can enter the respective cup 4220, 4222 along the entrance ramp 4240 and exit the respective cup 4220, 4222 along the exit ramp 4242. At an apex 4246 between the entrance ramp 4240 and the exit ramp 4242, the tips of the staple legs are deformed toward the staple base to assume the formed configuration, such as a B-form or modified B-form, for example. The pocket 4206b also defines a bridge 4244 between the proximal cup 4220 and the distal cup 4222. The bridge 4244 is offset from the non-forming portion 4208. More specifically, the bridge 4244 is positioned below or recessed relative to the non-forming portion 4208.

Figure 51C:
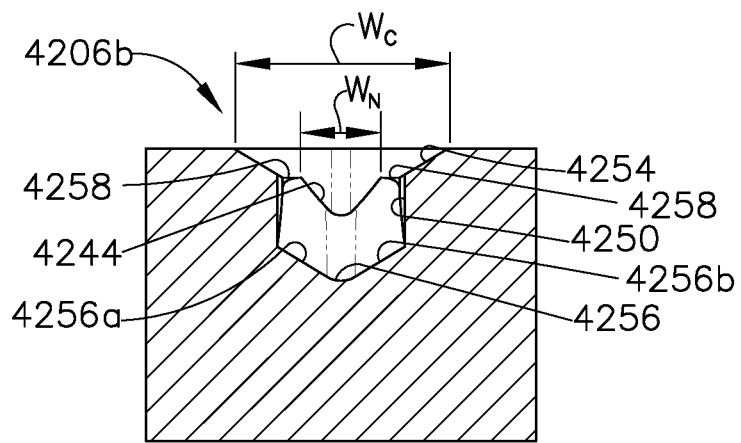
Figure 51B:
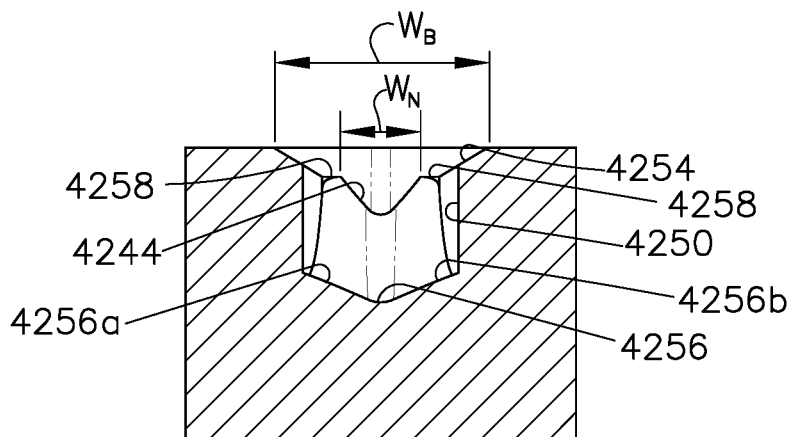
Figure 51A:
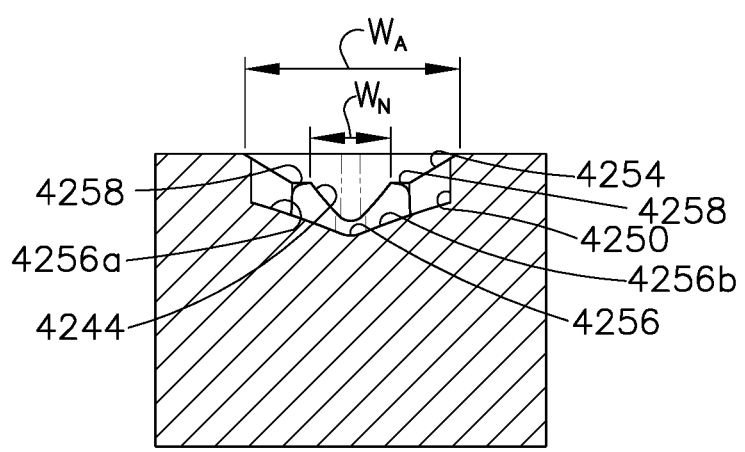

Referring primarily to FIGS. 51A-51C, the pocket 4206b includes sidewalls 4250, which are oriented perpendicular to the non-forming portion 4208 of the staple-forming surface 4202. The sidewalls 4250 narrow toward the neck portion 4224. Consequently, the widest portion of the cups 4220, 4222 is at the proximal and distal ends of the sidewalls 4250. The widened region provides an enlarged footprint for receiving the tip of a staple leg. As the cups 4220, 4222 narrow toward the neck portion 4224, the cups 4220, 4222 are configured to funnel and/or guide the tips of the staple legs toward and/or along the pocket axis PA and into a formed configuration.

The cups 4220, 4222 also include extended landing zones 4230, 4232, respectively, which further enlarge the footprint of the cups 4220, 4222. The proximal extended landing zone 4230 extends proximally along the pocket axis PA, and the distal extended landing zone 4232 extends distally along the pocket axis PA. In the pocket 4206b, the extended landing zones 4230 and 4232 define a substantially triangular perimeter. Moreover, the extended landing zones 4230 and 4232 terminate along the respective pocket axis PA at a corner. In other instances, the extended landing zones 4230 and 4232 can define straight or contoured perimeters, for example, and can extend laterally and/or longitudinally from the cups 4220 and 4222, for example.

Figure 49:
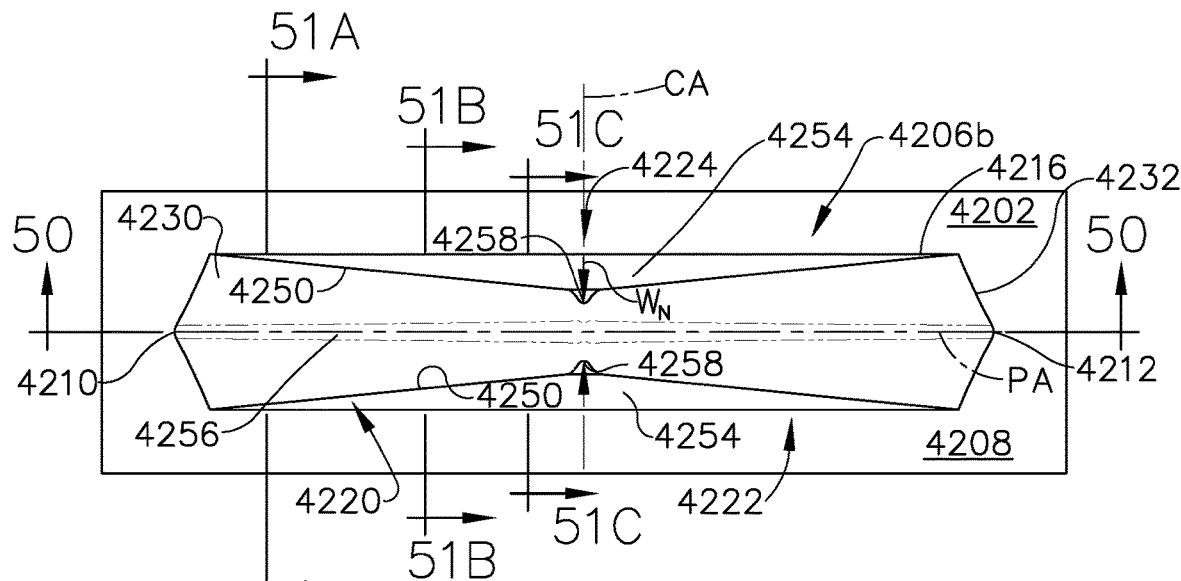
FIG. 49 is a detail view of a pocket of FIG. 48.

Additionally, the pocket 4206b includes a trough 4256 in the bottom surface thereof. The trough 4256 is configured to constrain and guide the staple legs as they move to the deformed configuration. In the depicted embodiment, the trough 4256 spans between the sidewalls 4250 and defines the entire bottom surface of the pocket 4206b. The trough 4256 extends from the proximal cup 4220 over the bridge 4224 and into the distal cup 4222. In other instances, the trough 4256 may not extend across the bridge 4244 of the pocket 4206b. The trough 4256 includes two ramped surfaces 4256a and 4256b that extend downward away from the non-forming portion 4208 and meet along the pocket axis PA (FIG. 49). As depicted in FIGS. 51A-51C, the trough 4256 defines a steeper gradient along the bridge 4244 than in the cups 4220, 4222. In other instances, the gradient can be uniform along the length of the trough 4256 and/or can be steeper in the cups 4220, 4222 than along the bridge 4244, for example.

Still referring to FIGS. 51A-51C, the pocket 4206b also defines a chamfered edge 4254 along the sides of the pocket 4206b. In the pocket 4206b, the chamfered edge 4254 defines the overall width of the pocket 4206b. The overall width of the pocket 4206b is uniform. For example, the width $W_A$ (FIG. 51A) is equal to the width $W_B$ (FIG. 51B) and the width $W_C$ (FIG. 51C). In other instances, the widths $W_A$, $W_B$, and/or $W_C$ may not be equal. Because the sidewalls 4250 narrow toward the neck portion 4224, the width of the chamfered edge 4254 correspondingly expands toward the neck portion 4224 to maintain the same overall pocket width. The pocket 4206b also includes projections or knobs 4258 which extend toward the pocket axis PA at the neck portion 4224 of the pocket 4206b. The knobs 4258 further narrow the neck portion 4224 to a width $W_N$. The trough 4256 spans the bottom surface of the neck portion 4224 across the width $W_N$.

Referring again to FIG. 49, the pocket 4206b is symmetric about the pocket axis PA. For example, the perimeter 4216 of the pocket 4206b is symmetric about the pocket axis PA. Moreover, the pocket 4206b is symmetric about a central axis CA through the neck portion 4224 and perpendicular to the pocket axis PA. For example, the perimeter 4216 of the pocket 4206b is symmetric about the central axis CA, and the proximal cup 4220 has the same geometry as the distal cup 4222. In other instances, the proximal cup 4220 can be different than the distal cup 4222. For example, referring again to FIG. 50, the distal depth $D_2$ can be less than the proximal depth $D_1$ to accommodate for variations in gap distance between the anvil and the staple cartridge and/or tissue flow, as described herein.

Referring again to FIG. 48, each pocket 4206 extends toward the neck portion 4224 of an adjacent pocket 4206. For example, the intermediate pockets 4206b are aligned with the neck portions 4224 of the inner pockets 4206a and the outer pockets 4206c. More specifically, the proximal landing zones 4230 of the intermediate pockets 4206b are aligned with the neck portion 4224 of an adjacent outer staple 4206c, and the distal landing zones 4232 of the intermediate pockets 4206b are aligned with the neck portion 4224 of an adjacent inner staple 4206a. Moreover, the inner pockets 4206a and the outer pockets 4206b extend toward the neck portion 4224 of one of the intermediate pockets 4206b. More specifically, the distal landing zones 4232 of the inner pockets 4206a are aligned with the neck portion 4224 of an adjacent intermediate pocket 4206b, and the proximal landing zones 4230 of the outer pockets 4206c are aligned with the neck portion 4224 of an adjacent intermediate pocket 4206b.

Referring now to FIGS. 52-55C, staple-forming pockets 4306 in a portion of an anvil 4300 are depicted. The pockets 4306 and arrangement thereof in the anvil 4300 are similar in many aspects to the pockets 3906 and arrangement thereof in the anvil 3900. For example, the anvil 4300 includes a staple-forming surface 4302 and a longitudinal slot 4304. The longitudinal slot 4304 extends along the longitudinal axis LA of the anvil 4300. In certain instances, a firing element and/or cutting element can translate through the longitudinal slot 4304 during at least a portion of a firing stroke. The staple-forming pockets 4306 are defined in the staple-forming surface 4302. The staple-forming surface 4302 also includes a non-forming portion 4308 that extends around the pockets 4306. The non-forming portion 4308 extends entirely around each pocket 4306 in FIG. 52. In other words, the non-forming portion 4308 surrounds the staple-forming pockets 4306. In other instances, at least a portion of two or more adjacent pockets 4306 can be in abutting contact such that a non-forming portion 4308 is not positioned therebetween.

The forming ratio of the staple-forming surface 4302 can be optimized. By optimizing the forming ratio, more staples can be formed and/or formed to their desired configurations. In certain instances, the surface area of the non-forming portion 4308 of the anvil 4300 can be minimized with respect to the staple-forming pockets 4306. Additionally or alternatively, the footprint of the staple-forming pockets 4306 can be extended or enlarged to maximize the portion of the staple-forming surface 4302 that is designed to catch and form the staples.

Figure 52:
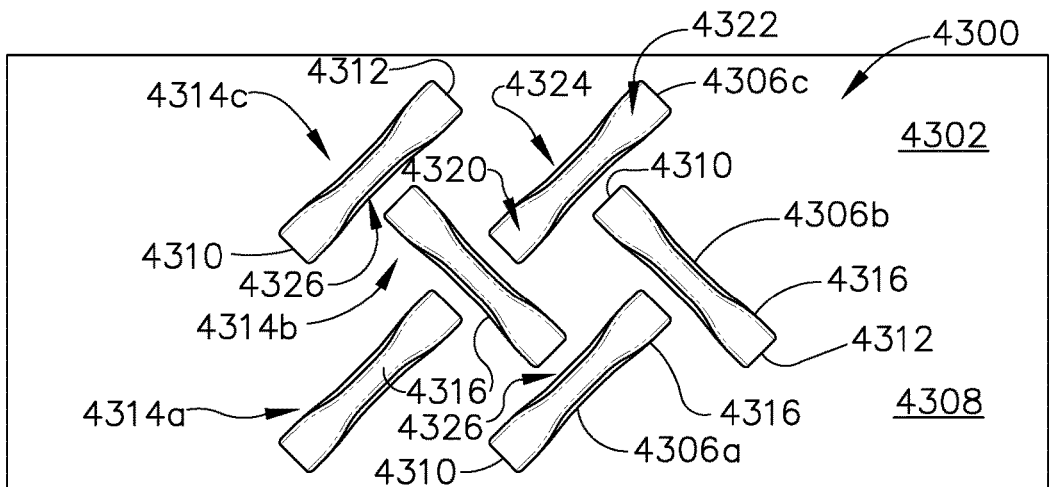
FIG. 52 is a plan view of a portion of an anvil having a plurality of staple-forming pockets defined therein.

The pockets 4306 depicted in FIG. 52 are arranged in an inner row 4314a, an intermediate row 4314b, and an outer row 4314c on a first side of the longitudinal slot 4304. Inner pockets 4306a are positioned in the inner row 4314a, intermediate pockets 4306b are positioned in the intermediate row 4314b, and outer pockets 4306c are positioned in the outer row 4314c. Similar to the anvil 3800, the pockets 4306 are arranged in a herringbone arrangement along the staple-forming surface 4302 of the anvil 4300. Although not shown in FIG. 52, in at least one instance, the pockets 4306 on the opposing side of the slot 4304 can form a mirror image reflection of the pockets 4306 on the first side of the longitudinal slot 4304. In other instances, the arrangement of pockets 4306 in the staple-forming surface 4302 can be asymmetrical relative to the slot 4304 and, in certain instances, the anvil 4300 may not include the longitudinal slot 4304. In various instances, the pockets 4306 can be arranged in less than or more than three rows on each side of the slot 4304.

The pockets 4306 depicted in FIG. 52 are identical. Each pocket 4306 defined in the staple-forming surface 4302 has the same geometry. In other instances, the geometry of the pockets 4306 can vary row-to-row and/or longitudinally along the length of the anvil 4300. For example, in certain instances, the depth of the pockets 4306 or portions thereof can vary along the length of the anvil 4300 to accommodate for variations in gap distance between the anvil and the staple cartridge along the length of an end effector and/or tissue flow, as described herein.

An exemplary pocket 4306b is shown in FIGS. 53-55C. The pocket 4306b has a first end, or proximal end, 4310 and a second end, or distal end, 4312. A pocket axis PA (FIG. 53) extends between the proximal end 4310 and the distal end 4312 of the pocket 4306b. The pocket 4306b includes a perimeter 4316, which defines the boundary of the pocket 4306b. The perimeter 4316 includes rounded corners at the proximal and distal ends of the pockets 4306. The pocket 4306b also includes a proximal cup 4320, a distal cup 4322, and a neck portion 4324 connecting the proximal cup 4320 and the distal cup 4322. When a staple is driven into forming contact with the staple-forming surface 4302, the proximal cup 4320 is aligned with a proximal staple leg, and the distal cup 4322 is aligned with a distal staple leg. The cups 4320, 4322 are configured to direct or funnel the staple legs toward the pocket axis PA and a central portion of the pocket 4306, such as the neck portion 4324, and to deform the staple legs into the formed configuration.

Figure 54:
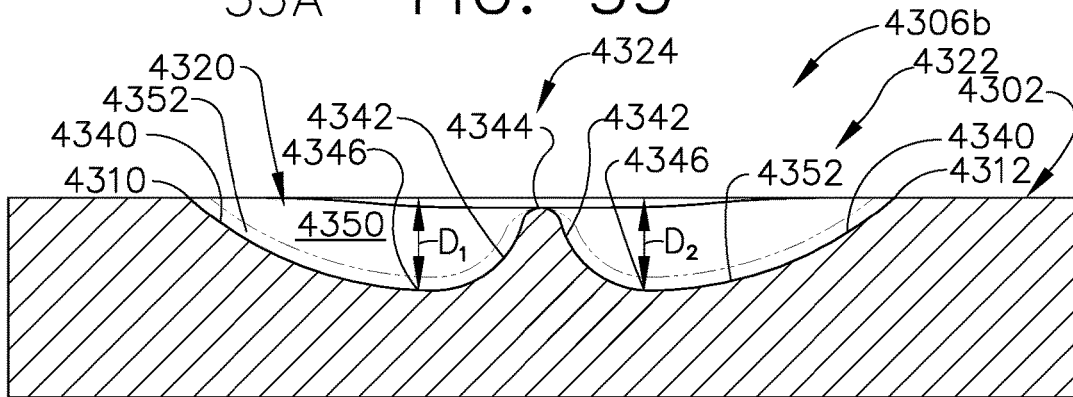
FIGS. 54-55C are cross-sectional views of the pocket of FIG. 53.

Referring primarily to FIG. 54, each cup 4320, 4322 of the pocket 4306b defines an entrance ramp 4340 and an exit ramp 4342. The exit ramp 4342 is steeper than the entrance ramp 4340. When forming a staple, the tip of a staple leg can enter the respective cup 4320, 4322 along the entrance ramp 4340 and exit the respective cup 4320, 4322 along the exit ramp 4342. At an apex 4346 between the entrance ramp 4340 and the exit ramp 4342, the tips of the staple legs are deformed toward the staple base to assume the formed configuration, such as a B-form or modified B-form, for example. The pocket 4306b also defines a bridge 4344 between the proximal cup 4320 and the distal cup 4322. The bridge 4344 is offset from the non-forming portion 4308. More specifically, the bridge 4344 is positioned below or recessed relative to the non-forming portion 4308.

Figure 55C:
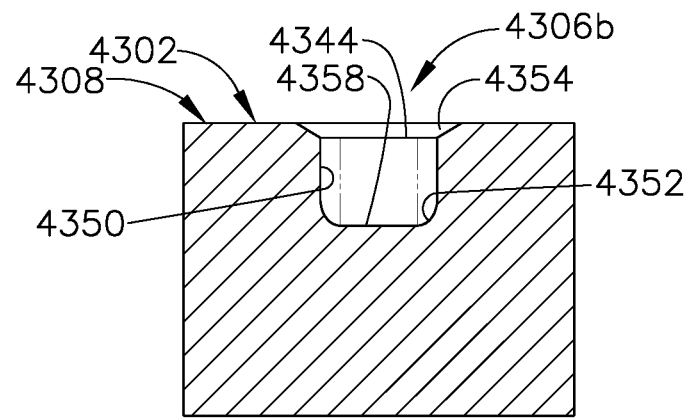
Figure 55B:
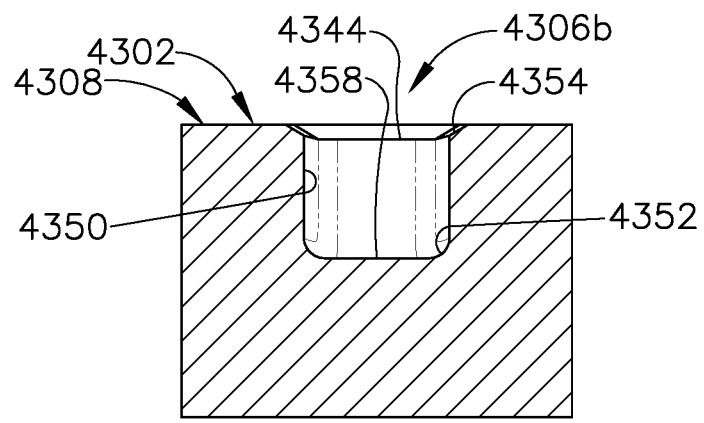
Figure 55A:
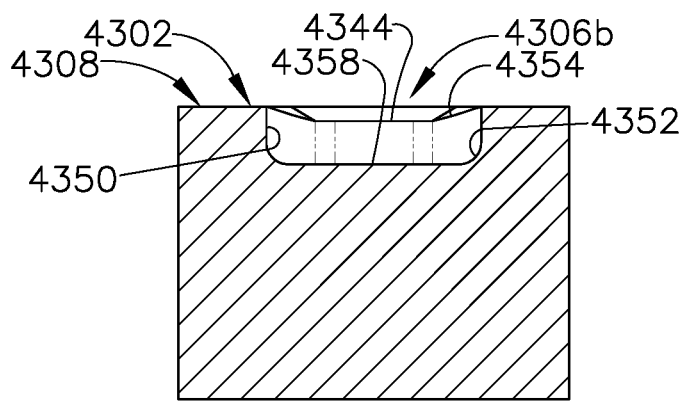

Referring primarily to FIGS. 55A-55C, the pocket 4306b includes sidewalls 4350, which are oriented perpendicular to the non-forming portion 4308 of the staple-forming surface 4302. The sidewalls 4350 narrow between the outer ends of each cup 4320, 4322 and the neck portion 4324. More specifically, the sidewalls 4350 extend along an inward contour to define a contour in the perimeter 4316 of the pocket 4306b. The widest portion of the cups 4320, 4322 is at the proximal and distal ends of the sidewalls 4350. The widened region provides an enlarged footprint for receiving the tip of a staple leg. As the cups 4320, 4322 narrow toward the neck portion 4324, the cups 4320, 4322 are configured to funnel and/or guide the tips of the staple legs toward and/or along the pocket axis PA and into a formed configuration.

The pocket 4306b defines a chamfered edge 4354 along the sides of the pocket 4306b. In the pocket 4306b, the chamfered edge 4354 defines the overall width of the pocket 4306b, which narrows toward the neck portion 4324. The pocket 4306b also defines a fillet 4352 (FIGS. 55A-55C) between the sidewalls 4350 and the bottom surface 4358 the pocket 4306b. The fillets 4352 are configured to guide the staple legs along the desired path in the pocket 4306b. For example, if a staple leg lands along the chamfer 4352, the fillet corner 4352 can smoothly guide the staple leg toward the pocket axis PA.

Referring again to FIG. 53, the pocket 4306b is symmetric about the pocket axis PA. For example, the perimeter 4316 of the pocket 4306b is symmetric about the pocket axis PA. Moreover, the pocket 4306b is symmetric about a central axis CA through the neck portion 4324 and perpendicular to the pocket axis PA. For example, the perimeter 4316 of the pocket 4306b is symmetric about the central axis CA, and the proximal cup 4320 has the same geometry as the distal cup 4322. In other instances, the proximal cup 4320 can be different than the distal cup 4322. For example, referring again to FIG. 54, the distal depth $D_2$ can be less than the proximal depth $D_1$ to accommodate for variations in gap distance between the anvil and the staple cartridge and/or tissue flow, as described herein.

Figure 53:
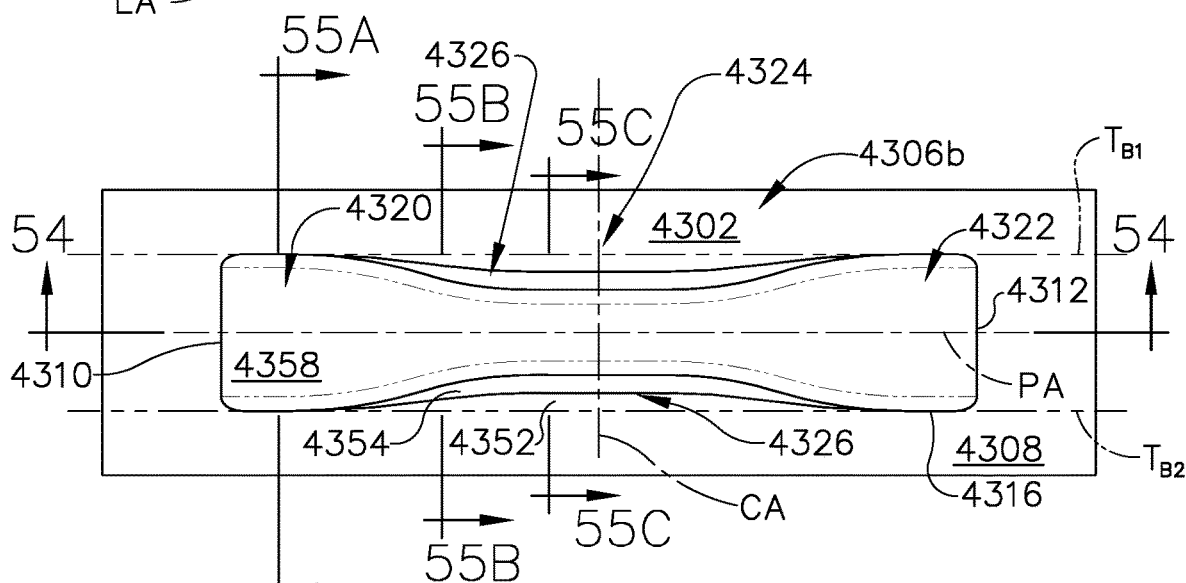
FIG. 53 is a detail view of a pocket of FIG. 52.

Referring again to FIG. 53, the neck portion 4324 of the pocket 4306b is narrower than the proximal and distal cups 4320 and 4322. The narrowed perimeter 4316 of the pocket 4306b defines a receiving peninsula 4326 between a portion of the proximal cup 4320 and a portion of the distal cup 4322. Owing to the symmetry of the pocket 4306b, symmetrical receiving peninsulas 4326 are positioned on each side of the pocket 4306b. The receiving peninsulas 4326 are bounded by the perimeter 4316 of the pocket 4306b and a tangent axis (e.g., $T_{B1}$ and $T_{B2}$), which is tangential to the widest portion of the proximal and distal cups 4320 and 4322 on a side of the pocket 4306b. A first tangent axis $T_{B1}$ is positioned on a first side of the pocket 4306b and a second tangent axis $T_{B2}$ is positioned on the opposite side of the pocket 4306b. The first and second tangent axes $T_{B1}$ and $T_{B2}$ depicted in FIG. 53 are parallel to the pocket axis PA.

Referring again to FIG. 52, each pocket 4306 extends toward the receiving peninsula 4326 of an adjacent pocket 4306. For example, the intermediate pockets 4306b are aligned with the neck portions 4324 of the inner pockets 4306a and the outer pockets 4306c. Moreover, the inner pockets 4306a and the outer pockets 4306b extend toward the receiving peninsula 4326 of one of the intermediate pockets 4306b. More specifically, the inner pockets 4306a are aligned with the neck portion 4324 of an adjacent intermediate pocket 4306b, and the outer pockets 4306c are aligned with the neck portion 4324 of an adjacent intermediate pocket 4306b. In certain instances, a portion of the pockets 4306 can extend into the receiving peninsula 4326 of an adjacent pocket 4306. Similar to the pockets 3906 in the anvil 3900, the geometry of the pockets 4306 facilitates the close arrangement of the pockets 4306 in the staple-forming surface 4302. The "forming ratio" is the ratio of the non-forming portion 4308 to the forming portion, i.e., the pockets 4306. In at least one instance, the forming ratio can be at least 1:1, for example.

Referring now to FIGS. 56-59C, staple-forming pockets 4406 in a portion of an anvil 4400 are depicted. The pockets 4406 and arrangement thereof in the anvil 4400 are similar in many aspects to the pockets 4306 and arrangement thereof in the anvil 4300. For example, the anvil 4400 includes a staple-forming surface 4402 and a longitudinal slot 4404. The longitudinal slot 4404 extends along the longitudinal axis LA of the anvil 4400. In certain instances, a firing element and/or cutting element can translate through the longitudinal slot 4404 during at least a portion of a firing stroke. The staple-forming pockets 4406 are defined in the staple-forming surface 4402. The staple-forming surface 4402 also includes a non-forming portion 4408 that extends around the pockets 4406. The non-forming portion 4408 extends entirely around each pocket 4406 in FIG. 56. In other words, the non-forming portion 4408 surrounds the staple-forming pockets 4406. In other instances, at least a portion of two or more adjacent pockets 4406 can be in abutting contact such that a non-forming portion 4408 is not positioned therebetween. Additionally, the non-forming portion 4406 extends through each pocket 4406, as described herein.

The forming ratio of the staple-forming surface 4402 can be optimized. By optimizing the forming ratio, more staples can be formed and/or formed to their desired configurations. In certain instances, the surface area of the non-forming portion 4408 of the anvil 4400 can be minimized with respect to the staple-forming pockets 4406. Additionally or alternatively, the footprint of the staple-forming pockets 4406 can be extended or enlarged to maximize the portion of the staple-forming surface 4402 that is designed to catch and form the staples.

Figure 56:
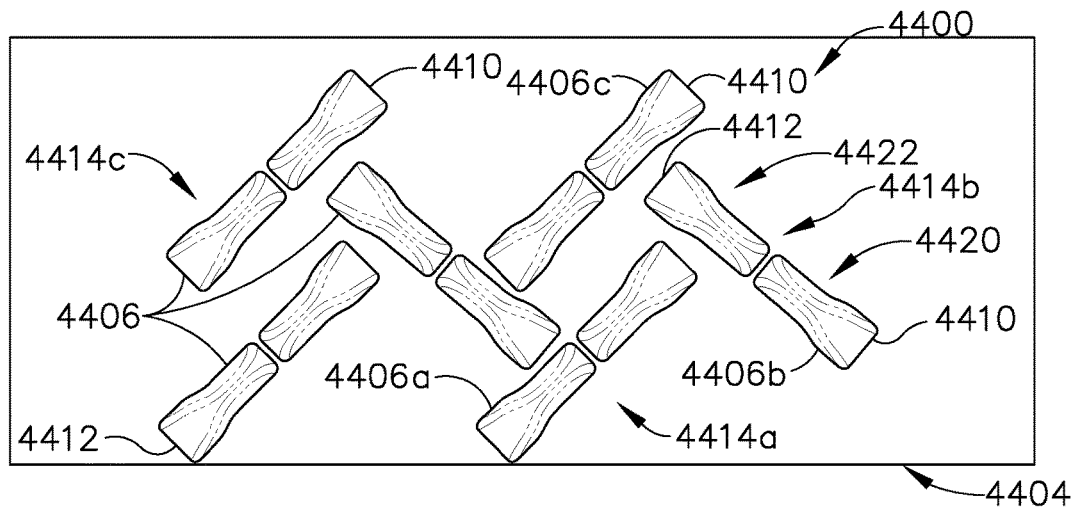
FIG. 56 is a plan view of a portion of an anvil having a plurality of staple-forming pockets defined therein.

The pockets 4406 depicted in FIG. 56 are arranged in an inner row 4414a, an intermediate row 4414b, and an outer row 4414c on a first side of the longitudinal slot 4404. Inner pockets 4406a are positioned in the inner row 4414a, intermediate pockets 4406b are positioned in the intermediate row 4414b, and outer pockets 4406c are positioned in the outer row 4414c. Similar to the anvil 3800, the pockets 4406 are arranged in a herringbone arrangement along the staple-forming surface 4402 of the anvil 4400. Although not shown in FIG. 56, in at least one instance, the pockets 4406 on the opposing side of the slot 4404 can form a mirror image reflection of the pockets 4406 on the first side of the longitudinal slot 4404. In other instances, the arrangement of pockets 4406 in the staple-forming surface 4402 can be asymmetrical relative to the slot 4404 and, in certain instances, the anvil 4400 may not include the longitudinal slot 4404. In various instances, the pockets 4406 can be arranged in less than or more than three rows on each side of the slot 4404.

The pockets 4406 depicted in FIG. 56 are identical. Each pocket 4406 defined in the staple-forming surface 4402 has the same geometry. In other instances, the geometry of the pockets 4406 can vary row-to-row and/or longitudinally along the length of the anvil 4400. For example, in certain instances, the depth of the pockets 4406 or portions thereof can vary along the length of the anvil 4400 to accommodate for variations in gap distance between the anvil and the staple cartridge along the length of an end effector and/or tissue flow, as described herein.

An exemplary pocket 4406b is shown in FIGS. 57-59C. The pocket 4406b has a first end, or proximal end, 4410 and a second end, or distal end, 4412. A pocket axis PA (FIG. 57) extends between the proximal end 4410 and the distal end 4412 of the pocket 4406b. The pocket 4406b includes a perimeter 4416, which defines the boundary of the pocket 4406b. The perimeter 4416 includes rounded corners at the proximal and distal ends 4410 and 4412 of the pocket 4406b. The pocket 4406b also includes a proximal cup 4420 and a distal cup 4422. A portion of the non-forming portion 4408 extends between the proximal cup 4420 and the distal cup 4422. In other words, the pocket 4406b includes two separate and discrete cups 4420 and 4422 in the staple-forming surface 4402. When a staple is driven into forming contact with the staple-forming surface 4402, the proximal cup 4420 is aligned with a proximal staple leg, and the distal cup 4422 is aligned with a distal staple leg. The cups 4420, 4422 are configured to direct or funnel the staple legs toward the pocket axis PA and a central portion of the pocket 4406 and to deform the staple legs into the formed configuration.

Figure 58:
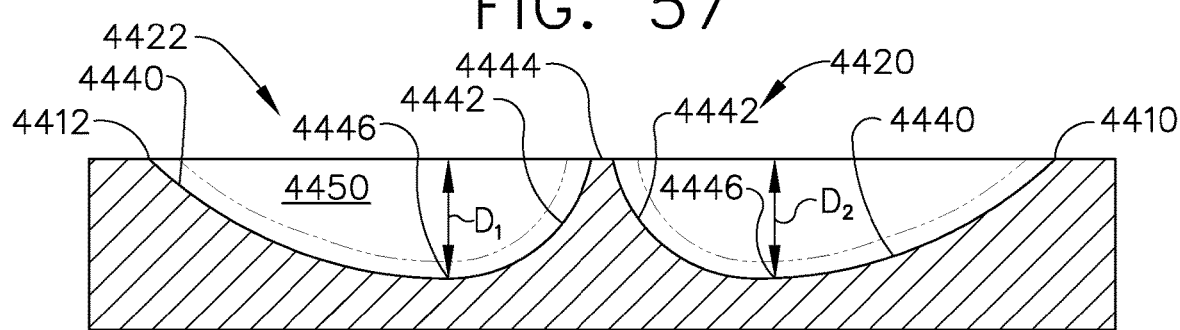
FIGS. 58-59C are cross-sectional views of the pocket of FIG. 57.

Referring primarily to FIG. 58, each cup 4420, 4422 of the pocket 4406b defines an entrance ramp 4440 and an exit ramp 4442. The exit ramp 4442 is steeper than the entrance ramp 4440. When forming a staple, the tip of a staple leg can enter the respective cup 4420, 4422 along the entrance ramp 4440 and exit the respective cup 4420, 4422 along the exit ramp 4442. At an apex 4446 between the entrance ramp 4440 and the exit ramp 4442, the tips of the staple legs are deformed toward the staple base to assume the formed configuration, such as a B-form or modified B-form, for example. The pocket 4406b also defines a bridge 4444 between the proximal cup 4420 and the distal cup 4422. The bridge 4444 is aligned with the non-forming portion 4408. More specifically, the bridge 4444 is a planar extension of the non-forming portion 4408, which extends between the proximal and distal cups 4420, 4422.

Figure 59C:
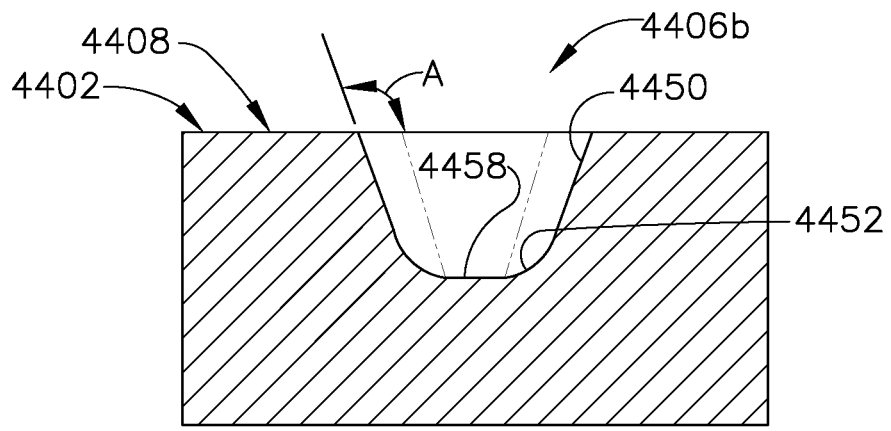
Figure 59B:
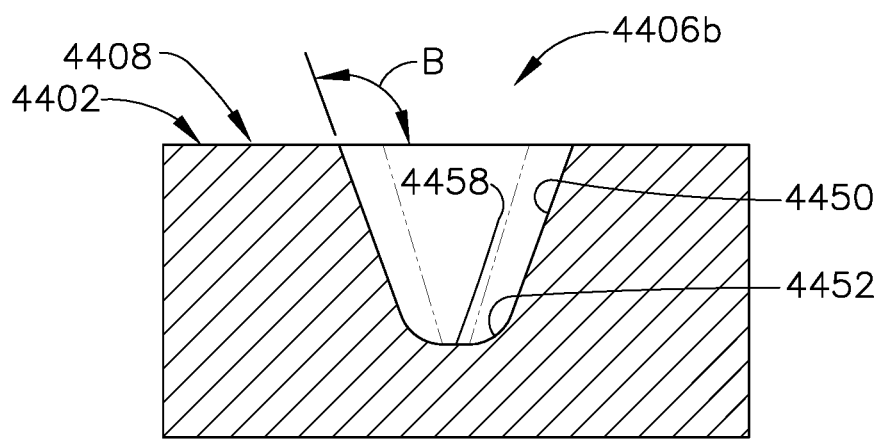
Figure 59A:
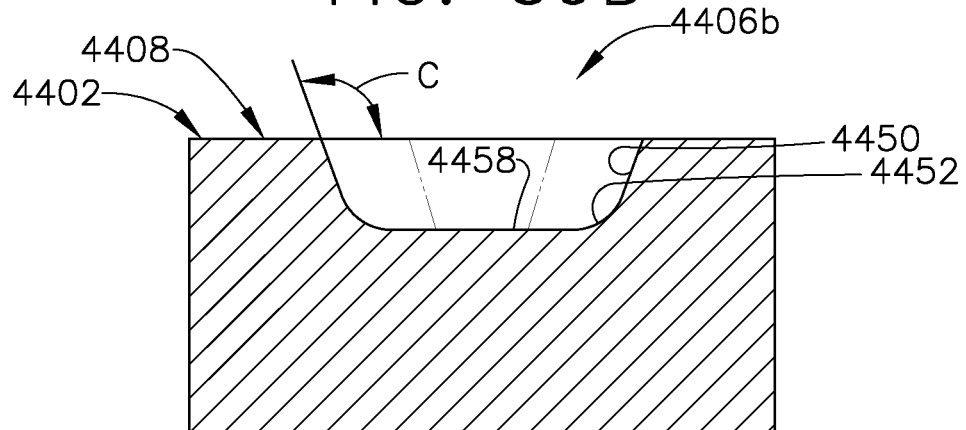

Referring primarily to FIGS. 59A-59C, the pocket 4406b includes sidewalls 4450, which are oriented at an angle relative to the non-forming portion 4408 of the staple-forming surface 4402. More specifically, the sidewalls 4450 are obliquely oriented relative to the non-forming portion 4408. Moreover, the angular orientation of the sidewalls 4450 is constant along the length of the cups. For example, the angles A, B, and C depicted in FIGS. 59A, 59B, and 59C, respectively, are equal. In other instances, one of more of the angles A, B, and C can be different. The sidewalls 4450 narrow between the outer ends of each cup 4420, 4422 and inner ends of the cups 4420, 4422. More specifically, the sidewalls 4450 extend along an inward contour to define a contour in the perimeter 4416 of the pocket 4406b. The widest portion of the cups 4420, 4422 is at the proximal and distal ends of the pocket 4406b. The widened region provides an enlarged footprint for receiving the tip of a staple leg. As the cups 4420, 4422 narrow toward the bridge 4444, the cups 4420, 4422 are configured to funnel and/or guide the tips of the staple legs toward and/or along the pocket axis PA and into a formed configuration.

The pocket 4406b defines a fillet 4452 (FIGS. 59A-59C) between the sidewalls 4450 and the bottom surface 4458 of the pocket 4406b. The fillets 4452 are configured to guide the staple legs along the desired path in the pocket 4406b. For example, if a staple leg lands along the fillet 4452, the fillet 4452 can smoothly guide the staple leg toward the pocket axis PA.

Referring again to FIG. 57, the pocket 4406b is symmetric about the pocket axis PA. For example, the perimeter 4416 of the pocket 4406b is symmetric about the pocket axis PA. Moreover, the pocket 4406b is symmetric about a central axis CA between the proximal and distal cups 4420 and 4422 and perpendicular to the pocket axis PA. For example, the perimeter 4416 of the pocket 4406b is symmetric about the central axis CA, and the proximal cup 4420 has the same geometry as the distal cup 4422. In other instances, the proximal cup 4420 can be different than the distal cup 4422. For example, referring again to FIG. 58, the distal depth $D_2$ can be less than the proximal depth $D_1$ to accommodate for variations in gap distance between the anvil and the staple cartridge and/or tissue flow, as described herein.

Figure 57:
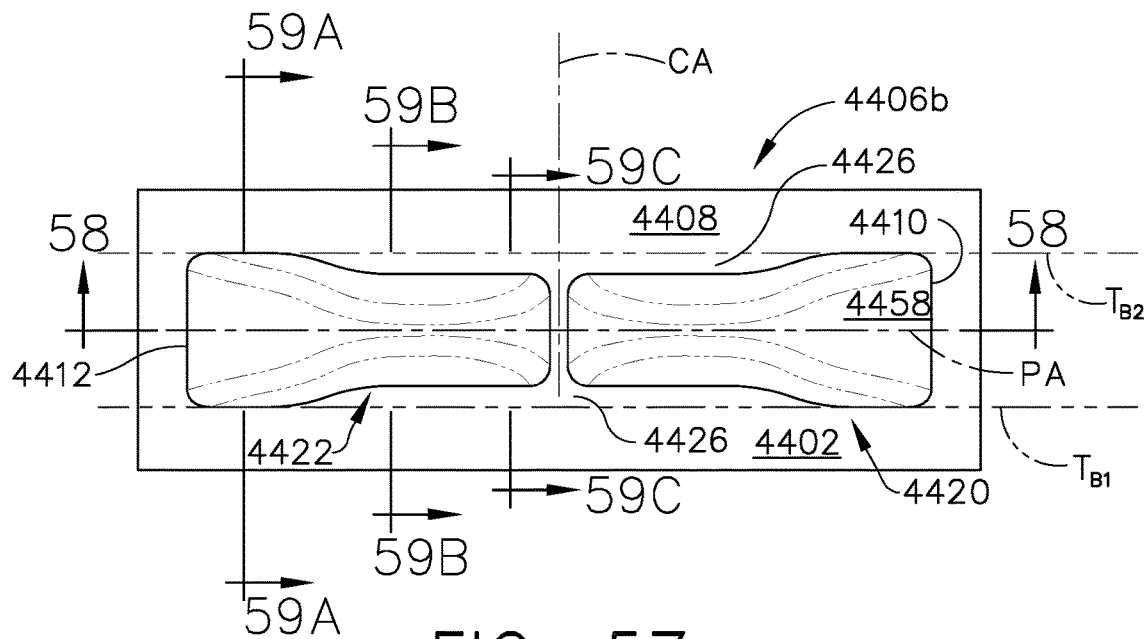
FIG. 57 is a detail view of a pocket of FIG. 56.

Referring again to FIG. 57, the central portion of the pocket 4406b is narrower than the proximal and distal ends 4410 and 4412 of the cups 4420 and 4422, respectively. The narrowed perimeter 4416 of the pocket 4406b defines a receiving peninsula 4426 between a portion of the proximal cup 4420 and a portion of the distal cup 4422. Owing to the symmetry of the pocket 4406b, symmetrical receiving peninsulas 4426 are positioned on each side of the pocket 4406b. The receiving peninsulas 4426 are bounded by the perimeter 4416 of the pocket 4406b and a tangent axis (e.g., $T_{B1}$ and $T_{B2}$), which is tangential to the widest portion of the proximal and distal cups 4420 and 4422 on a side of the pocket 4406b. A first tangent axis $T_{B1}$ is positioned on a first side of the pocket 4406b and a second tangent axis $T_{B2}$ is positioned on the opposite side of the pocket 4406b. The first and second tangent axes $T_{B1}$ and $T_{B2}$ depicted in FIG. 57 are parallel to the pocket axis PA.

Referring again to FIG. 56, each pocket 4406 extends toward the receiving peninsula 4426 of an adjacent pocket 4406. For example, the intermediate pockets 4406b are aligned with the central portion of the inner pockets 4406a and the outer pockets 4406c. Moreover, the inner pockets 4406a and the outer pockets 4406b extend toward the receiving peninsula 4426 of one of the intermediate pockets 4406b. More specifically, the inner pockets 4406a are aligned with the central portion of an adjacent intermediate pocket 4406b, and the outer pockets 4406c are aligned with the central portion of an adjacent intermediate pocket 4406b. In certain instances, a portion of the pockets 4406 can extend into the receiving peninsula 4426 of an adjacent pocket 4406. Similar to the pockets 3906 in the anvil 3900, the geometry of the pockets 4406 facilitates the close arrangement of the pockets 4406 in the staple-forming surface 4402. The "forming ratio" of the staple-forming surface 4402 is the ratio of the non-forming portion 4408 to the forming portion, i.e., the pockets 4406. The forming ratio of the staple-forming surface 4402 is about 2.56:1. In other instances, the forming ratio can be less than 2.56:1 or more than 2.56:1. For example, in at least one instance, more than 50% of the staple-forming surface 4402 can be covered with staple-forming pockets 4406.

Referring now to FIGS. 60-63C, staple-forming pockets 4506 in a portion of an anvil 4500 are depicted. The pockets 4506 and arrangement thereof in the anvil 4500 are similar in many aspects to the pockets 3906 and arrangement thereof in the anvil 3900. For example, the anvil 4500 includes a staple-forming surface 4502 and a longitudinal slot 4504. The longitudinal slot 4504 extends along the longitudinal axis LA of the anvil 4500. In certain instances, a firing element and/or cutting element can translate through the longitudinal slot 4504 during at least a portion of a firing stroke. The staple-forming pockets 4506 are defined in the staple-forming surface 4502. The staple-forming surface 4502 also includes a non-forming portion 4508 that extends around the pockets 4506. The non-forming portion 4508 extends entirely around each pocket 4506 in FIG. 60. In other words, the non-forming portion 4508 surrounds the staple-forming pockets 4506. In other instances, at least a portion of two or more adjacent pockets 4506 can be in abutting contact such that a non-forming portion 4508 is not positioned therebetween.

The forming ratio of the staple-forming surface 4502 can be optimized. By optimizing the forming ratio, more staples can be formed and/or formed to their desired configurations. In certain instances, the surface area of the non-forming portion 4508 of the anvil 4500 can be minimized with respect to the staple-forming pockets 4506. Additionally or alternatively, the footprint of the staple-forming pockets 4506 can be extended or enlarged to maximize the portion of the staple-forming surface 4502 that is designed to catch and form the staples.

Figure 60:
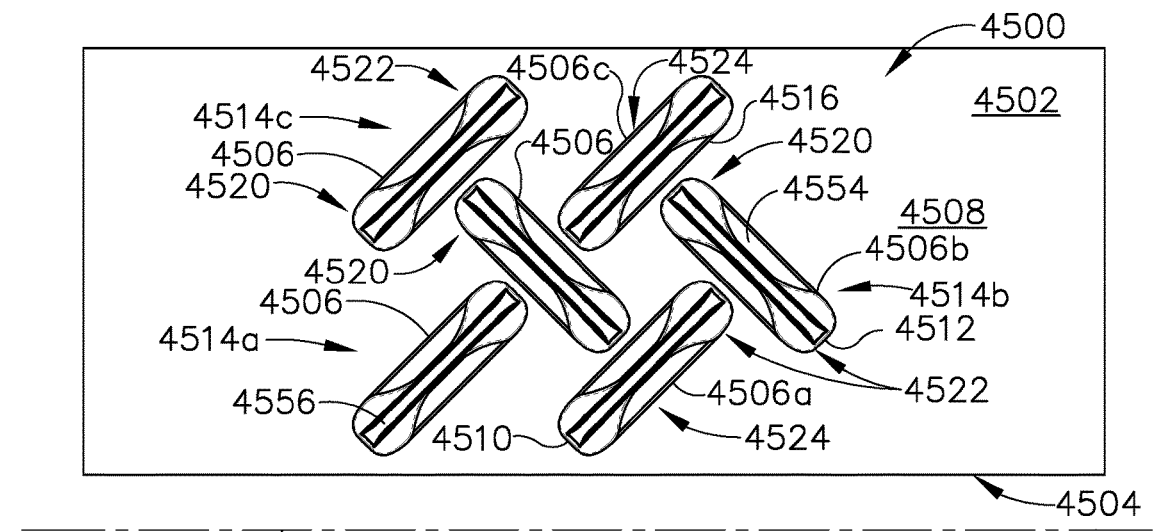
FIG. 60 is a plan view of a portion of an anvil having a plurality of staple-forming pockets defined therein.
Figure 61:
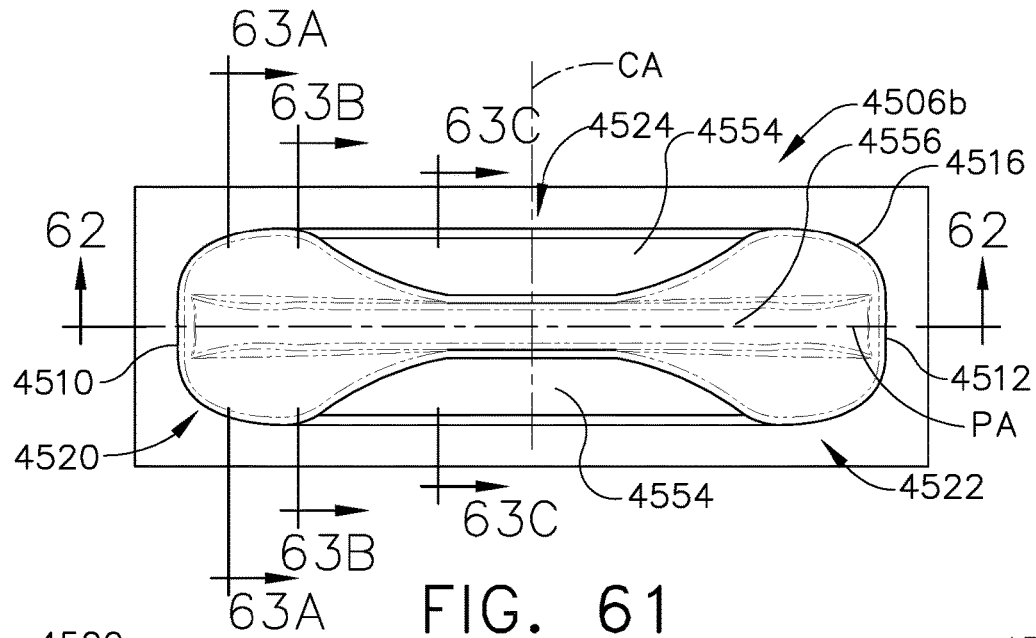
FIG. 61 is a detail view of a pocket of FIG. 60.

The pockets 4506 depicted in FIG. 60 are arranged in an inner row 4514a, an intermediate row 4514b, and an outer row 4514c on a first side of the longitudinal slot 4504. Inner pockets 4506a are positioned in the inner row 4514a, intermediate pockets 4506b are positioned in the intermediate row 4514b, and outer pockets 4506c are positioned in the outer row 4514c. Similar to the anvil 3800, the pockets 4506 are arranged in a herringbone arrangement along the staple-forming surface 4502 of the anvil 4500. Although not shown in FIG. 60, in at least one instance, the pockets 4506 on the opposing side of the slot 4504 can form a mirror image reflection of the pockets 4506 on the first side of the longitudinal slot 4504. In other instances, the arrangement of pockets 4506 in the staple-forming surface 4502 can be asymmetrical relative to the slot 4504 and, in certain instances, the anvil 4500 may not include the longitudinal slot 4504. In various instances, the pockets 4506 can be arranged in less than or more than three rows on each side of the slot 4504.

The pockets 4506 depicted in FIG. 60 are identical. Each pocket 4506 defined in the staple-forming surface 4502 has the same geometry. In other instances, the geometry of the pockets 4506 can vary row-to-row and/or longitudinally along the length of the anvil 4500. For example, in certain instances, the depth of the pockets 4506 or portions thereof can vary along the length of the anvil 4500 to accommodate for variations in gap distance between the anvil and the staple cartridge along the length of an end effector and/or tissue flow, as described herein.

An exemplary pocket 4506b is shown in FIGS. 61-63C. The pocket 4506b has a first end, or proximal end, 4510 and a second end, or distal end, 4512. A pocket axis PA (FIG. 61) extends between the proximal end 4510 and the distal end 4512 of the pocket 4506b. The pocket 4506b includes a perimeter 4516, which defines the boundary of the pocket 4506b. Similar to the pockets 4306, the perimeter 4516 includes rounded corners at the proximal and distal ends 4510 and 4512 of the pocket 4506b. The pocket 4506b also includes a proximal cup 4520, a distal cup 4522, and a neck 4524 extending between the proximal cup 4520 and the distal cup 4522. When a staple is driven into forming contact with the staple-forming surface 4502, the proximal cup 4520 is aligned with a proximal staple leg, and the distal cup 4522 is aligned with a distal staple leg. The cups 4520, 4522 are configured to direct or funnel the staple legs toward the pocket axis PA and a central portion of the pocket 4506, such as the neck 4524, and to deform the staple legs into the formed configuration.

Figure 62:
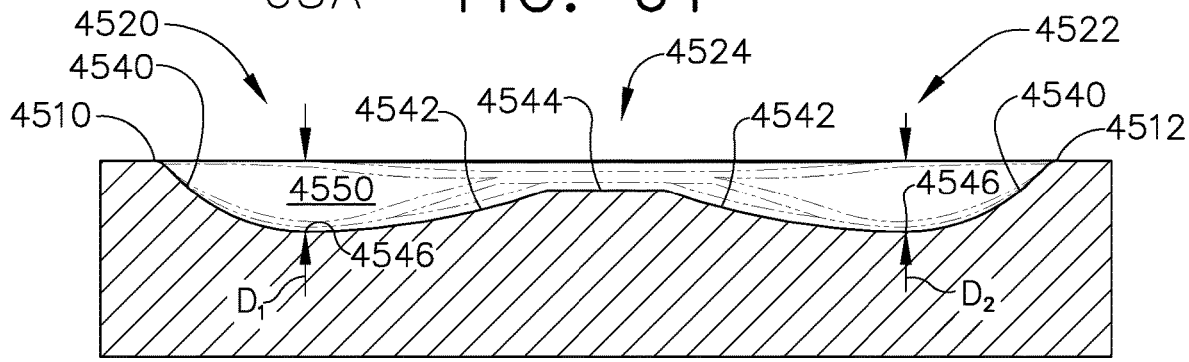
FIGS. 62-63C are cross-sectional views of the pocket of FIG. 61.

Referring primarily to FIG. 62, each cup 4520, 4522 of the pocket 4506b defines an entrance ramp 4540 and an exit ramp 4542. The entrance ramp 4540 is steeper than the exit ramp 4542. When forming a staple, the tip of a staple leg can enter the respective cup 4520, 4522 along the entrance ramp 4540 and exit the respective cup 4520, 4522 along the exit ramp 4542. At an apex 4546 between the entrance ramp 4540 and the exit ramp 4542, the tips of the staple legs are deformed toward the staple base to assume the formed configuration, such as a B-form or modified B-form, for example. The pocket 4506b also defines a bridge 4544 between the proximal cup 4520 and the distal cup 4522. The bridge 4544 is offset from the non-forming portion 4508. More specifically, the bridge 4544 is positioned below or recessed relative to the non-forming portion 4508.

Figure 63C:
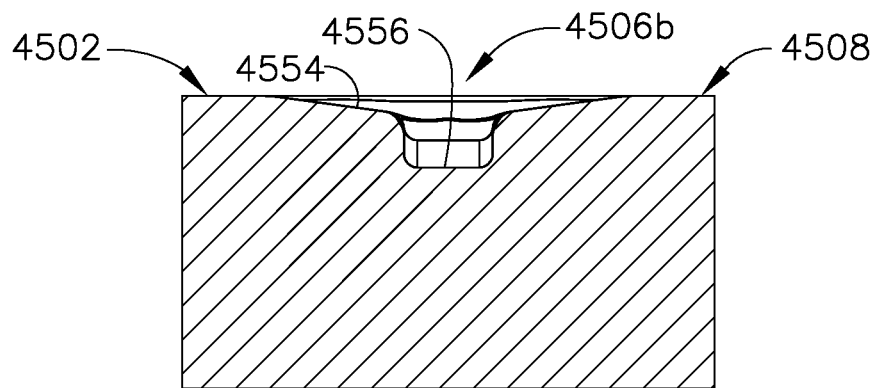
Figure 63B:
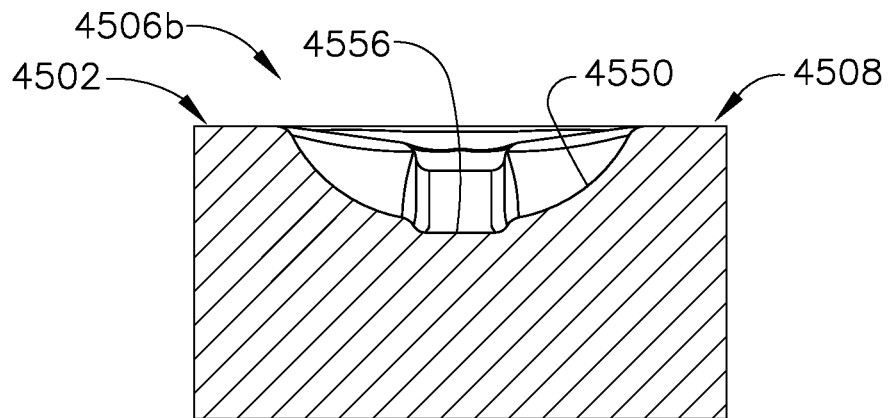
Figure 63A:
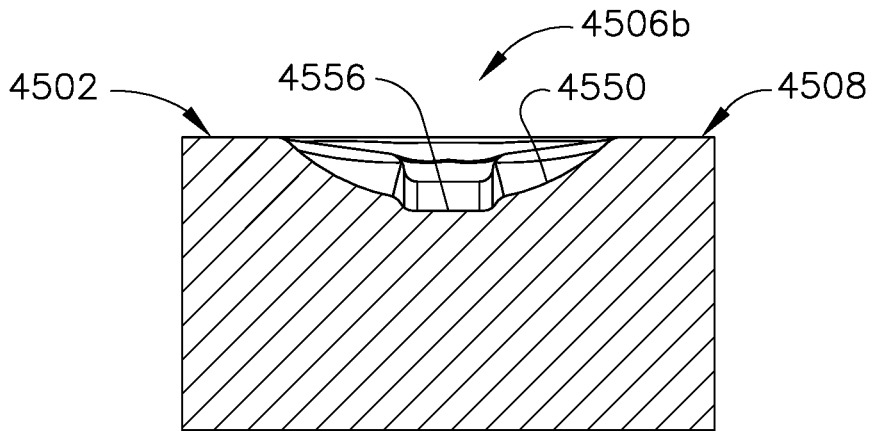

Referring primarily to FIGS. 63A-63C, the pocket 4506b includes contoured or arced walls 4550. The walls 4550 form each cup 4520, 5422 into a wide, rounded basin for receiving and forming the staple legs. Additionally, the pocket 4506b includes a groove 4556 along the bottom surface. The walls 4550 arc downward into the anvil 4500 between the non-forming surface 4508 and the groove 4556. For example, the sidewalls 4550 seamlessly transition to a bottom surface of the pocket 4506b. The groove 4556 extends along the bottom surface from the proximal cup 4520 over the bridge 4524 and into the distal cup 4522. The groove 4556 is configured to constrain and guide the staple legs as they move to the deformed configuration. In various instances, the diameter of the groove 4556 can be less than the diameter of the staple engaged with the groove 4556. In end effectors in which different staple geometries are utilized with the same staple-forming pocket geometry, the width of the groove in the pocket can be less than the smallest diameter staple.

The contoured walls 4550 narrow between the outer ends of each cup 4520, 4522 and the neck 4524. More specifically, the walls 4550 extend along an inward contour to define a contour in the perimeter 4516 of the pocket 4506b. The widened region provides an enlarged footprint for receiving the tip of a staple leg. As the cups 4520, 4522 narrow toward the bridge 4544, the cups 4520, 4522 are configured to funnel and/or guide the tips of the staple legs toward and/or along the pocket axis PA and into a formed configuration.

The pocket 4506b also defines a chamfered edge 4554 along a portion of the sides of the pocket 4506b. As the sidewalls 4550 narrow toward the neck portion 4524, the width of the chamfered edge 4554 correspondingly expands toward the neck portion 4224 to maintain the overall pocket width.

Referring again to FIG. 61, the pocket 4506b is symmetric about the pocket axis PA. For example, the perimeter 4516 of the pocket 4406b is symmetric about the pocket axis PA. Moreover, the pocket 4506b is symmetric about a central axis CA through the neck portion 4524 and perpendicular to the pocket axis PA. For example, the perimeter 4516 of the pocket 4506b is symmetric about the central axis CA, and the proximal cup 4520 has the same geometry as the distal cup 4522. In other instances, the proximal cup 4520 can be different than the distal cup 4522. For example, referring again to FIG. 62, the distal depth $D_2$ can be less than the proximal depth $D_1$ to accommodate for variations in gap distance between the anvil and the staple cartridge and/or tissue flow, as described herein.

Referring again to FIG. 60, each pocket 4506 extends toward the neck portion 4524 of an adjacent pocket 4506. For example, the intermediate pockets 4506b are aligned with the neck portions 4524 of the inner pockets 4506a and the outer pockets 4506c. Moreover, the inner pockets 4506a and the outer pockets 4506b extend toward the neck portion 4524 of one of the intermediate pockets 4506b.

Staple-forming pockets can include extended landing zones for receiving the tips of the staple legs when the staples are fired into forming contact with the anvil. In certain instances, the extended landing zones can extend laterally and/or longitudinally from the cups of the staple-forming pockets, as described herein. The profile, or perimeter, of the staple-forming pockets can nest with the profile, or perimeter, of one or more adjacent staple-forming pockets. For example, at least a portion of the perimeter of a staple-forming pocket can extend along a contour or path that matches, tracks, follows and/or parallels a portion of the perimeter of one or more adjacent staple-forming pockets. Such tracking portions or adjacent perimeters can define concentric profiles.

In various instances, the surface area of a staple-forming pocket having one or more extended landing zones can be greater than the surface area of a staple-forming pocket without the one or more extended landing zones. For example, extended landing zones can increase the surface area of a staple-forming pocket by at least 10%. Extended landing zones can increase the surface area of a staple-forming pocket by 15% or 25%, for example. In other instances, extended landing zones can increase the surface area of a staple-forming pocket by less than 10%, such as 5%, for example. Certain staple-forming pockets described herein can have a greater surface area than the staple-forming pockets in an anvil having six rows of parallel staple-forming pockets but that is otherwise identical to certain anvils described herein having six rows of angularly-oriented staple-forming pockets. In still other instances, a staple-forming pocket having extended landing zones may also include narrowed and/or otherwise reduced portions having a surface area that is equal to or greater than the surface area of the extended landing zones.

In certain instances, the staple-forming pockets can be asymmetrical. For example, the staple-forming pockets can be asymmetrical relative to a pocket axis extending between a proximal end and a distal end of the pocket and/or can be asymmetrical relative to a central axis extending perpendicular to the pocket axis and transecting a central portion of the pocket. The asymmetry of the staple-forming pockets can facilitate nesting of the pockets and/or can maximize the surface area of the pockets in a staple-forming surface, for example.

Referring now to FIGS. 64-67C, staple-forming pockets 5006 in a portion of an anvil 5000 are depicted. Similar to the anvil 3800, the pockets 5006 are arranged in a herringbone arrangement along the staple-forming surface 5002 of the anvil 5000. The anvil 5000 includes a staple-forming surface 5002 and a longitudinal slot 5004. The longitudinal slot 5004 extends along the longitudinal axis LA of the anvil 5000. In certain instances, a firing element and/or a cutting element can translate through the longitudinal slot 5004 during at least a portion of a firing stroke. The staple-forming pockets 5006 are defined in the staple-forming surface 5002. The staple-forming surface 5002 also includes a non-forming portion 5008 that extends around the pockets 5006. The non-forming portion 5008 extends entirely around each pocket 5006. In other words, the non-forming portion 5008 surrounds the staple-forming pockets 5006. In other instances, at least a portion of two or more adjacent pockets 5006 can be in abutting contact such that a non-forming portion 5008 is not positioned therebetween.

The forming ratio of the staple-forming surface 5002 can be optimized. By optimizing the forming ratio, more staples can be formed and/or formed to their desired configurations. In certain instances, the surface area of the non-forming portion 5008 of the anvil 5000 can be minimized with respect to the staple-forming pockets 5006. Additionally or alternatively, the footprint of the staple-forming pockets 5006 can be extended or enlarged to maximize the portion of the staple-forming surface 5002 that is designed to catch and form the staples.

Figure 64:
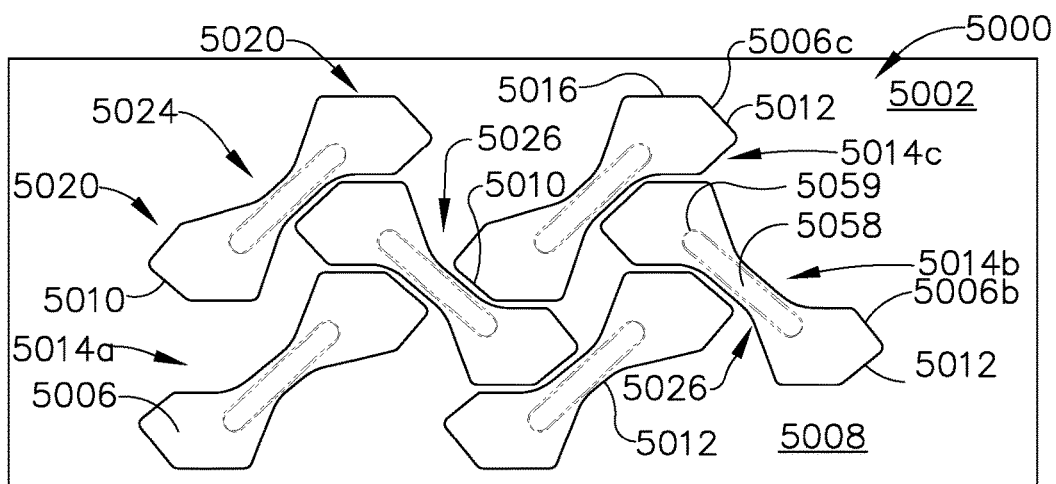
FIG. 64 is a plan view of a portion of an anvil having a plurality of staple-forming pockets defined therein.

The pockets 5006 depicted in FIG. 64 are arranged in an inner row 5014a, an intermediate row 5014b, and an outer row 5014c on a first side of the longitudinal slot 5004. Inner pockets 5006a are positioned in the inner row 5014a, intermediate pockets 5006b are positioned in the intermediate row 5014b, and outer pockets 5006c are positioned in the outer row 5014c. Although not shown in FIG. 64, in at least one instance, the pockets 5006 on the opposing side of the slot 5004 can form a mirror image reflection of the pockets 5006 on the first side of the longitudinal slot 5004. In other instances, the arrangement of pockets 5006 in the staple-forming surface 5002 can be asymmetrical relative to the slot 5004 and, in certain instances, the anvil 5000 may not include the longitudinal slot 5004. In various instances, the pockets 5006 can be arranged in less than or more than three rows on each side of the slot 5004.

The inner pockets 5006a are identical, the intermediate pockets 5006b are identical, and the outer pockets 5006c are identical; however, the inner pockets 5006a are different than the intermediate pockets 5006b and the outer pockets 5006c, and the intermediate pockets 5006b are different than the outer pockets 5006c. In other words, the pockets 5006 in each row 5014a, 5014b, and 5014c are different. Extended landing zones 5030 and 5032 of the pockets 5006a, 5006b, and 5006c, which are described herein, contribute to the different geometries thereof. The shape and size of the extended landing zones 5030 and 5032 are confined by the perimeter 5016 of adjacent, nested pockets 5006.

Although the pockets 5006 in each row 5014a, 5014b, and 5014c are different, the pockets 5006 can be configured to form staples to the same, or substantially the same, formed shape. In other instances, the pockets 5006 can be configured to form staples to different formed shapes, such as to different heights and/or configurations. In certain instances, the pockets 5006 can vary longitudinally within each row 5014a, 5014b, and 5014c. For example, in certain instances, the depth of the pockets 5006 or portions thereof can vary along the length of the anvil 5000 to accommodate for variations in gap distance between the anvil and the staple cartridge along the length of an end effector and/or tissue flow, as described herein.

In certain instances, the pockets 5006 can be configured to engage different geometry staples. For example, staples having different unformed heights and/or different diameters can be formed by the pockets 5006 in the anvil 5000. In certain instances, the geometry of the staples can vary longitudinally, and the pockets 5006 can be configured to form the different geometry staples. For example, the unformed height of the staples and/or the wire diameter can vary along the length of the anvil 5000.

An exemplary intermediate pocket 5006b is shown in FIGS. 64-67C. The pocket 5006b has a first end, or proximal end, 5010 and a second end, or distal end, 5012. A pocket axis PA (FIG. 65) extends between the proximal end 5010 and the distal end 5012 of the pocket 5006b. The pocket 5006b includes a perimeter 5016, which defines the boundary of the pocket 5006b. The perimeter 5016 includes linear portions and contoured portions. More specifically, the perimeter 5016 includes linear portions and contoured corners therebetween at which the linear portions change directions. Referring again to FIG. 64, at least a portion of the perimeter 5016 of each pocket 5006 closely tracks or parallels at least a portion of the perimeter of one or more adjacent pockets 5006.

The pocket 5006b includes a proximal cup 5020, a distal cup 5022, and a neck 5024 extending between the proximal cup 5020 and the distal cup 5022. When a staple is driven into forming contact with the staple-forming surface 5002, the proximal cup 5020 is aligned with a proximal staple leg, and the distal cup 5022 is aligned with a distal staple leg.

The cups 5020 and 5022 are configured to direct or funnel the staple legs toward the pocket axis PA and the central portion of the pocket 5006, such as the neck portion 5024, and to deform the staple legs into the formed configuration.

Figure 66:
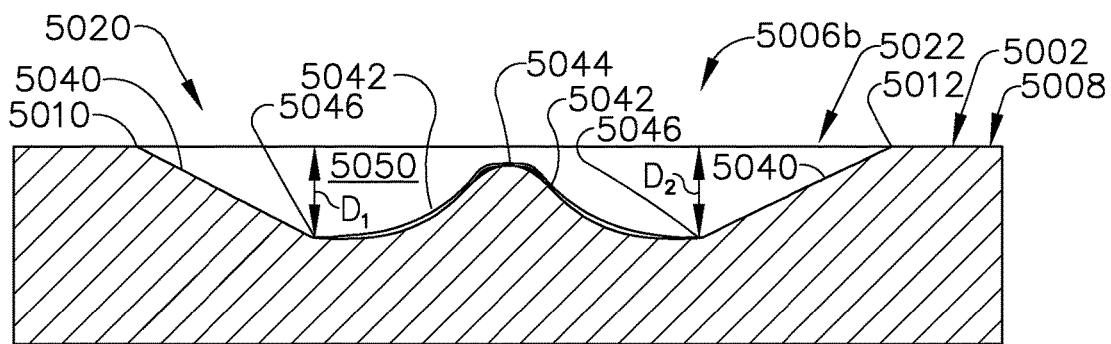
FIGS. 66-67C are cross-sectional views of the pocket of FIG. 65.

Referring primarily to FIG. 66, each cup 5020, 5022 of the pocket 5006b defines an entrance ramp 5040 and an exit ramp 5042. When forming a staple, the tip of a staple leg can enter the respective pocket 5020, 5022 along the entrance ramp 5040 and exit the respective pocket 5020, 5022 along the exit ramp 5042. At an apex 5046 between the entrance ramp 5040 and the exit ramp 5042, the tips of the staple legs are deformed toward the staple base to assume the formed configuration, such as a B-form or modified B-form, for example. The pocket 5006b also defines a bridge 5044 in the neck portion 5024 between the proximal cup 5020 and the distal cup 5022. The bridge 5044 is offset from the non-forming portion 5008. More specifically, the bridge 5044 is positioned below or recessed relative to the non-forming portion 5008.

Figure 67C:
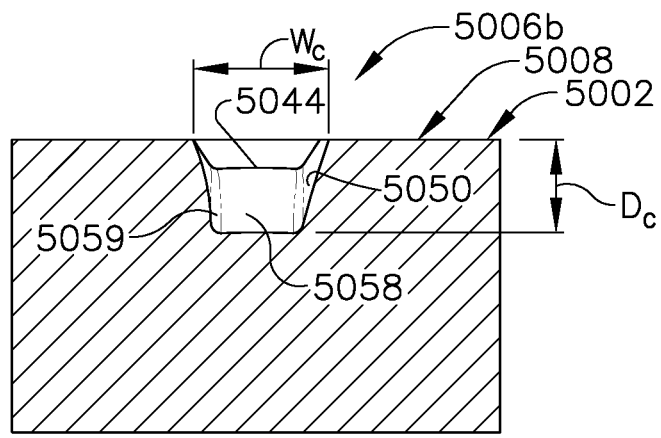
Figure 67B:
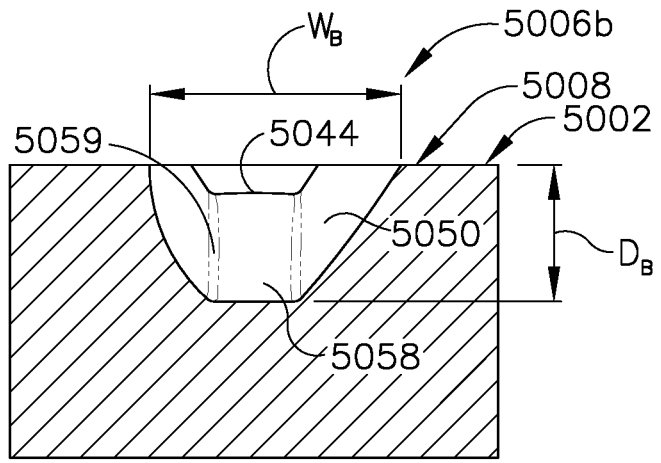
Figure 67A:
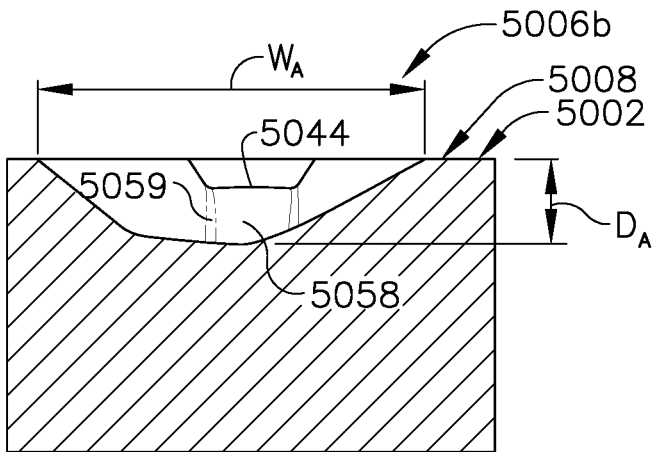

Referring primarily to FIGS. 67A-67C, the pocket 5006b includes sidewalls 5050, which extend from the non-forming portion 5008 to the bottom surface 5058. The sidewalls 5050 include linear portions and contoured portions. The sidewalls 5050 widen toward a central region 5021 (FIG. 65) of each cup 5020, 5022, and narrow from the central region 5021 of each cup 5020, 5022 toward the neck portion 5024. The widened central region 5021 provides an enlarged footprint for receiving the tip of a staple leg. As the cups 5020, 5022 narrow toward the neck 5024, the cups 5020, 5022 are configured to funnel and/or guide the staple legs and tips thereof toward and/or along the pocket axis PA and into a formed configuration.

Figure 65:
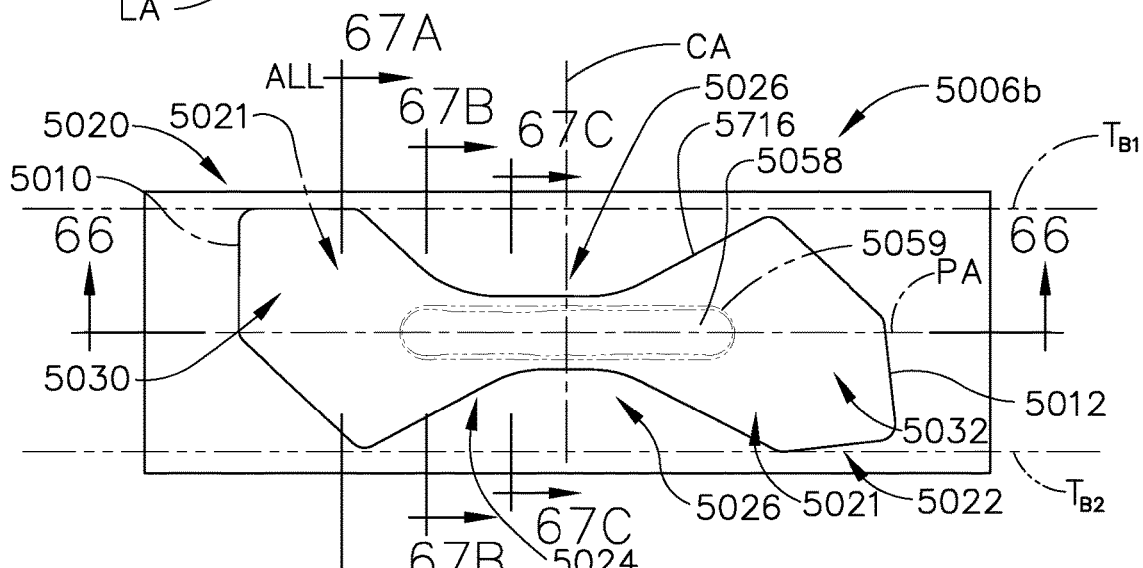
FIG. 65 is a detail view of a pocket of FIG. 64.

FIG. 67A is taken along the plane ALL in FIG. 65, which corresponds to the anticipated landing location (ALL) of a staple leg. For example, the tip of a staple leg can be expected to land in the proximal cup 5020 at and/or near the intersection of the plane ALL and the pocket axis PA. At the plane ALL, the pocket 5006b defines a width $W_A$ and a depth $D_A$. The cross-section in FIG. 67B is taken across a transition between the proximal cup 5020 and the neck 5024. FIG. 67B depicts the pocket 5006b defining a width $W_B$ and a depth $D_B$. The width $W_B$ is less than the width $W_A$, and the depth $D_B$ is greater than the depth $D_A$. In other words, the pocket 5006b narrows and deepens from the plane ALL in the proximal cup 5020 toward the neck 5024. The comparatively large width $W_A$ at the plane ALL is configured to provide a wide receptacle or basin for receiving the staple leg. The cross-section in FIG. 67C is taken across the neck portion 5024. FIG. 67C depicts the pocket 5006b defining a width $W_C$ and a depth $D_C$. The width $W_C$ is less than the width $W_B$, and the depth $D_C$ is less than the depth $D_B$. In other words, the pocket 5006b continues to narrow, and becomes shallower in the neck 5024 across the bridge 5044.

The bottom surface 5058 of the pocket 5006b is a flat surface, which is bounded by an arcuate fillet 5059 therearound. In certain instances, the bottom surface 5058 can have a groove defined along at least a portion thereof. In other instances, the bottom surface 5058 can form a trough. In still other instances, the bottom surface can include hump or ridge along at least a portion thereof, such as across the bridge 5044, for example.

Referring primarily now to FIG. 65, the pocket 5006b includes a proximal extended landing zone 5030 and a distal extended landing zone 5032. The proximal extended landing zone 5030 is positioned in a proximal portion of the proximal cup 5020, and the distal extended landing zone 5032 is positioned in a distal portion of the distal cup 5022. More specifically, the extended landing zones 5030 and 5032 are positioned beyond the anticipated landing location of a staple. For example, the proximal extended landing zone 5030 is positioned proximal to the plane ALL and, in instances where the tip of a staple leg lands beyond the plane ALL, the proximal extended landing zones 5030 can catch the staple leg and direct it toward the pocket axis PA and/or toward the neck portion 5024. The landing zones 5030 and 5032 define a generally polygonal shape and, more specifically, a quadrilateral with rounded corners. In other instances, the landing zones 5030 and 5032 can be triangular or substantially triangular and, in still other instances, can define an arcuate or bulbous profile, for example.

The geometry of the extended landing zones 5030 and 5032 is constrained by the perimeter 5016 of the adjacent staple-forming pockets 5006. For example, the extended landing zones 5030 and 5032 can extend toward and/or into nearly abutting contact with one or more adjacent staple-forming pockets. The extended landing zones 5030 and 5032 and/or other portions of the pocket 5006b can track and/or extend parallel to adjacent staple-forming pockets 5006. In other instances, the extended landing zones 5030 and 5032 can abut one or more adjacent staple-forming pockets 5006.

Referring again to FIG. 65, the pocket 5006b is asymmetric about the pocket axis PA. For example, the perimeter 5016 of the pocket 5006b is asymmetric about the pocket axis PA. Moreover, the pocket 5006b is asymmetric about a central axis CA through the neck portion 5024 and perpendicular to the pocket axis PA. For example, the perimeter 5016 of the pocket 5006b is asymmetric about the central axis CA, and the proximal cup 5020 has a different geometry than the distal cup 5022. Although the proximal cup 5020 and the distal cup 5022 are different, the pocket 5006b can be configured to form symmetric staples. For example, referring again to FIG. 66, the distal depth $D_2$ can be less than the proximal depth $D_1$ to accommodate for variations in gap distance between the anvil and the staple cartridge and/or tissue flow, as described herein. The formed height of the proximal and distal legs of a staple can be equal. In other instances, the pocket 5006 can be configured to form asymmetric staples.

Referring again to FIG. 65, the neck portion 5024 is narrower than the proximal and distal cups 5020 and 5022. The narrowed perimeter 5016 of the pocket 5006b at the neck portion 5024 defines a receiving peninsula 5026 between a portion of the proximal cup 5020 and a portion of the distal cup 5022. Receiving peninsulas 5026 are positioned on each side of the pocket 5006b. The receiving peninsulas 5026 are bounded by the perimeter 5016 of the pocket 5006b and a tangent axis (e.g., $T_{B1}$ and $T_{B2}$), which is tangential to the widest portions of the proximal and distal cups 5020 and 5022 on each side of the pocket 5006. A first tangent axis $T_{B1}$ is positioned on a first side of the pocket 5006b and a second tangent axis $T_{B2}$ is positioned on the opposite side of the pocket 5006b. The first and second tangent axes $T_{B1}$ and $T_{B2}$ depicted in FIG. 67 are parallel to the pocket axis PA. In other instances, one or both of the tangent axes $T_{B1}$ and $T_{B2}$ may not be parallel to the pocket axis PA.

Referring again to FIG. 64, the perimeters 5016 of the pockets 5006 are nested or interlocked along the staple-forming surface 5002. In particular, each pocket 5006 extends into the receiving peninsula 5026 of an adjacent pocket 5006. For example, the intermediate pockets 5006b are nested between the inner pockets 5006a and the outer pockets 5006c. Stated differently, the intermediate pockets 5006b extend into the receiving peninsula 5026 of an adjacent inner pocket 5006a and into the receiving peninsula 5026 of an adjacent outer pocket 5006c. Moreover, the inner pockets 5006a and the outer pockets 5006b are nested with the intermediate pockets 5006b. More specifically, the inner pockets 5006a extend into the receiving peninsula 5026 of an adjacent intermediate pocket 5006b, and the outer pockets 5006c extend into the receiving peninsula 5026 of an adjacent intermediate pocket 5006b. In various instances, the distal extended landing zone 5032 of the intermediate pocket 5006b is positioned in the receiving peninsula 5026 of an inner pocket 5006a, the proximal extended landing zone 5030 of the intermediate pocket 5006b is positioned in the receiving peninsula 5026 of an outer pocket 5006c, the distal extended landing zone 5032 of an inner pocket 5006a is positioned in the receiving peninsula 5026 of an intermediate pocket 5006b, and the proximal extended landing zone 5030 of the outer pocket 5006c is positioned in the receiving peninsula 5026 of an intermediate pocket 5006b.

The geometry of the pockets 5006 facilitates the nesting of the pockets 5006 in the staple-forming surface 5002. For example, because the pockets 5006 include a narrowed neck portion 5024 between two enlarged cups 5020 and 5022, one of the enlarged cups 5020, 5022 of another pocket 5006 can be positioned adjacent to the narrowed neck portion 5024. For example, one of the enlarged cups 5020, 5022 can be aligned with and/or received by a portion of an adjacent pocket 5006. In such instances, the surface area of the staple-forming surface 5002 that is covered by the pockets 5006 can be optimized. The "forming ratio" of the staple-forming surface 5002 is the ratio of the non-forming portion 5008 to the forming portion, i.e., the pockets 5006. The forming ratio of the staple-forming surface 5002 is about 1:1. In other instances, the forming ratio can be less than 1:1 or more than 1:1. For example, in at least one instance, more than 50% of the staple-forming surface 5002 can be covered with staple-forming pockets 5006. In another instances, more than 60% or more than 75% of the stapling-forming surface 5002 can be covered with staple-forming pockets 5006.

Referring now to FIGS. 68-71C, staple-forming pockets 5106 in a portion of an anvil 5100 are depicted. Similar to the anvil 3800, the pockets 5106 are arranged in a herringbone arrangement along the staple-forming surface 5102 of the anvil 5100. The anvil 5100 includes a staple-forming surface 5102 and a longitudinal slot 5104. The longitudinal slot 5104 extends along the longitudinal axis LA of the anvil 5100. In certain instances, a firing element and/or a cutting element can translate through the longitudinal slot 5104 during at least a portion of a firing stroke. The staple-forming pockets 5106 are defined in the staple-forming surface 5102. The staple-forming surface 5102 also includes a non-forming portion 5108 that extends around the pockets 5106. The non-forming portion 5108 extends entirely around each pocket 5106. In other words, the non-forming portion 5108 surrounds the staple-forming pockets 5106. In other instances, at least a portion of two or more adjacent pockets 5106 can be in abutting contact such that a non-forming portion 5108 is not positioned therebetween.

The forming ratio of the staple-forming surface 5102 can be optimized. By optimizing the forming ratio, more staples can be formed and/or formed to their desired configurations. In certain instances, the surface area of the non-forming portion 5108 of the anvil 5100 can be minimized with respect to the staple-forming pockets 5106. Additionally or alternatively, the footprint of the staple-forming pockets 5106 can be extended or enlarged to maximize the portion of the staple-forming surface 5102 that is designed to catch and form the staples.

Figure 68:
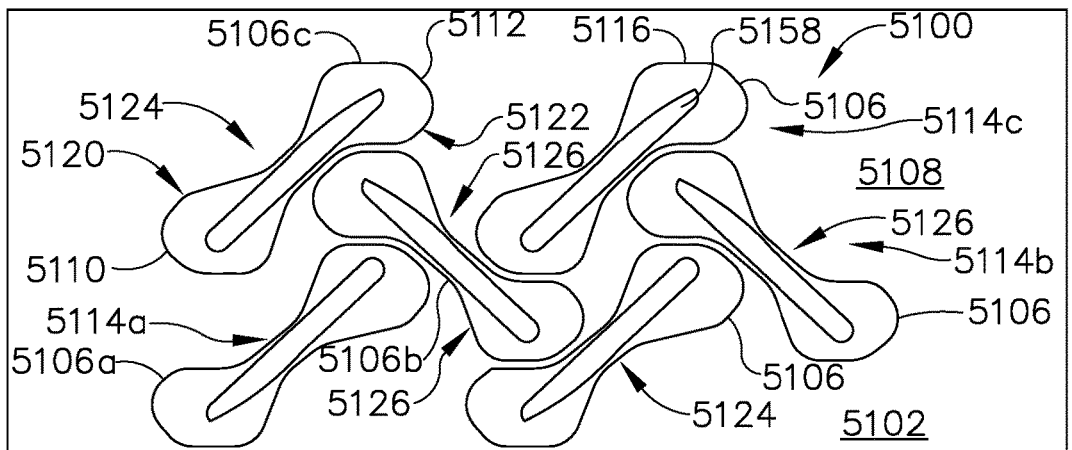
FIG. 68 is a plan view of a portion of an anvil having a plurality of staple-forming pockets defined therein.

The pockets 5106 depicted in FIG. 68 are arranged in an inner row 5114a, an intermediate row 5114b, and an outer row 5114c on a first side of the longitudinal slot 5104. Inner pockets 5106a are positioned in the inner row 5114a, intermediate pockets 5106b are positioned in the intermediate row 5114b, and outer pockets 5106c are positioned in the outer row 5114c. Although not shown in FIG. 68, in at least one instance, the pockets 5106 on the opposing side of the slot 5104 can form a mirror image reflection of the pockets 5106 on the first side of the longitudinal slot 5104. In other instances, the arrangement of pockets 5106 in the staple-forming surface 5102 can be asymmetrical relative to the slot 5104 and, in certain instances, the anvil 5100 may not include the longitudinal slot 5104. In various instances, the pockets 5106 can be arranged in less than or more than three rows on each side of the slot 5104.

The inner pockets 5106a are identical, the intermediate pockets 5106b are identical, and the outer pockets 5106c are identical; however, the inner pockets 5106a are different than the intermediate pockets 5106b and the outer pockets 5106c, and the intermediate pockets 5106b are different than the outer pockets 5106c. In other words, the pockets 5106 in each row 5114a, 5114b, and 5114c are different. In other instances, the pockets 5106 in two or more of the rows can be the same. For example, the inner pockets 5106a can be the same as the outer pockets 5106c. Extended landing zones 5130 and 5132 of the pockets 5106a, 5106b, and 5106c, which are described herein, can contribute to the different geometries thereof. Moreover, the shape and size of the extended landing zones 5130 and 5132 are confined by the perimeter 5116 of the adjacent, nested pockets 5106. The landing zones 5130 and 5132 define an arcuate profile. In other instances, the landing zones 5030 and 5032 can be polygonal and/or include one or more linear and/or contoured portions.

Although the pockets in each row 5114a, 5114b, and 5114c are different, the pockets 5106 can be configured to form staples to the same, or substantially the same, formed shape. In other instances, the pockets 5106 can be configured to form staples to different formed shapes, such as to different heights and/or configurations. In certain instances, the pockets 5106 can vary longitudinally within each row 5114a, 5114b, and 5114c. For example, in certain instances, the depth of the pockets 5106 or portions thereof can vary along the length of the anvil 5100 to accommodate for variations in gap distance between the anvil and the staple cartridge along the length of an end effector and/or tissue flow, as described herein.

An exemplary intermediate pocket 5106b is shown in FIGS. 68-71C. The pocket 5106b has a first end, or proximal end, 5110 and a second end, or distal end, 5112. A pocket axis PA (FIG. 69) extends between the proximal end 5110 and the distal end 5112 of the pocket 5106b. The pocket 5106b includes a perimeter 5116, which defines the boundary of the pocket 5106b. The perimeter 5116 includes linear portions and contoured portions. More specifically, the perimeter 5116 includes linear portions and contoured corners therebetween at which the linear portions change directions. Referring again to FIG. 68, at least a portion of the perimeter 5116 of each pocket 5106 closely tracks or parallels at least a portion of the perimeter of one or more adjacent pockets 5106. The rounded perimeter 5116 of the pocket 5106b can provide a smoother profile, which can be easier to coin and/or stamp in the staple-forming surface 5102 than pockets having sharp corners, for example.

The pocket 5106b includes a proximal cup 5120, a distal cup 5122, and a neck portion 5124 extending between the proximal cup 5120 and the distal cup 5122. When a staple is driven into forming contact with the staple-forming surface 5102, the proximal cup 5120 is aligned with a proximal staple leg, and the distal cup 5122 is aligned with a distal staple leg. The cups 5120 and 5122 are configured to direct or funnel the staple legs toward the pocket axis PA and the central portion of the pocket 5106, such as the neck portion 5124, and to deform the staple legs into the formed configuration.

Figure 70:
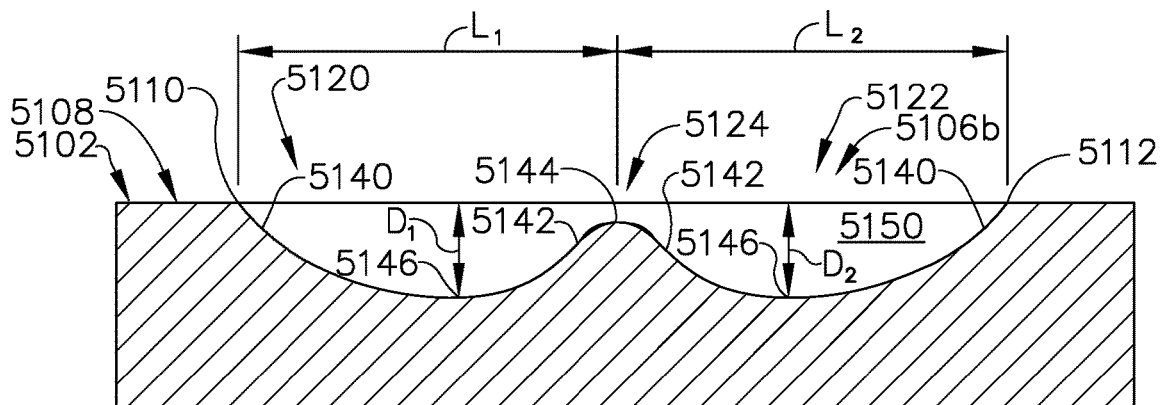
FIGS. 70-71C are cross-sectional views of the pocket of FIG. 69.

Referring primarily to FIG. 70, each cup 5120, 5122 of the pocket 5106b defines an entrance ramp 5140 and an exit ramp 5142. When forming a staple, the tip of a staple leg can enter the respective pocket 5120, 5122 along the entrance ramp 5140 and exit the respective pocket 5120, 5122 along the exit ramp 5142. At an apex 5146 between the entrance ramp 5140 and the exit ramp 5142, the tips of the staple legs are deformed toward the staple base to assume the formed configuration, such as a B-form or modified B-form, for example. The pocket 5106b also defines a bridge 5144 in the neck portion 5124 between the proximal cup 5120 and the distal cup 5122. The bridge 5144 is offset from the non-forming portion 5108. More specifically, the bridge 5144 is positioned below or recessed relative to the non-forming portion 5108.

Figure 71C:
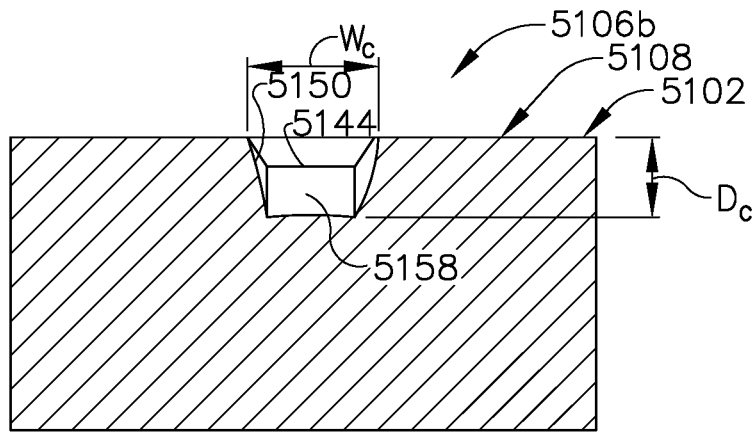
Figure 71B:
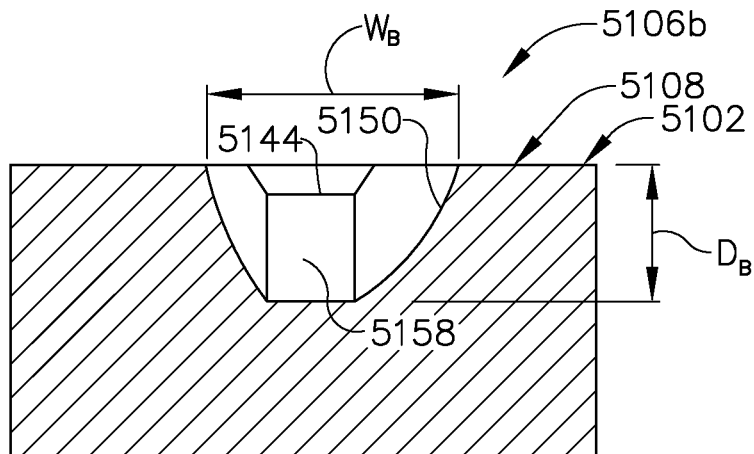
Figure 71A:
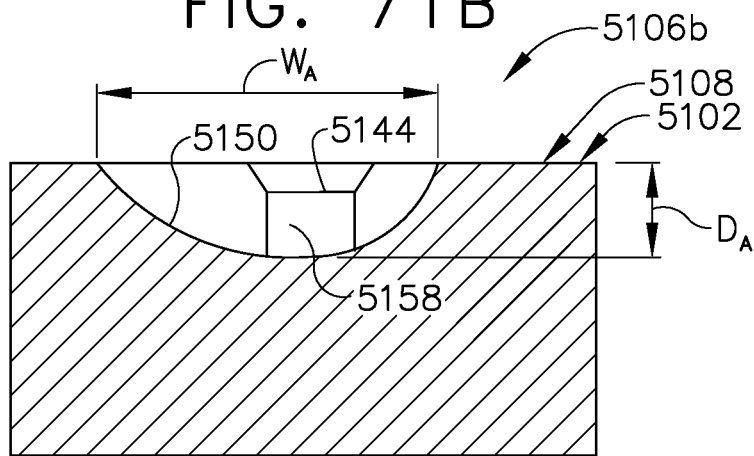

Referring primarily to FIGS. 71A-71C, the pocket 5106b includes sidewalls 5150, which extend from the non-forming portion 5108. The sidewalls 5150 include linear portions and contoured portions. The sidewalls 5150 widen toward a central region 5121 (FIG. 69) of each cup 5120, 5122, and narrow from the central region 5121 of each cup 5120, 5122 toward the neck portion 5124. The widened central region 5121 provides an enlarged footprint for receiving the tip of a staple leg. As the cups 5120, 5122 narrow toward the neck 5124, the cups 5120, 5122 are configured to funnel and/or guide the staple legs and tips thereof toward and/or along the pocket axis PA and into a formed configuration.

Figure 69:
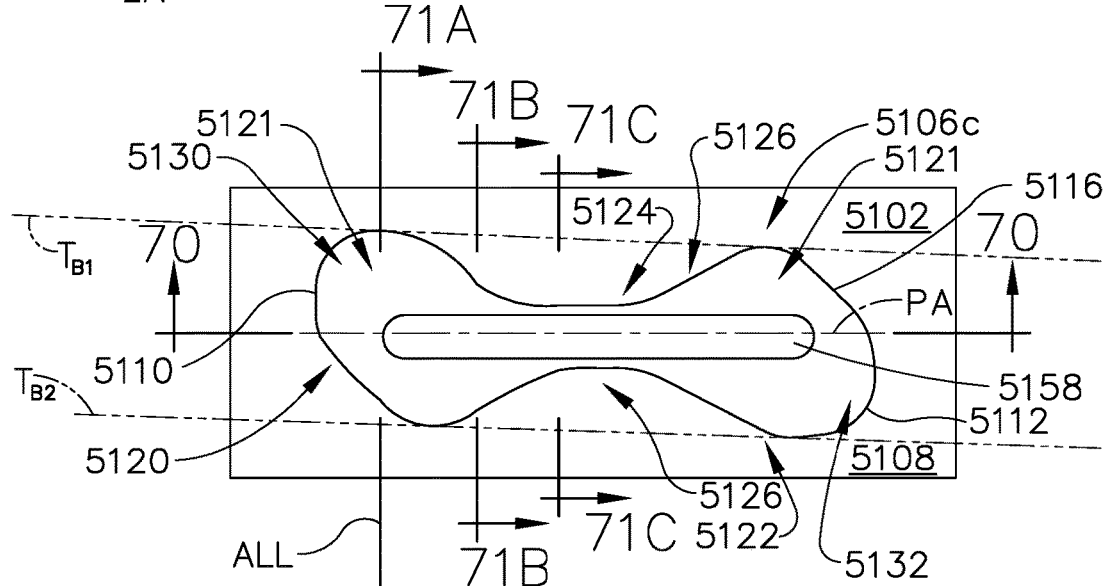
FIG. 69 is a detail view of a pocket of FIG. 68.

FIG. 71A is taken along the plane ALL in FIG. 69, which corresponds to the anticipated landing location of a staple leg. For example, the tip of a staple leg can be expected to land in the proximal cup 5120 at and/or near the intersection of the plane ALL and the pocket axis PA. At the plane ALL, the pocket 5106b defines a width $W_A$ and a depth $D_A$. The cross-section in FIG. 71B is taken across a transition between the proximal cup 5120 and the neck 5124. FIG. 71B depicts the pocket 5106b defining a width $W_B$ and a depth $D_B$. The width $W_B$ is less than the width $W_A$, and the depth $D_B$ is greater than the depth $D_A$. In other words, the pocket 5106b narrows and deepens from the plane ALL in the proximal cup 5120 toward the neck 5124. The comparatively large width $W_A$ at the plane ALL is configured to provide a wide basin or receptacle for receiving the staple leg. The cross-section in FIG. 71C is taken across the neck portion 5124. FIG. 71C depicts the pocket 5106b defining a width $W_C$ and a depth $D_C$. The width $W_C$ is less than the width $W_B$, and the depth $D_C$ is less than the depth $D_B$. In other words, the pocket 5106b continues to narrow, and becomes shallower in the neck 5124 across the bridge 5144.

The bottom surface 5158 of the pocket 5106b is a flat surface. In other instances, the bottom surface 5158 can have a groove defined along at least a portion thereof. In still instances, the bottom surface 5158 can form a trough and/or can include hump or ridge along at least a portion thereof, such as across the bridge 5144, for example.

Referring primarily now to FIG. 69, the pocket 5106b includes a proximal extended landing zone 5130 and a distal extended landing zone 5132. The proximal extended landing zone 5130 is positioned in a proximal portion of the proximal cup 5120, and the distal extended landing zone 5132 is positioned in a distal portion of the distal cup 5122. More specifically, the extended landing zones 5130 and 5132 are positioned beyond the anticipated landing location of a staple. For example, the proximal extended landing zone 5130 is positioned proximal to the plane ALL and, in instances where the tip of a staple leg lands beyond the plane ALL, the proximal extended landing zone 5130 can catch the staple leg and direct it toward the pocket axis PA and/or toward the neck portion 5124.

The geometry of the extended landing zones 5130 and 5132 is constrained by the perimeter 5016 of the adjacent staple-forming pockets 5106. For example, the extended landing zones 5130 and 5132 can extend toward and/or into nearly abutting contact with one of more adjacent staple-forming pockets. The extended landing zones 5130 and 5132 and/or other portions of the pocket 5106b can extend parallel to adjacent staple-forming pockets 5106. In other instances, the extended landing zones 5130 and 5132 can abut one or more adjacent staple-forming pockets 5106.

Referring again to FIG. 69, the pocket 5106b is asymmetric about the pocket axis PA. For example, the perimeter 5116 of the pocket 5106b is asymmetric about the pocket axis PA. Moreover, the pocket 5106b is asymmetric about a central axis CA through the neck portion 5124 and perpendicular to the pocket axis PA. For example, the perimeter 5116 of the pocket 5106b is asymmetric about the central axis CA, and the proximal cup 5120 has a different geometry than the distal cup 5122. Although the proximal cup 5120 and the distal cup 5122 are different, the pocket 5106b can be configured to form symmetric staples. For example, referring again to FIG. 70, the distal depth $D_2$ can be less than the proximal depth $D_1$ to accommodate for variations in gap distance between the anvil and the staple cartridge and/or tissue flow, as described herein. Accordingly, the formed height of the proximal and distal legs of a staple can be equal. In other instances, the pocket 5106 can be configured to form asymmetric staples.

Referring again to FIG. 69, the neck portion 5124 is narrower than the proximal and distal cups 5120 and 5122. The narrowed perimeter 5116 of the pocket 5106b at the neck portion 5124 defines a receiving peninsula 5126 between a portion of the proximal cup 5120 and a portion of the distal cup 5122. Receiving peninsulas 5126 are positioned on each side of the pocket 5106b. The receiving peninsulas 5126 are bounded by the perimeter 5116 of the pocket 5106b and a tangent axis (e.g., $T_{B1}$ or $T_{B2}$), which is tangential to the widest portions of the proximal and distal cups 5120 and 5122 on each side of the pocket 5106. A first tangent axis $T_{B1}$ is positioned on a first side of the pocket 5106b and a second tangent axis $T_{B2}$ is positioned on the opposite side of the pocket 5106b. The first and second tangent axes $T_{B1}$ and $T_{B2}$ depicted in FIG. 69 are skewed relative to the pocket axis PA. In other instances, one or both of the tangent axes $T_{B1}$ and $T_{B2}$ can be parallel to the pocket axis PA.

Referring again to FIG. 68, the perimeters 5116 of the pockets 5106 are nested or interlocked along the staple-forming surface 5102. In particular, each pocket 5106 extends into the receiving peninsula 5126 of an adjacent pocket 5106. For example, the intermediate pockets 5106b are nested between the inner pockets 5106a and the outer pockets 5106c. Stated differently, the intermediate pockets 5106b extend into the receiving peninsula 5126 of an adjacent inner pocket 5106a and into the receiving peninsula 5126 of an adjacent outer pocket 5106c. Moreover, the inner pockets 5106a and the outer pockets 5106b are nested with the intermediate pockets 5106b. More specifically, the inner pockets 5106a extend into the receiving peninsula 5126 of an adjacent intermediate pocket 5106b, and the outer pockets 5106c extend into the receiving peninsula 5126 of an adjacent intermediate pocket 5106b. In various instances, the distal extended landing zone 5132 of the intermediate pocket 5106b is positioned in the receiving peninsula 5126 of an inner pocket 5106a, the proximal extended landing zone 5130 of the intermediate pocket 5106b is positioned in the receiving peninsula 5126 of an outer pocket 5106c, the distal extended landing zone 5132 of an inner pocket 5106a is positioned in the receiving peninsula 5126 of an intermediate pocket 5106b, and the proximal extended landing zone 5130 of the outer pocket 5106c is positioned in the receiving peninsula 5126 of an intermediate pocket 5106b.

The geometry of the pockets 5106 facilitates the nesting of the pockets 5106 in the staple-forming surface 5102. For example, because the pockets 5106 include a narrowed neck portion 5124 between two enlarged cups 5120 and 5122, one of the enlarged cups 5120, 5122 of another pocket 5106 can be positioned adjacent to the narrowed neck portion 5124. For example, one of the enlarged cups 5120, 5122 can be aligned with and/or received by a portion of an adjacent pocket 5106. In such instances, the surface area of the staple-forming surface 5102 that is covered by the pockets 5106 can be optimized. For example, the surface area of the staple-forming surface 5102 that is covered by the pockets 5106 is maximized. The "forming ratio" of the staple-forming surface 5102 is the ratio of the non-forming portion 5108 to the forming portion, i.e., the pockets 5106. In at least one instance, the forming ratio can be at least 1:1, for example. In certain instances, more than 60% or more than 75% of the staple-forming surface 5102 can be covered by staple-forming pockets 5106.

Referring now to FIGS. 72-76C, staple-forming pockets 5206 in a portion of an anvil 5200 are depicted. Similar to the anvil 3800, the pockets 5206 are arranged in a herringbone arrangement along the staple-forming surface 5202 of the anvil 5200. The anvil 5200 includes a staple-forming surface 5202 and a longitudinal slot 5204. The longitudinal slot 5204 extends along the longitudinal axis LA of the anvil 5200. In certain instances, a firing element and/or a cutting element can translate through the longitudinal slot 5204 during at least a portion of a firing stroke. The staple-forming pockets 5206 are defined in the staple-forming surface 5202. The staple-forming surface 5202 also includes a non-forming portion 5208 that extends around the pockets 5206. The non-forming portion 5208 extends entirely around each pocket 5206. In other words, the non-forming portion 5208 surrounds the staple-forming pockets 5206. In other instances, at least a portion of two or more adjacent pockets 5206 can be in abutting contact such that a non-forming portion 5208 is not positioned therebetween.

The forming ratio of the staple-forming surface 5202 can be optimized. By optimizing the forming ratio, more staples can be formed and/or formed to their desired configurations. In certain instances, the surface area of the non-forming portion 5208 of the anvil 5200 can be minimized with respect to the staple-forming pockets 5206. Additionally or alternatively, the footprint of the staple-forming pockets 5206 can be extended or enlarged to maximize the portion of the staple-forming surface 5202 that is designed to catch and form the staples.

Figure 72:
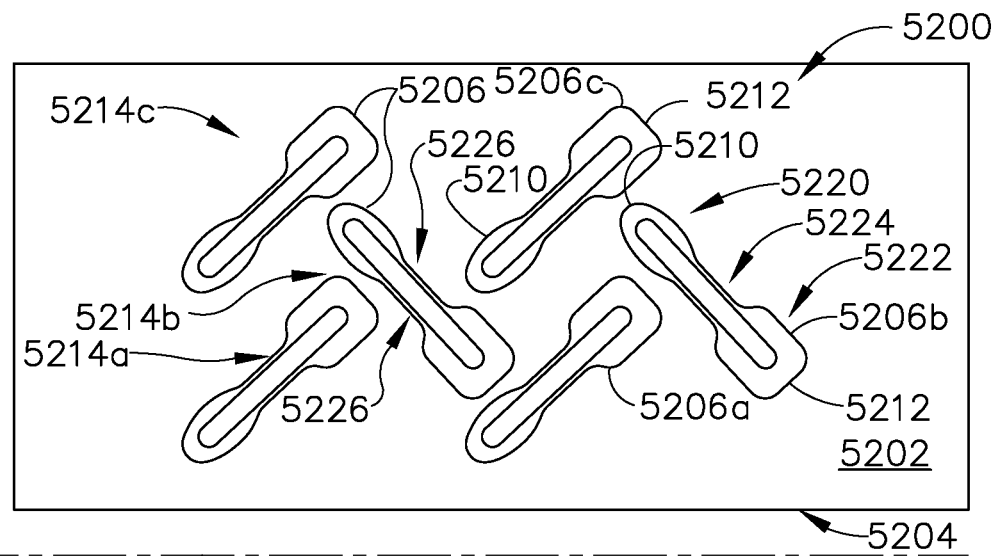
FIG. 72 is a plan view of a portion of an anvil having a plurality of staple-forming pockets defined therein.

The pockets 5206 depicted in FIG. 72 are arranged in an inner row 5214a, an intermediate row 5214b, and an outer row 5214c on a first side of the longitudinal slot 5204. Inner pockets 5206a are positioned in the inner row 5214a, intermediate pockets 5206b are positioned in the intermediate row 5214b, and outer pockets 5206c are positioned in the outer row 5214c. Although not shown in FIG. 72, in at least one instance, the pockets 5206 on the opposing side of the slot 5204 can form a mirror image reflection of the pockets 5206 on the first side of the longitudinal slot 5204. In other instances, the arrangement of pockets 5206 in the staple-forming surface 5202 can be asymmetrical relative to the slot 5204 and, in certain instances, the anvil 5200 may not include the longitudinal slot 5204. In various instances, the pockets 5206 can be arranged in less than or more than three rows on each side of the slot 5204.

The pockets 5206 depicted in FIG. 72 are identical. Each pocket 5206 defined in the staple-forming surface 5202 has the same geometry. In other instances, the geometry of the pockets 5206 can vary row-to-row and/or longitudinally along the length of the anvil 5200. For example, in certain instances, the depth of the pockets 5206 can vary along the length of the anvil 5200 to accommodate for variations in gap distance between the anvil and the staple cartridge along the length of an end effector and/or tissue flow, as described herein.

The pockets 5206 can be configured to form staples to the same, or substantially the same, formed shape. As described herein, the pockets 5206 can be configured to form each staple to the same asymmetrical shape. In other instances, the pockets 5206 can be configured to form staples to different formed shapes, such as to different heights and/or configurations.

An exemplary intermediate pocket 5206b is shown in FIGS. 73-76C. The pocket 5206b has a first end, or proximal end, 5210 and a second end, or distal end, 5212. A pocket axis PA (FIG. 72) extends between the proximal end 5210 and the distal end 5212 of the pocket 5206b. The pocket 5206b includes a perimeter 5216, which defines the boundary of the pocket 5206b. The perimeter 5216 includes linear portions and contoured portions.

The pocket 5206b includes a proximal cup 5220, a distal cup 5222, and a neck 5224 extending between the proximal cup 5220 and the distal cup 5222. When a staple is driven into forming contact with the staple-forming surface 5202, the proximal cup 5220 is aligned with a proximal staple leg, and the distal cup 5222 is aligned with a distal staple leg. The cups 5220 and 5222 are configured to direct or funnel the staple legs toward the pocket axis PA and the central portion of the pocket 5206, such as the neck portion 5224, and to deform the staple legs into the formed configuration. In other instances, the cup 5222 can be proximal to the cup 5220.

Referring primarily to FIG. 70, each cup 5220 and 5222 of the pocket 5206b defines an entrance ramp 5240a and 5240b, respectively, and an exit ramp 5242a and 5242b, respectively. When forming a staple, the tip of a staple leg can enter the respective pocket 5220, 5222 along the entrance ramp 5240a, 5240b and exit the respective pocket 5220, 5222 along the exit ramp 5242a, 5242b. At an apex 5246a, 5246b, respectively, between the entrance ramp 5240a, 5240b and the exit ramp 5242a, 5242b, the tips of the staple legs are deformed toward the staple base to assume the formed configuration, such as a B-form or modified B-form, for example. The pocket 5206b also defines a bridge 5244 between the proximal cup 5220 and the distal cup 5222. The bridge 5244 is offset from the non-forming portion 5208. More specifically, the bridge 5244 is positioned below or recessed relative to the non-forming portion 5208.

Referring again to FIG. 73, the pocket 5206b is symmetric about the pocket axis PA. For example, the perimeter 5216 of the pocket 5206b is symmetric about the pocket axis PA. Moreover, the pocket 5206b is asymmetric about a central axis CA through the neck portion 5224 and perpendicular to the pocket axis PA. For example, the perimeter 5216 of the pocket 5206b is asymmetric about the central axis CA, and the proximal cup 5220 has a different geometry than the distal cup 5222. The asymmetry of the cups 5220 and 5222 is configured to form asymmetric staples. For example, referring again to FIG. 74, the distal depth $D_2$ is less than the proximal depth $D_1$, which is configured to form a staple having a greater formed height at the proximal leg than at the distal leg. The distal depth $D_2$ can be about 0.002 inches less than the proximal depth $D_1$. In other instances, the difference between the distal depth $D_2$ and the proximal depth $D_1$ can be greater than and/or less than 0.002 inches. In certain instances, the difference can be between one percent and ten percent of the staple diameter. For example, the difference can be about two percent of the staple diameter. In other instances, the formed height of the staple can be greater at the distal leg than the proximal leg. The length of each cup 5220, 5222 is also different. For example, the distal length $D_2$ is greater than the proximal length $D_1$ in FIG. 74. Additionally, the incline of the entrance ramps 5240a and 5240b in the pocket 5206b are different, and the incline of the exit ramps 5242a and 5242b in the pocket 5206b are also different.

In various instances, the reduced depth in a portion of the pocket 5206b can improve the stiffness of the anvil. For example, because the distal depth $D_2$ is less than the proximal depth $D_1$, the anvil 5200 is comprised of more material, which can increase the stiffness thereof. Moreover, because the increased material is in a distal portion of the anvil 5200, such portion can have an increased stiffness, which can limit bowing or deformation of the anvil toward the distal end.

The difference in geometry of the proximal and distal cups 5220 and 5222, respectively, can accommodate for tissue movement or flow. More specifically, when tissue is clamped against the anvil 5200, fluid in the clamped tissue can flow or move toward adjacent, unclamped tissue. The tissue can flow laterally toward the longitudinal sides of the anvil 5200, distally toward the distal end of the anvil 5200, and/or proximally toward the proximal end of the anvil 5200. In certain instances, tissue can flow relative to the anvil 5200 when the cutting edge is advanced distally through the tissue. In such instances, tissue may flow laterally, distally, and/or proximally, but it primarily flows distally due to the distal movement of the cutting edge. In instances where the cutting edge moves proximally to incise tissue, the movement or flow of the tissue would be generally proximal during the cutting stroke. The different geometries of the proximal and distal cups 5220 and 5222, respectively, can accommodate for the flow of the tissue, which can shift or skew the staple legs embedded therein.

Referring primarily to FIGS. 75A-76C, the pocket 5206b includes sidewalls 5250, which extend from the non-forming portion 5208. The cups 5220, 5222 are configured to funnel and/or guide the staple legs and tips thereof toward and/or along the pocket axis PA and into a formed configuration. Owing to the different geometries of the proximal and distal cups 5220 and 5222, the path of the proximal staple leg can be different than the path of the distal staple leg when driven into forming contact with the pocket 5206b. In certain instances, the asymmetrical staple pockets 5206b can form asymmetrical staples from symmetrical unformed staples. Additionally or alternatively, asymmetrical unformed staples can be formed into asymmetrical formed staples by the staple pockets 5206b.

Figure 73:
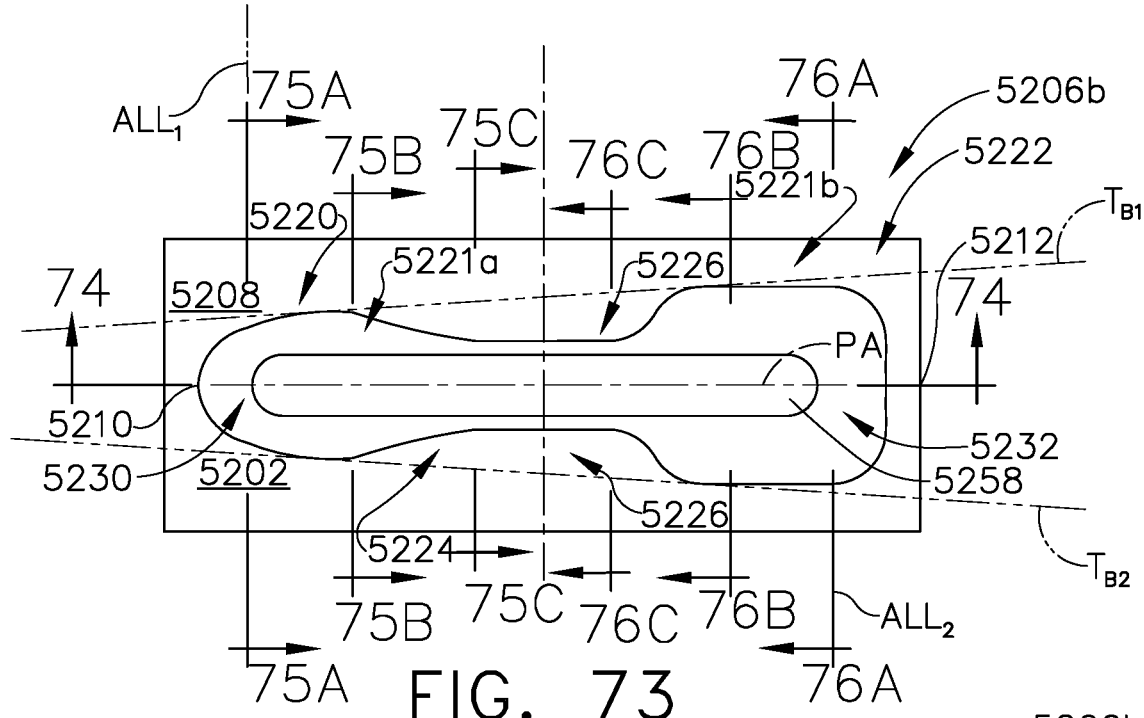
FIG. 73 is a detail view of a pocket of FIG. 72.
Figure 74:
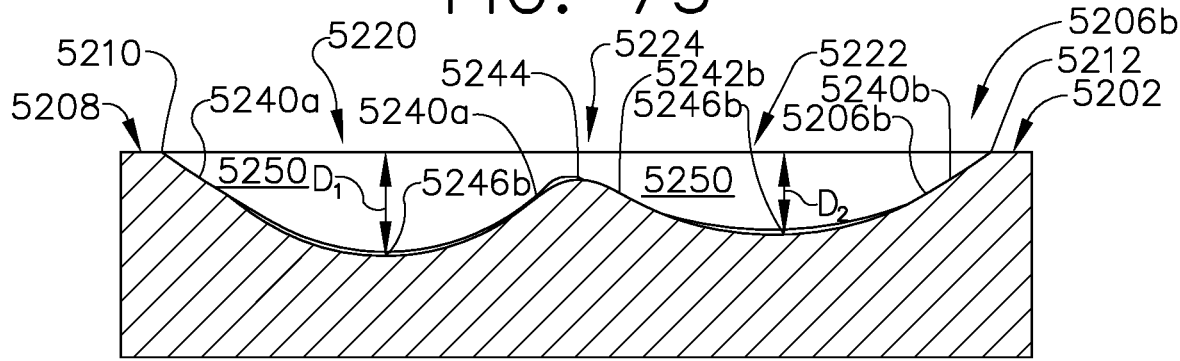
FIGS. 74-76C are cross-sectional views of the pocket of FIG. 76.
Figure 75C:
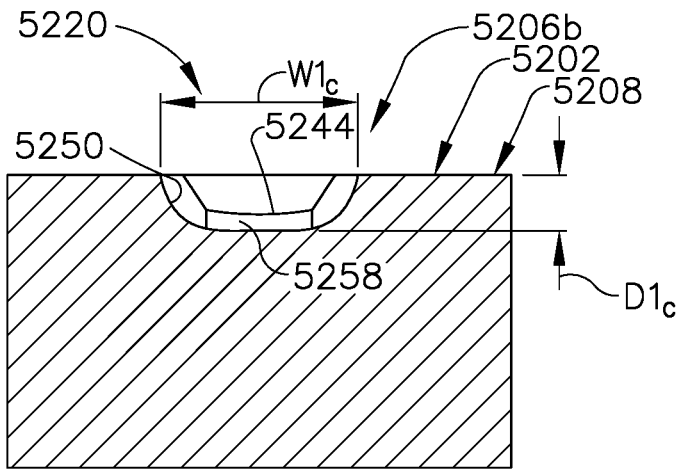
Figure 75B:
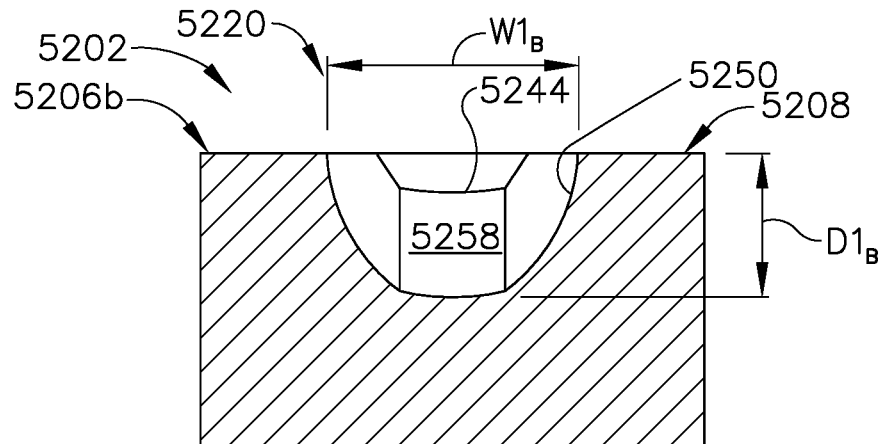
Figure 75A:
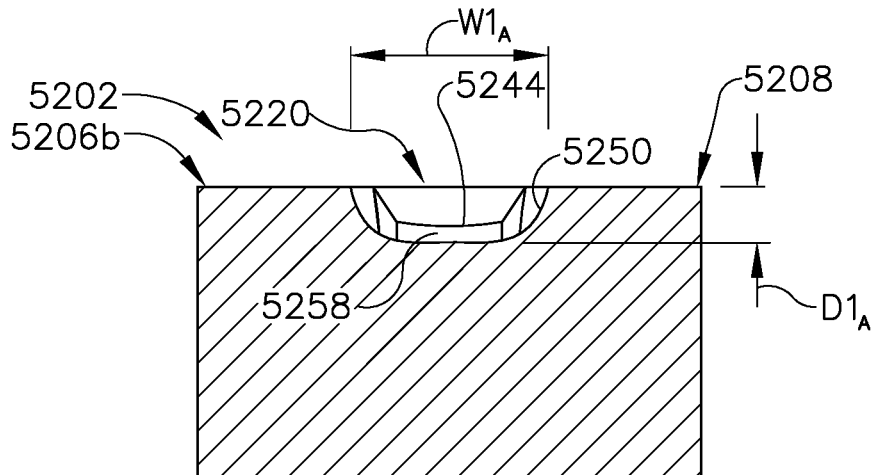

FIG. 75A is taken along the plane $ALL_1$ in FIG. 73, which corresponds to the anticipated landing location of a proximal staple leg. For example, the tip of a proximal staple leg can be expected to land in the proximal cup 5220 at and/or near the intersection of the plane $ALL_1$ and the pocket axis PA. At the plane $ALL_1$, the proximal cup 5220 defines a width $W1_A$ and a depth $D1_A$. The cross-section in FIG. 75B is taken across a transition between the proximal cup 5220 and the neck 5224. FIG. 75B depicts the proximal cup 5220 defining a width $W1_B$ and a depth $D1_B$. The width $W1_B$ is greater than the width $W1_A$, and the depth $D1_B$ is greater than the depth $D1_A$. In other words, the proximal cup 5220 widens and deepens from the plane $ALL_1$ in the proximal cup 5220 toward the neck 5224. The cross-section in FIG. 75C is taken across a proximal end of the neck portion 5224. FIG. 75C depicts the pocket 5206b defining a width $W1_C$ and a depth $D1_C$. The width $W1_C$ is less than the width $W1_B$, and the depth $D1_C$ is less than the depth $D1_B$. In other words, the pocket 5206b continues to narrow, and becomes shallower in the neck 5224 across the bridge 5244.

Figure 76C:
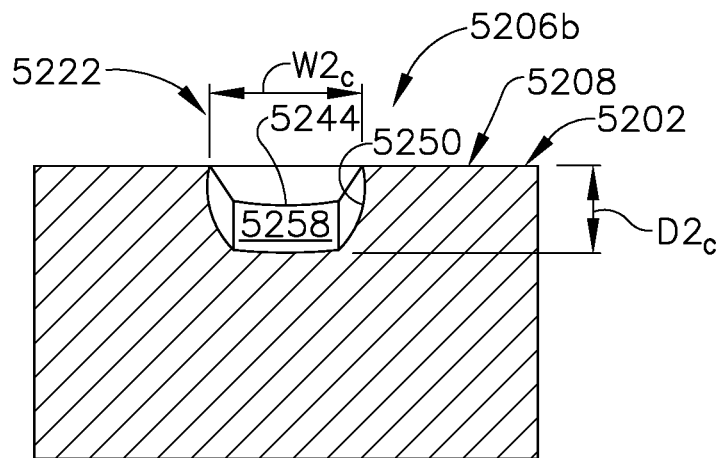
Figure 76B:
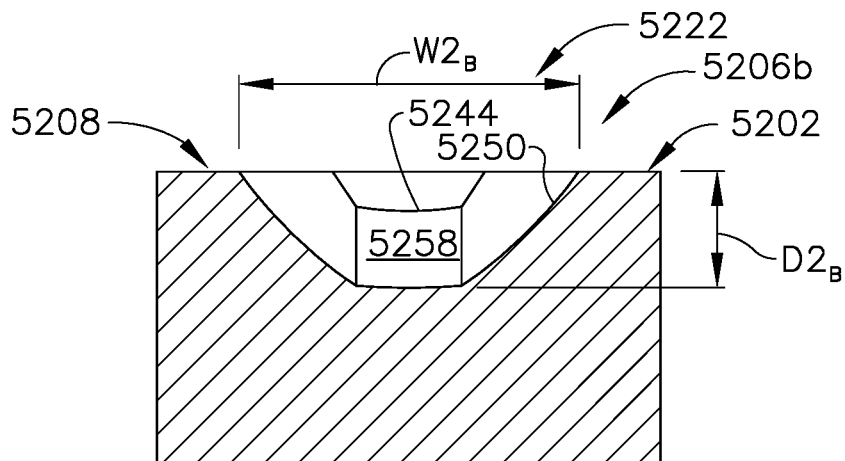
Figure 76A:
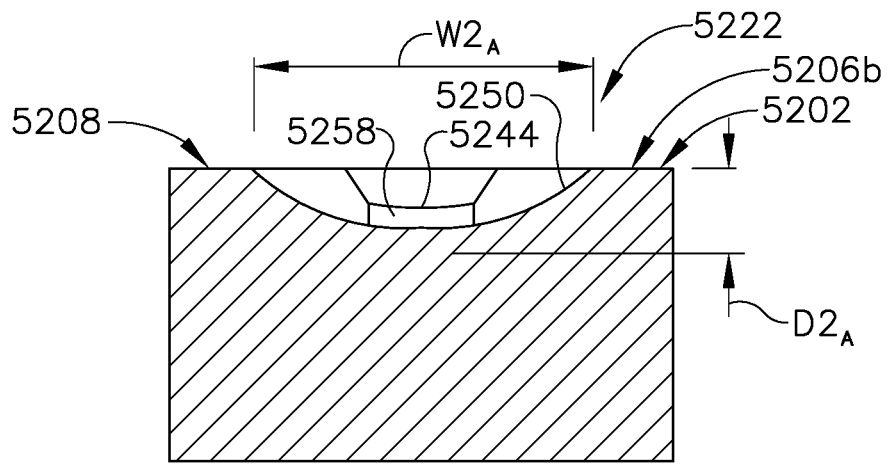

FIG. 76A is taken along the plane $ALL_2$ in FIG. 73, which corresponds to the anticipated landing location of a distal staple leg. For example, the tip of a distal staple leg can be expected to land in the distal cup 5222 at and/or near the intersection of the plane $ALL_2$ and the pocket axis PA. At the plane $ALL_2$, the distal cup 5222 defines a width $W2_A$ and a depth $D2_A$. The width $W2_A$ is different than the width $W1_A$, and the depth $D2_A$ is different than the depth $D1_A$. The cross-section in FIG. 76B is taken across a transition between the distal cup 5222 and the neck 5224. FIG. 76B depicts the distal cup 5222 defining a width $W2_B$ and a depth $D2_B$. The width $W2_B$ is different than the width $W1_B$, and the depth $D2_B$ is different than the depth $D1_B$. The width $W2_B$ is less than the width $W2_A$, and the depth $D2_B$ is greater than the depth $D2_A$. In other words, the distal cup 5222 narrows and deepens from the plane $ALL_2$ in the distal cup 5222 toward the neck 5224. The cross-section in FIG. 76C is taken across a distal end of the neck portion 5224. FIG. 76C depicts the pocket 5206b defining a width $W2_C$ and a depth $D2_C$. The width $W2_C$ is different than the width $W1_C$, and the depth $D2$ is different than the depth $D1_C$. The width $W2_C$ is less than the width $W2_B$, and the depth $D2$ is less than the depth $D2_B$. In other words, the pocket 5206b continues to narrow, and becomes shallower in the neck 5224 across the bridge 5244.

The bottom surface 5258 of the pocket 5206b is a flat surface. In other instances, the bottom surface 5258 can have a groove defined along at least a portion thereof. In still other instances, the bottom surface 5258 can form a trough and/or can include a hump or ridge along at least a portion thereof, such as across the bridge 5244, for example.

Referring primarily now to FIG. 73, the pocket 5206b includes a proximal extended landing zone 5230 and a distal extended landing zone 5232. The proximal extended landing zone 5230 is positioned in a proximal portion of the proximal cup 5220, and the distal extended landing zone 5232 is positioned in a distal portion of the distal cup 5222. More specifically, the extended landing zones 5230 and 5232 are positioned beyond the anticipated landing location of a staple. For example, the proximal extended landing zone 5230 is positioned proximal to the plane $ALL_1$ and, in instances where the tip of a staple leg lands beyond the plane ALL$_1$, the proximal extended landing zones 5230 can catch the staple leg and direct it toward the pocket axis PA and/or toward the neck portion 5224. The distal extended landing zone 5232 is positioned distal to the plane ALL$_2$ and, in instances where the tip of a staple leg lands beyond the plane ALL$_2$, the distal extended landing zones 5232 can catch the staple leg and direct it toward the pocket axis PA and/or toward the neck portion 5224. In certain instances, the geometry of the extended landing zones 5230, 5232 can be constrained or limited by the geometry of the adjacent, nested staple-forming pockets 5206.

Referring again to FIG. 73, the neck portion 5224 is narrower than the proximal and distal cups 5220 and 5222. The narrowed perimeter 5216 of the pocket 5206b at the neck portion 5224 defines a receiving peninsula 5226 between a portion of the proximal cup 5220 and a portion of the distal cup 5222. Receiving peninsulas 5226 are positioned on each side of the pocket 5206b. The receiving peninsulas 5226 are bounded by the perimeter 5216 of the pocket 5206b and a tangent axis (e.g., T$_{B1}$ and T$_{B2}$), which is tangential to the widest portions of the proximal and distal cups 5220 and 5222 on each side of the pocket 5206. A first tangent axis T$_{B1}$ is positioned on a first side of the pocket 5206b and a second tangent axis T$_{B2}$ is positioned on the opposite side of the pocket 5206b. The first and second tangent axes T$_{B1}$ and T$_{B2}$ depicted in FIG. 73 are skewed relative to the pocket axis PA. In other instances, one or both of the tangent axes T$_{B1}$ and T$_{B2}$ can be parallel to the pocket axis PA.

In various instances, the geometry of the pockets 5206 can facilitate the nesting and/or the close arrangement of the pockets 5206 in the staple-forming surface 5202. For example, the surface area of the staple-forming surface 5202 that is covered by the pockets 5206 can be optimized. The "forming ratio" of the staple-forming surface 5202 is the ratio of the non-forming portion 5208 to the forming portion, i.e., the pockets 5206. In at least one instance, the forming ratio can be at least 1:1, for example.

As described herein, the arrangement of staple cavities and staples in a staple cartridge for an end effector can correspond to or match the arrangement of staple-forming pockets in an anvil of the end effector. More specifically, the angular orientation and spacing of each staple cavity can match the angular orientation and spacing of a respective staple-forming pocket. For example, when the staple cavities are arranged in a herringbone pattern, the staple-forming pockets can be arranged in a corresponding herringbone pattern.

In certain instances, an end effector can include a staple cartridge having an arrangement of staple cavities and an anvil having a non-corresponding arrangement of staple-forming pockets. For example, the staple cavities can be obliquely oriented relative to a longitudinal axis and the staple-forming pockets can be oriented parallel to the longitudinal axis. In certain instances, an end effector can be configured to receive different staple cartridges having different arrangements of staple cavities, for example, and the anvil of the end effector may not be compatible with all of the different staple cartridges and permutations of staple cavities therein. In such instances, the anvil can be retrofit or adapted with an attachment, such as an anvil plate, having a suitable arrangement of staple-forming pockets.

Figure 77:
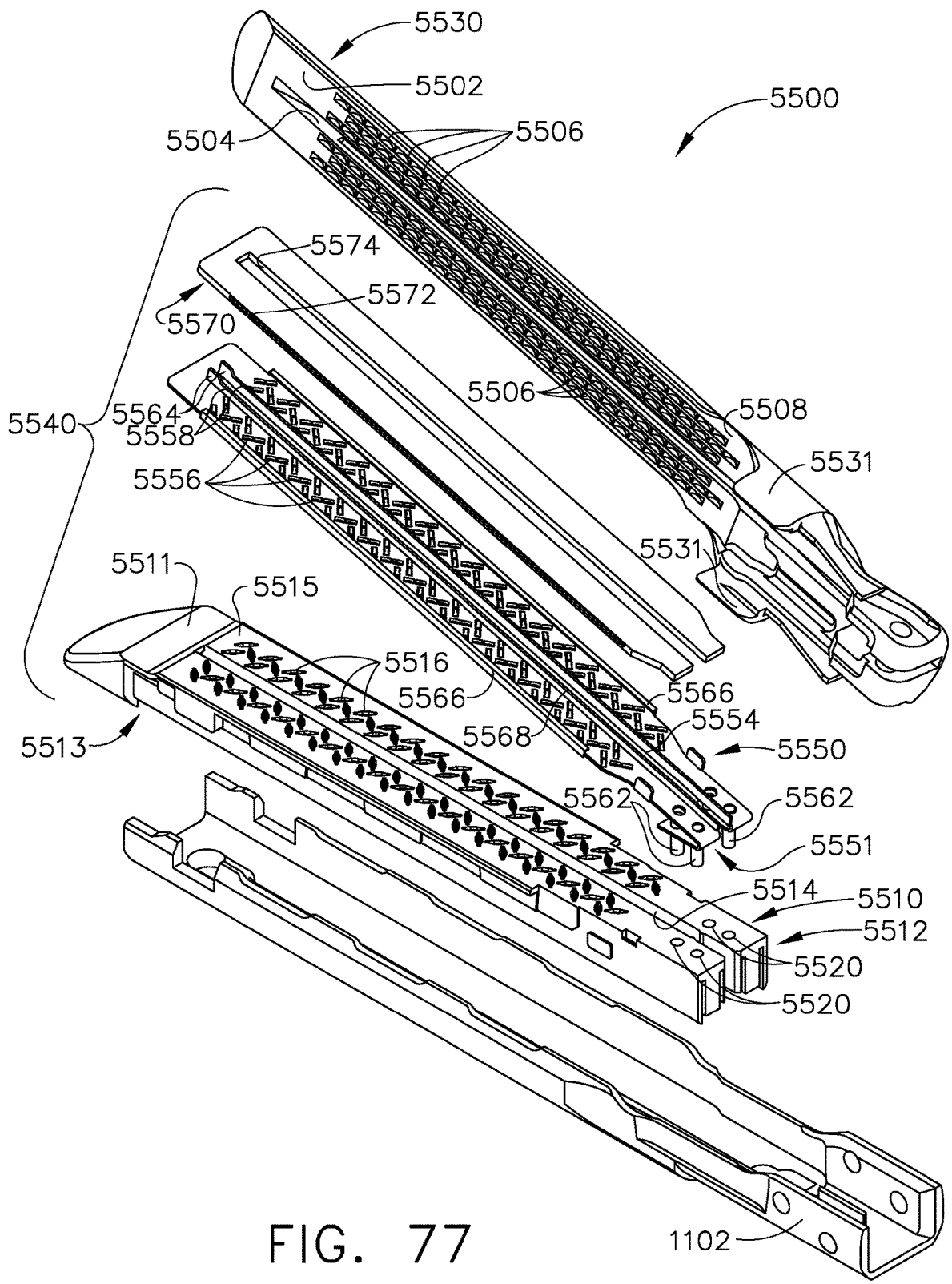
FIG. 77 is an exploded perspective view of an end effector and an adaptor assembly.
Figure 78:
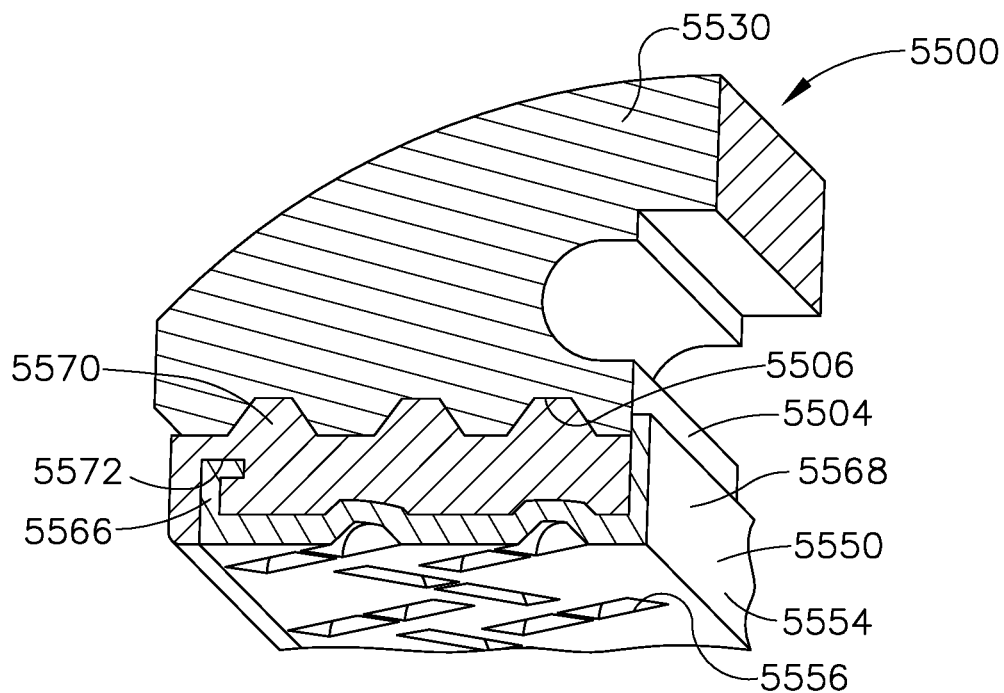
FIG. 78 is a cross-sectional perspective view of a portion of the end effector and the adaptor assembly of FIG. 77.
Figure 79:
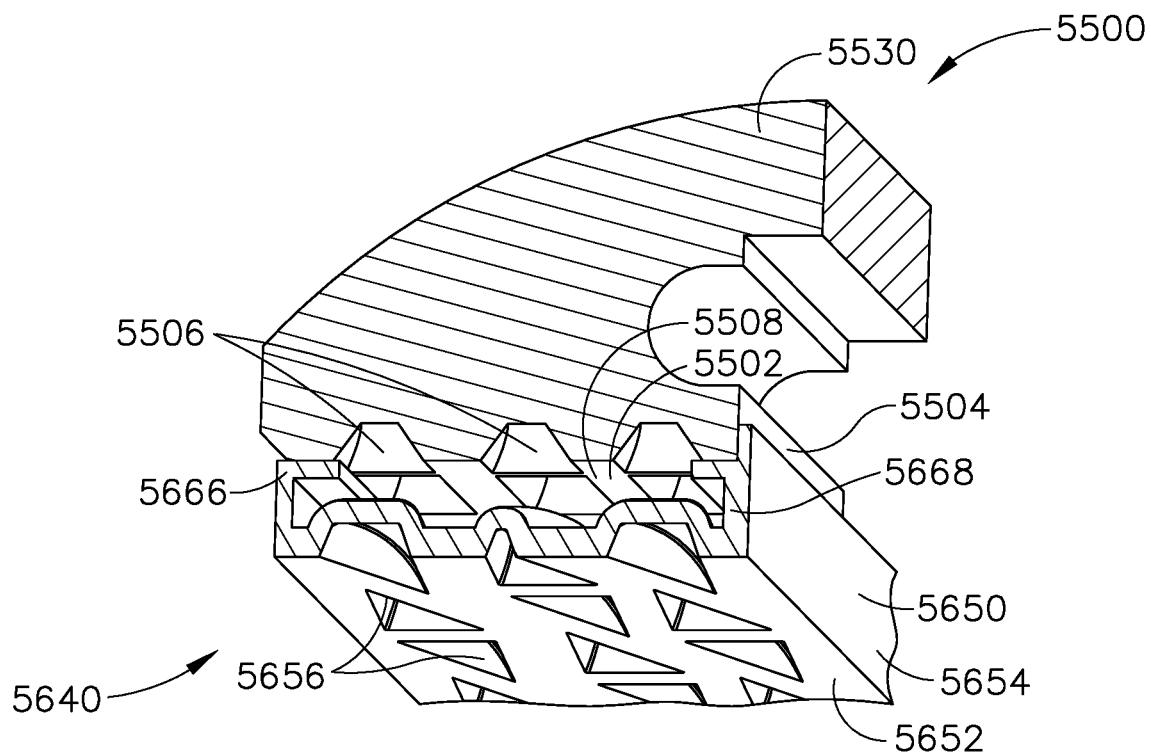
FIG. 79 is a cross-sectional perspective view of a portion of the end effector of FIG. 77 and an adaptor assembly.

A surgical end effector 5500 is depicted in FIGS. 77-79. Similar to the end effector 1100 (FIGS. 1-4), the end effector 5500 includes the elongate channel 1102, which is configured to operably support a staple cartridge 5510 therein. The staple cartridge 5510 is similar in many aspects to the staple cartridge 1110. For example, the staple cartridge includes a staple cartridge body 5511 having a deck 5515. A longitudinal slot 5514 extends through the deck 5515 from a proximal end portion 5512 of the body 5511 toward a distal end portion 5513 of the body 5511. Angularly-oriented staple cavities 5516 are defined in the cartridge body 5511 and each staple cavity 5516 defines an opening in the deck 5515. The opening of each staple cavity 5516 is oriented at an oblique angle relative to the longitudinal slot 5514. The staple cavities 5516 are arranged in a herringbone pattern. Staples are removably positioned in the staple cavities.

The end effector 5500 also includes an anvil 5530 that is pivotally supported relative to the elongate channel 1102. The anvil 5530 is similar in many aspects to the anvil 1130. For example, the anvil 5530 includes a staple-forming surface 5502 and a longitudinal slot 5504. In certain instances, a firing element and/or a cutting element, such as the sled assembly 1120 and/or the firing member 1760 (FIG. 4), for example, can translate through the longitudinal slot 5504 during at least a portion of a firing stroke. Tissue stops 5531 extend downward toward the staple cartridge 5510 to control the positioning of tissue between the proximal end portion 5512 of the cartridge body 5511 and the anvil 5530. Staple-forming pockets 5506 are defined in the staple-forming surface 5502, which also includes a non-forming portion 5508 that extends around the pockets 5506. The staple-forming pockets 5506 are oriented parallel to the longitudinal slot 5504. In other words, the arrangement of staple-forming pockets 5506 does not match or correspond to the arrangement of staple cavities 5516. If staples were fired from the staple cartridge 5510 into forming contact with the anvil 5530, the majority of such staples would likely be unformed and/or malformed.

The end effector 5500 includes an adaptor assembly 5540, which is configured to adapt the anvil 5530 to a suitable arrangement of staple-forming pockets. The staple cartridge 5510 is part of the adaptor assembly 5540. The adaptor assembly 5540 also includes an anvil plate 5550 and connecting material 5570. A proximal portion of the anvil plate 5550 forms a spring 5551 at which the anvil plate 5550 is attached to the staple cartridge 5510. As such, the anvil plate 5550 is configured to pivot downward toward the staple cartridge 5510 at the proximal spring 5551 when a closing motion is applied to the anvil plate 5550, such as by the anvil 5530, for example. The spring 5551 can bias the anvil plate 5550 toward the configuration shown in FIG. 77, which can facilitate the releasable attachment of the adaptor assembly 5540 to the anvil 5530.

The arrangement of staple-forming pockets in the anvil plate 5550 corresponds to the arrangement of staple cavities 5516 in the staple cartridge. The anvil plate 5550 includes a staple-forming surface 5502 and a longitudinal slot 5554, which is aligned with the longitudinal slot 5504 in the anvil 5530 and the longitudinal slot 5514 in the staple cartridge 5510 when the adaptor assembly 5540 is installed in the end effector 5500. Staple-forming pockets 5556 are defined in the staple-forming surface 5502 and a non-forming portion 5558 (FIG. 77) extends around the staple-forming pockets 5556. In the illustrated embodiment, the staple-forming pockets 5556 are oriented at oblique angles relative to the longitudinal slot 5554. More specifically, the staple-forming pockets 5556 are arranged in a herringbone pattern, which corresponds to the herringbone pattern of the staple cavities 5516. The anvil plate 5550 can be a sheet of metal in which the arrangement of staple-forming pockets has been stamped.

The arrangement of staple-forming pockets 5556 in the anvil plate 5550 corresponds to the arrangement of staple cavities 5516 in the staple cartridge. In other words, each staple-forming pocket 5556 in the anvil plate 5550 corresponds to the angle and position of a staple cavity 5516. The reader will appreciate that a staple cartridge can include a variety of different arrangements of staple cavities, and various exemplary arrangements of staple cavities are described herein. For example, a staple cartridge can include a longitudinally-repetitive pattern of obliquely-oriented staple cavities and/or one or more parallel and/or angularly-offset staple cavities. Additionally or alternatively, a staple cartridge can include multiple distinct patterns of staple cavities. In still other instances, the arrangement of staple cavities can vary laterally and/or longitudinally along the cartridge body. Whatever the arrangement of staple cavities in a staple cartridge, a corresponding arrangement of staple-forming pockets can be provided by the complementary anvil plate 5550 of the adaptor assembly 5540.

The anvil plate 5500 is connectable to the staple cartridge 5510, and the connecting material 5570 is attached to the anvil plate 5500. In use, when the staple cartridge 5510 is inserted into the elongate channel 1102, the anvil plate 5500 and the connecting material 5570 of the adaptor assembly 5540 are also disposed between the elongate channel 1102 and the anvil 5530. In certain instances, the anvil 5530 can be pivoted downward toward the elongate channel 1102 to secure or otherwise attach the anvil plate 5550 to the staple-forming surface 5502 of the anvil 5530 with the connecting material 5570. Additionally or alternatively, the spring member 5551 can bias the anvil plate 5550 and the connecting material 5570 thereon into and/or toward attachment with the anvil 5530. When the adaptor assembly 5540 is installed in the end effector 5500, the anvil 5530 has effectively been retrofit or adapted for use with the staple cartridge 5510.

The staple cartridge 5510 and the anvil plate 5550 may include alignment features for aligning the staple cavities 5516 in the staple cartridge 5510 with the corresponding staple-forming pockets 5556 in the anvil plate 5500. For example, the staple cartridge 5510 includes alignment apertures 5520 (FIG. 77), and the anvil plate 5550 includes alignment posts or pins 5562. The alignment pins 5562 are received by the alignment apertures 5520 to position the anvil plate 5550 relative to the staple cartridge 5510. For example, the alignment pins 5562 can be press fit into the alignment apertures 5520. The connection between the alignment apertures 5520 and the alignment pins 5562 is configured to longitudinally align the staple cartridge 5510 and the anvil plate 5550, for example.

In certain instances, the manufacturer and/or distributor can provide the assembly 5540 pre-assembled. For example, the anvil plate 5550 can be press fit into engagement with the staple cartridge 5510 before a surgeon or assistant thereto obtains the assembly 5540 for a surgical procedure. In other instances, the surgeon and/or assistant thereto can assemble the assembly 5540.

The anvil plate 5550 also includes alignment features for aligning the anvil plate 5550 with the anvil 5530. For example, the anvil plate 5550 includes distal alignment flanges 5564. The distal alignment flanges 5564 are received by the longitudinal slot 5504 in the anvil 5530 to position the anvil plate 5550 relative to the anvil 5530. For example, the distal alignment flanges 5564 can be press fit into the longitudinal slot 5504. The connection between the alignment flanges 5564 and the longitudinal slot 5504 is configured to laterally align the anvil plate 5550 and the anvil 5530, for example.

The connecting material 5570 is a flexible material. For example, the connecting material 5570 can comprise an elastomer and/or low density polyethylene. In various instances, the connecting material 5570 can be an overmold on the anvil plate 5550. When adhered or otherwise secured to the anvil 5530, the connecting material 5570 is configured to assume a deformed configuration that matches the profile of the staple-forming surface 5502. For example, the unformed configuration of the connecting material 5570 is depicted in FIG. 77 and the formed configuration of the connecting material 5570 is depicted in FIG. 78. Referring primarily to FIG. 78, the connecting material 5570 flows into and fills the staple-forming pockets 5506. In other words, the staple-forming pockets 5506 imprint in the connecting material 5570. In such instances, the connecting material 5570 can fortify the anvil plate 5550 during a forming process. For example, the connecting material 5570 between the anvil plate 5550 and the anvil 5530 can provide a backing for the anvil plate 5550 to prevent and/or limit deformation of the anvil plate 5550 relative to the anvil 5530 when the anvil plate 5550 is impacted and subjected to other forces during use.

The connecting material 5570 includes a channel 5572. The channel 5572 extends along a portion of the length thereof. Although not shown in FIG. 77, a similar channel 5572 can be defined in the connecting material 5570 along the opposite side of the adaptor assembly 5540. A lip 5566 of the anvil plate 5550 is positioned in the channel 5572. The lip 5566 is substantially U-shaped. In other instances, the lip 5566 can be L-shaped, linear, and/or contoured, for example. The anvil plate 5500 also includes an inner ridge 5568, which is aligned with a longitudinal slot 5574 (FIG. 77) in the connecting material 5570 and the longitudinal slot 5504 in the anvil 5530. The ridge 5568 is configured to facilitate the alignment of the adaptor assembly 5540 along the length of the end effector 5500. In various instances, the connecting material 5570 can be molded over the anvil plate 5550. For example, the connecting material 5570 can be molded around the lip 5566 and/or the ridge 5568.

A portion of the end effector 5500 is also depicted in FIG. 79. An adaptor assembly 5640 is installed in the end effector 5500 in FIG. 79. The adaptor assembly 5640 is similar in many aspects to the adaptor assembly 5540. For example, the adaptor assembly 5640 includes an anvil plate 5650 having a staple-forming surface 5652 and a longitudinal slot 5654, which is aligned with the longitudinal slot 5504 in the anvil 5530. Staple-forming pockets 5656 are defined in the staple-forming surface 5652 and a non-forming portion 5658 extends around the staple-forming pockets 5656. The staple-forming pockets 5656 are oriented at oblique angles relative to the longitudinal slot 5654. More specifically, the staple-forming pockets 5656 are arranged in a herringbone pattern, which corresponds to the herringbone pattern of the staple cavities 5516 (FIG. 77). The anvil plate 5650 can be a sheet of metal in which the arrangement of staple-forming pockets has been stamped.

The adaptor assembly 5640 does not include a deformable material, such as the deformable material 5570. Rather, the anvil plate 5650 is configured to directly engage the anvil 5530. The anvil plate 5650 includes a lip 5666, which is positioned against the staple-forming surface 5502. The lip 5666 is substantially U-shaped. In other instances, the lip 5666 can be L-shaped, linear, and/or contoured, for example. The anvil plate 5600 also includes an inner ridge 5668, which is aligned with the longitudinal slot 5504 in the anvil 5530. The ridge 5668 is configured to facilitate the alignment of the adaptor assembly 5640 along the length of the end effector 5600.

In other instances, the anvil plate 5650 can be embedded in the staple-forming surface 5502 of the anvil 5530. For example, staple-forming pockets 5656 of the anvil plate 5650 can at least partially nest within the staple-forming pockets 5506 in the anvil 5530. Although the arrangement, quantity, and/or geometry of the staple-forming pockets 5656 are different than the arrangement, quantity, and/or geometry of the staple-forming pockets 5506, portions of the staple-forming pockets 5656 can be positioned within portions of the staple-forming pockets 5506.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719, for example, discloses several examples of a robotic surgical instrument system in greater detail.

EXAMPLES

Example 1

A staple cartridge comprising a longitudinal axis, a cartridge body, wherein a plurality of staple cavities are defined in the cartridge body, wherein a majority of the plurality of staple cavities are arranged in a longitudinally-repetitive pattern, wherein the plurality of staple cavities further comprises an irregular staple cavity, and wherein the irregular staple cavity is angularly-offset from the staple cavities in the longitudinally-repetitive pattern, and a plurality of staples positioned in the staple cavities.

Example 2

The staple cartridge of Example 1, further comprising a firing element configured to translate between a proximal position and a distal position in the cartridge body, wherein the longitudinally-repetitive pattern extends distally beyond the distal position of the firing element.

Example 3

The staple cartridge of Examples 1 or 2, wherein the longitudinally-repetitive pattern consists of a pattern of staple cavities obliquely oriented relative to the longitudinal axis.

Example 4

The staple cartridge of Examples 1, 2, or 3, wherein the cartridge body comprises a deck, wherein each staple cavity defines an opening in the deck, and wherein the openings of the staple cavities in the pattern form a herringbone pattern.

Example 5

The staple cartridge of Examples 1, 2, 3, or 4, wherein the opening of the irregular staple cavity comprises a proximal end and a distal end, wherein a staple cavity axis extends between the proximal end and the distal end, and wherein the staple cavity axis is parallel to the longitudinal axis.

Example 6

A staple cartridge comprising a longitudinal axis and a cartridge body, wherein a plurality of staple cavities are defined in the cartridge body, wherein the plurality of staple cavities are arranged in a plurality of patterns, and wherein the plurality of patterns comprises a first pattern comprising a longitudinally-repetitive pattern of staple cavities angularly oriented relative to the longitudinal axis and a second pattern, wherein the second pattern is laterally aligned with the first pattern and longitudinally offset from the first pattern, and wherein the second pattern is different than the first pattern. The staple cartridge further comprises a plurality of staples positioned in the staple cavities.

Example 7

The staple cartridge of Example 6, wherein the cartridge body comprises a deck, and wherein the longitudinally-repetitive pattern comprises a first staple cavity defining a first opening in the deck and a second staple cavity defining a second opening in the deck, wherein the second opening is obliquely oriented relative to the first opening.

Example 8

The staple cartridge of Examples 6 or 7, wherein the longitudinally-repetitive pattern comprises a herringbone pattern.

Example 9

The staple cartridge of Examples 6, 7, or 8, wherein the second pattern comprises a third staple cavity defining a third opening in the deck, and wherein the third opening is obliquely oriented relative to the first opening and the second opening.

Example 10

The staple cartridge of Examples 6, 7, 8, or 9, wherein the second pattern further comprises a fourth staple cavity defining a fourth opening in the deck, and wherein the fourth opening is parallel to the third opening.

Example 11

The staple cartridge of Example 10, further comprising a plurality of staple drivers comprising a first driver positioned in the third staple cavity and comprising a first ramp profile and a second driver positioned in the fourth staple cavity and comprising a second ramp profile, wherein the first driver is connected to the second driver, and wherein the first ramp profile is different than the second ramp profile.

Example 12

The staple cartridge of Examples 10 or 11, wherein the fourth opening is longitudinally staggered relative to the third opening.

Example 13

The staple cartridge of Examples 6, 7, 8, 9, 10, 11, or 12, wherein the second pattern comprises a proximal pattern.

Example 14

The staple cartridge of Examples 6, 7, 8, 9, 10, 11, 12, or 13, wherein the plurality of patterns further comprises a third pattern laterally aligned with the first pattern and longitudinally offset from the first pattern, and wherein the third pattern is different than the first pattern.

Example 15

The staple cartridge of Example 14, wherein the first pattern is positioned intermediate the second pattern and the third pattern.

Example 16

The staple cartridge of Examples 14 or 15, further comprising a cutting edge configured to move relative to the cartridge body during a firing stroke, wherein the cutting edge is configured to move between a proximal position and a distal position, and wherein the third pattern is positioned distal to the distal position of the cutting edge.

Example 17

An end effector for stapling tissue comprising, the end effector comprising a staple cartridge comprising a cartridge body, wherein a plurality of staple cavities are defined in the cartridge body, wherein the plurality of staple cavities are arranged in a plurality of patterns. The plurality of patterns comprises a first pattern comprising a longitudinally-repetitive pattern of staple cavities angularly oriented relative to a longitudinal axis and a second pattern, wherein the second pattern is longitudinally offset from the first pattern, and wherein the second pattern is different than the first pattern. The end effector further comprises a cutting edge configured to move between a proximal position and a distal position and a tissue stop, wherein the first pattern extends between the tissue stop and the distal position of the cutting edge.

Example 18

The end effector of Example 17, wherein the second pattern comprises a plurality of parallel staple cavities.

Example 19

The end effector of Examples 17 or 18, wherein the parallel staple cavities are obliquely oriented relative to the staple cavities in the first pattern.

Example 20

The end effector of Examples 17, 18, or 19, further comprising an anvil, wherein the tissue stop comprises a pair of sidewalls extending from the anvil toward the staple cartridge.

Example 21

An end effector for use with a surgical stapler, the end effector comprising a staple cartridge comprising a plurality of staples, wherein the plurality of staples comprises a first staple, and wherein the first staple comprises a proximal leg and a distal leg and an anvil comprising a staple-forming surface, wherein a plurality of pockets are defined in the staple-forming surface, wherein the plurality of pockets comprises a first pocket. The first pocket comprises a proximal cup, wherein the proximal leg is aligned with the proximal cup and a distal cup, wherein the distal leg is aligned with the distal cup, and wherein the first pocket is asymmetric relative to a central axis transecting the first pocket equidistant between the proximal cup and the distal cup.

Example 22

The end effector of Example 21, wherein the first pocket is obliquely oriented relative to a longitudinal axis defined by the end effector.

Example 23

The end effector of Examples 21 or 22, wherein each pocket comprises a perimeter, wherein the plurality of pockets comprises a second pocket, and wherein a portion of the perimeter of the first pocket is adjacently nested with a portion of the perimeter of the second pocket.

Example 24

The end effector of Examples 21, 22, or 23, wherein the first pocket is configured to form a staple to an asymmetric configuration.

Example 25

The end effector of Examples 21, 22, 23, or 24, wherein the first pocket is asymmetric relative to a first pocket axis extending between the proximal cup and the distal cup perpendicular to the central axis.

Example 26

An end effector for use with a surgical stapler, the end effector comprising a staple cartridge comprising a plurality of staples, wherein the plurality of staples comprises a first staple, and wherein the first staple comprises a first proximal leg and a first distal leg, and an anvil comprising a staple-forming surface, wherein a plurality of pockets are defined in the staple-forming surface, wherein the plurality of pockets comprises a first pocket. The first pocket comprises a first proximal cup, wherein the first proximal leg is aligned with the first proximal cup, and a first distal cup, wherein the first distal leg is aligned with the first distal cup, wherein the first distal cup is laterally offset from the first proximal cup, and wherein the first pocket is asymmetric relative to a first pocket axis extending between the first proximal cup and the first distal cup.

Example 27

The end effector of Example 26, wherein the plurality of pockets comprises a second pocket, and wherein the second pocket comprises a second proximal cup and a second distal cup, wherein the second distal cup is laterally offset from the second proximal cup, and wherein the second pocket is asymmetric relative to a second pocket axis extending between the second proximal cup and the second distal cup.

Example 28

The end effector of Example 27, wherein the second pocket axis is angularly oriented relative to the first pocket axis.

Example 29

The end effector of Examples 27 or 28, wherein the first pocket axis and the second pocket axis are obliquely oriented relative to a longitudinal axis defined by the end effector.

Example 30

The end effector of Examples 27, 28, or 29, wherein the plurality of staples further comprises a second staple, wherein the second staple comprises a second proximal leg and a second distal leg, wherein the second proximal leg is aligned with the second proximal cup, and wherein the second distal leg is aligned with the second distal cup.

Example 31

The end effector of Examples 27, 28, 29, or 30, wherein the second distal cup is nested adjacent to the first pocket between the first proximal cup and the first distal cup.

Example 32

The end effector of Examples 26, 27, 28, 29, 30, or 31, wherein the plurality of pockets comprises a plurality of nested pockets.

Example 33

The end effector of Examples 26, 27, 28, 29, 30, 31, or 32, wherein the first proximal cup comprises a first geometry, wherein the first distal cup comprises a second geometry, and wherein the second geometry is different than the first geometry.

Example 34

The end effector of Examples 26, 27, 28, 29, 30, 31, or 32, wherein the staple-forming surface comprises a non-forming planar surface surrounding at least a portion of the pockets, wherein the first proximal cup comprises a proximal depth relative to the non-forming planar surface, wherein the first distal cup comprises a distal depth relative to the non-forming planar surface, and wherein the distal depth is different than the proximal depth.

Example 35

The end effector of Example 34, wherein the proximal depth is greater than the distal depth.

Example 36

An end effector for use with a surgical stapler, the end effector comprising a staple cartridge comprising a plurality of staples, wherein the plurality of staples comprises a first staple, wherein the first staple comprises a first proximal leg and a first distal leg, and wherein the first distal leg is laterally offset from the first proximal leg, and an anvil comprising a staple-forming surface, wherein a plurality of pockets are defined in the staple-forming surface, wherein the plurality of pockets comprises a first pocket. The first pocket comprises a first proximal cup comprising a proximal geometry, wherein the first proximal leg is aligned with the first proximal cup, and a first distal cup comprising a distal geometry, wherein the first distal leg is aligned with the first distal cup, and wherein distal geometry is different than the proximal geometry.

Example 37

The end effector of Example 36, wherein the first proximal cup is configured to form the first proximal leg to a first height, wherein the first distal cup is configured to form the first distal leg to a second height, and wherein the second height is different than the first height.

Example 38

The end effector of Examples 36 or 37, wherein the first proximal cup comprises a first depth, wherein the second distal cup comprises a second depth, and wherein the first depth is different than the second depth.

Example 39

The end effector of Examples 36, 37, or 38, wherein the first proximal cup comprises a first entrance angle and a first exit angle, wherein the first distal cup comprises a second entrance angle and a second exit angle, wherein the first entrance angle is different than the second entrance angle, and wherein the first exit angle is different than the second exit angle.

Example 40

The end effector of Examples 36, 37, 38, or 39, wherein the first proximal cup comprises a first width, wherein the second distal cup comprises a second width, and wherein the first width is different than the second width.

Example 41

The end effector of Examples 36, 37, 38, 39, or 40, wherein the plurality of pockets comprises a second pocket, and wherein the second pocket is different than the first pocket.

Example 42

The end effector of Example 41, wherein the plurality of pockets are arranged in a plurality of rows comprising a first row comprising the first pocket and a second row comprising the second pocket, wherein the second pocket is not parallel to the first pocket.

Example 43

An end effector comprising a staple cartridge and an anvil comprising a longitudinal axis and a staple-forming surface, wherein a plurality of staple-forming pockets are defined in the staple-forming surface. The plurality of staple-forming pockets comprises a first pocket obliquely oriented relative to the longitudinal axis, a second pocket obliquely oriented relative to the longitudinal axis and the first pocket, and a third pocket obliquely oriented relative to the longitudinal axis, the first pocket, and the second pocket.

Example 44

The end effector of Example 43, wherein a slot is defined at least partially through the anvil along the longitudinal axis, wherein the first pocket is spaced a first distance from the slot, wherein the second pocket is spaced a second distance from the slot, wherein the third pocket is spaced a third distance from the slot, and wherein the first distance, the second distance, and the third distance are different.

Example 45

The end effector of Examples 43 or 44, wherein the first pocket is positioned in an inner row, wherein the second pocket is positioned in an intermediate row, wherein the third pocket is positioned in an outer row, and wherein the first pocket is longitudinally staggered from the third pocket and longitudinally overlapping the third pocket.

Example 46

The end effector of Examples 43, 44, or 45, wherein the second pocket is laterally spaced apart from the first pocket by a first lateral distance, wherein the second pocket is laterally spaced apart from the third pocket by a second lateral distance, and wherein the second lateral distance is different than the first lateral distance.

Example 47

The end effector of Examples 43, 44, 45, or 46, wherein the staple cartridge comprises a plurality of staples comprising a first staple positioned for forming contact with the first pocket, a second staple positioned for forming contact with the second pocket, wherein the first staple laterally overlaps the first staple by a first distance, and a third staple positioned for forming contact with the third pocket, wherein the third staple laterally overlaps the second staple by a second distance, and wherein the second distance is different than the first distance.

Example 48

A staple cartridge comprising a cartridge body comprising a longitudinal slot, wherein a plurality of staple cavities are defined in the cartridge body, wherein the staple cavities are obliquely oriented relative to the longitudinal slot, wherein the staple cavities are arranged in a plurality of rows comprising a first row positioned on a first side of the longitudinal slot, a second row positioned on the first side of the longitudinal slot, wherein the staple cavities in the first row laterally overlap the staple cavities in the second row by a first distance, and a third row positioned on the first side of the longitudinal slot, wherein the staple cavities in the second row laterally overlaps the staple cavities in the third row by a second distance, and wherein the second distance is different than the first distance.

Example 49

The staple cartridge of Example 48, wherein the staple cavities in the first row are oriented at a first angle relative to the longitudinal slot, wherein the staple cavities in the second row are oriented at a second angle relative to the longitudinal slot, wherein the staple cavities in the third row are oriented at a third angle relative to the longitudinal slot, and wherein the first angle, the second angle, and the third angle are different.

Example 50

The staple cartridge of Example 49, wherein the second angle is a supplementary angle to the first angle.

Example 51

The staple cartridge of Examples 49 or 50, wherein the third angle is greater than the first angle.

Example 52

The staple cartridge of Examples 48, 49, or 50, wherein the second distance is greater than the first distance.

Example 53

The staple cartridge of Examples 48, 49, 50, 51, or 52, further comprising a plurality of staples positioned in the plurality of staple cavities.

Example 54

The staple cartridge of Example 53, wherein the staples comprise a staple length, and wherein the first distance and the second distance are less than one-third the staple length.

Example 55

The staple cartridge of Examples 53 or 54, wherein the staples comprise a diameter, and wherein the first distance and the second distance are greater than the diameter.

Example 56

The staple cartridge of Examples 48, 49, 50, 51, 52, 53, 54, or 55, wherein the first row comprises an inner row, wherein the second row comprises an intermediate row, and wherein the third row comprises an outer row.

Example 57

The staple cartridge of Example 56, wherein the staple cavities in the inner row are at least partially longitudinally staggered relative to the staple cavities in the outer row.

Example 58

A staple cartridge comprising a cartridge body comprising a longitudinal slot, wherein a plurality of staple cavities are defined in the cartridge body, and a plurality of staples positioned in the plurality of staple cavities, wherein the staples are obliquely oriented relative to the longitudinal slot, and wherein the plurality of staples comprises a first group of staples arranged in a first row, a second group of staples arranged in a second row, wherein the first group of staples in the first row laterally overlap the second group of staples in the second row by a first distance, and a third group of staples arranged in a third row, wherein the second group of staples in the second row laterally overlaps the third group of staples in the third row by a second distance, and wherein the second distance is different than the first distance.

Example 59

The staple cartridge of Example 58, wherein the staples in the first row are oriented at a first angle relative to the longitudinal slot, wherein the staples in the second row are oriented at a second angle relative to the longitudinal slot, wherein the staples in the third row are oriented at a third angle relative to the longitudinal slot, and wherein the first angle, the second angle, and the third angle are different.

Example 60

The staple cartridge of Examples 58 or 59, wherein the second distance is greater than the first distance.

Example 61

The staple cartridge of Examples 58, 59, or 60, wherein the staples comprise a staple length, and wherein the first distance and the second distance are less than one-third the staple length.

Example 62

The staple cartridge of Examples 58, 59, 60, or 61, wherein the staples comprise a diameter, and wherein the first distance and the second distance are greater than the diameter.

Example 63

The staple cartridge of Examples 58, 59, 60, 61, or 62, wherein the first row comprises an inner row, wherein the second row comprises an intermediate row, and wherein the third row comprises an outer row.

Example 64

The staple cartridge of Example 63, wherein the staple cavities in the inner row are at least partially longitudinally staggered relative to the staple cavities in the outer row.

Example 65

A staple cartridge comprising a cartridge body comprising a longitudinal slot, wherein a plurality of staple cavities are defined in the cartridge body, and a plurality of staples positioned in the plurality of staple cavities, wherein the staples are obliquely oriented relative to the longitudinal slot, and wherein the plurality of staples comprises a first group of staples arranged in an inner row, a second group of staples arranged in an intermediate row, wherein the inner row is laterally offset from the intermediate row by a first distance, and a third group of staples arranged in an outer row, wherein the outer row is laterally offset from the intermediate row by a second distance, and wherein the second distance is different than the first distance.

Example 66

The staple cartridge of Example 65, wherein the staples in the inner row are oriented at a first angle relative to the longitudinal slot, wherein the staples in the intermediate row are oriented at a second angle relative to the longitudinal slot, wherein the staples in the outer row are oriented at a third angle relative to the longitudinal slot, and wherein the first angle, the second angle, and the third angle are different.

Example 67

The staple cartridge of Examples 65 or 66, wherein each staple in the first group is longitudinally offset from an adjacent the staple in the second group by a first longitudinal distance, wherein each staple in the third group is longitudinally offset from an adjacent the staple in the third group by a second longitudinal distance, and wherein the second longitudinal distance is different than the first longitudinal distance.

Example 68

An adaptor for use with an end effector having an anvil comprising a first arrangement of staple-forming pockets, the adaptor comprising a staple cartridge comprising a plurality of staples and an anvil plate comprising a second arrangement of staple-forming pockets, wherein the second arrangement of staple-forming pockets is different than the first arrangement of staple-forming pockets.

Example 69

The adaptor of Example 68, wherein the anvil plate further comprises an alignment feature configured to engage the anvil.

Example 70

The adaptor of Examples 68 or 69, wherein the anvil plate further comprises an alignment post positioned in an alignment aperture in the staple cartridge.

Example 71

The adaptor of Examples 68, 69, or 70, wherein the anvil plate further comprises an alignment ridge aligned with a longitudinal slot in the anvil.

Example 72

The adaptor of Examples 68, 69, 70, or 71, further comprising a spring connection between the staple cartridge and the anvil plate.

Example 73

The adaptor of Examples 68, 69, 70, 71, or 72, further comprising a deformable material.

Example 74

The adaptor of Example 73, wherein the deformable material comprises an overmold on the anvil plate.

Example 75

The adaptor of Examples 68, 69, 70, 71, 72, 73, or 74, wherein the anvil plate comprises a stamped metal sheet.

Example 76

The adaptor of Examples 68, 69, 70, 71, 72, 73, 74, or 75, wherein the second arrangement of staple-forming pockets are partially nested in the first arrangement of staple-forming pockets.

Example 77

The adaptor of Examples 68, 69, 70, 71, 72, 73, 74, 75, or 76, wherein the first arrangement of staple-forming pockets comprises a plurality of rows of parallel staple-forming pockets, and wherein the second arrangement of staple-forming pockets comprises a plurality of rows of angled staple-forming pockets.

Example 78

The adaptor of Example 77, wherein the staple cartridge comprises a cartridge body, wherein a plurality of staple cavities are defined in the cartridge body, and wherein the staple cavities are arranged in a plurality of angled rows corresponding to the plurality of rows of angled staple-forming pockets.

Example 79

An adaptor for use with an end effector having a staple-forming anvil, the adaptor comprising a staple cartridge comprising a plurality of staple cavities and a plurality of staples positioned in the staple cavities. The adaptor further comprises an anvil plate, wherein the anvil plate is movable between an open position and a closed position relative to the staple cartridge. The anvil plate comprises a plurality of staple-forming pockets, wherein each staple is aligned with a corresponding the staple-forming pocket when the anvil plate is in the closed position, and an alignment feature configured to engage the staple-forming anvil.

Example 80

The adaptor of Example 79, further comprising a deformable overmold on the anvil plate.

Example 81

The adaptor of Examples 79 or 80, wherein the anvil plate comprises a stamped metal sheet.

Example 82

The adaptor of Examples 79, 80, or 81, wherein the staple cavities are arranged in a herringbone pattern, and wherein the staple-forming pockets are arranged in a corresponding herringbone pattern.

Example 83

An adaptor for use with an end effector having an anvil comprising a plurality of first staple-forming pockets, the adaptor comprising a staple cartridge comprising a plurality of staple cavities and a plurality of staples positioned in the staple cavities, wherein the plurality of staples are misaligned with the first staple-forming pockets. The adaptor further comprises an anvil plate comprising a plurality of second staple-forming pockets, wherein the staples are aligned with the second staple-forming pockets.

Example 84

The adaptor of Example 83, further comprising a deformable overmold on the anvil plate.

Example 85

The adaptor of Examples 83 or 84, wherein the anvil plate comprises a stamped metal sheet.

Example 86

The adaptor of Examples 83, 84, or 85, wherein the second staple-forming pockets are partially nested in the first staple-forming pockets.

Example 87

The adaptor of Examples 83, 84, 85, or 86, wherein the first staple-forming pockets are arranged in a plurality of rows of parallel staple-forming pockets, and wherein the second staple-forming pockets are arranged in a plurality of rows of angled staple-forming pockets.

Example 88

A method comprising obtaining a staple cartridge comprising a plurality of staples, wherein each staple comprises a base and a leg extending from the base and firing the staples from the staple cartridge, wherein the staples are fired into tissue in a staple line. The staple line comprises a first portion comprising a first flexibility and a second portion longitudinally offset from the first portion, wherein the second portion comprises a second flexibility, and wherein the second flexibility is different than the first flexibility.

Example 89

The method of Example 88, further comprising selecting the staple cartridge from at least two different staple cartridges.

Example 90

The method of Example 89, wherein the at least two different staple cartridges comprise different arrangements of staple cavities.

Example 91

The method of Examples 88, 89, or 90, wherein the first portion comprises a distal portion.

Example 92

The method of Examples 88, 89, 90, or 91, wherein the first portion is laterally offset from the second portion.

Example 93

The method of Examples 88, 89, 90, 91, or 92, wherein the first portion comprises a first row of staples, and wherein the second portion comprises a second row of staples.

Example 94

A method comprising obtaining a staple cartridge comprising a plurality of staples, wherein each staple comprises a base and a leg extending from the base and firing the staples from the staple cartridge, wherein the staples are fired into tissue in a staple line. The staple line comprises a first length comprising a first group of the staples, wherein the bases of the staples in the first group are arranged in a herringbone pattern, and a second length comprising a second group of the staples, wherein the second length is longitudinally offset from the first length, and wherein the bases of the staples in the first group are arranged in parallel.

Example 95

The method of Example 94, wherein the first length comprises a first flexibility, wherein the second length comprises a second flexibility, and wherein the second flexibility is different than the first flexibility.

Example 96

The method of Examples 94 or 95, wherein the first length is more flexible than the second length.

Example 97

The method of Examples 94, 95, or 96, further comprising selecting the staple cartridge from at least two different staple cartridges.

Example 98

The method of Example 97, wherein the at least two different staple cartridges comprise different arrangements of staple cavities.

Example 99

A method comprising obtaining an adaptor assembly comprising a staple cartridge and an anvil plate, wherein the anvil plate comprises a plurality of first staple-forming pockets, and wherein the plurality of first staple-forming pockets are arranged in a first arrangement, and installing the adaptor assembly in an end effector, wherein the end effector comprises an anvil comprising a plurality of second staple-forming pockets, wherein the second staple-forming pockets are arranged in a second arrangement, and wherein the second arrangement is different than the first arrangement.

Example 100

The method of Example 99, wherein the first arrangement comprises a herringbone pattern of pockets.

Example 101

The method of Examples 99 or 100, wherein the second arrangement comprises a parallel pattern of pockets.

Example 102

The method of Examples 99, 100, or 101, wherein the staple cartridge comprises a plurality of staple cavities arranged in a corresponding herringbone pattern.

Example 103

The method of Examples 99, 100, 101, or 102, wherein the staple cartridge comprises a plurality of staples arranged in a corresponding herringbone pattern.

Example 104

The method of Example 103, further comprising driving the staples into forming contact with the second staple-forming pockets in the adaptor assembly.

Example 105

The method of Examples 99, 100, 101, 102, 103, or 104, wherein the adaptor assembly comprises a deformable material, and wherein the installing step further comprises forming the deformable material to a deformed configuration that corresponds to a profile of the anvil.

Example 106

The method of Examples 99, 100, 101, 102, 103, 104, or 105, wherein the installing step further comprises aligning features on the anvil plate with features on the anvil.

Example 107

The method of Examples 99, 100, 101, 102, 103, 104, 105, or 106, further comprising clamping tissue between the staple cartridge and the anvil plate.

Example 108

An end effector for use with a surgical stapler, the end effector comprising a staple cartridge comprising a plurality of staples, wherein the plurality of staples comprises a first staple and a second staple, and wherein the second staple is obliquely oriented relative to the first staple, and an anvil comprising a staple-forming surface, wherein a plurality of pockets are defined in the staple-forming surface, and wherein the pockets cover more than 50% of the staple-forming surface.

Example 109

The end effector of Example 108, wherein each pocket comprises a perimeter, and wherein the perimeters are adjacently nested along the staple-forming surface.

Example 110

The end effector of Examples 108 or 109, wherein each pocket comprises a proximal cup, a distal cup, and a neck extending between the proximal cup and the distal cup.

Example 111

The end effector of Example 110, wherein the plurality of pockets comprises a first pocket in a first row, a second pocket in a second row, and a third pocket in a third row, and wherein the second pocket comprises a proximal extended landing zone extending toward the neck of the first pocket.

Example 112

The end effector of Examples 110 or 111, wherein the second pocket further comprises a distal extended landing zone extending toward the neck of the third pocket.

Example 113

An end effector for use with a surgical stapler, the end effector comprising a staple cartridge comprising a plurality of staples, wherein the plurality of staples comprises a first staple and a second staple, and wherein the second staple is angularly oriented with respect to the first staple, and an anvil comprising a staple-forming surface, wherein a plurality of pockets are defined in the staple-forming surface, and wherein the plurality of pockets comprises a first pocket aligned with the first staple, wherein the first pocket comprises a first proximal cup and a first distal cup, and a second pocket aligned with the second staple, wherein the second pocket comprises a second proximal cup and a second distal cup, wherein the first distal cup extends into a receiving peninsula defined between a portion of the second proximal cup and a portion of the second distal cup.

Example 114

The end effector of Example 113, wherein the staple-forming surface comprises a non-forming portion extending around the pockets, and wherein the non-forming portion covers less than 50% of the staple-forming surface.

Example 115

The end effector of Examples 113 or 114, wherein the first pocket further comprises a first neck extending between the first proximal cup and the first distal cup, and wherein the second pocket further comprises a second neck extending between the second proximal cup and the second distal cup.

Example 116

The end effector of Example 115, wherein the first neck is narrower than the first proximal cup and the first distal cup, and wherein the second neck is narrower than the second proximal cup and the second distal cup.

Example 117

The end effector of Examples 113, 114, 115, or 116, wherein the first distal cup extends laterally toward the second pocket.

Example 118

The end effector of Examples 113, 114, 115, 116, or 117, wherein the first distal cup extends longitudinally toward the second pocket.

Example 119

The end effector of Examples 113, 114, 115, 116, 117, or 118, wherein the first distal cup comprises an extended landing zone disposed in the receiving peninsula.

Example 120

The end effector of Examples 113, 114, 115, 116, 117, 118, or 119, wherein the plurality of pockets further comprises a third pocket aligned with a third staple, wherein the third pocket comprises a third proximal cup and a third distal cup, and wherein the second proximal cup extends into a second receiving peninsula between a portion of the third proximal cup and a portion of the third distal cup.

Example 121

The end effector of Example 120, wherein the pockets are arranged in a plurality of rows, and wherein the plurality of rows comprises an inner row comprising the first pocket, an intermediate row comprising the second pocket, wherein the second pocket is offset from the first pocket, and an outer row comprising the third pocket, wherein the third pocket is aligned with the first pocket.

Example 122

An end effector for use with a surgical stapler, the end effector comprising a staple cartridge comprising a plurality of staples, wherein the plurality of staples comprises a first staple and a second staple, and wherein the second staple is angularly oriented with respect to the first staple, and an anvil comprising a staple-forming surface, wherein a plurality of pockets are defined in the staple-forming surface, wherein the plurality of pockets are arranged in a plurality of rows, and wherein the plurality of rows comprises a first row comprising a first pocket aligned with the first staple, wherein the first pocket comprises a narrow-most region, and a second row comprising a second pocket aligned with the second staple, wherein the second pocket comprises a proximal end and a distal end, and wherein a pocket axis extending between the proximal end and the distal end transects the narrow-most region of the first pocket.

Example 123

The end effector of Example 122, wherein the first pocket comprises a perimeter, and wherein the second pocket nests in the perimeter of the first pocket.

Example 124

The end effector of Examples 122 or 123, wherein the staple-forming surface comprises a non-forming portion extending around the pockets, wherein the non-forming portion comprises less than 50% of the staple-forming surface.

Example 125

The end effector of Examples 122, 123, or 124, wherein the second pocket comprises a groove extending along the pocket axis.

Example 126

The end effector of Examples 122, 123, 124, or 125, wherein the staple-forming portion comprises a non-forming portion extending around the pockets, wherein the second pocket comprises a sidewall extending between the proximal end and the distal end, and wherein the sidewall is oriented at a constant angle relative to the non-forming portion from the proximal end to the distal end.

Example 127

The end effector of Examples 122, 123, 124, 125, or 126, wherein the second pocket comprises a chamfered perimeter.

Example 128

A staple cartridge comprising a cartridge body comprising a longitudinal slot, wherein a plurality of staple cavities are defined in the cartridge body, and wherein the staple cavities are obliquely oriented relative to the longitudinal slot, and a plurality of staples positioned in the staple cavities, wherein the staple cavities in the cartridge body are arranged in a plurality of rows. The plurality of rows comprises a first row positioned on a first side of the longitudinal slot, a second row positioned on the first side of the longitudinal slot, wherein the staples positioned in the staple cavities in the first row are longitudinally spaced from the staples positioned in the staple cavities in the second row by a first distance, and a third row positioned on the first side of the longitudinal slot, wherein the staples positioned in the staple cavities in the third row are longitudinally spaced from the staples positioned in the staple cavities in the second row by a second distance, and wherein the second distance is different than the first distance.

Example 129

The staple cartridge of Example 128, wherein the second row is positioned intermediate the first row and the third row.

Example 130

The staple cartridge of Examples 128 or 129, wherein the staples in the staple cavities in the first row longitudinally overlap the staples in the staple cavities in the second row by the first distance, and wherein the staples in the staple cavities in the third row longitudinally overlap the staples in the staple cavities in the second row by the second distance.

Example 131

The staple cartridge of Examples 128, 129, or 130, wherein the second distance is zero.

Example 132

The staple cartridge of Examples 128, 129, 130, or 131, wherein the plurality of staples comprises a first staple positioned in one of the staple cavities in the first row, wherein the first staple comprises a first base comprising a first length, and a third staple positioned in one of the staple cavities in the third row, wherein the third staple comprises a third base comprising a third length, and wherein the third length is different than the first length.

Example 133

The staple cartridge of Example 132, wherein the plurality of staples further comprises a second staple positioned in one of the staple cavities in the second row, wherein the second staple comprises a second base comprising a second length, and wherein the second length is different than the first length and the third length.

Example 134

The staple cartridge of Examples 128, 129, 130, 131, 132, or 133, wherein the staple cavities in the first row are oriented at a first angle relative to the longitudinal slot, wherein the staple cavities in the second row are oriented at a second angle relative to the longitudinal slot, and wherein the staple cavities in the third row are oriented at a third angle relative to the longitudinal slot.

Example 135

The staple cartridge of Example 134, wherein the second angle is different than the first angle and the third angle.

Example 136

The staple cartridge of Examples 134 or 135, wherein the second angle is 180 degrees offset from the first angle.

Example 137

The staple cartridge of Examples 134, 135, or 136, wherein the third angle is different than the first angle.

Example 138

A staple cartridge comprising a cartridge body comprising a longitudinal slot, wherein a plurality of staple cavities are defined in the cartridge body, wherein the staple cavities are obliquely oriented relative to the longitudinal axis, wherein each staple cavity comprises a proximal end and a distal end, wherein the plurality of staple cavities are arranged in a plurality of rows. The plurality of rows comprises a first row positioned on a first side of the longitudinal slot, a second row positioned on the first side of the longitudinal slot, wherein the proximal and distal ends of the staple cavities in the second row are longitudinally offset relative to the proximal and distal ends of the staple cavities in the first row, and a third row positioned on the first side of the longitudinal slot, wherein the proximal and distal ends of the staple cavities in the third row are longitudinally offset relative to the proximal and distal ends of the staple cavities in the first row and the second row.

Example 139

The staple cartridge of Example 138, wherein the staple cavities in the third row at least partially longitudinally overlap the staple cavities in the first row.

Example 140

The staple cartridge of Examples 138 or 139, wherein the staple cavities in the second row at least partially longitudinally overlap the staple cavities in the third row.

Example 141

The staple cartridge of Examples 138, 139, or 140, wherein the staple cavities in the second row at least partially longitudinally overlap the staple cavities in the first row.

Example 142

The staple cartridge of Examples 138, 139, 140, or 141, further comprising a plurality of staples positioned in the staple cavities, wherein the plurality of staples comprises a first staple positioned in one of the staple cavities in the first row, wherein the first staple comprises a first base comprising a first length, and a third staple positioned in one of the staple cavities in the third row, wherein the third staple comprises a third base comprising a third length, and wherein the third length is greater than the first length.

Example 143

The staple cartridge of Example 142, wherein the plurality of staples further comprises a second staple positioned in one of the staple cavities in the second row, wherein the second staple comprises a second base comprising a second length, and wherein the second length is different than the first length and the third length.

Example 144

The staple cartridge of Examples 138, 139, 140, 141, 142, or 143, wherein the staple cavities in the first row are oriented at a first angle relative to the longitudinal slot, wherein the staple cavities in the second row are oriented at a second angle relative to the longitudinal slot, and wherein the staple cavities in the third row are oriented at a third angle relative to the longitudinal slot.

Example 145

The staple cartridge of Example 144, wherein the second angle is different than the first angle and the third angle.

Example 146

The staple cartridge of Examples 144 or 145, wherein the third angle is different than the first angle.

Example 147

A staple cartridge comprising a cartridge body comprising a longitudinal slot, wherein a plurality of staple cavities are defined in the cartridge body, wherein the staple cavities are angularly oriented relative to the longitudinal slot, wherein the staple cavities are arranged in a plurality of rows. The plurality of rows comprises a first row positioned on a first side of the longitudinal slot, a second row positioned on the first side of the longitudinal slot, wherein the staples in the first row longitudinally overlap the staples in the second row by a first distance, and a third row positioned on the first side of the longitudinal slot, wherein the staples in the third row longitudinally overlap the staples in the second row by a second distance, and wherein the second distance is different than the first distance. The staple cartridge further comprises a plurality of staples positioned in the staple cavities.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES; now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012; now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A staple cartridge, comprising:
   a longitudinal slot extending along a longitudinal axis, wherein the longitudinal axis defines a first side and a second side of the staple cartridge;
   a cartridge body, wherein staple cavities are defined in said cartridge body, wherein each staple cavity comprises a longitudinal length with respect to said longitudinal axis;
   wherein a first plurality of said staple cavities are arranged in a longitudinally-repetitive pattern on said first side, and wherein said longitudinally-repetitive pattern comprises staples cavities at different angular orientations with respect to said longitudinal axis;
   wherein a second plurality of said staple cavities are positioned on said first side, wherein said second plurality of said staple cavities comprises a first staple cavity angularly-offset from said staple cavities in said longitudinally-repetitive pattern, wherein said first staple cavity defines a first axis that is parallel to the longitudinal axis, wherein said second plurality of said staple cavities are distal to said first plurality of said staple cavities with respect to said longitudinal axis, and wherein none of said longitudinal lengths of said second plurality of said staple cavities longitudinally overlap said longitudinal lengths of said first plurality of said staple cavities with respect to said longitudinal axis;
   wherein a third plurality of said staple cavities are positioned on said first side, wherein said third plurality of said staple cavities comprises a second staple cavity angularly-offset from said staple cavities in said longitudinally-repetitive pattern, wherein said second staple cavity defines a second axis that is parallel to the longitudinal axis, wherein said third plurality of said staples cavities are proximal to said first plurality of said staple cavities with respect to said longitudinal axis, and wherein none of said longitudinal lengths of said third plurality of said staple cavities longitudinally overlap said longitudinal lengths of said first plurality of said staple cavities with respect to said longitudinal axis; and
a plurality of staples positioned in said staple cavities.

2. The staple cartridge of claim 1, further comprising a firing element configured to translate between a proximal position and a distal position in said cartridge body, wherein said longitudinally-repetitive pattern extends distally beyond the distal position of said firing element.

3. The staple cartridge of claim 1, wherein said longitudinally-repetitive pattern consists of a pattern of staple cavities obliquely oriented relative to the longitudinal axis.

4. The staple cartridge of claim 3, wherein said cartridge body comprises a deck, wherein each said staple cavity defines an opening in said deck, and wherein said openings of said staple cavities in said longitudinally-repetitive pattern form a herringbone pattern.

5. A staple cartridge, comprising:
a longitudinal slot extending along a longitudinal axis, wherein the longitudinal axis defines a first side and a second side of the staple cartridge;
a cartridge body, wherein staple cavities are defined in said cartridge body, wherein each staple cavity comprises a longitudinal length with respect to said longitudinal axis, wherein said staple cavities are arranged in a plurality of patterns, and wherein said plurality of patterns comprises:
a first pattern on said first side, wherein said first pattern comprises a first plurality of longitudinally-repetitive staple cavities angularly oriented relative to said longitudinal axis; and
a second pattern on said first side, wherein said second pattern comprises a second plurality of said staple cavities, wherein said second pattern is distal to said first pattern with respect to said longitudinal axis, wherein said second pattern is different than said first pattern, wherein none of said longitudinal lengths of said second plurality of said staple cavities longitudinally overlap said longitudinal lengths of said first plurality of longitudinally-repetitive staple cavities with respect to said longitudinal axis, and wherein said second pattern comprises a first cavity defining a first axis that is parallel to the longitudinal axis;
a third pattern on said first side, wherein said third pattern comprises a third plurality of said staple cavities, wherein said third pattern is proximal to said first pattern with respect to said longitudinal axis, wherein said third pattern is different than said first pattern, and wherein none of said longitudinal lengths of said third plurality of said staple cavities longitudinally overlap said longitudinal lengths of said first plurality of longitudinally-repetitive staple cavities with respect to said longitudinal axis, and wherein said third pattern comprises a second cavity defining a second axis that is parallel to the longitudinal axis; and
a plurality of staples positioned in said staple cavities.

6. The staple cartridge of claim 5, wherein said cartridge body comprises a deck, and wherein said first pattern comprises;
a plurality of obliquely-oriented staple cavity openings in said deck.

7. The staple cartridge of claim 6, wherein said first pattern comprises a herringbone pattern.

8. The staple cartridge of claim 5, further comprising a plurality of staple drivers comprising:
a first driver comprising a first ramp profile; and
a second driver comprising a second ramp profile, wherein said first driver is connected to said second driver, and wherein said first ramp profile is different than said second ramp profile.

9. The staple cartridge of claim 5, further comprising a cutting edge configured to move relative to said cartridge body during a firing stroke, wherein said cutting edge is configured to move between a proximal position and a distal position, and wherein said second pattern is positioned distal to said distal position of said cutting edge.

10. A staple cartridge, comprising:
a longitudinal axis;
a cartridge body, wherein staple cavities are defined in said cartridge body, wherein each staple cavity comprises a longitudinal length with respect to said longitudinal axis, wherein said staple cavities are arranged in a plurality of patterns, and wherein said plurality of patterns comprises:
a first pattern comprising a first plurality of staple cavities angularly oriented relative to said longitudinal axis, wherein said first pattern comprises a longitudinally-repetitive pattern, and wherein said longitudinally-repetitive pattern comprises a herringbone pattern;
a second pattern comprising a second plurality of said staple cavities, wherein said second pattern is distal to said first pattern with respect to said longitudinal axis, wherein said second pattern is different than said first pattern, and wherein none of said longitudinal lengths of said second plurality of said staple cavities longitudinally overlap said longitudinal lengths of said first plurality of staple cavities with respect to said longitudinal axis;
a third pattern comprising a third plurality of said staple cavities, wherein said third pattern is proximal to said first pattern with respect to said longitudinal axis, wherein said third pattern is different than said first pattern, and wherein none of said longitudinal lengths of said third plurality of said staple cavities longitudinally overlap said longitudinal lengths of said first plurality of staple cavities with respect to said longitudinal axis; and
a plurality of staples positioned in said staple cavities;
wherein said cartridge body further comprises a deck, and wherein said longitudinally-repetitive pattern comprises:
a first staple cavity defining a first opening in said deck; and
a second staple cavity defining a second opening in said deck, wherein said second opening is obliquely oriented relative to said first opening;
wherein said second pattern comprises a third staple cavity defining a third opening in said deck, and wherein said third opening is obliquely oriented relative to said first opening and said second opening;
wherein said second pattern further comprises a fourth staple cavity defining a fourth opening in said deck, wherein said fourth opening is parallel to said third opening, and wherein said fourth opening is longitudinally staggered relative to said third opening.

11. An end effector for stapling tissue, the end effector comprising:
a staple cartridge comprising a cartridge body, wherein staple cavities are defined in said cartridge body, wherein each staple cavity comprises a longitudinal length with respect to a longitudinal axis, wherein said staple cavities are arranged in a plurality of patterns, and wherein said plurality of patterns comprises:

a first pattern comprising a first plurality of longitudinally-repetitive staple cavities angularly oriented relative to the longitudinal axis;

a second pattern comprising a second plurality of said staple cavities, wherein said second pattern is distal to said first pattern with respect to the longitudinal axis, wherein said second pattern is different than said first pattern, and wherein none of said longitudinal lengths of said second plurality of said staple cavities longitudinally overlap said longitudinal lengths of said first plurality of longitudinally-repetitive staple cavities with respect to the longitudinal axis, and wherein said second pattern comprises a first staple cavity defining a first axis that is parallel to the longitudinal axis; and a third pattern comprising a third plurality of said staple cavities, wherein said third pattern is proximal to said first pattern with respect to said longitudinal axis, wherein said third pattern is different than said first pattern, and wherein none of said longitudinal lengths of said third plurality of said staple cavities longitudinally overlap said longitudinal lengths of said first plurality of longitudinally-repetitive staple cavities with respect to said longitudinal axis, and wherein said third pattern comprises a second staple cavity defining a second axis that is parallel to the longitudinal axis;

a cutting edge configured to move between a proximal position and a distal position; and a tissue stop, wherein said first pattern extends between said tissue stop and the distal position of said cutting edge.

12. The end effector of claim 11, wherein said second pattern comprises a plurality of parallel staple cavities.

13. The end effector of claim 12, wherein said parallel staple cavities are obliquely oriented relative to said staple cavities in said first pattern.

14. The end effector of claim 11, further comprising an anvil, wherein said tissue stop comprises a pair of sidewalls extending from said anvil toward said staple cartridge.

\* \* \* \* \*